US012319724B2

(12) United States Patent
Wu et al.

(10) Patent No.: US 12,319,724 B2
(45) Date of Patent: *Jun. 3, 2025

(54) IL2 AGONISTS AND METHODS OF USE THEREOF

(71) Applicant: Regeneron Pharmaceuticals, Inc., Tarrytown, NY (US)

(72) Inventors: Jiaxi Wu, Elsmford, NY (US); Tong Zhang, Fort Lee, NJ (US); Maria del Pilar Molina-Portela, Bronx, NY (US); Eric Smith, New York, NY (US); Chia-Yang Lin, Scarsdale, NY (US); Thomas Craig Meagher, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/843,243

(22) Filed: Jun. 17, 2022

(65) Prior Publication Data

US 2022/0362395 A1 Nov. 17, 2022

Related U.S. Application Data

(63) Continuation of application No. PCT/US2020/066096, filed on Dec. 18, 2020.

(60) Provisional application No. 62/951,831, filed on Dec. 20, 2019.

(51) Int. Cl.
| | |
|---|---|
| *A61K 39/00* | (2006.01) |
| *A61K 35/17* | (2015.01) |
| *A61K 38/20* | (2006.01) |
| *A61K 39/12* | (2006.01) |
| *A61K 40/11* | (2025.01) |
| *A61K 40/31* | (2025.01) |
| *A61K 40/42* | (2025.01) |
| *A61K 40/46* | (2025.01) |
| *A61K 47/68* | (2017.01) |
| *A61P 35/00* | (2006.01) |
| *C07K 14/55* | (2006.01) |
| *C07K 14/705* | (2006.01) |
| *C07K 14/715* | (2006.01) |
| *C07K 14/725* | (2006.01) |
| *C07K 14/74* | (2006.01) |
| *A61K 38/00* | (2006.01) |

(52) U.S. Cl.
CPC .............. *C07K 14/55* (2013.01); *A61K 35/17* (2013.01); *A61K 38/2013* (2013.01); *A61K 39/0011* (2013.01); *A61K 40/11* (2025.01); *A61K 40/31* (2025.01); *A61K 40/4234* (2025.01); *A61K 40/46* (2025.01); *A61K 47/6849* (2017.08); *A61P 35/00* (2018.01); *C07K 14/7051* (2013.01); *C07K 14/70517* (2013.01); *C07K 14/70539* (2013.01); *C07K 14/7155* (2013.01); *A61K 38/00* (2013.01); *A61K 2239/50* (2023.05); *A61K 2239/55* (2023.05); *A61K 2239/57* (2023.05); *C07K 2319/30* (2013.01)

(58) Field of Classification Search
None
See application file for complete search history.

(56) References Cited

U.S. PATENT DOCUMENTS

| | | | |
|---|---|---|---|
| 6,348,192 B1 | 2/2002 | Chan et al. | |
| 6,689,353 B1 | 2/2004 | Wang et al. | |
| 6,955,807 B1 | 10/2005 | Shanafelt et al. | |
| 6,967,092 B1 | 11/2005 | McKearn et al. | |
| 7,404,956 B2 | 7/2008 | Peters et al. | |
| 8,012,465 B2 | 9/2011 | Elias et al. | |
| 8,124,084 B2 | 2/2012 | Lefrancois et al. | |
| 8,349,311 B2 | 1/2013 | Wittrup et al. | |
| 8,518,697 B2 | 8/2013 | Hansen et al. | |
| 8,734,774 B2 | 5/2014 | Frelinger et al. | |
| 8,895,020 B2 | 11/2014 | Hansen et al. | |
| 8,945,571 B2 | 2/2015 | Mössner et al. | |
| 8,992,937 B2 | 3/2015 | Hansen et al. | |
| 9,206,243 B2 | 12/2015 | Leó n Monzón et al. | |
| 9,266,938 B2 | 2/2016 | Ast et al. | |
| 9,359,415 B2 | 6/2016 | Alvarez et al. | |
| 9,447,159 B2 | 9/2016 | Ast et al. | |
| 9,931,413 B2 | 4/2018 | Chang et al. | |
| 10,174,091 B1 | 1/2019 | Higginson-Scott et al. | |
| 10,174,092 B1 | 1/2019 | Higginson-Scott et al. | |
| 10,407,481 B2 | 9/2019 | Alvarez | |
| 10,464,993 B2 | 11/2019 | Lefrancois et al. | |
| 10,556,952 B2 | 2/2020 | Davis et al. | |
| 10,696,724 B2 | 6/2020 | Winston et al. | |
| 10,787,494 B2 | 9/2020 | Struthers et al. | |
| 10,927,158 B2 * | 2/2021 | Seidel, III | C07K 14/55 |
| 10,927,161 B2 * | 2/2021 | Seidel, III | C07K 16/2818 |

(Continued)

FOREIGN PATENT DOCUMENTS

| | | |
|---|---|---|
| CA | 2831008 | 11/2012 |
| CA | 3098653 A1 * | 11/2019 |

(Continued)

OTHER PUBLICATIONS

Biology Dictionary (2022, 4 pages) (Year: 2022).*

(Continued)

*Primary Examiner* — Michael Szperka
*Assistant Examiner* — Marianne Dibrino
(74) *Attorney, Agent, or Firm* — Biospark Intellectual Property Law

(57) ABSTRACT

The present disclosure relates to IL2 agonists with improved therapeutic profiles.

13 Claims, 63 Drawing Sheets
Specification includes a Sequence Listing.

(56) References Cited

U.S. PATENT DOCUMENTS

| | | |
|---|---|---|
| 10,946,068 B2 | 3/2021 | Higginson-Scott et al. |
| 10,961,310 B2 | 3/2021 | Viney et al. |
| 11,053,294 B2 | 7/2021 | Karow et al. |
| 11,225,520 B2 | 1/2022 | Novina et al. |
| 11,359,000 B2 | 6/2022 | Struthers et al. |
| 11,725,034 B2 * | 8/2023 | Wu .................. A61K 38/2013 424/134.1 |
| 2003/0166163 A1 | 9/2003 | Gillies |
| 2015/0258260 A1 | 9/2015 | Tuseth |
| 2017/0037102 A1 | 2/2017 | Greve |
| 2017/0204154 A1 | 7/2017 | Greve |
| 2017/0216403 A1 | 8/2017 | Wittrup et al. |
| 2017/0233448 A1 | 8/2017 | Malek |
| 2017/0368169 A1 | 12/2017 | Loew et al. |
| 2018/0125941 A1 | 5/2018 | Greve |
| 2018/0228842 A1 | 8/2018 | Garcia et al. |
| 2018/0265584 A1 | 9/2018 | Viney et al. |
| 2018/0326010 A1 | 11/2018 | Codarri Deak et al. |
| 2019/0062395 A1 | 2/2019 | Merchant et al. |
| 2019/0119345 A1 | 4/2019 | Krupnick et al. |
| 2019/0169254 A1 | 6/2019 | Higginson-Scott et al. |
| 2019/0241638 A1 | 8/2019 | Bernett et al. |
| 2019/0300592 A1 | 10/2019 | Struthers et al. |
| 2019/0389933 A1 | 12/2019 | Bernett et al. |
| 2020/0140512 A1 | 5/2020 | Bernett et al. |
| 2020/0316118 A1 | 10/2020 | Jounaidi et al. |
| 2021/0094996 A1 | 4/2021 | Viney et al. |
| 2021/0130430 A1 | 5/2021 | Winston et al. |
| 2021/0238246 A1* | 8/2021 | Hernández García .................. C07K 14/56 |
| 2021/0269496 A1 | 9/2021 | Rios et al. |
| 2021/0277085 A1 | 9/2021 | Higginson-Scott et al. |
| 2021/0340209 A1 | 11/2021 | Yue et al. |
| 2021/0380699 A1 | 12/2021 | Campbell et al. |
| 2022/0002370 A1 | 1/2022 | Karow et al. |
| 2022/0125884 A1 | 4/2022 | Baca et al. |
| 2022/0227837 A1 | 7/2022 | Li |
| 2022/0235133 A1 | 7/2022 | Li et al. |
| 2022/0289806 A1 | 9/2022 | Xu et al. |
| 2022/0324933 A1 | 10/2022 | Li |
| 2022/0378933 A1 | 12/2022 | Li et al. |
| 2022/0402989 A1 | 12/2022 | Wu et al. |

FOREIGN PATENT DOCUMENTS

| | | |
|---|---|---|
| EP | 1362062 B1 | 5/2005 |
| EP | 2882777 B1 | 10/2018 |
| EP | 3660039 A1 | 6/2020 |
| EP | 3233920 B1 | 8/2020 |
| WO | 2003048334 A2 | 6/2003 |
| WO | WO2009103965 A1 | 8/2009 |
| WO | 2010020766 A2 | 2/2010 |
| WO | 2010085495 A1 | 7/2010 |
| WO | 2012088446 A1 | 6/2012 |
| WO | WO2013184942 A1 | 12/2013 |
| WO | WO2014121087 A1 | 8/2014 |
| WO | 2014153111 A2 | 9/2014 |
| WO | WO2014186469 A2 | 11/2014 |
| WO | WO2015118016 A1 | 8/2015 |
| WO | WO2016022671 A1 | 2/2016 |
| WO | 2016164937 A2 | 10/2016 |
| WO | 2017127514 A1 | 7/2017 |
| WO | WO2018023093 | 2/2018 |
| WO | 2018089420 A1 | 5/2018 |
| WO | 2018170168 A1 | 9/2018 |
| WO | 2018170288 A1 | 9/2018 |
| WO | 2018176505 A1 | 10/2018 |
| WO | WO2018184964 A1 | 10/2018 |
| WO | WO2018184965 A1 | 10/2018 |
| WO | 2018215938 A1 | 11/2018 |
| WO | WO2018217989 A1 | 11/2018 |
| WO | 2017220989 A1 | 12/2018 |
| WO | 2018226750 A1 | 12/2018 |
| WO | 2019010224 A1 | 1/2019 |
| WO | 2019104092 A1 | 5/2019 |
| WO | WO2019112852 A1 | 6/2019 |
| WO | WO2019112854 A1 | 6/2019 |
| WO | 2019051127 A9 | 8/2019 |
| WO | 2019173832 A2 | 9/2019 |
| WO | 2019191295 A1 | 10/2019 |
| WO | 2019168791 A3 | 11/2019 |
| WO | WO 2019/214757 A1 * | 11/2019 |
| WO | WO2019246392 A1 | 12/2019 |
| WO | 2020020783 A1 | 1/2020 |
| WO | WO2020018715 | 1/2020 |
| WO | 2020057645 A1 | 3/2020 |
| WO | 2020061142 A1 | 3/2020 |
| WO | 2020005819 A8 | 4/2020 |
| WO | 2020070150 A1 | 4/2020 |
| WO | WO2020092554 | 5/2020 |
| WO | 2020132136 A1 | 6/2020 |
| WO | 2020132138 A1 | 6/2020 |
| WO | 2020132368 A1 | 6/2020 |
| WO | WO2020131547 | 6/2020 |
| WO | WO2020136060 | 7/2020 |
| WO | WO2020236875 A1 | 11/2020 |
| WO | WO2021011353 A1 | 1/2021 |
| WO | WO2021034890 A1 | 2/2021 |
| WO | WO2021119516 A1 | 6/2021 |
| WO | WO2021127487 A2 | 6/2021 |
| WO | WO2021168192 A2 | 8/2021 |
| WO | WO2021258213 | 12/2021 |
| WO | WO2022236292 A2 | 11/2022 |

OTHER PUBLICATIONS

De Weerd and Nguyen (Immunol. Cell Biol., 2012, 90: 483-491) (Year: 2012).*
Stauber et al (PNAS, 2006, 103: 2788-2793) (Year: 2006).*
Emboss Needle (2022) (Year: 2022).*
HLA Nomenclature (2015) (Year: 2015).*
Wieczorek et al (Front. Immunol. 2017, vol. 8, article 292: 1-16) (Year: 2017).*
Pullen et al (J. Immunol. 1994, 152: 3445-3451) (Year: 1994).*
Marrack et al (Ann. Rev. Immunol. 2008, 26:171-203) (Year: 2008).*
Singh et al (J. Immunol. 2017, 199: 2203-2213) (Year: 2017).*
Liu et al (MHC Complex: Interaction with Peptides. IN: eLS. John Wiley & Songs, Ltd: Chinchester, DOI: 10.1002/9780470015902. a0000922.pub2, 2011, pp. 1-12) (Year: 2011).*
HLA Nomenclature 2023, 2 pages (Year: 2023).*
Greten et al (JIM, 2002, 271: 125-135) (Year: 2002).*
Schutz et al (Immunity, inflammation and Disease, 2014, 2(3): 181-192) (Year: 2014).*
Chen et al (Immunol. Res. 2012, 53: 182-190) (Year: 2012).*
Barouch et al (JEM, 1995, 182: 1847-1856) (Year: 1995).*
Augusto and Hollenbach (Curr. Opin. Immunol. 2022, 76: 102178, pp. 1-8) (Year: 2022).*
Riemer et al (JBC, 2010, 285(38): 29608-29622) (Year: 2010).*
Lim et al (Exp. Hematol., 2006, 34: 296-307) (Year: 2006).*
Bownds et al (J. Immunother. 2001, 24(1): 1-9) (Year: 2001).*
Dubrovina et al (Blood, 2012, 120(8): 1633-1646) (Year: 2012).*
Riley et al (J. Immunotherapy, 2001, 24(3): 212-220) (Year: 2001).*
Written Opinion mailed May 17, 2022 in PCT/US2020/066096.
Written Opinion mailed May 17, 2022 in PCT/US2020/066086.
Stauber et al., 2005 "Cyrstal structure of the Il-2 signaling complex: Paradigm for a heterotrimeric cytokine receptor" PNAS 103(8): 2788-2793.
International Search Report and Written Opinion dated Jun. 28, 2021 in PCT/US2020/066086.
International Search Report and Written Opinion dated Apr. 21, 2021 in PCT/US2020/066096.
Carmenate et al., 2013, "Human IL-2 Mutein with Higher Antitumor Efficacy Than Wild Type IL-2" J Immunol 190:6230-6238.
Card et al., 2004, "A soluble single-chain T-cell receptor IL-2 fusion protein retains WC-restricted peptide specificity and IL-2 bioactivity", Cancer Immunology 53(4): 345-357.

(56) References Cited

OTHER PUBLICATIONS

Hernandez et al., 2020, "Amplification of neoantigen-specific antitumor responses using a long-lasting IL-2 fusion protein" J Immunol 204 (1 Supplement) 239.9.
Hutmacher et al., 2019, "Targeted Delivery of IL2 to the Tumor Stroma Potentiates the Action of Immune Checkpoint Inhibitors by Preferential Activation of NK and CD8 T Cells" 7(4): 572-583.
Klein et al., 2017 "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines", Oncoimmunology 6(3): ep1277306.
Kontermann et al., 2011, "Strategies for extended serum half-life of protein therapeutics" Current Opinion in Biotechnology 22(6): 868-876.
Melder et al., 2005 "Pharmacokinetics and in vitro and in vivo anti-tumor response of an interleukin-2-human serum albumin fusion protein in mice" Cancer Immunology, Immunology 54: 535-547.
Millington et al., 2012, "Effects of an agonist interleukin-2/Fc fusion protein, a mutant antagonist interleukin-15/Fc fusion protein, and sirolimus on cardiac allograft survival in non-human primates" The Journal of Heart and Lung Transplantation 31(4): 427-435.
Mullard, 2021, "Restoring IL-2 to its cancer immunotherapy glory" Nature Reviews Drug Discovery 20(3): 163-165.
Puskas et al., 2011, "Development of an attenuated interleukin-2 fusion protein that can be activated by tumour-expressed proteases" Immunology 133: 206-220.
Quayle et al., 2020, "CUE-101, a Novel E7-pHLA-IL2-Fc Fusion Protein, Enhances Tumor Antigen-Specific T-Cell Activation for the Treatment of HPV16-Drive Malignancies" Clin Cancer Res. 26(8): 1953-64.
Soriano et al., 2019 "A novel engineered fusion protein effectively targets and expands disease specific anti-tumor T-cells." Summit (PEGS). Poster.
Stoklasek et al., 2006, Combined IL-15/IL-15Rα Immunotherapy Maximizes IL-15 Activity In Vivo, J Immunol., 177(9): 6072-6080.
Sun et al., 2019, "A next-generation tumor-targeting IL-2 preferentially promotes tumor-infiltrating CD8 T-cell response and effective tumor control" Nature Communications 10:3874, pp. 1-12.
Van Krinks et al., 2019 "KY1043, a novel PD-L1 IL-2 immunocytokine directed towards CD25, delivers potent anti-tumour activity in vitro and in vivo." Society for Immunotherapy of Cancer (SITC). Poster, one page.
Ward et al., 2018, "IL-2/CD25: A Long-Acting Fusion Protein That Promotes Immune Tolerance by Selectively Targeting the IL-2 Receptor on Regulatory T Cells" The Journal of Immunology, 20 pages.
Weidle et al., 2014 "TCR-MHC/Peptide Interaction: Prospects for New Anti-tumoral Agents" Cancer Genomics & Proteomics 11:267-278.
Wrangle et al., 2018, "IL-2 and Beyond in Cancer Immunotherpy", Journal of Interferon and Cytokine Research 38(2): 45-68.
Arenas-Ramirez et al., 2015 "Interleukin-2: Biology, Design and Application" Trends in Immunology 36(12): 763-777.
Casadesús et al., 2020, "A rationally-engineered IL-2 improves the antitumor effect of anti-CD20 therapy" OncoImmunology, 9(1):1-12, 1770565.
Hernandez et al. "Sustained IL-2R signaling of limited duration by high-dose mIL-2/mCD25 fusion protein amplifies tumor-reactive CD8+ T cells to enhance antitumor immunity". Cancer Immunol Immunother 70, 909-921 (2021), published online Oct. 10, 2020.
Kosmac et al., "KY1043, a novel CD25-directed PD-L1 IL-2 immunocytokine, delivers potent anti-tumor activity in vivo via an expansion of a Tcf1hiPD-1+CD8+T cell population" Poster. Presented Jun. 22, 2020.
Lopes et al., 2020, "ALKS 4230: a novel engineered IL-2 fusion protein with an improved cellular selectivity profile for cancer immunotherapy" J Immunother Cancer. 8(1):1-13. e000673.

Malek et al., 2010 "Interleukin-2 Receptor Signaling: At the Interface between Tolerance and Immunity" Immunity 33:153-165.
Vidarsson et al., 2014 "IgG subclasses and allotypes: from structure to effector functions" Frontiers in Immunology, 5 (520): 1-17.
Wang et al., 2018 "IgG Fc engineering to modulate antibody effector functions" Protein Cell, 9(1):63-73.
Liu, Jun, and George F. Gao. "Major histocompatibility complex: Interaction with peptides." eLS (2011).
HLA Alleles Numbers 2015, 2 pages.
Marrack, Philippa, et al. "Evolutionarily conserved amino acids that control TCR-MHC interaction." Annu. Rev. Immunol. 26 (2008): 171-203.
Pullen, Jeffrey K., et al. "Recognition of a single amino acid change on the surface of a major transplantation antigen is in the context of self peptide." Journal of immunology (Baltimore, Md.: 1950) 152.7 (1994): 3445-3452.
Singh, Nishant K., et al. "Emerging concepts in TCR specificity: rationalizing and (maybe) predicting outcomes." The Journal of Immunology 199.7 (2017): 2203-2213.
Wieczorek, Marek, et al. "Major histocompatibility complex (MHC) class I and MHC class II proteins: conformational plasticity in antigen presentation." Frontiers in immunology 8 (2017): 292.
Cheung et al., "Antibody-IL-2 fusion proteins: a novel strategy for immune protection", Proceedings of the National Academy of Sciences (2019), 116(8):3100-3105.
Krieg et al., "Improved IL-2 immunotherapy by selective stimulation of IL-2 receptors on lymphocytes and endothelial cells", Proc Nat Acad Sci USA (2010), 107(26):11906-11.
Penichet et al., "Antibody-IL-2 fusion proteins: a novel strategy for immune protection", Human Antibodies (1997), 8(3):106-118.
Silva, John-Paul, et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469.
Zhang, Tong, et al. "The binding of an anti-PD-1 antibody to FcγRI has a profound impact on its biological functions." Cancer Immunology, Immunotherapy 67 (2018): 1079-1090.
NCBI Search Application-Cobalt Alignment IL-2 (Year: 2024) 2 pages.
NCBI Search Application-Cobalt Alignment Seq 4v9 (Year: 2024) 2 pages.
International Search Report and Written Opinion mailed Sep. 25, 2023 in PCT/US2023/067844 (11 pages).
International Search Report and Written Opinion mailed Jul. 25, 2023 in PCT/US2023/067532 (11 pages).
Antunes et al., 2018, "Structure-Based Methods for Binding Mode and Binding Affinity Prediction for Peptide-MHC Complexes," Current Topics in Medicinal Chemistry 18(26): 2239-2255.
Antunes et al., 2018, "General Prediction of Peptide-MHC Binding Modes Using Incremental Docking: A Proof of Concept," Scientific Reports 8(4327): 1-13.
Hatano et al., 2021, "Virus-Driven Carcinogenesis," Cancers 13(2625): 1-27.
Heemskerk et al., 2013, "The Cancer Antigenome," The EMBO Journal 32: 194-203.
Hsu et al., 2021, "A Cytokine Receptor-Masked IL2 Prodrug Selectively Activates Tumor-Infiltrating Lymphocytes for Potent Antitumor Therapy," Nature Communications 12(2768): 1-13.
Janeway et al., 2001, "The Major Histocompatibility Complex and Its Functions," Immunobiology: The Immune System in Health and Disease. 5th Edition. New York: Garland Science (11 pages).
"Definition of Agonist," NIH National Cancer Institute (Year: 2023) 1 page.
Rammensee et al., 1999, "SYFPEITHI: Database for MHC Ligands and Peptide Motifs," Immunogenetics 50: 213-219.
Schueler-Furman et al., 1998, "Knowledge-Based Structure Prediction of MHC Class I Bound Peptides: A Study of 23 Complexes," Folding & Design 3: 549-564.
Sequence Listing for SEQ ID No. 47-49 in PCT/US2019/021654 (WO2019173832) Year: 2019 (2 pages).
Vigneron et al., 2013, "Database of T Cell-Defined Human Tumor Antigens: The 2013 Update," Cancer Immunity 13: 1-6.

(56) References Cited

OTHER PUBLICATIONS

Xue et al., 2021, "Next-Generation Cytokines for Cancer Immunotherapy," Antibody Therapeutics 4(2): 123-133.
Zhang et al., 2014, "HPVdb: A Data Mining System for Knowledge Discovery in Human Papillomavirus with Applications in T Cell Immunology and Vaccinology," Database doi: 10.1093/database/bau031 1-12.

* cited by examiner

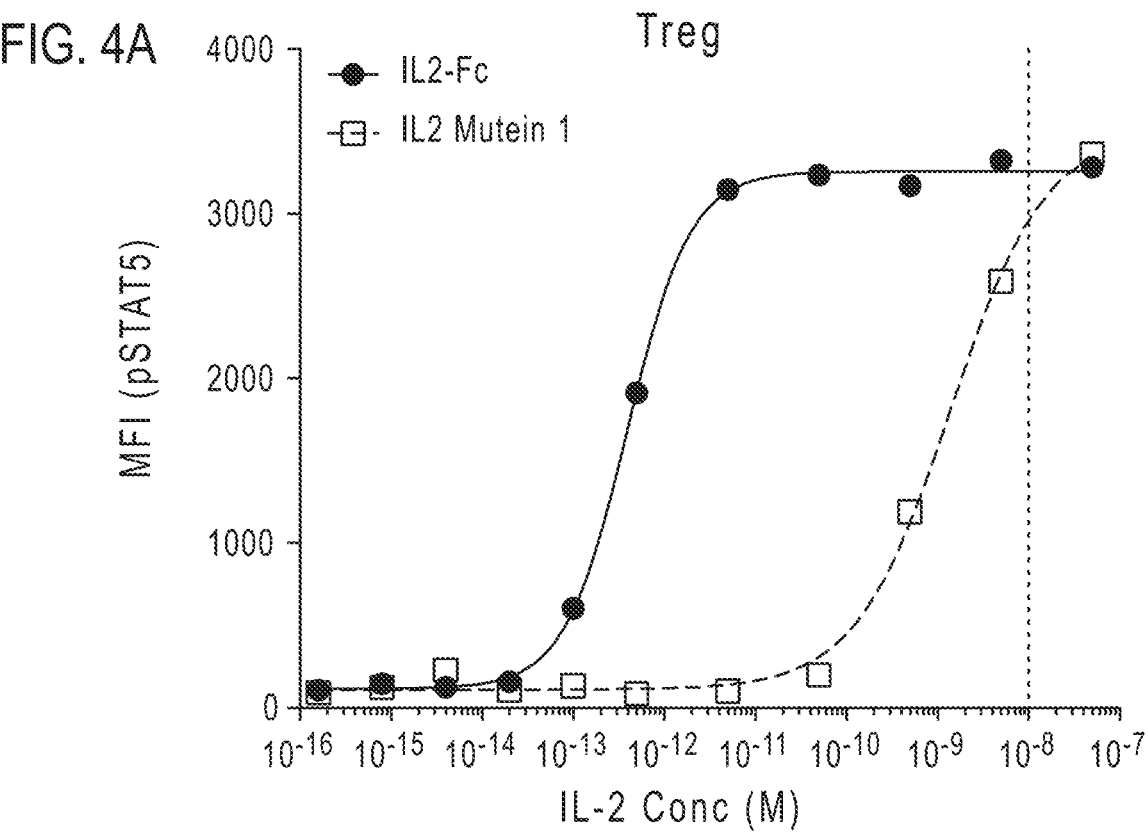
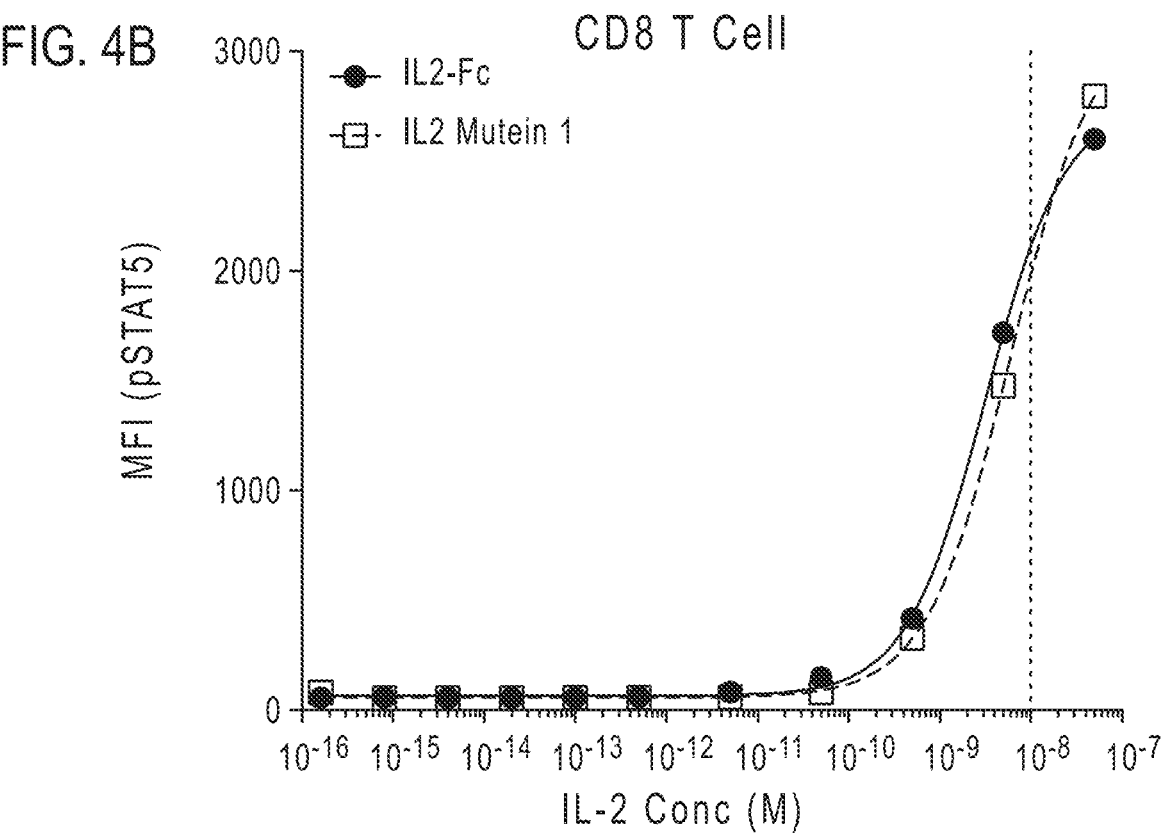

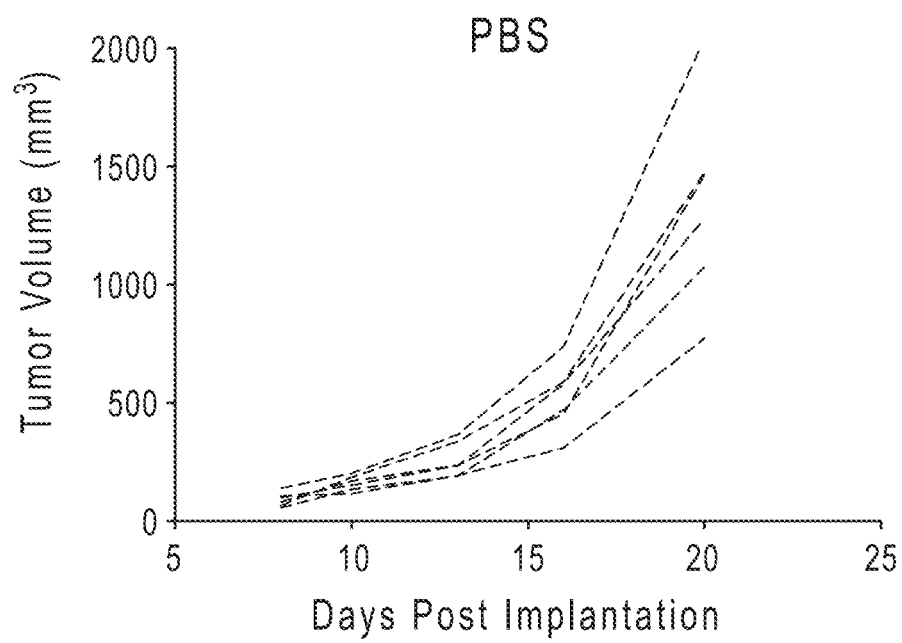
FIG. 7C.1
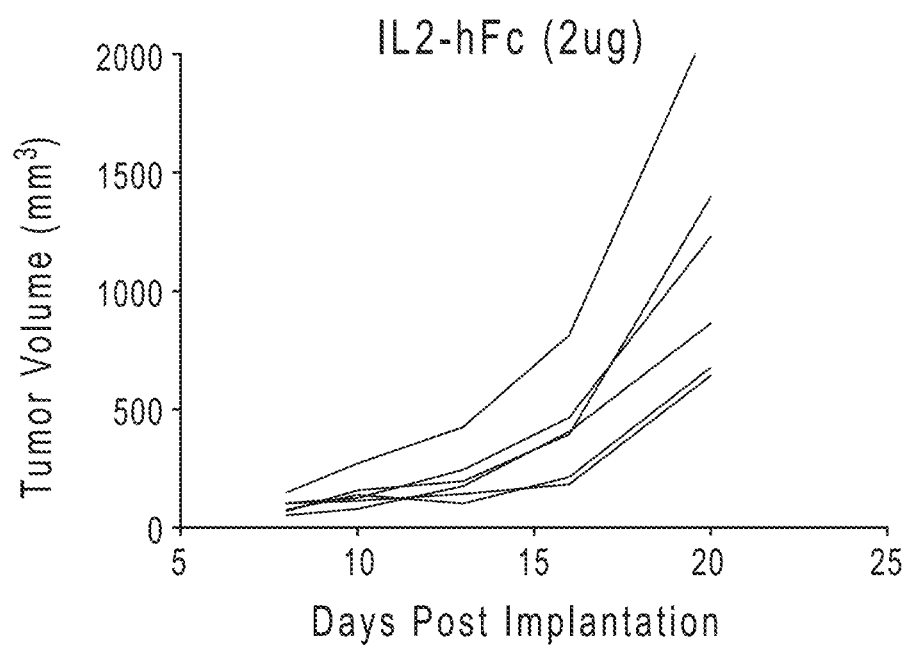
FIG. 7C.2

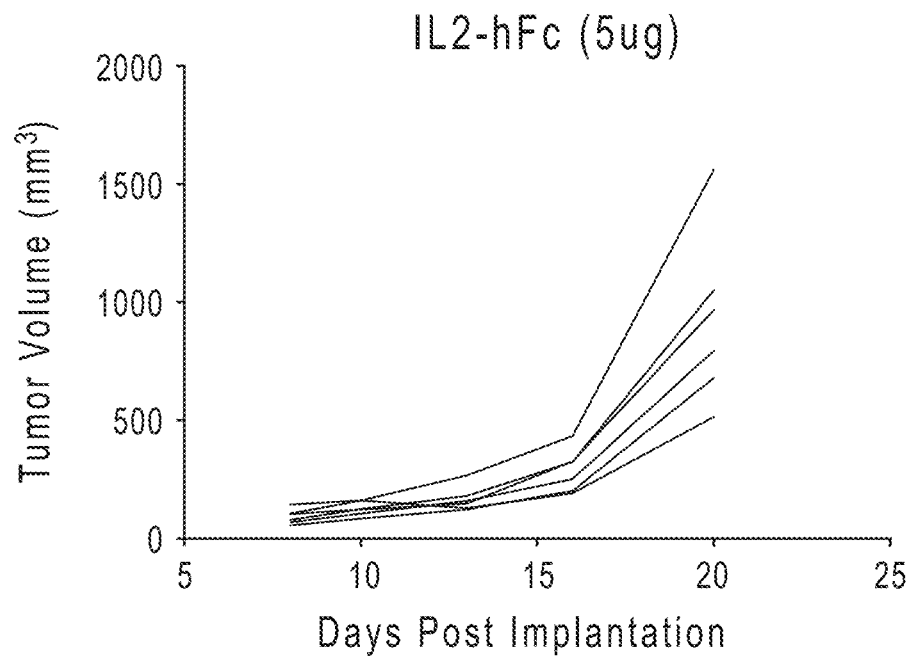
FIG. 7C.3
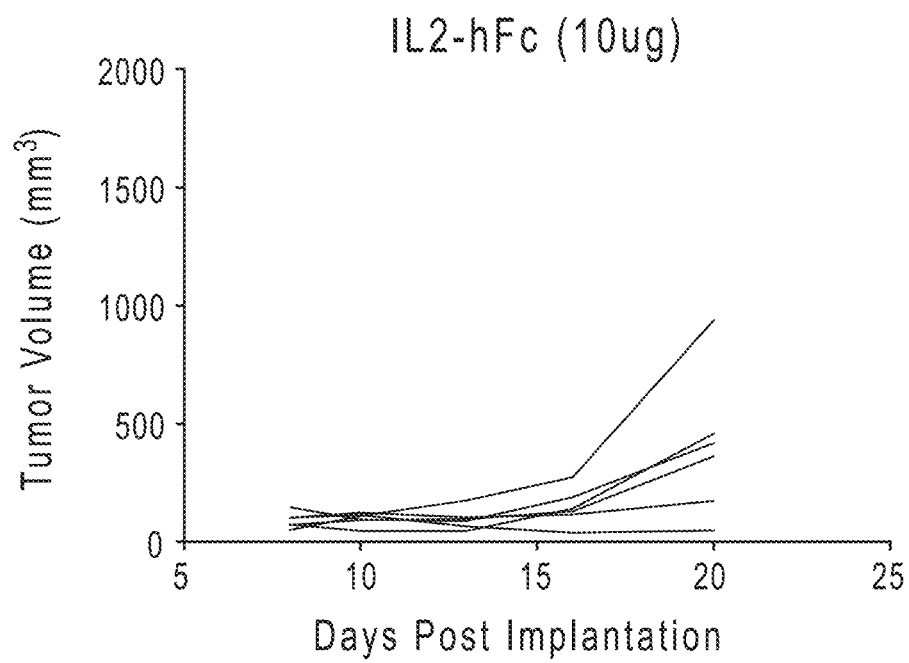
FIG. 7C.4

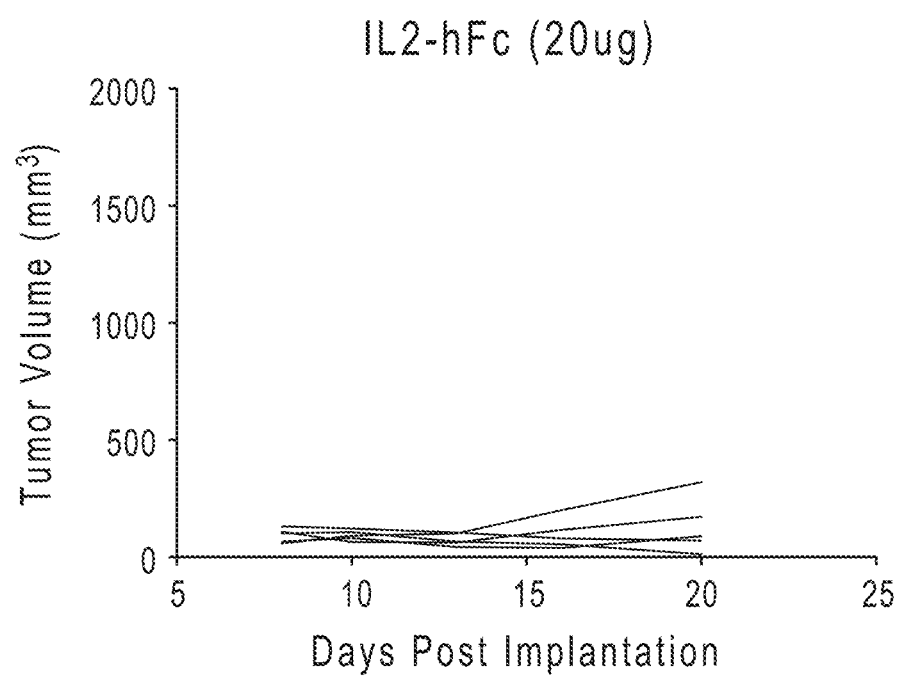
FIG. 7C.5

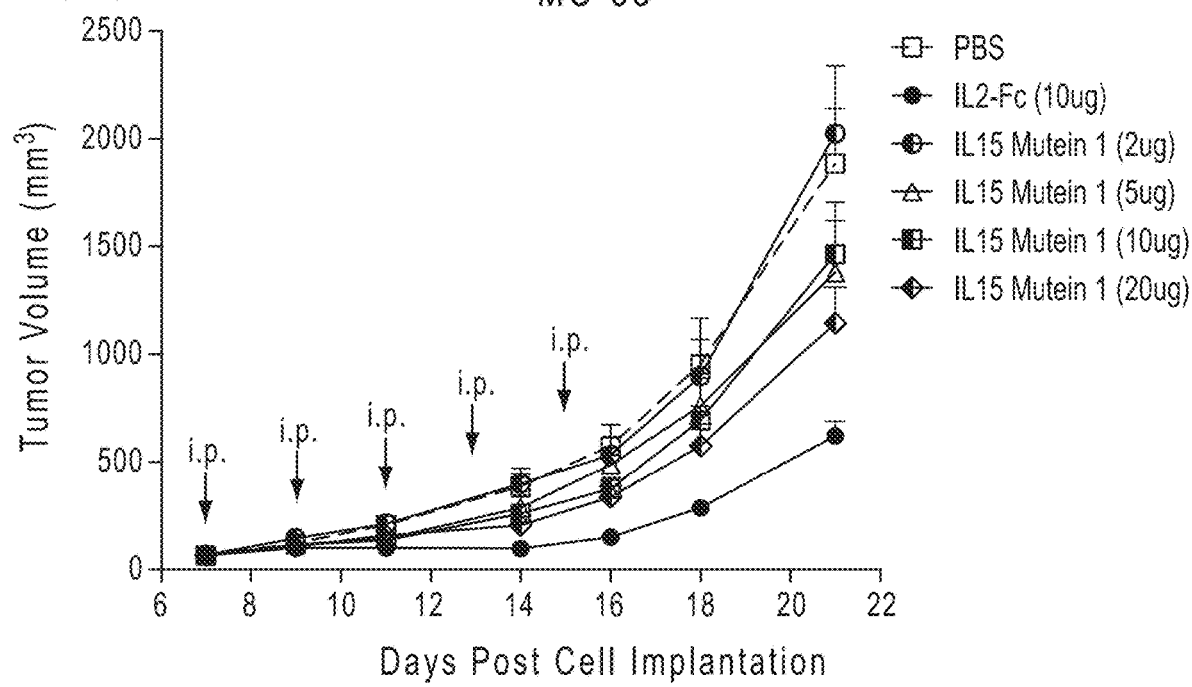
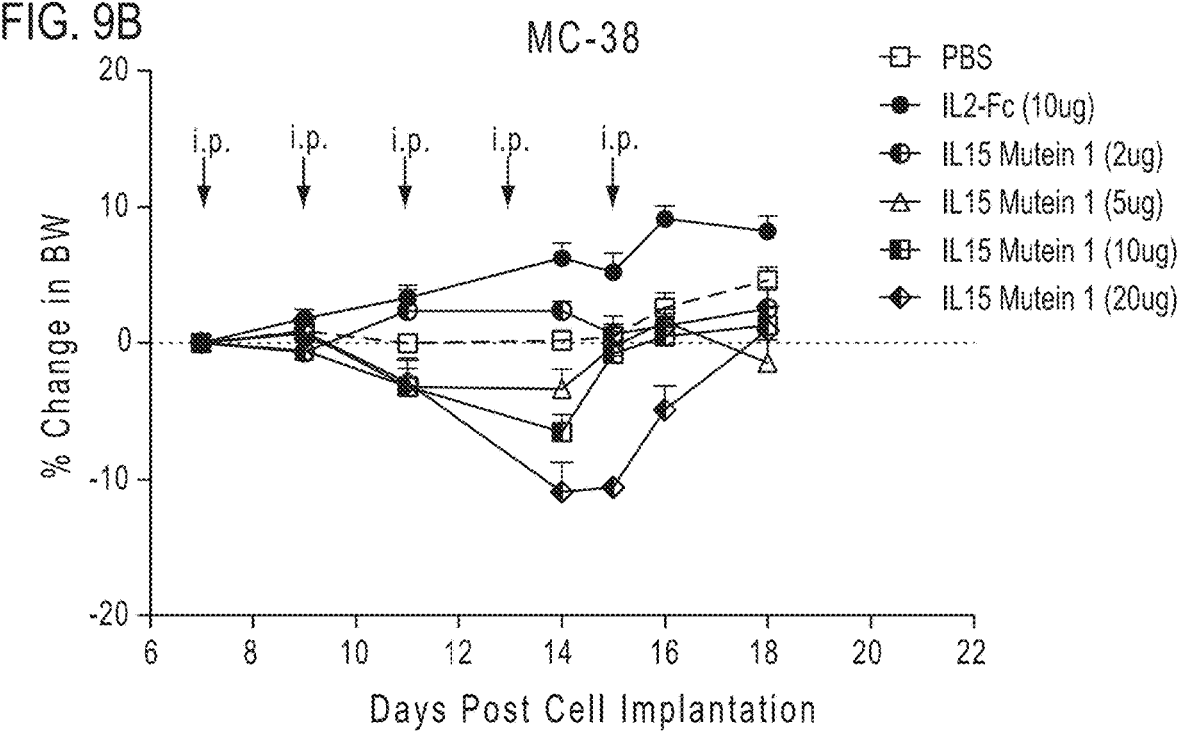

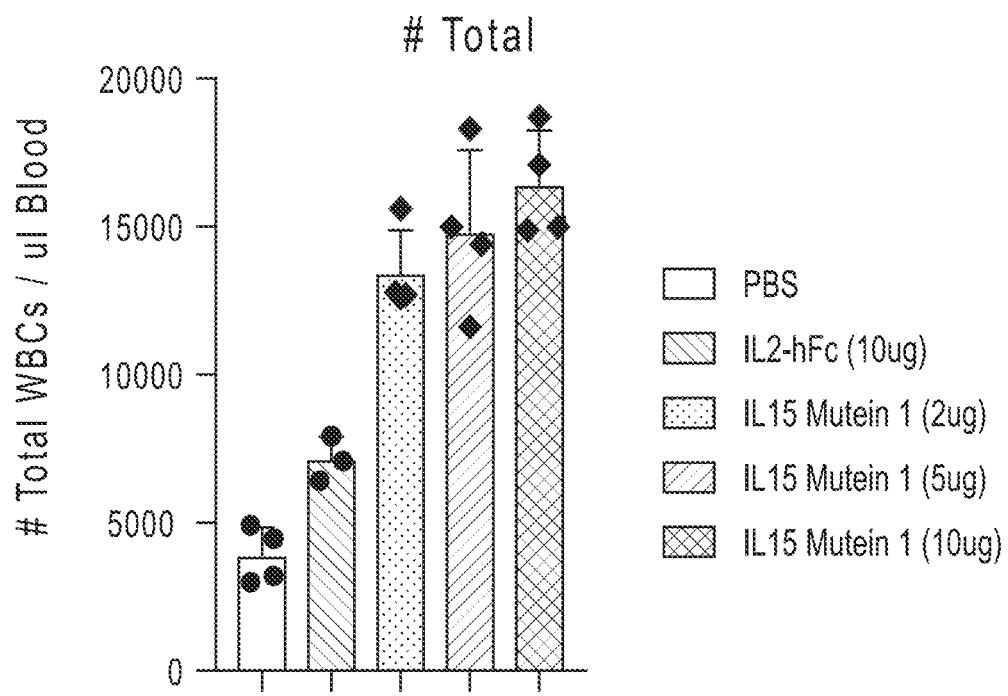
FIG. 9C.1
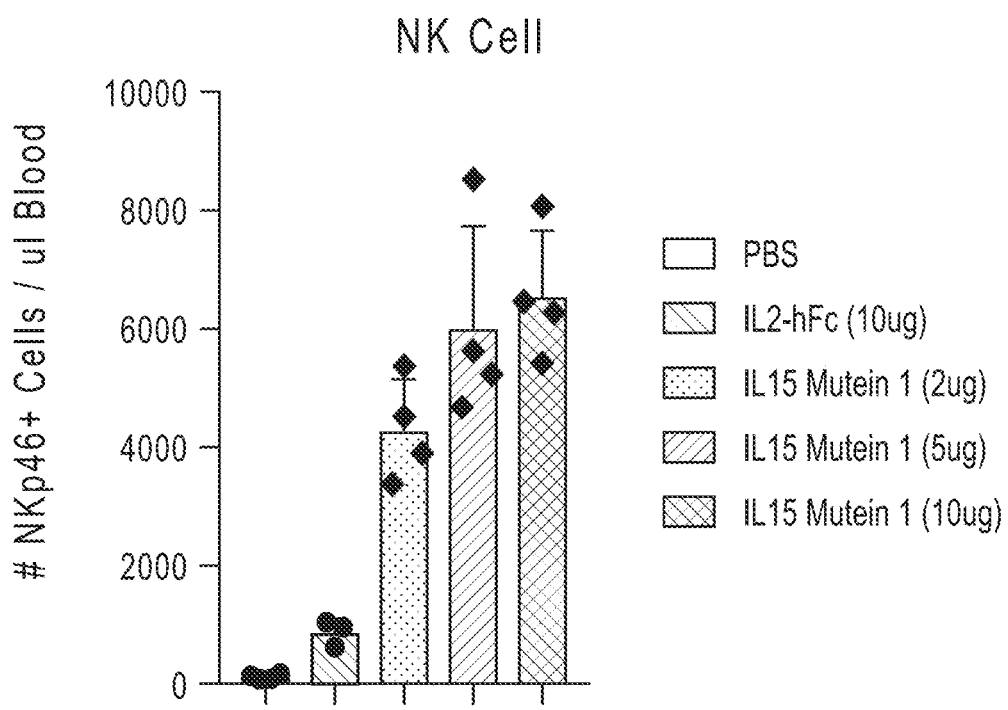
FIG. 9C.2

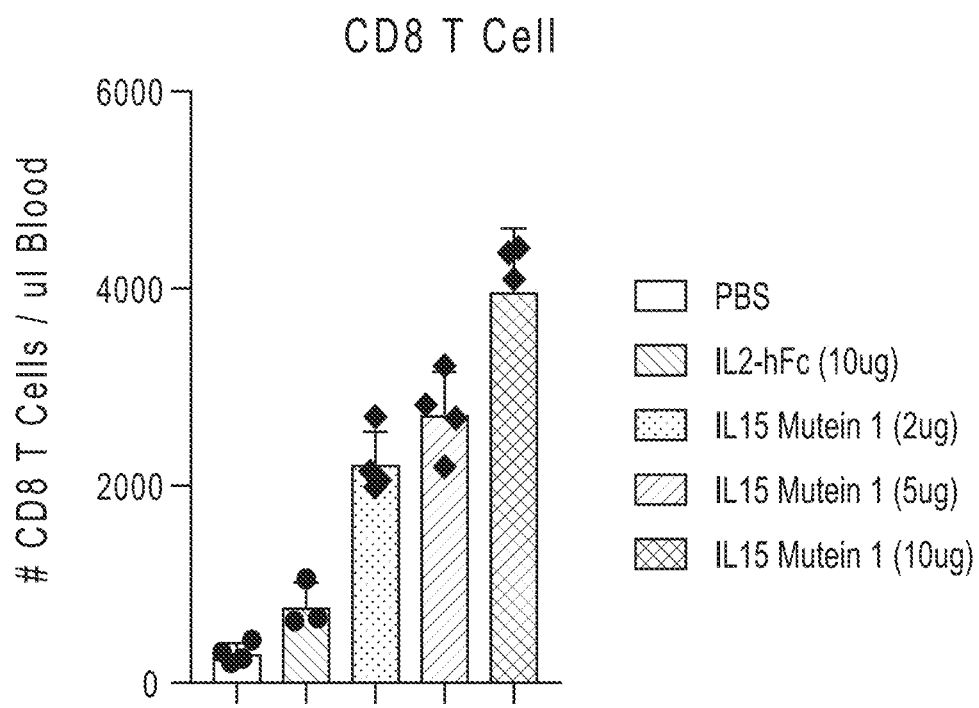
FIG. 9C.3
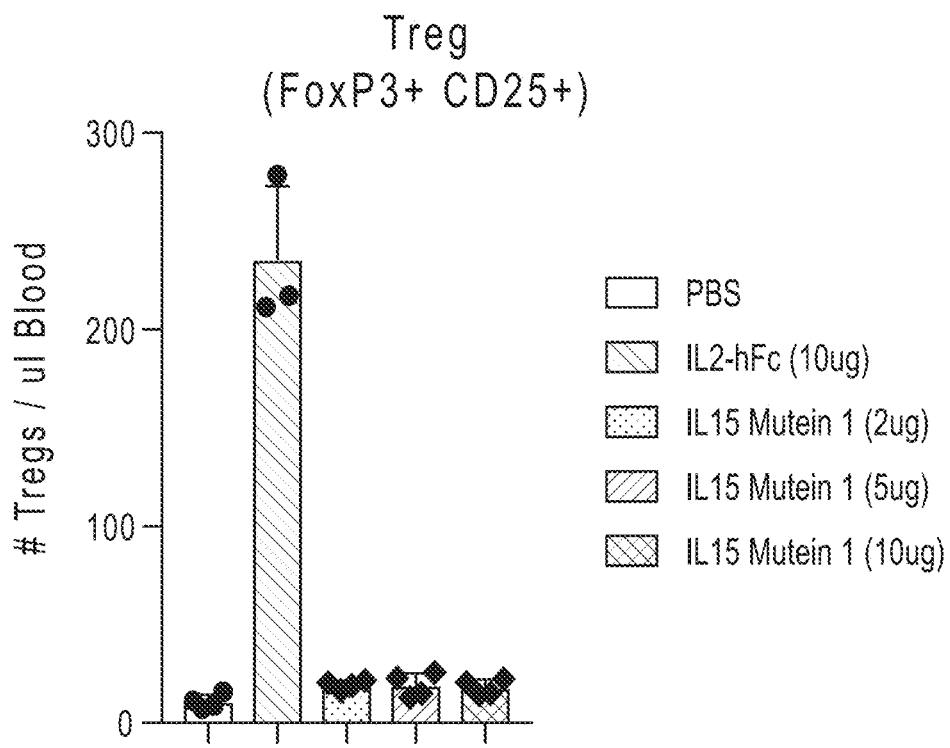
FIG. 9C.4

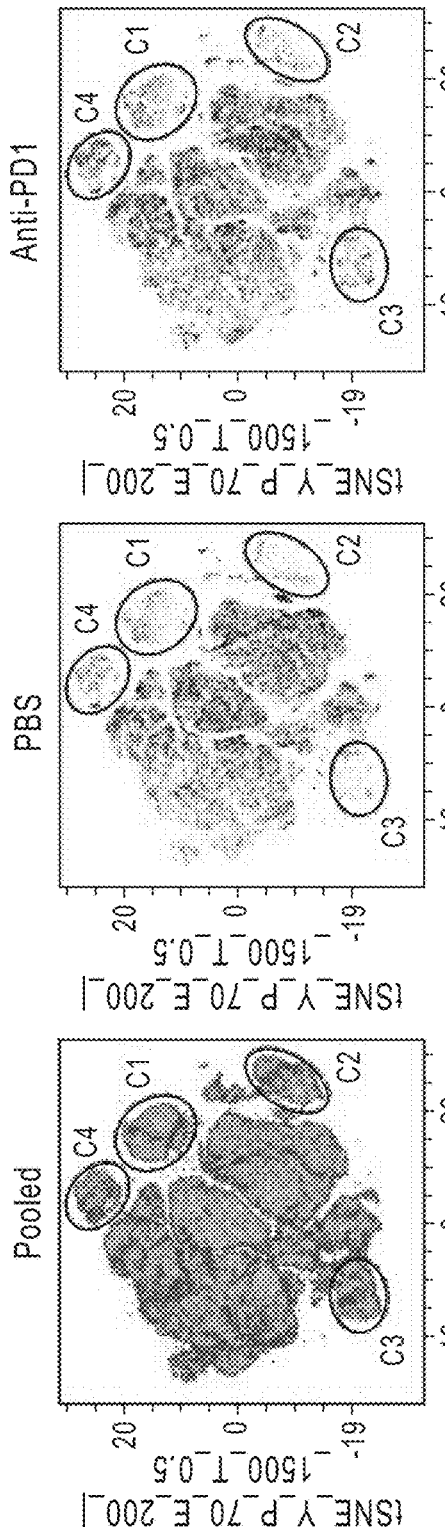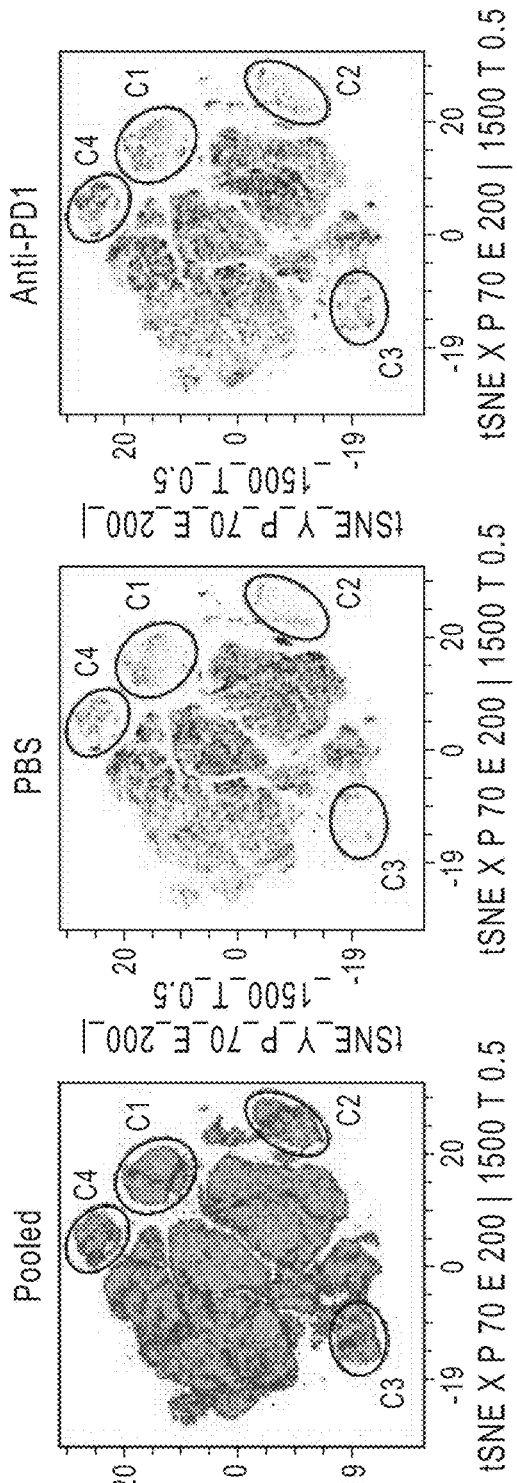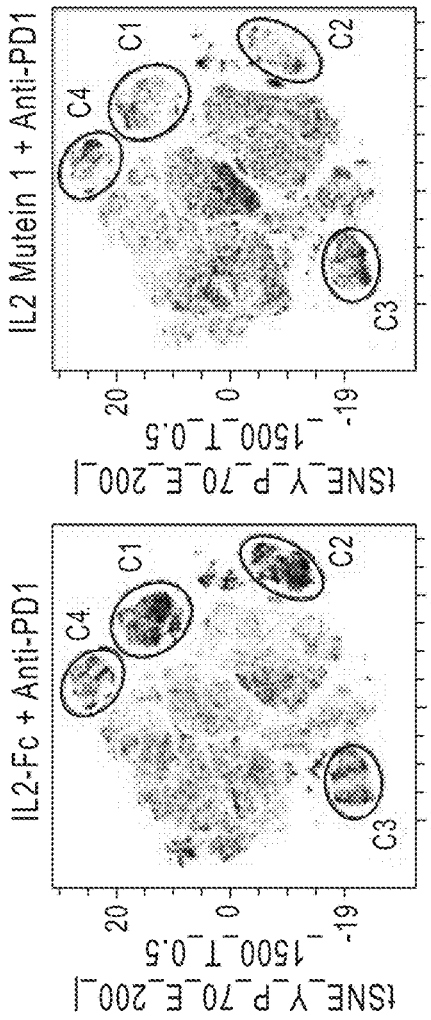
FIG. 10A.1 Pooled
FIG. 10A.2 PBS
FIG. 10A.3 Anti-PD1
FIG. 10A.4 IL2-Fc + Anti-PD1
FIG. 10A.5 IL2 Mutein 1 + Anti-PD1

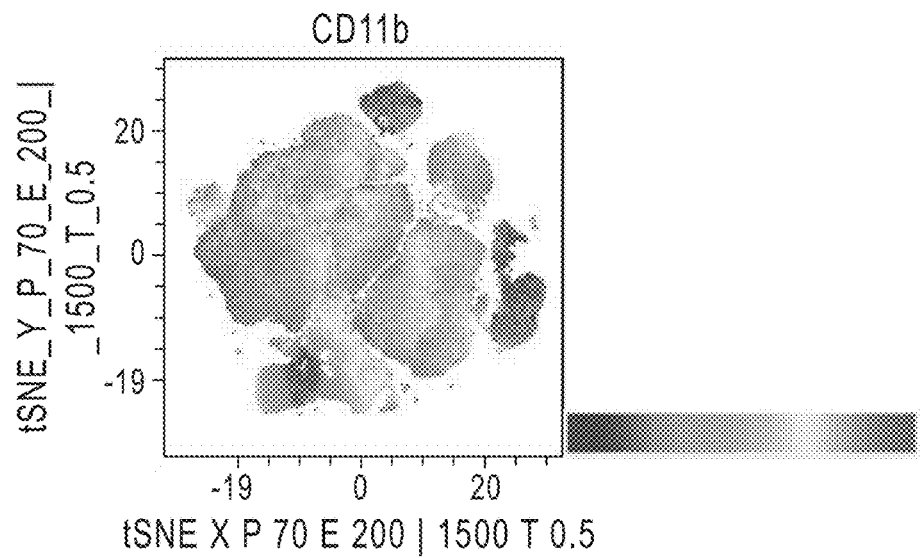
FIG. 10C.1
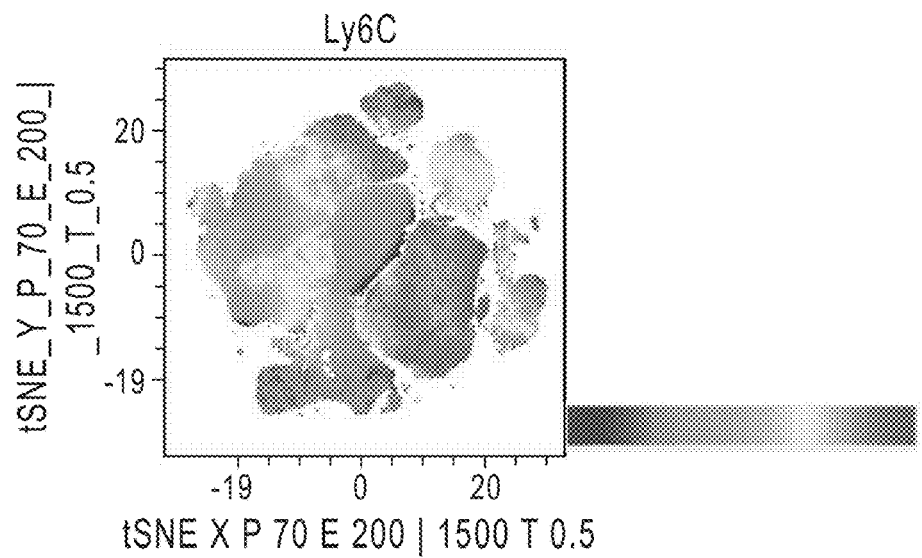
FIG. 10C.2
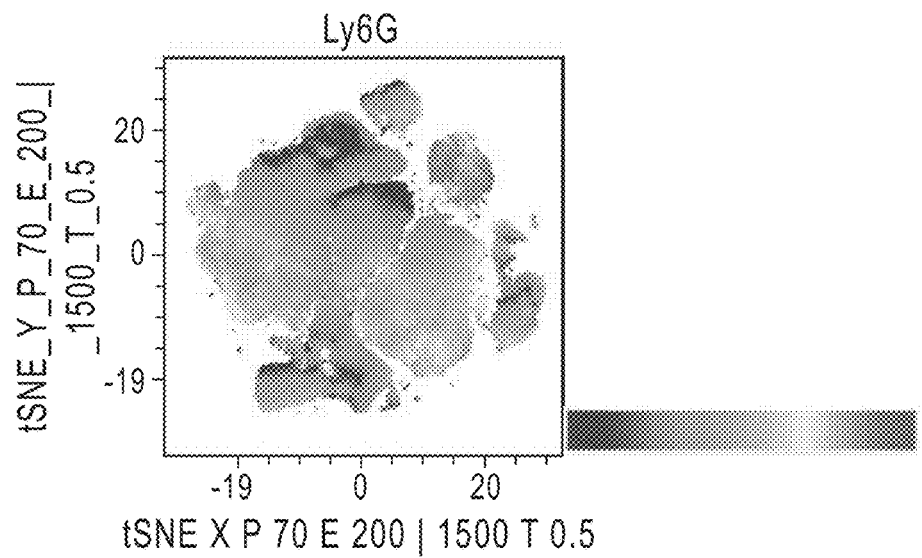
FIG. 10C.3

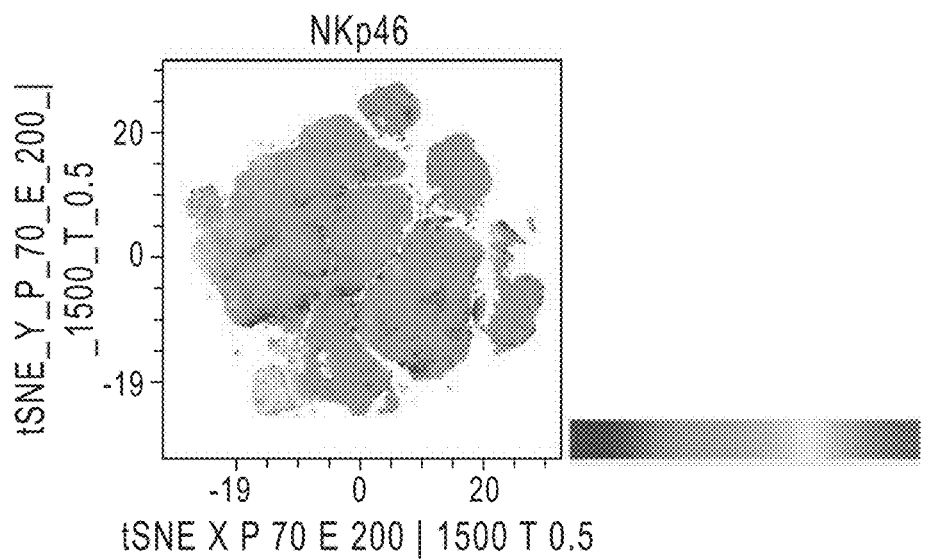
FIG. 10C.4
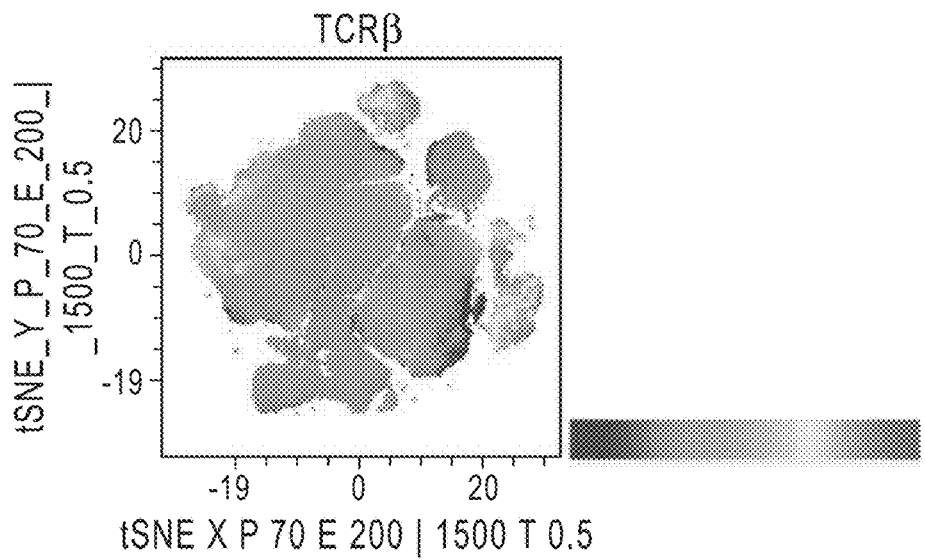
FIG. 10C.5
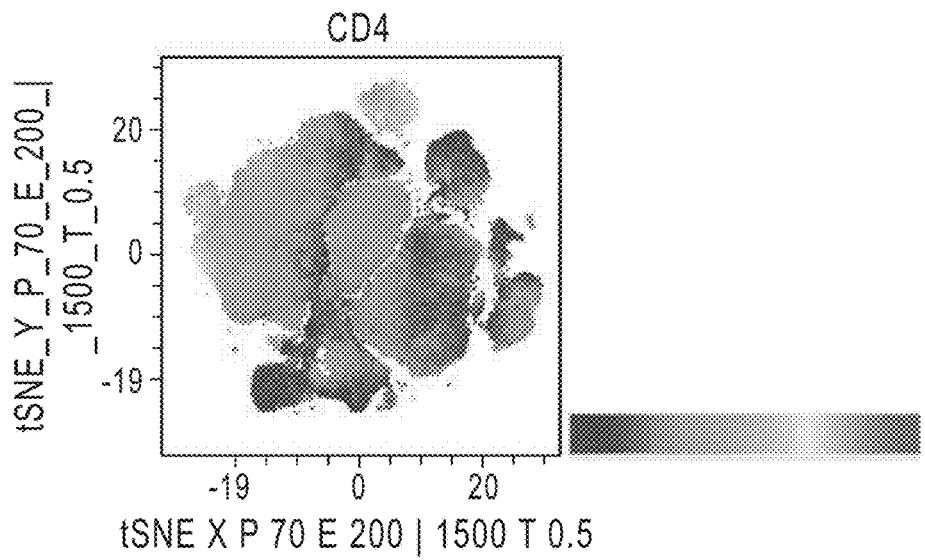
FIG. 10C.6

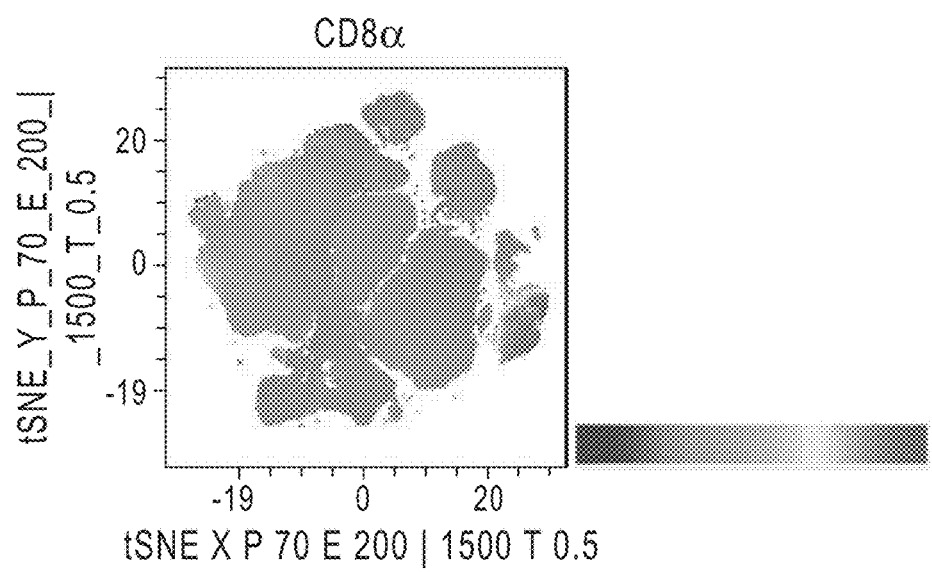
FIG. 10C.7

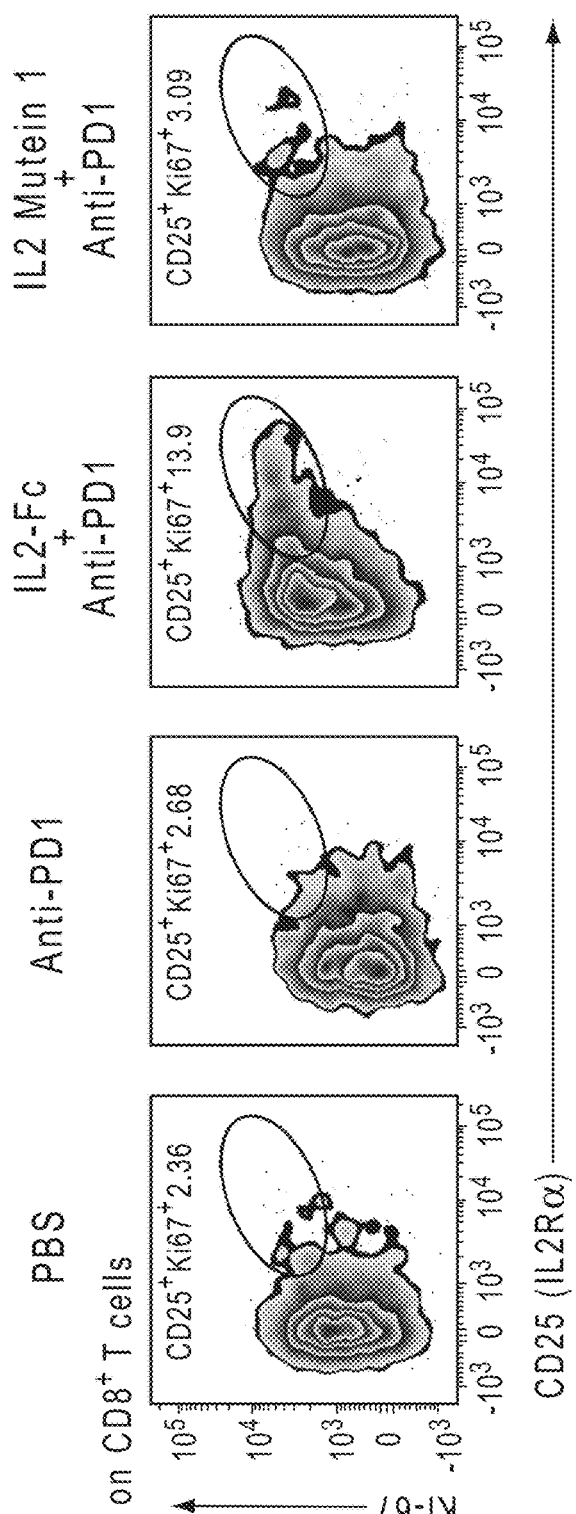
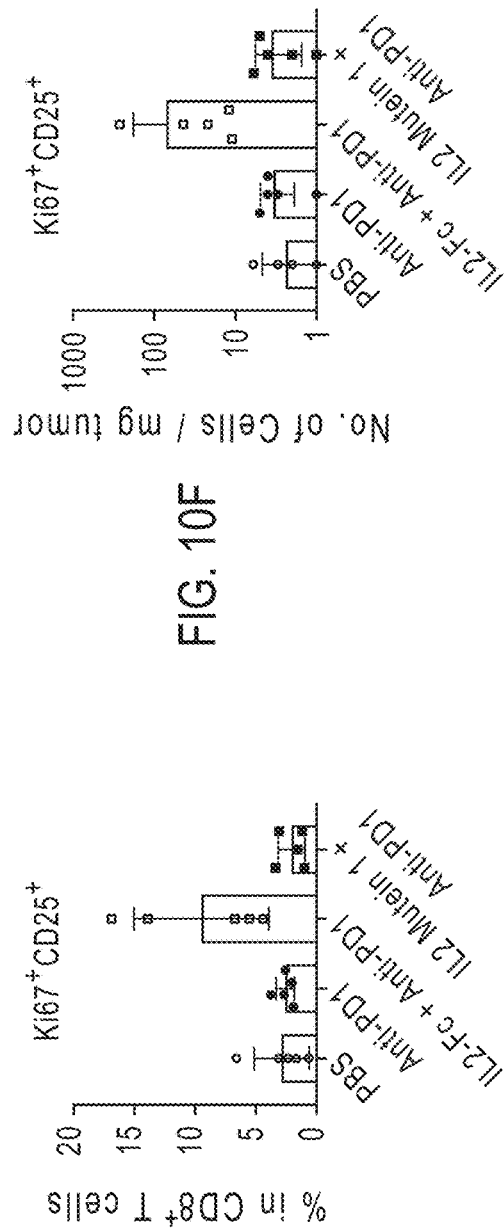
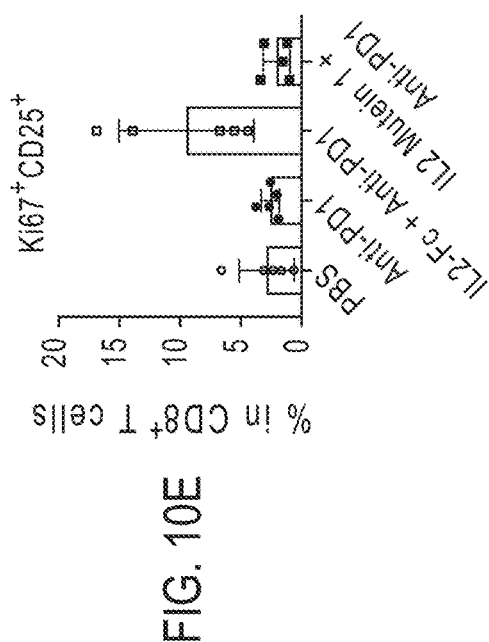
FIG. 10D
FIG. 10E
FIG. 10F

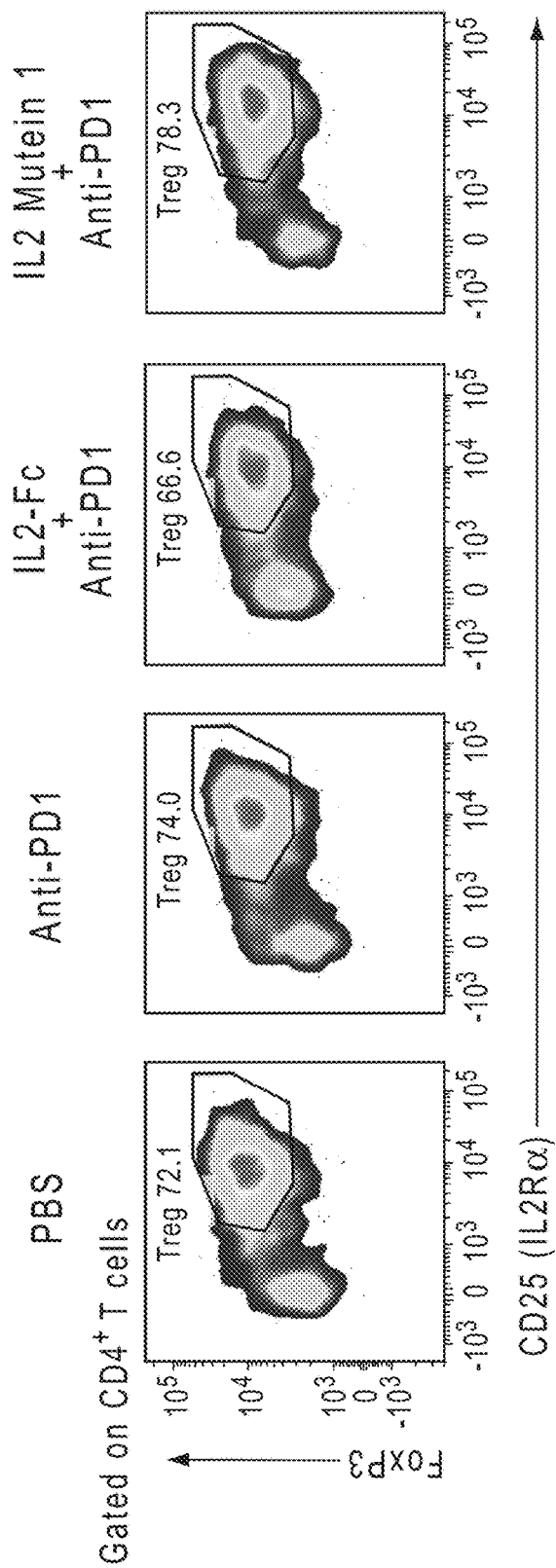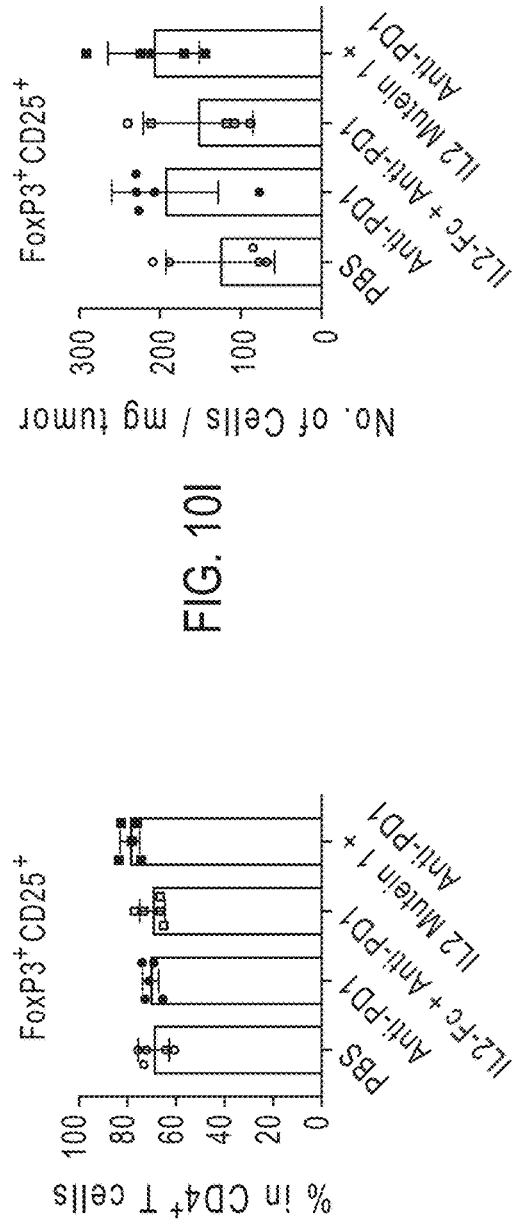
FIG. 10G
FIG. 10H
FIG. 10I

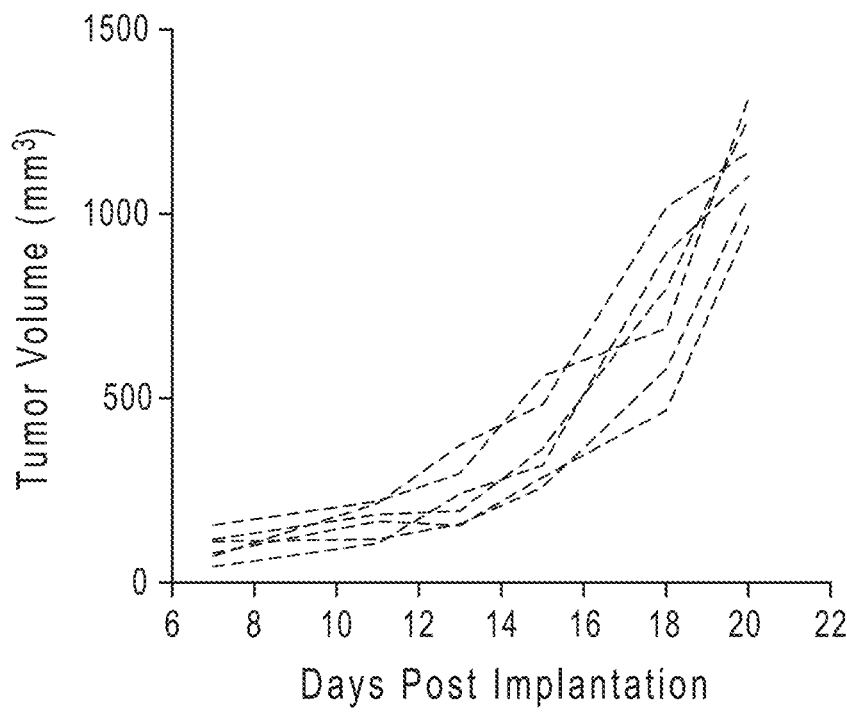
FIG. 18B.1
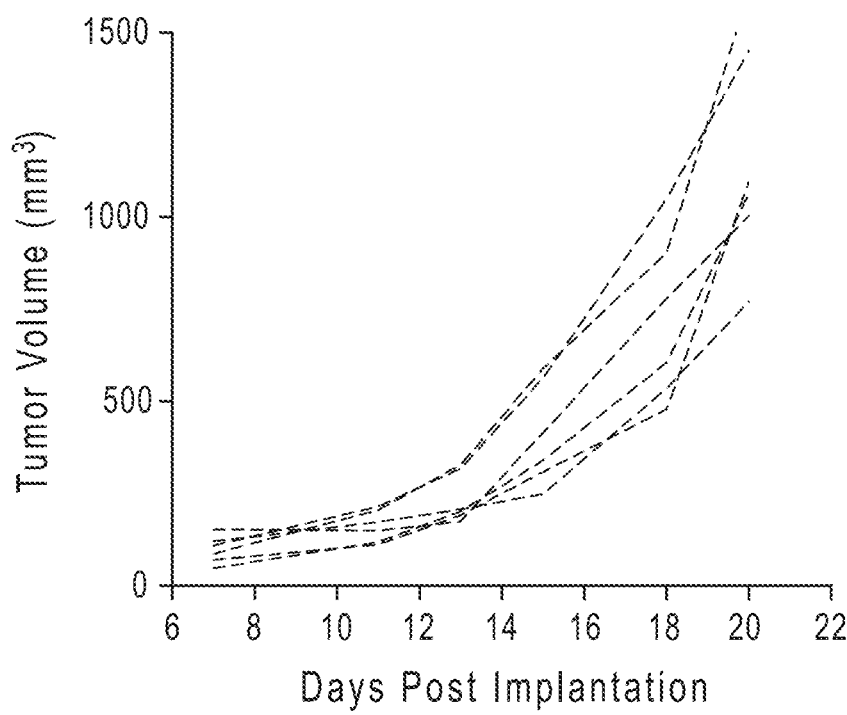
FIG. 18B.2

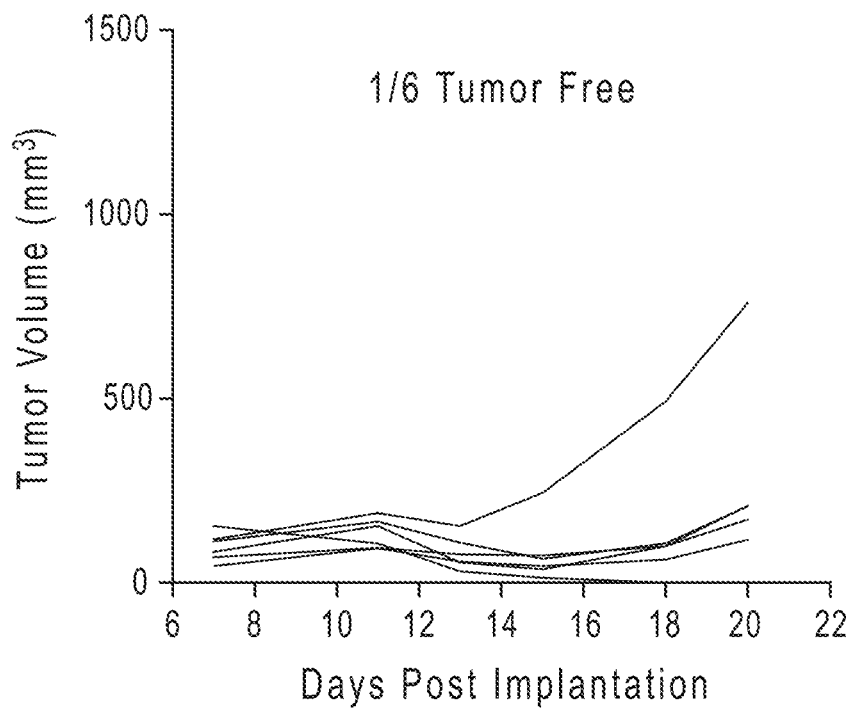
FIG. 18B.3
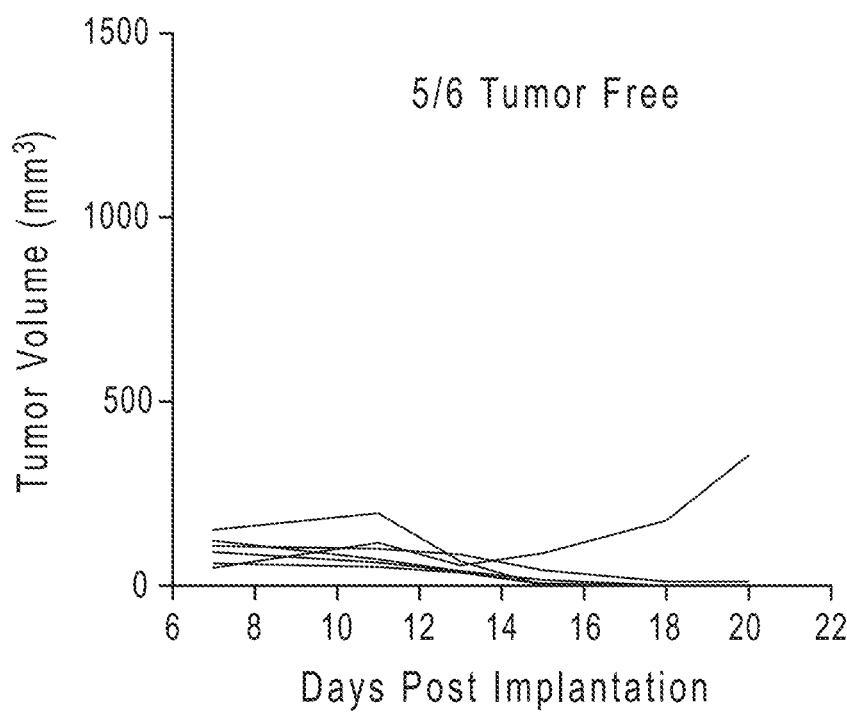
FIG. 18B.4

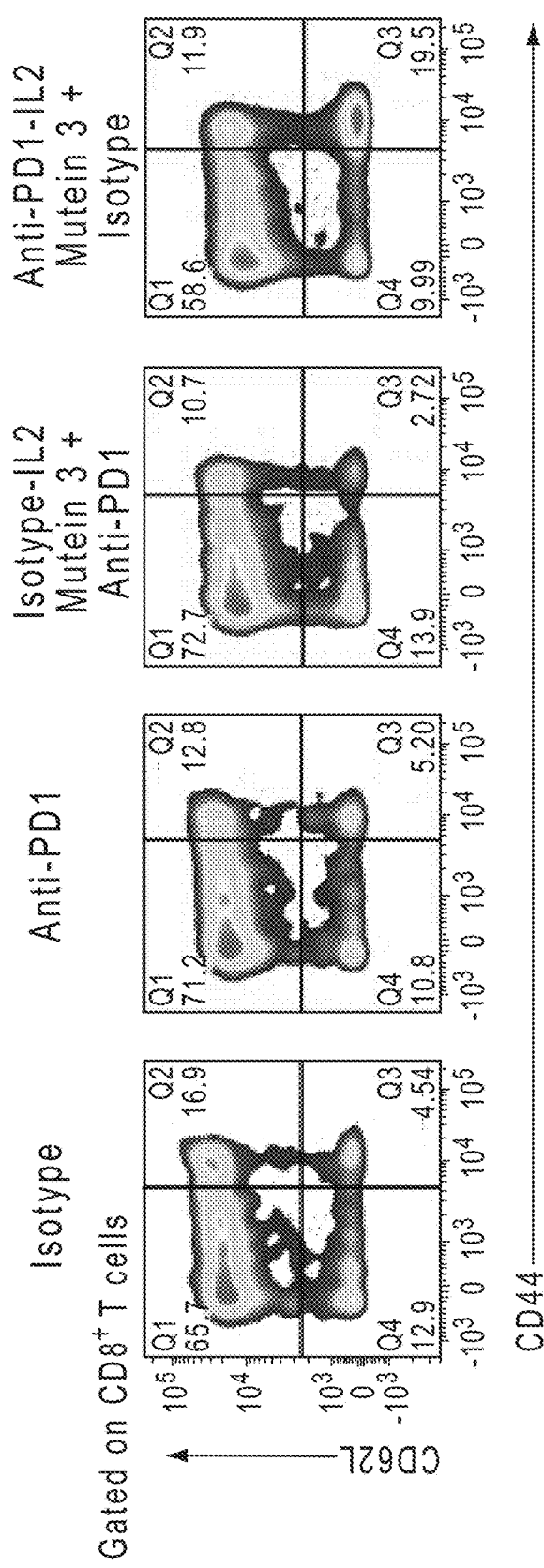
FIG. 18C.1
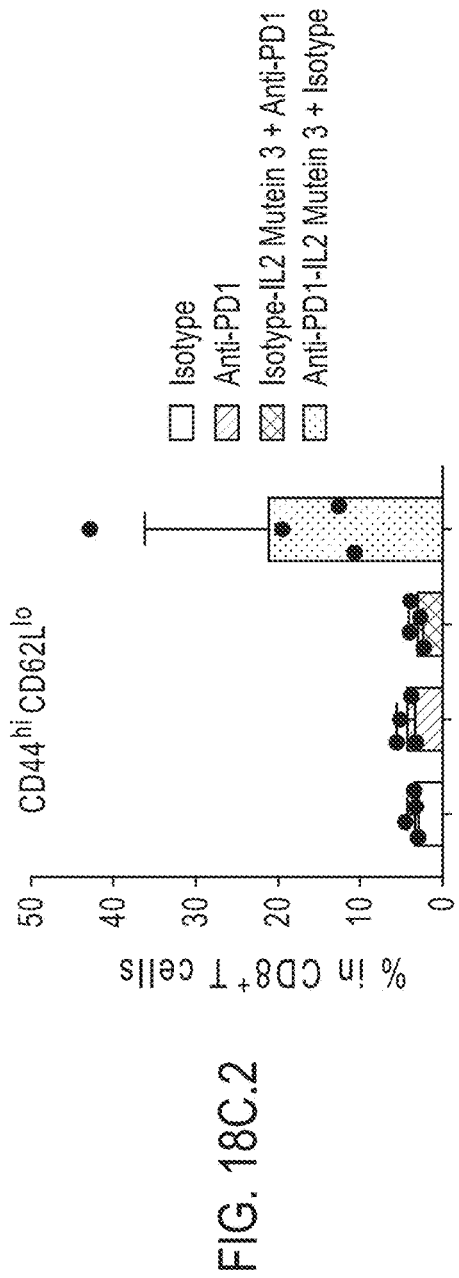
FIG. 18C.2

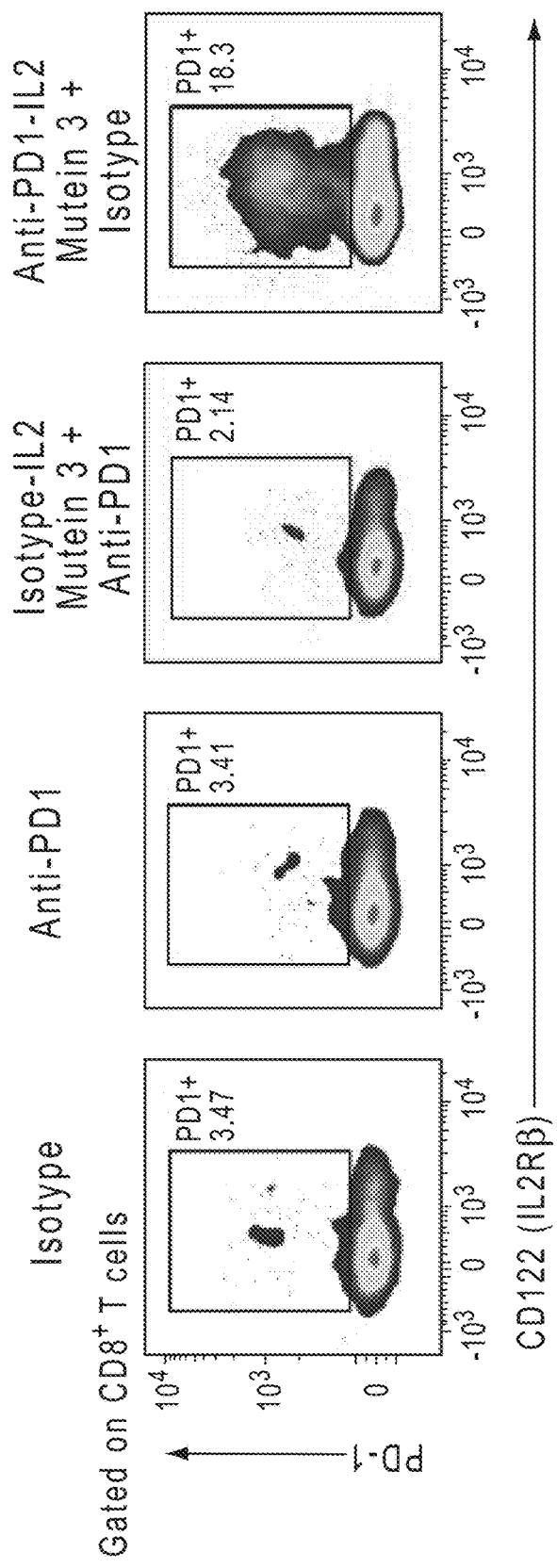
FIG. 18D.1
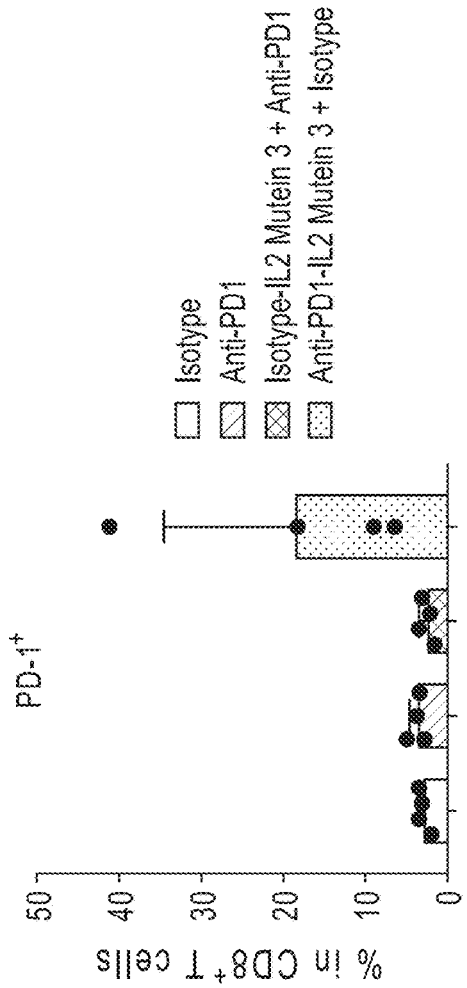
FIG. 18D.2

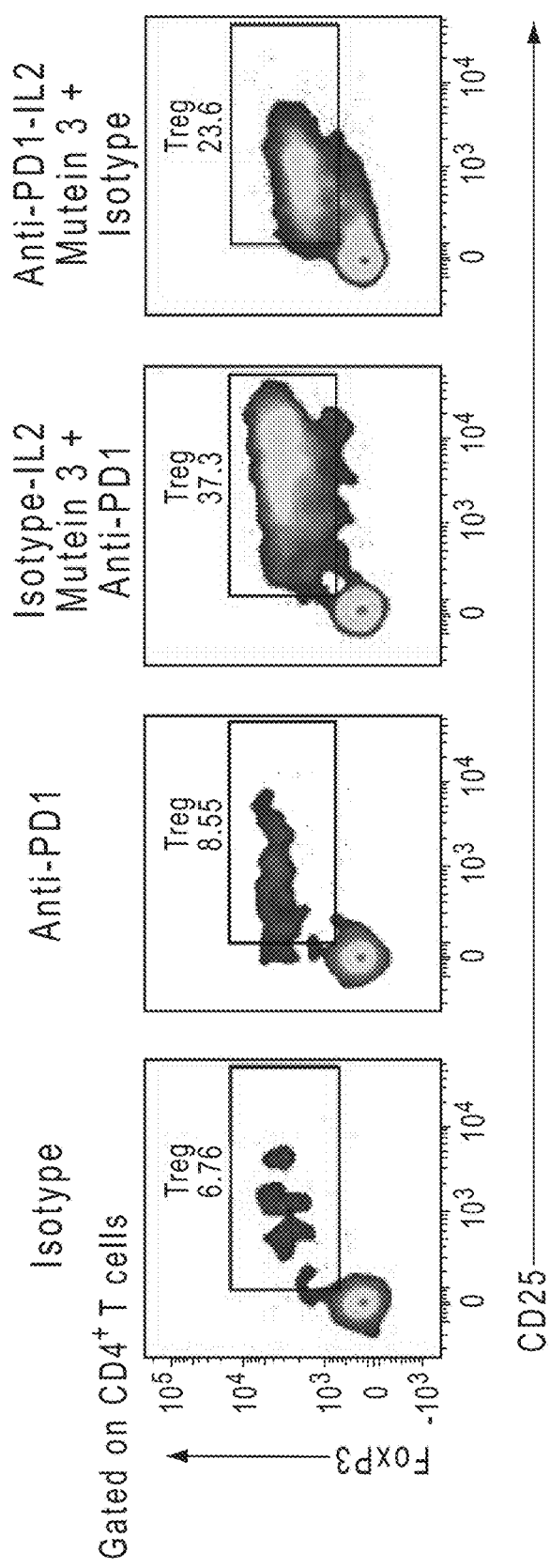
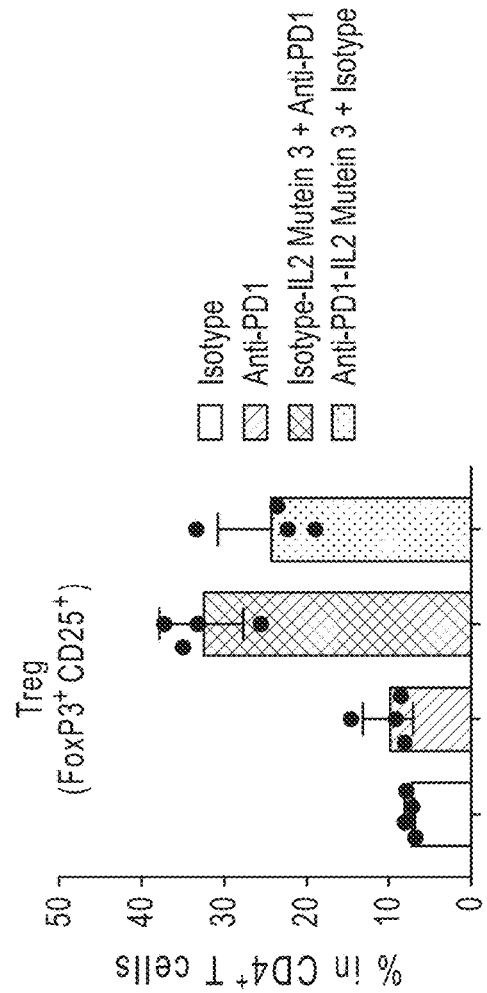
FIG. 18E.1
FIG. 18E.2

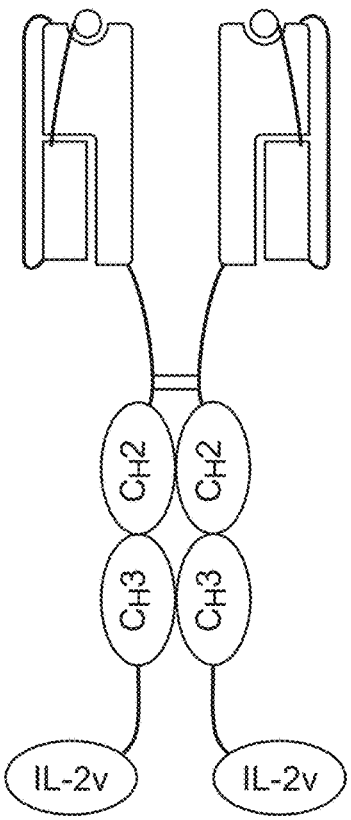
FIG. 22A.1
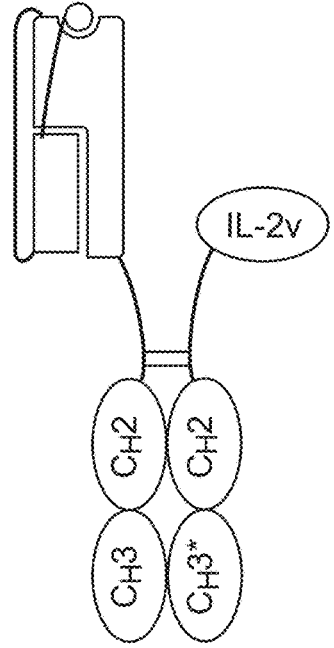
FIG. 22A.2
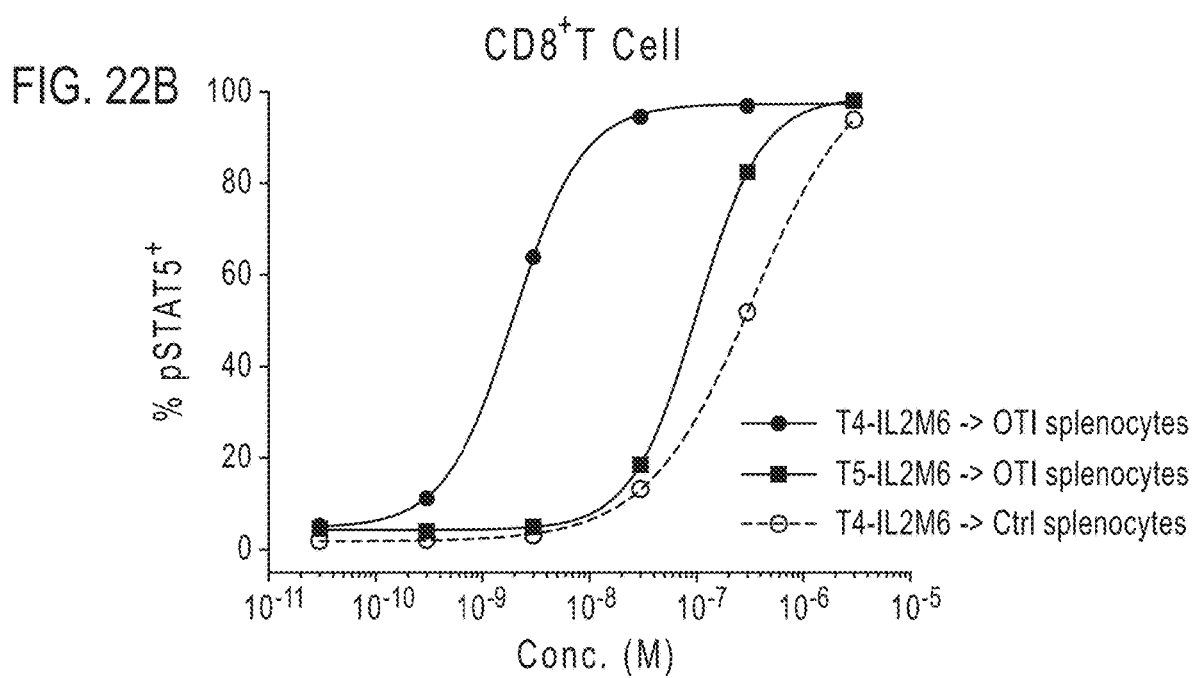
FIG. 22B

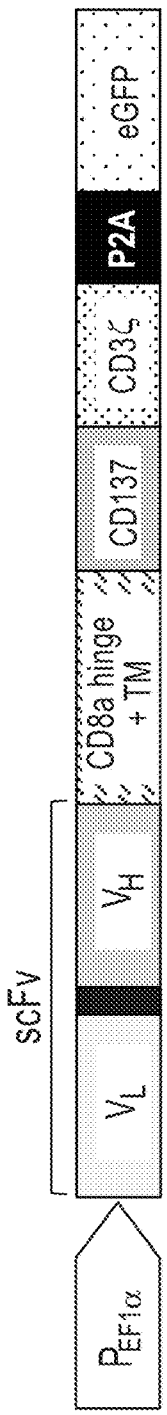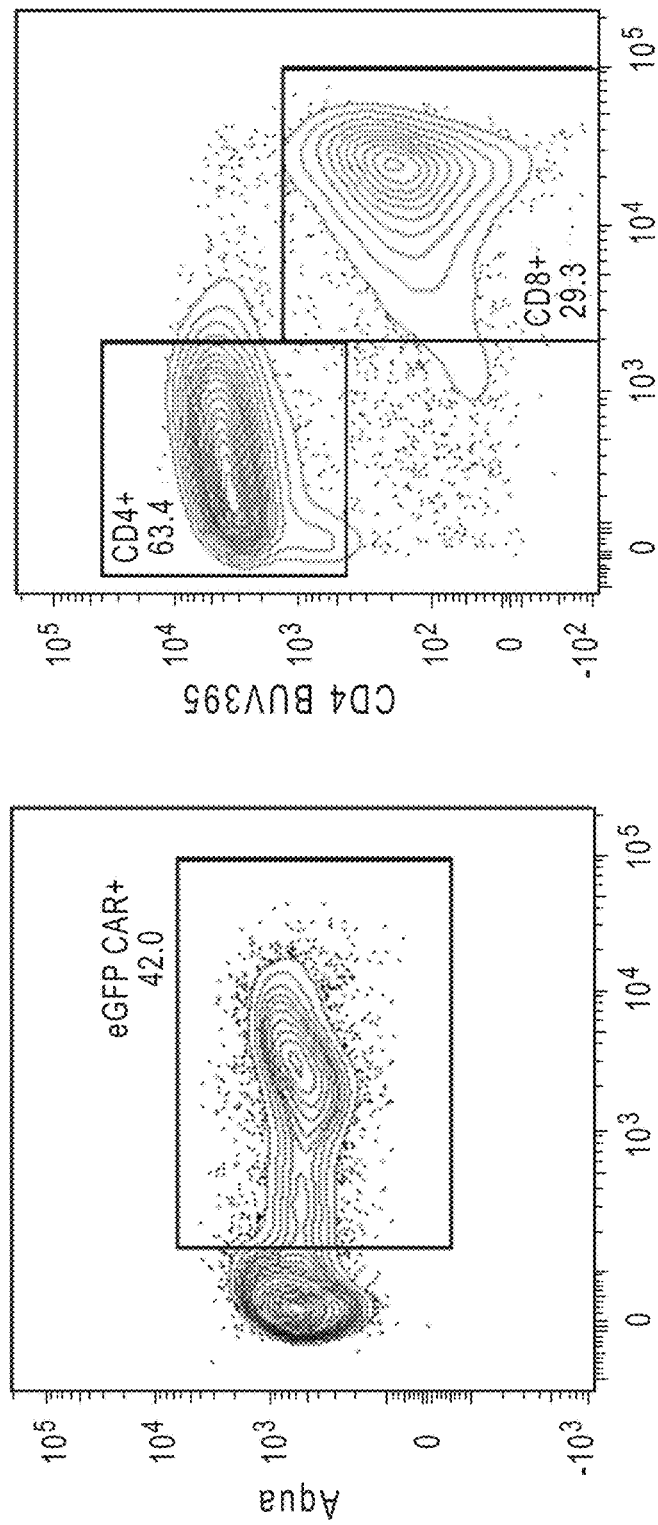
FIG. 25A
FIG. 25B
FIG. 25C

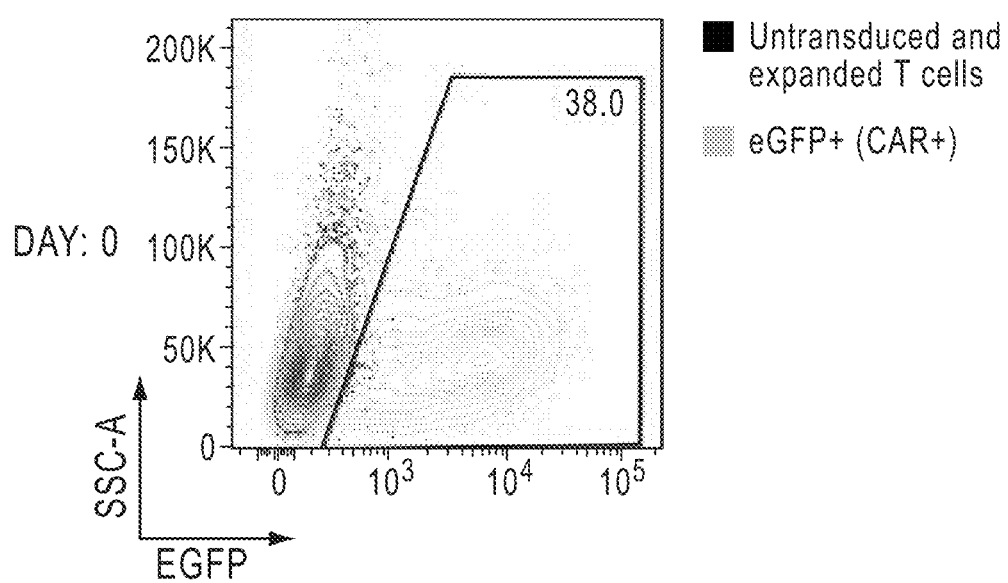
FIG. 28A.1

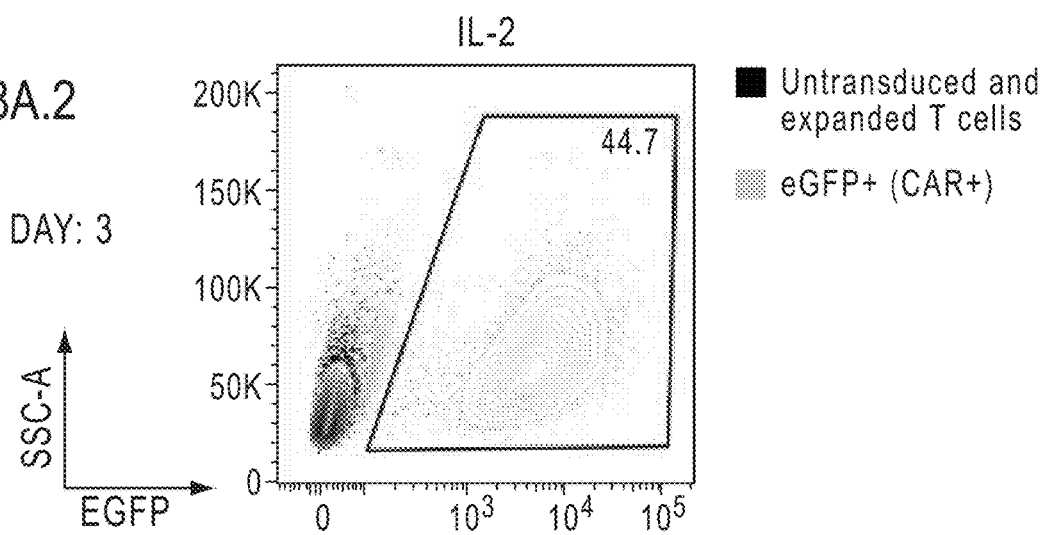
FIG. 28A.2
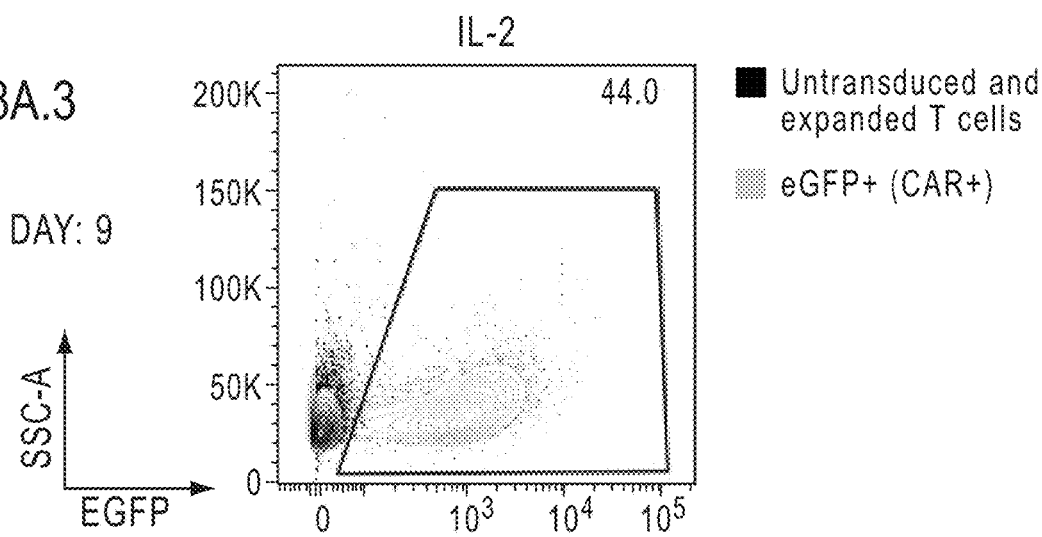
FIG. 28A.3
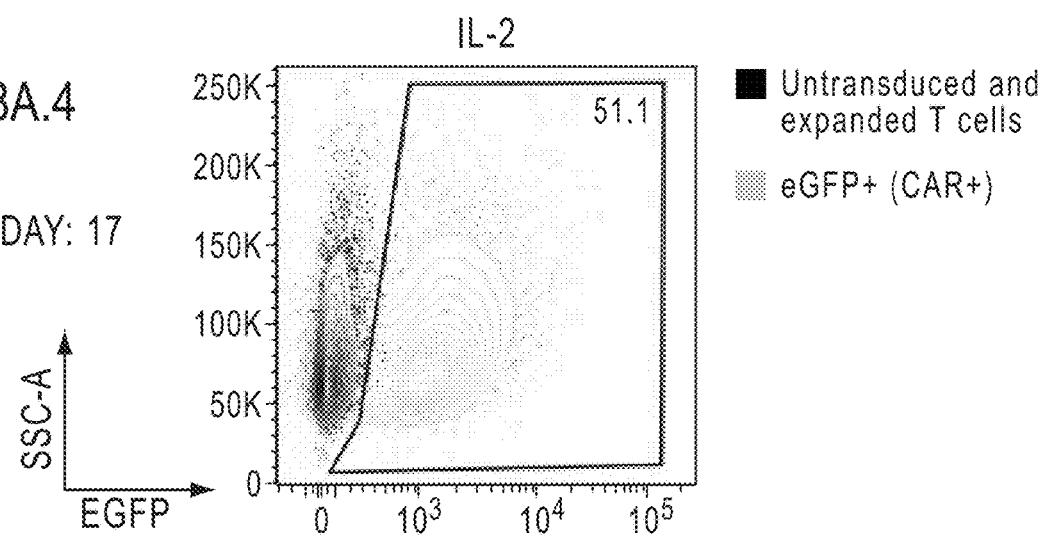
FIG. 28A.4

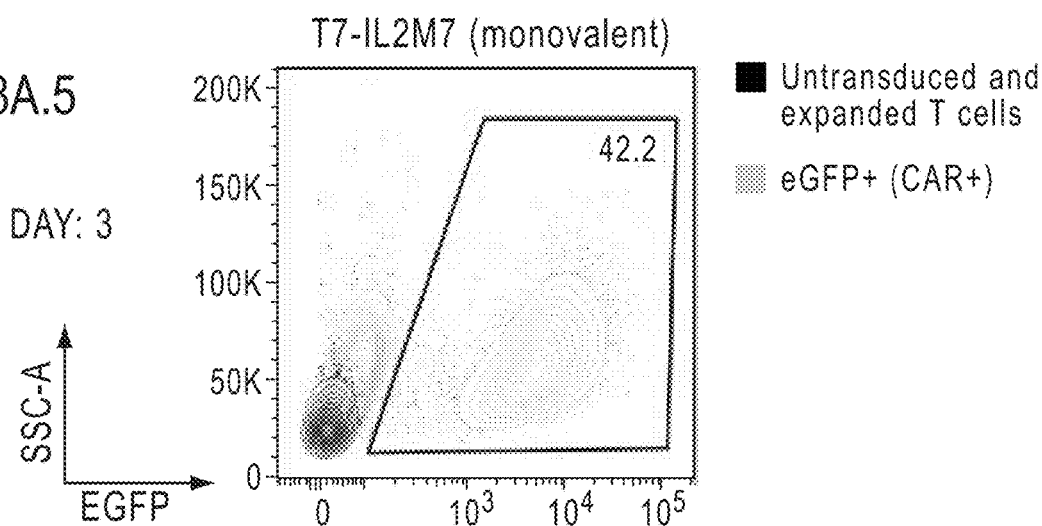
FIG. 28A.5 DAY: 3
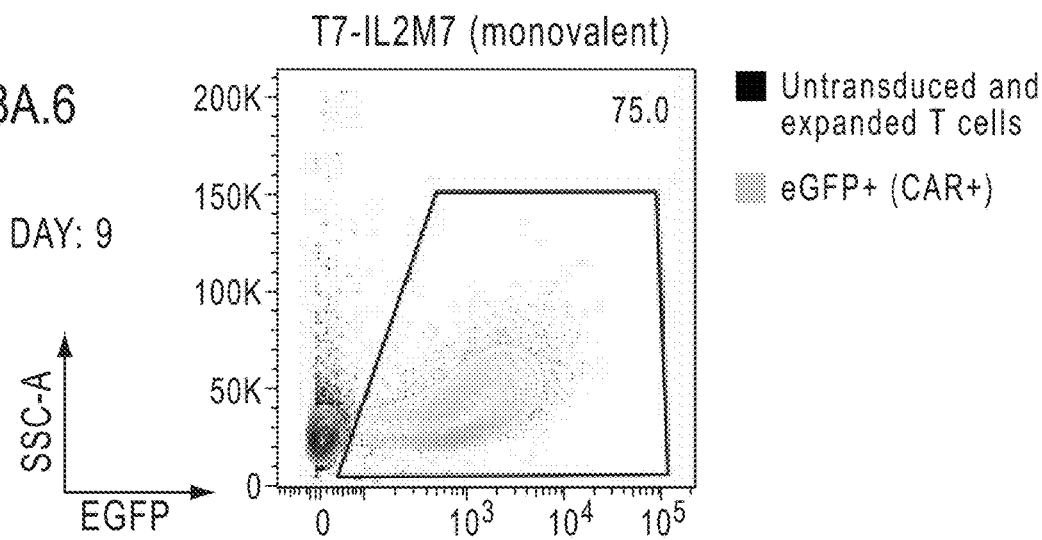
FIG. 28A.6 DAY: 9
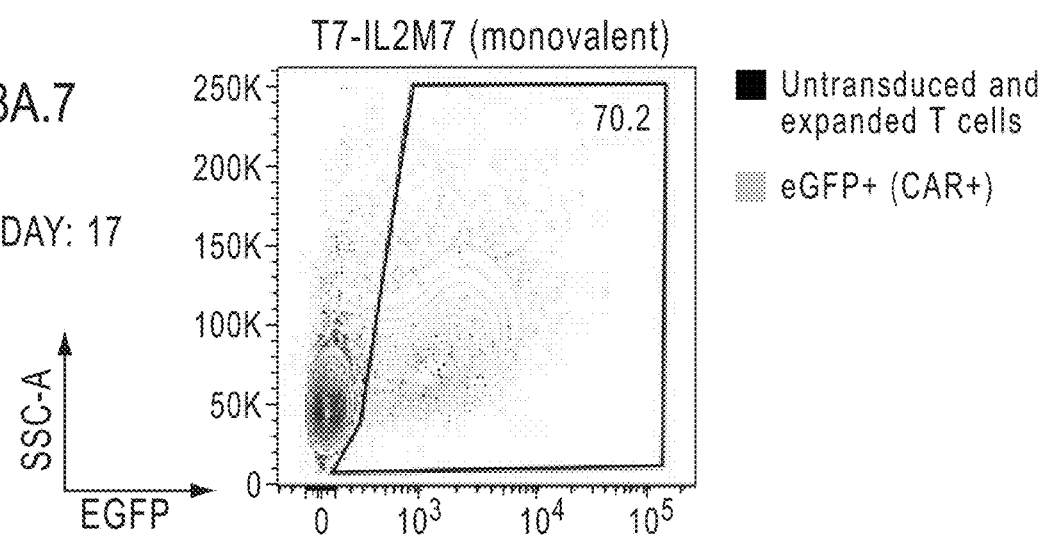
FIG. 28A.7 DAY: 17

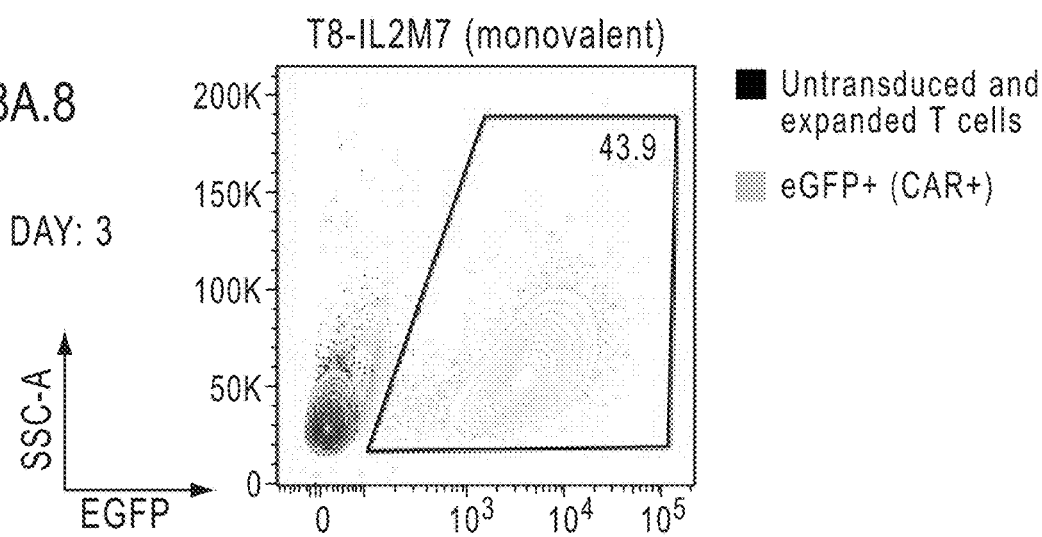
FIG. 28A.8
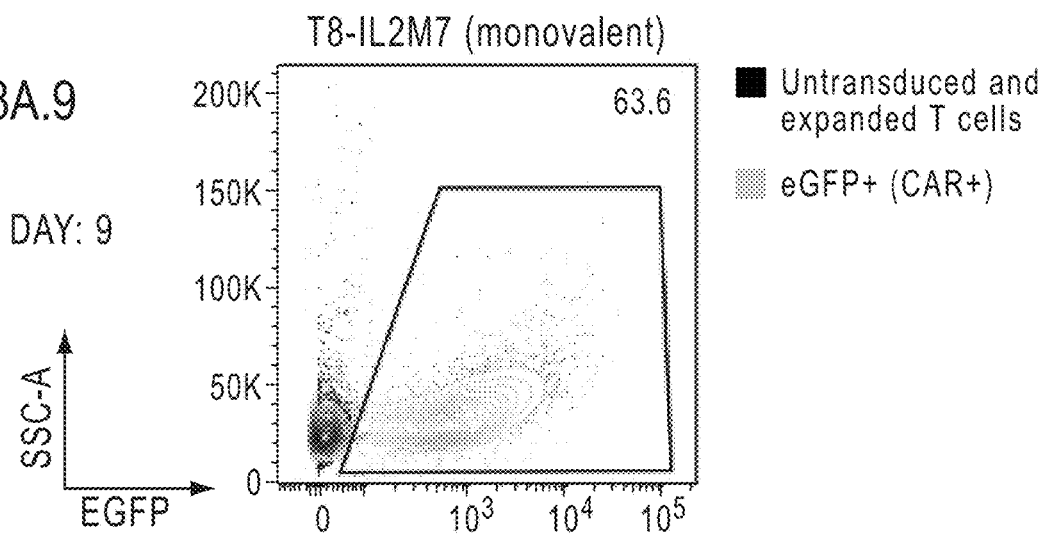
FIG. 28A.9
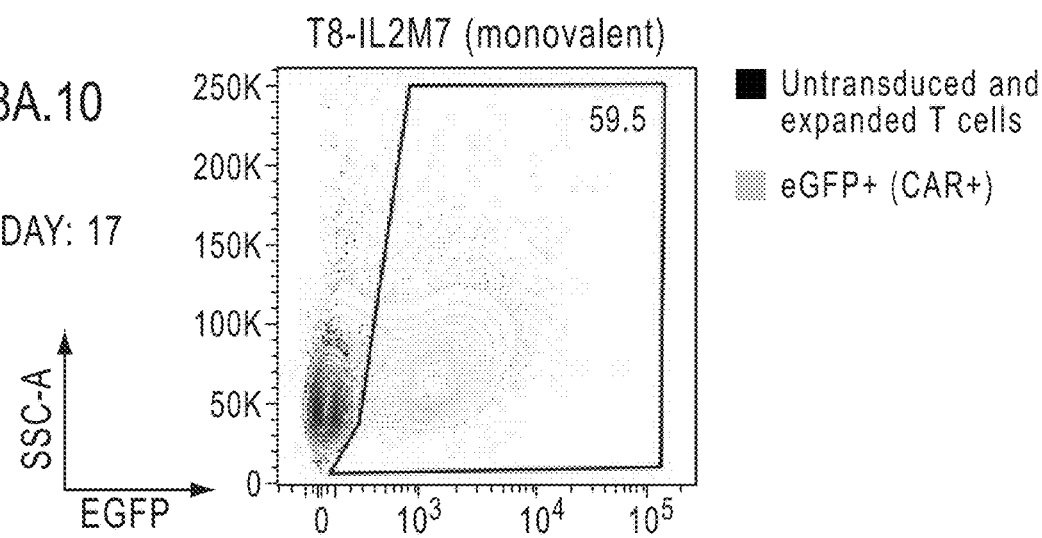
FIG. 28A.10

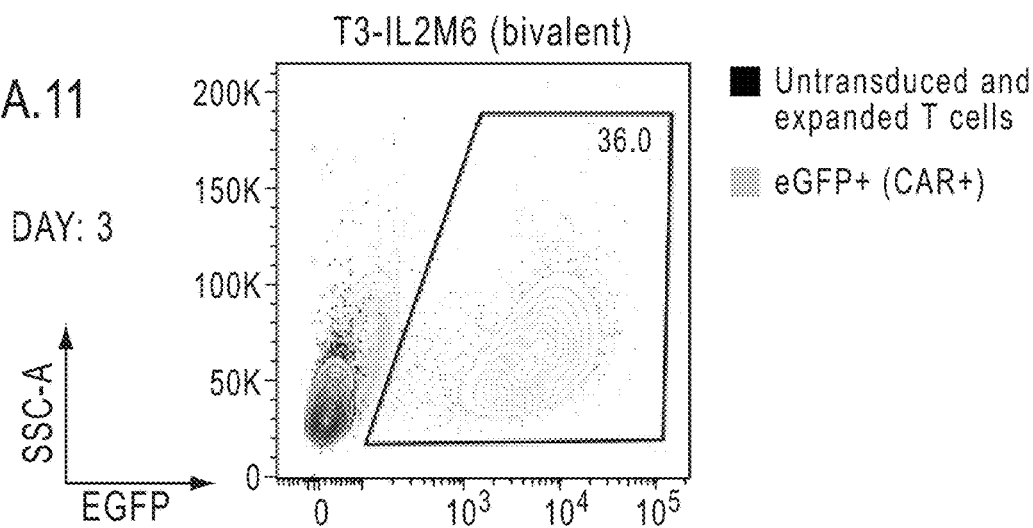
FIG. 28A.11
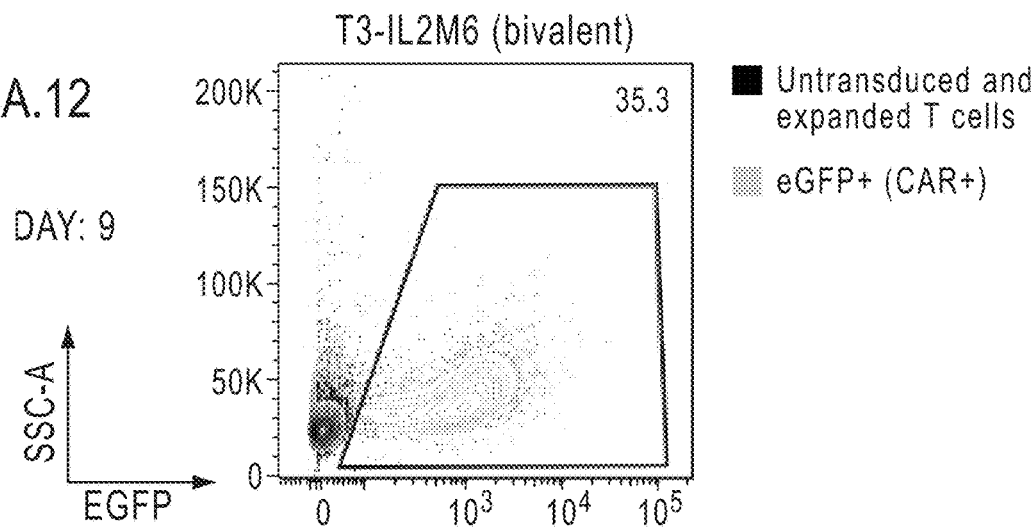
FIG. 28A.12
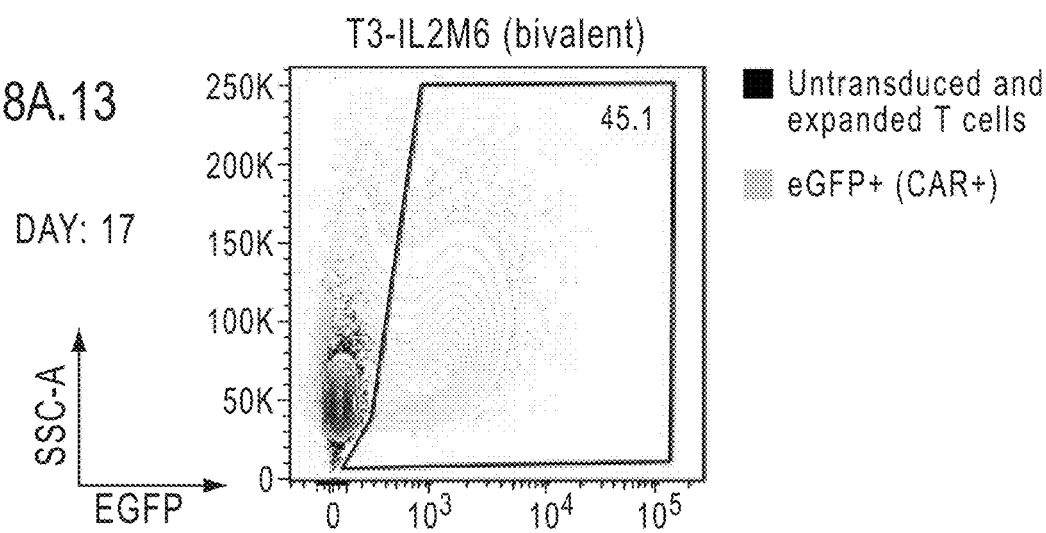
FIG. 28A.13

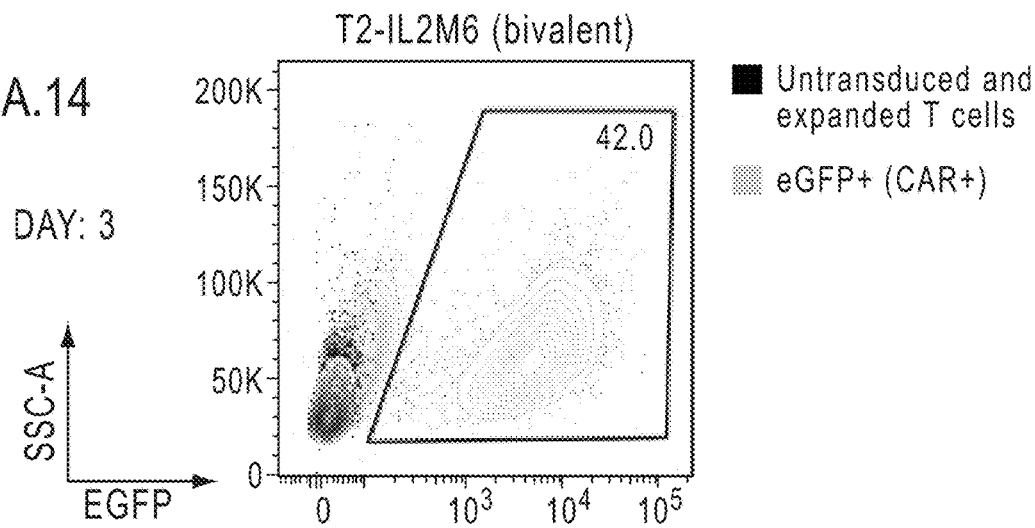
FIG. 28A.14 DAY: 3
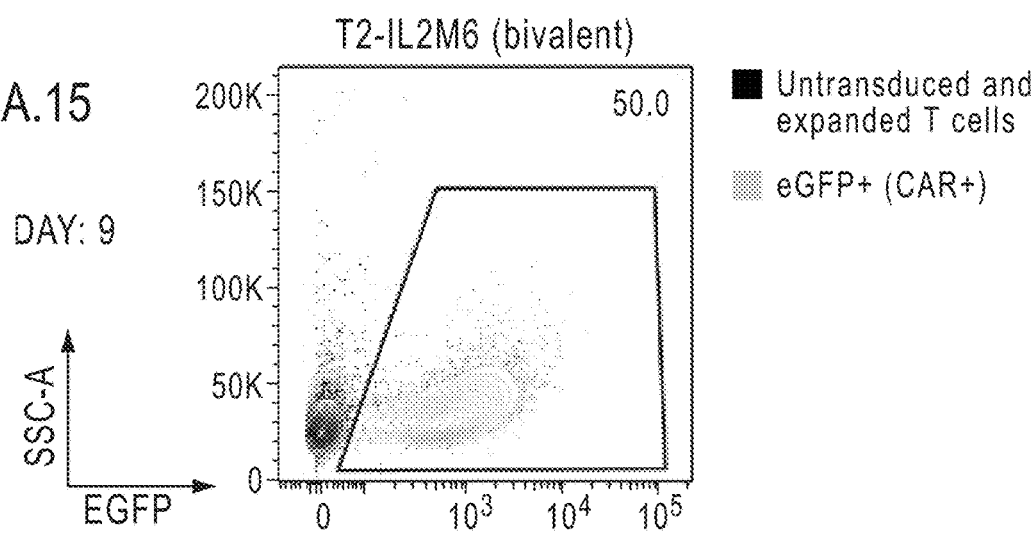
FIG. 28A.15 DAY: 9
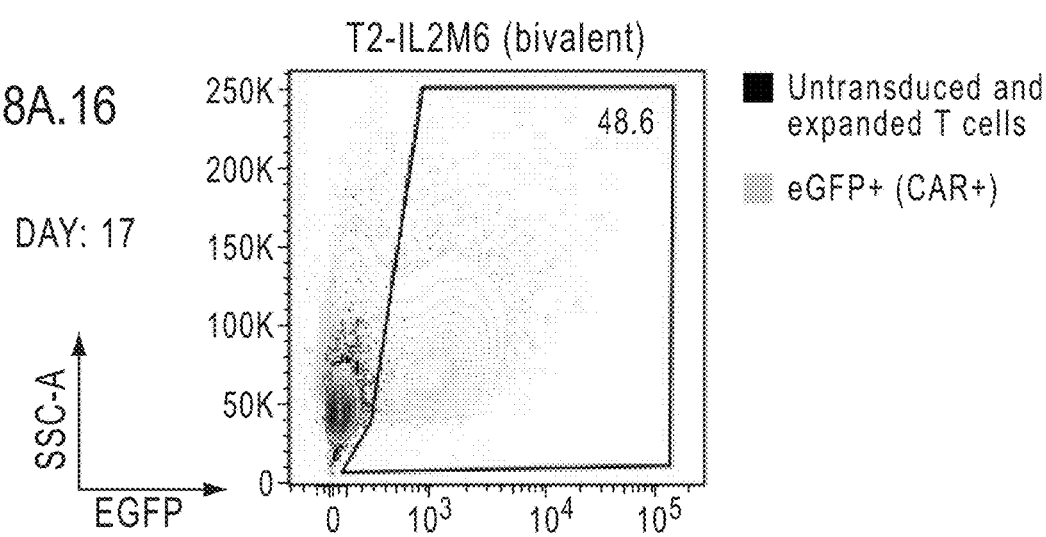
FIG. 28A.16 DAY: 17

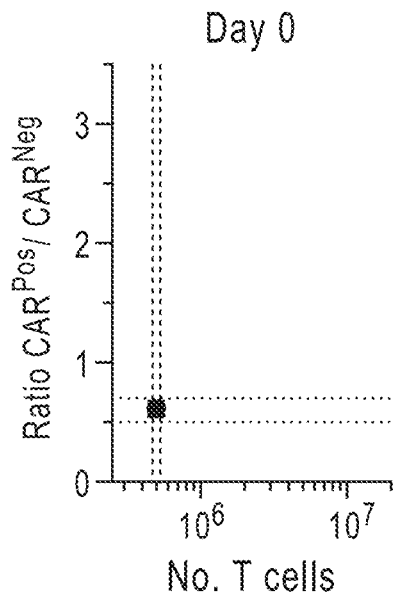
FIG. 28B.1
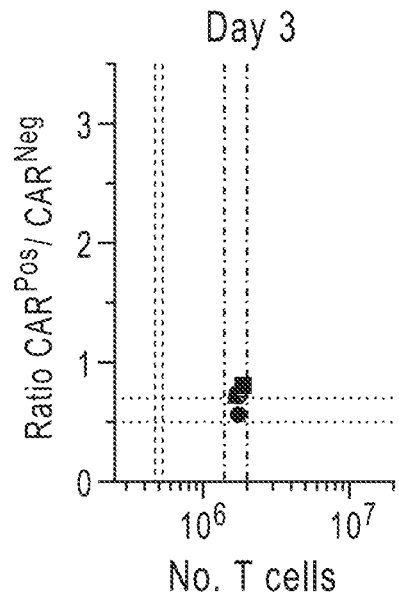
FIG. 28B.2
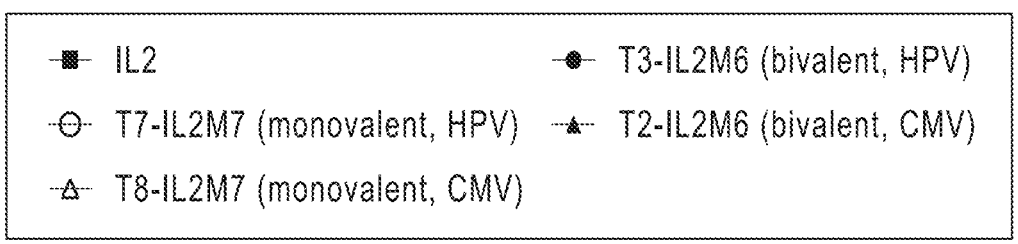
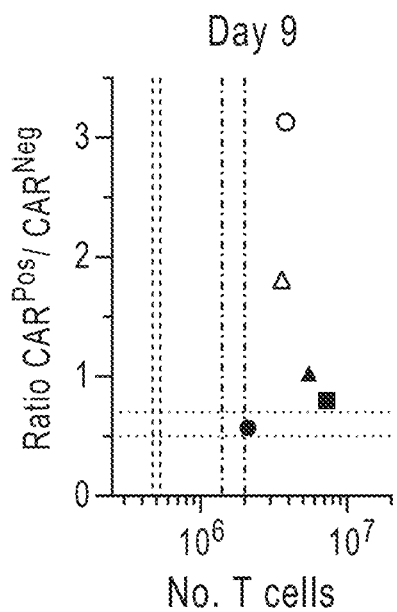
FIG. 28B.3
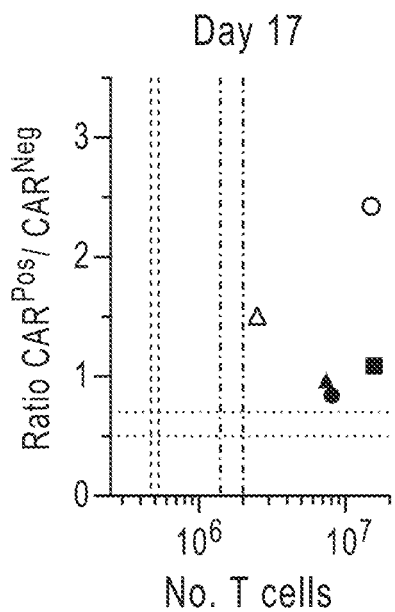
FIG. 28B.4

IL2 AGONISTS AND METHODS OF USE THEREOF

1. CROSS-REFERENCE TO RELATED APPLICATIONS

This application is a continuation of international application no. PCT/US2020/066096 filed Dec. 18, 2020, which claims the priority benefit of U.S. provisional application No. 62/951,831, filed Dec. 20, 2019, the contents of each of which are incorporated herein in their entireties by reference thereto.

2. SEQUENCE LISTING

The instant application contains a Sequence Listing which has been submitted electronically in ASCII format and is hereby incorporated by reference in its entirety. Said ASCII copy, created on Dec. 18, 2020, is named RGN-006D-WO_SL and is 162,034 bytes in size.

3. BACKGROUND

Interleukin 2 (IL-2 or IL2) is a pluripotent cytokine produced primarily by CD4$^+$ helper T cells. It stimulates the proliferation and differentiation of T cells, induces the generation of cytotoxic T lymphocytes (CTLs) and the differentiation of peripheral blood lymphocytes to cytotoxic cells and lymphokine-activated killer (LAK) cells, promotes cytokine and cytolytic molecule expression by T cells, facilitates the proliferation and differentiation of B-cells and the synthesis of immunoglobulin by B-cells, and stimulates the generation, proliferation and activation of natural killer (NK) cells (see Waldmann, 2009, Nat Rev Immunol 6:595-601 and Malek, 2008, Annu Rev Immunol 26:453-79).

IL2 has three different receptors: the high affinity receptor, the intermediate affinity receptor, and the low affinity receptor. The high affinity receptor has three subunits: the interleukin 2 receptor alpha (IL-2Rα; CD25), the interleukin 2 receptor beta (IL-2Rβ; CD122), and the interleukin 2 receptor gamma (IL-2Rγ; CD132; common gamma chain). The low affinity receptor is IL-2Rα, which is a 55 kD polypeptide (p55) that appears upon T cell activation and was originally called Tac (for T activation) antigen. IL-2Rα binds IL2 with a $K_D$ of approximately $10^{-8}$ M. Binding of IL2 to cells expressing only IL-2Rα does not lead to any detectable biologic response.

The intermediate affinity receptor is composed of IL-2Rβ and IL-2Rγ. IL-2Rβ is a member of the type I cytokine receptor family characterized by the two cysteine/WSXWS motif (SEQ ID NO:1). IL-2Rγ, a 64 kD polypeptide, is also known as the common gamma chain because it is shared among a number of cytokine receptors, including the receptor for interleukin-4 and interleukin-7. The intermediate affinity receptor also mediates interleukin 15 (IL-15 or IL15) signaling.

Resting immune cells are thought to express only the intermediate affinity receptor. Upon antigen receptor-mediated immune cell activation, e.g., of resting T cells, IL-2Rα is rapidly expressed. Once IL-2Rα binds IL2, it then sequentially engages IL-2Rβ and IL-2Rγ. IL2 binding by the IL-2Rαβγ complex results in signal transduction through a STAT5 and IL2 mediated growth stimulation of, inter alia, effector T cells that destroy virus-infected cells and tumor cells.

In addition to its stimulatory effects on effector T cells, IL2 mediates activation-induced cell death (AICD) in T cells (Lenardo et al., 1991, Nature 353:858-61). AICD is a process by which fully activated T cells undergo programmed cell death, resulting in tolerance not only to established normal self-antigens but also to persistent antigens such as tumor antigens.

IL2 is also involved in the maintenance of peripheral CD4+CD25$^+$ regulatory T (T$_{reg}$) cells (see, e.g., Fontenot et al., 2005, Nature Immunol 6:1142-51), which are also known as suppressor T cells. They suppress effector T cells from destroying their (self-)target, either through cell-cell contact by inhibiting T cell help and activation, or through release of immunosuppressive cytokines such as IL-10 or TGFβ. Depletion of T$_{reg}$ cells was shown to enhance IL2-induced anti-tumor immunity (Imai et al., 2007, Cancer Sci 98:416-23).

Due to its pleotropic effects, IL2 is not optimal for inhibiting tumor growth. The use of IL2 as an antineoplastic agent has been limited by the serious toxicities that accompany the doses necessary for a tumor response. Proleukin® (marketed by Prometheus Laboratories, San Diego, Calif.), is a recombinant form of IL2 that is approved for the treatment of metastatic melanoma and metastatic renal cancer, but its side effects are so severe that its use is only recommended in a hospital setting with access to intensive care. Patients receiving high-dose IL2 treatment frequently experience severe cardiovascular, pulmonary, renal, hepatic, gastrointestinal, neurological, cutaneous, haematological and systemic adverse events, which require intensive monitoring and in-patient management. The major side effect of IL2 therapy is vascular leak syndrome (VLS), which leads to the accumulation of interstitial fluid in the lungs and liver resulting in pulmonary edema and liver damage. There is no treatment for VLS other than withdrawal of IL2. Low-dose IL2 regimens have been tested in patients to avoid VLS, however, at the expense of suboptimal therapeutic results. It has been shown that IL2-induced pulmonary edema resulted from direct binding of IL2 to lung endothelial cells, which express low to intermediate levels of functional high affinity IL2 receptors (Krieg et al., 2010, Proc Nat Acad Sci USA 107:11906-11).

A variety of IL2 variants have been generated with the aim of reducing the toxicity of IL2 cancer therapy. The prevailing approach is the generation of IL2 molecules that allow IL2 binding to the intermediate affinity receptor but disfavor the association of IL2 with CD25 (thus termed CD122-biased). The rationale for this approach is two-fold. First, CD25 is prominently expressed on T$_{reg}$ cells, where the excess of CD25 could serve as a sink, thereby taking IL2 away from effector T cells. Second, endothelial cells, which mediate VLS, express CD25. In theory, reducing binding to CD25 (IL-2Rα) could redirect the IL2 signal to effector T cells, improving anti-tumor efficacy, and reduce VLS, thereby reducing toxicity. Strategies to obtain CD122-biased IL2 formulations include, for example, CD122-directed IL2 complexes, in which an anti-IL2 monoclonal antibody covers the CD25-binding site, IL2 muteins with a mutation at the CD25-binding site, and IL2 carrying polyethylene glycol (PEG) groups at the CD25-binding site. Onur and Arenas-Ramirez, 2019, Swiss Med Wkly 149:w14697.

Despite the general acceptance in the field of CD122 directed IL2 therapies being developed for cancer therapy, it has been surprisingly discovered that such molecules have poor therapeutic indices for cancer therapy, with high, toxic doses required to confer modest anti-cancer effects.

Thus, there is a need in the art for novel IL2 therapies with improved therapeutic efficacy and safety profiles.

4. SUMMARY

The present disclosure stems from a number of discoveries regarding the activities of IL2 molecules that impact anti-tumor efficacy. As shown herein, CD122 directed IL2 molecules have surprisingly only modest anti-tumor efficacy, even at high doses that result in apparent toxicity. This can be explained by a number of other discoveries. First, the inventors have discovered that while CD122 directed IL2 molecules were designed to preferentially expand NK and $CD8^+$ T cells relative to Treg cells, they primarily do so in the blood and spleen but to a much lesser extent in tumors, in contrast to wild IL2 preferentially expands $CD8^+$ T cells in the tumor but not in the periphery. In addition, $CD8^+$ T cells expanded by CD122-biased IL2 molecules are mostly $CD44^+CD62L^+$ central memory-like T cells and lack specificity against tumor cells, whereas wild type IL2 can expand $CD44^+CD62L^-$ effector $CD8^+$ T cells. Thus, the anti-tumor efficacy of these molecules is reduced relative to wild type IL2. Further, the inventors have discovered that tumor Treg cells are less responsive to IL2 than blood and spleen Treg cells. Thus, the adverse effects of non-CD122 directed forms of IL2 cancer therapy can be mitigated by directing such non-CD122 directed forms of IL2 to tumors, where Tregs are less responsive to IL2 and IL2 preferentially expands CD8+ T cells.

Further, the inventors have discovered that the therapeutic indices of a variety of IL2 molecules with various degrees of receptor attenuation can be improved by appropriately balancing the ability of an IL2 agonist to be localized to a site or cell type of interest (e.g., the tumor environment generally or tumor reactive T cells specifically) and modulating the level activity of the IL2 component at the site of interest and/or until it reaches the site or cell type of interest.

Based on the foregoing discoveries, the inventors have developed IL2 molecules (referred to herein as IL2 agonists) that are believed to be more effective than the CD122 directed IL2 molecules currently under development for the treatment of cancer. The IL2 agonists of the disclosure are not directed to CD122 and, in some instances, have reduced or minimized CD122 binding. The IL2 agonists of the disclosure have an IL2 moiety and (1) an optional tumor targeting moiety and/or (2) an optional multimerization, e.g., dimerization, moiety and/or (3) an optional stabilization moiety. The tumor targeting moiety, e.g., an antigen binding domain ("ABD") of an antibody, can, for example, bind to a target molecule present on the tumor surface (e.g., a tumor associated antigen), the tumor microenvironment, and/or tumor reactive lymphocytes.

IL2 moieties that can be used in the IL2 agonists of the disclosure are described in Section 6.3.

Targeting moieties that can be used in the IL2 agonists of the disclosure are described in Section 6.4.

Multimerization moieties that can be used in the IL2 agonists of the disclosure are described in Section 6.5.

Stabilization moieties that can be used in the IL2 agonists of the disclosure are described in Section 6.6.

Various exemplary configurations of the IL2 agonists of the disclosure are described in specific embodiments 1 to 166, 199 to 258 and 267 to 322, infra.

Linkers that can be used to connect different components of the IL2 agonists of the disclosures are described in Section 6.7.

The disclosure further provides nucleic acids encoding the IL2 agonists of the disclosure. The nucleic acids encoding the IL2 agonists can be a single nucleic acid (e.g., a vector encoding all polypeptide chains of an IL2 agonist) or a plurality of nucleic acids (e.g., two or more vectors encoding the different polypeptide chains of an IL2 agonist). The disclosure further provides host cells and cell lines engineered to express the nucleic acids and IL2 agonists of the disclosure. The disclosure further provides methods of producing an IL2 agonist of the disclosure. Exemplary nucleic acids, host cells, and cell lines, and methods of producing an IL2 agonist are described in Section 6.8 and specific embodiments 167 to 169, 259 to 261 and 323 to 325 infra.

The disclosure further provides pharmaceutical compositions comprising the IL2 agonists of the disclosure. Exemplary pharmaceutical compositions are described in Section 6.9 and specific embodiments 170, 262 and 326 infra.

Further provided herein are methods of using the IL2 agonists and the pharmaceutical compositions of the disclosure, e.g., for treating cancer and immune disorders. Exemplary methods are described in Section 6.10. The IL2 agonists of the disclosure are useful in combination therapy, for example as an adjunct to CART therapy. Exemplary combination therapy methods are disclosed in 6.11. Specific embodiments of the methods of treatment of the disclosure are described in specific embodiments 171 to 198, 263 to 266 and 327 to 346 infra.

5. BRIEF DESCRIPTION OF THE FIGURES

FIGS. 4A-4C show activity of IL2M1 on human PBMCs. IL2M1 has reduced activity on IL-2Rα+ Tregs (FIG. 4A), whereas it maintains the full activity on IL-2Rα− CD8+ T cells (FIG. 4B) and NK cells (FIG. 4C).

Figure 7A:
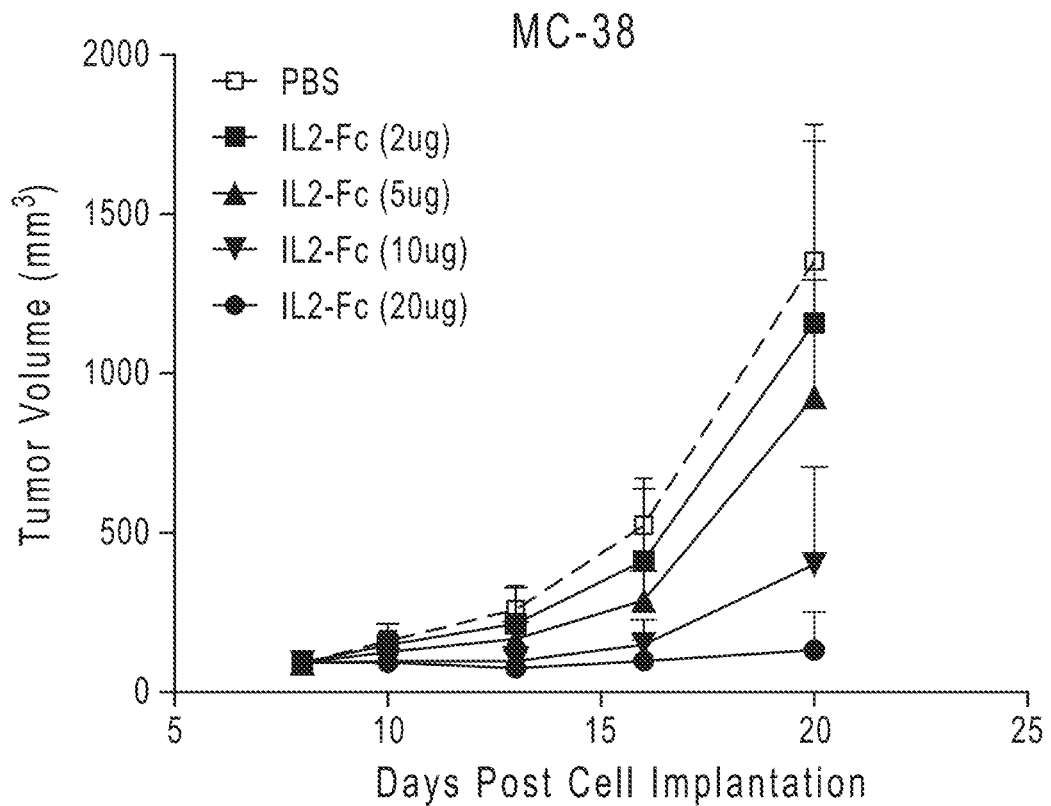
Figure 7B:
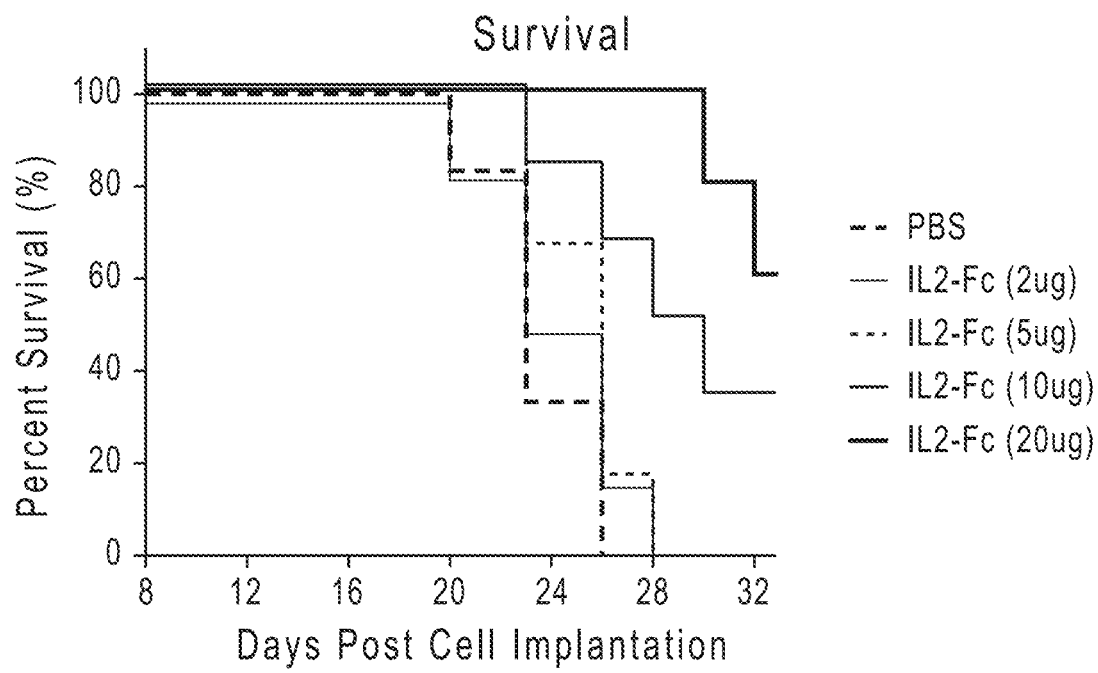

FIGS. 7A-7C.5 show that IL2M0 (referred to as IL2-Fc in figure) induces antitumor response in a dose dependent manner.

Figure 8A:
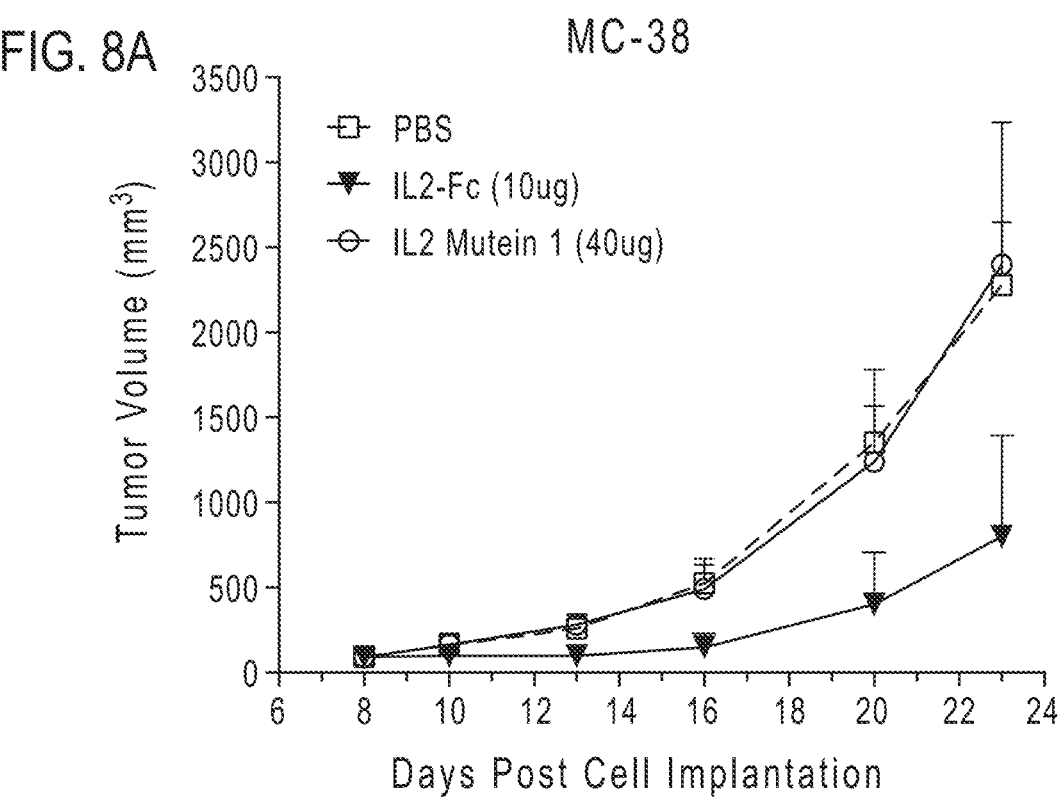
Figure 8B:
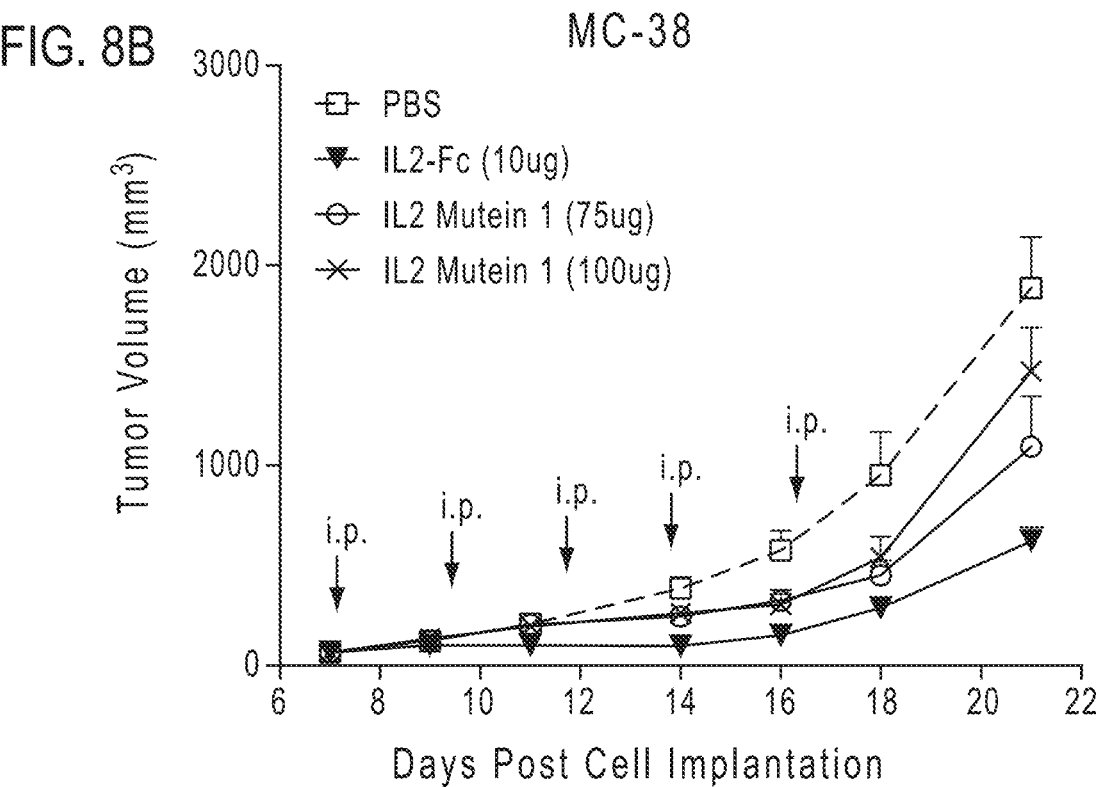
Figure 8C:
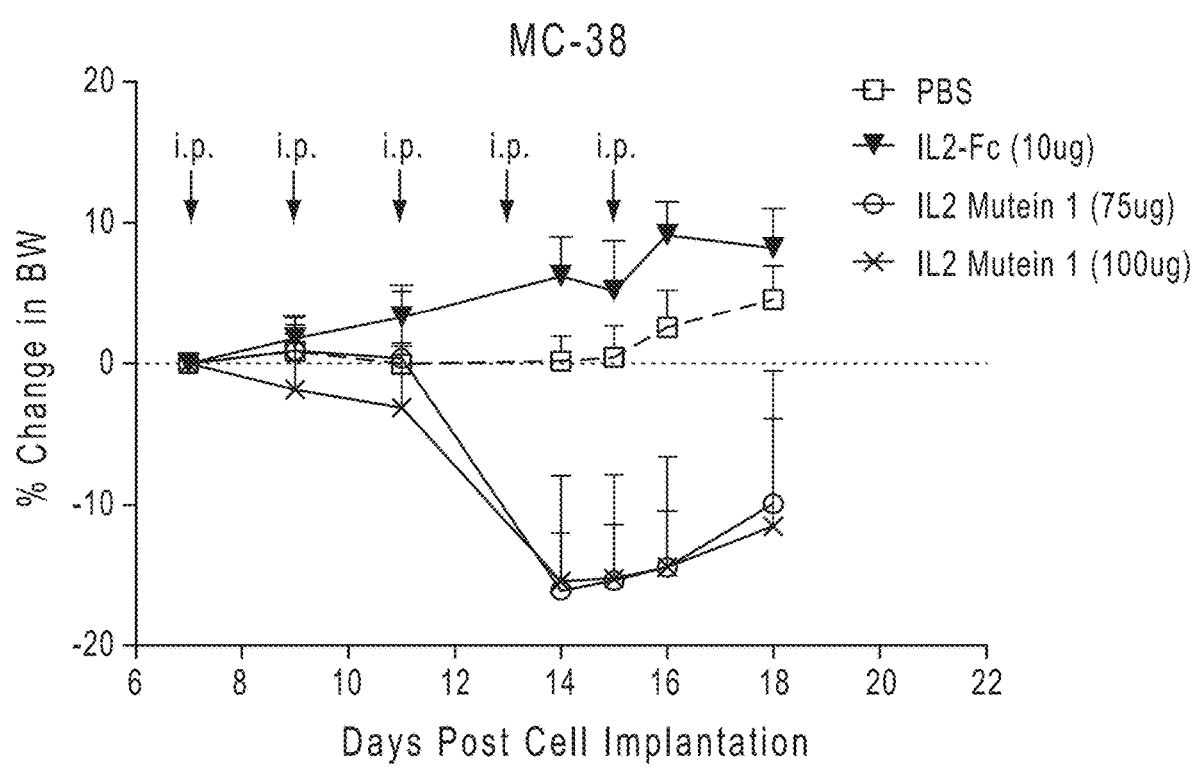

FIGS. 8A-8C show modest antitumor efficacy (FIG. 8A, 8B) and concomitant apparent toxicity (FIG. 8C) for IL2M1.

FIGS. 9A-9C.4 show modest antitumor efficacy (FIG. 9A) and concomitant apparent toxicity (FIG. 9B) for IL15M1, as well as the peripheral immune cell profile induced by IL15M1 (FIGS. 9C.1-C.4).

FIGS. 10A.1-10R show activity of IL2M0 (referred to as IL2-Fc in figure) and IL2M1 on proliferation of intratumoral and peripheral lymphocytes.

Figure 11A:
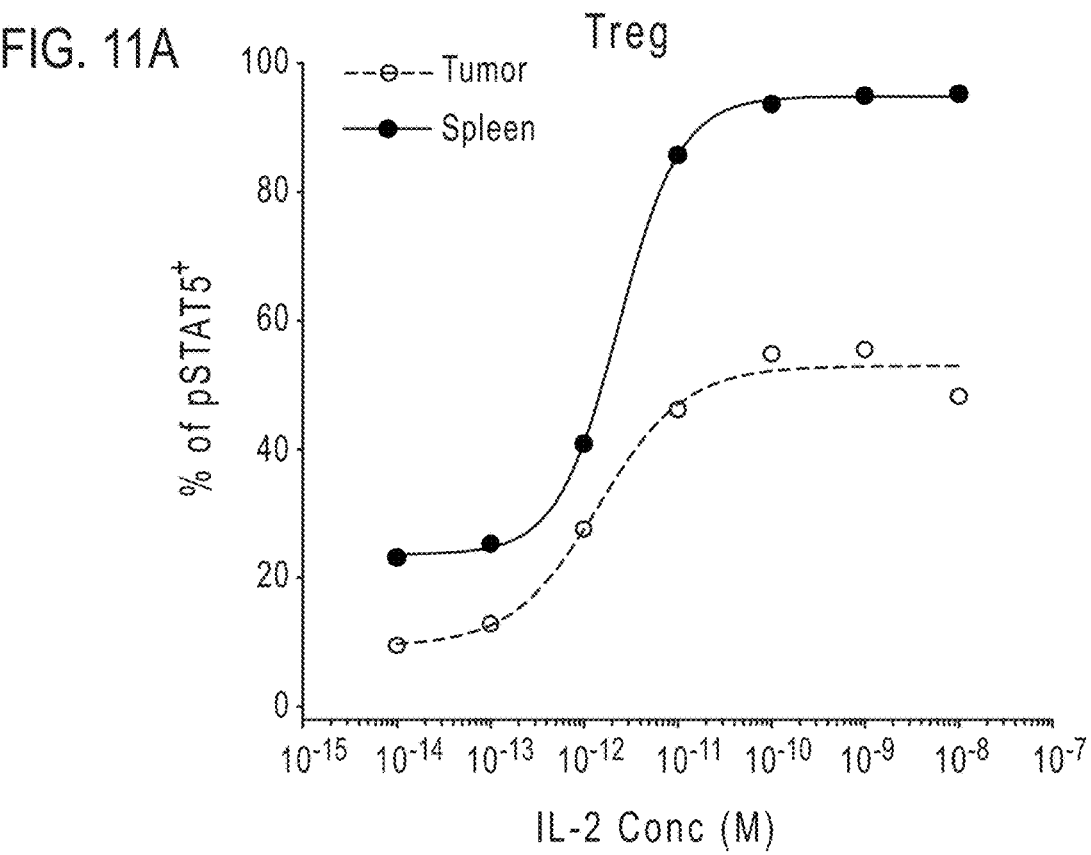
Figure 11B:
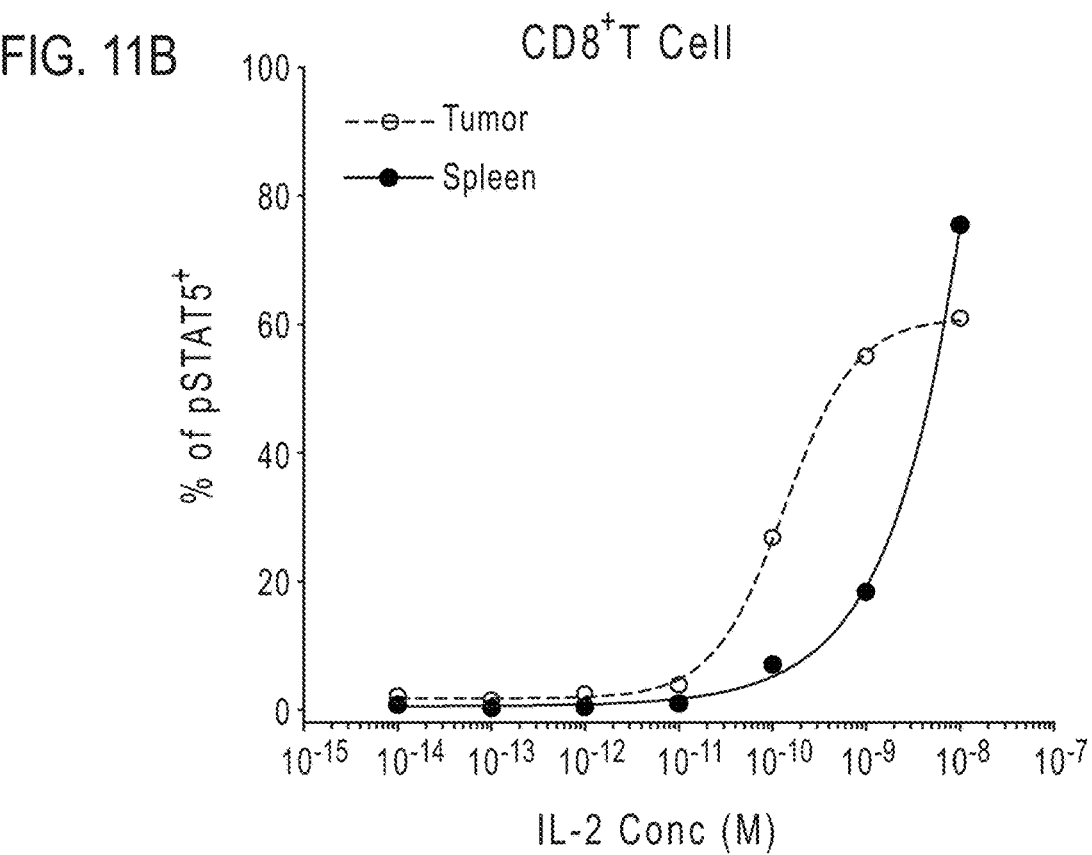

FIGS. 11A-11B show differential IL2 responsiveness of splenic and tumor-infiltrating Tregs and CD8+ T cells.

Figure 12A:
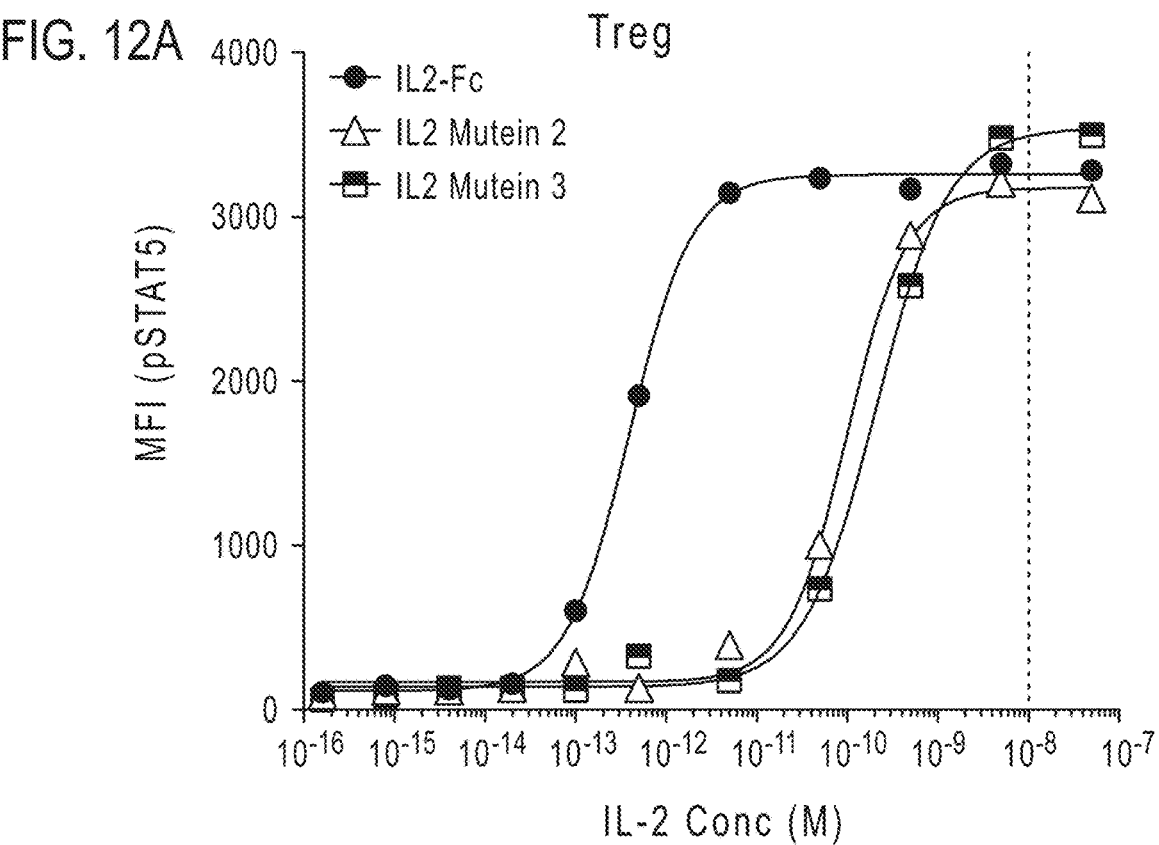
Figure 12B:
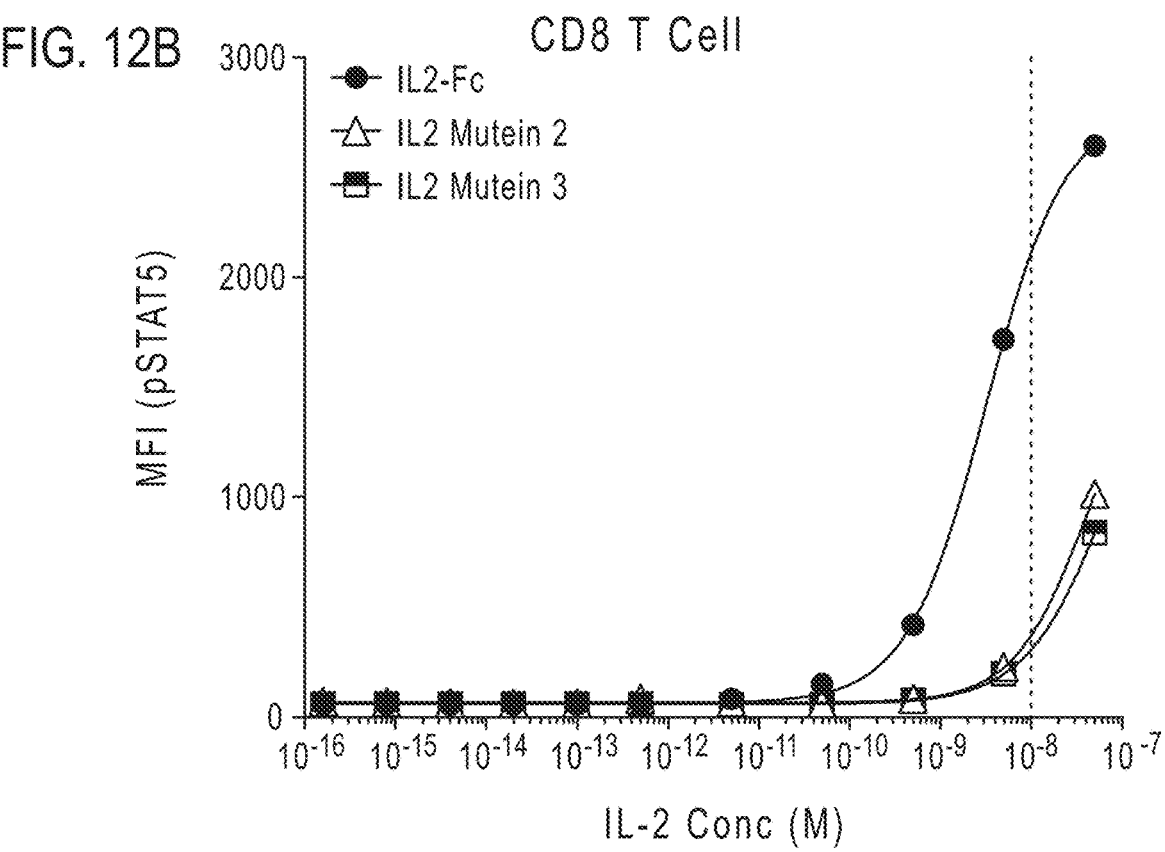
Figure 12C:
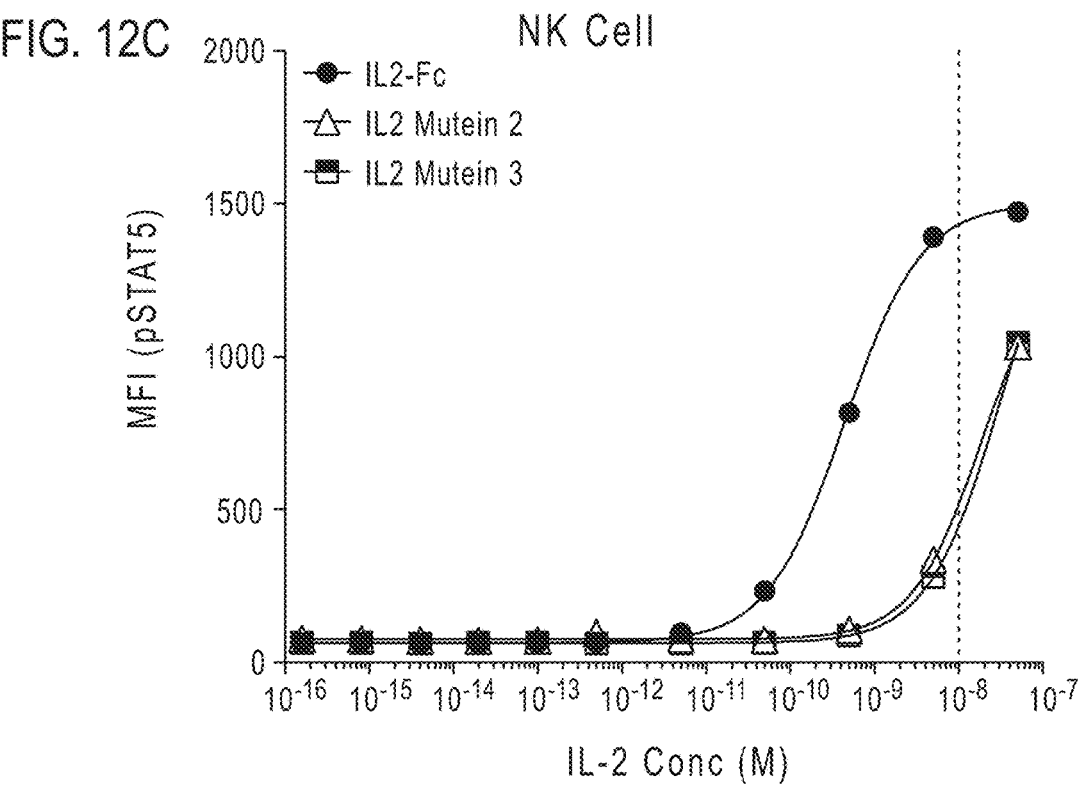
Figure 12D:
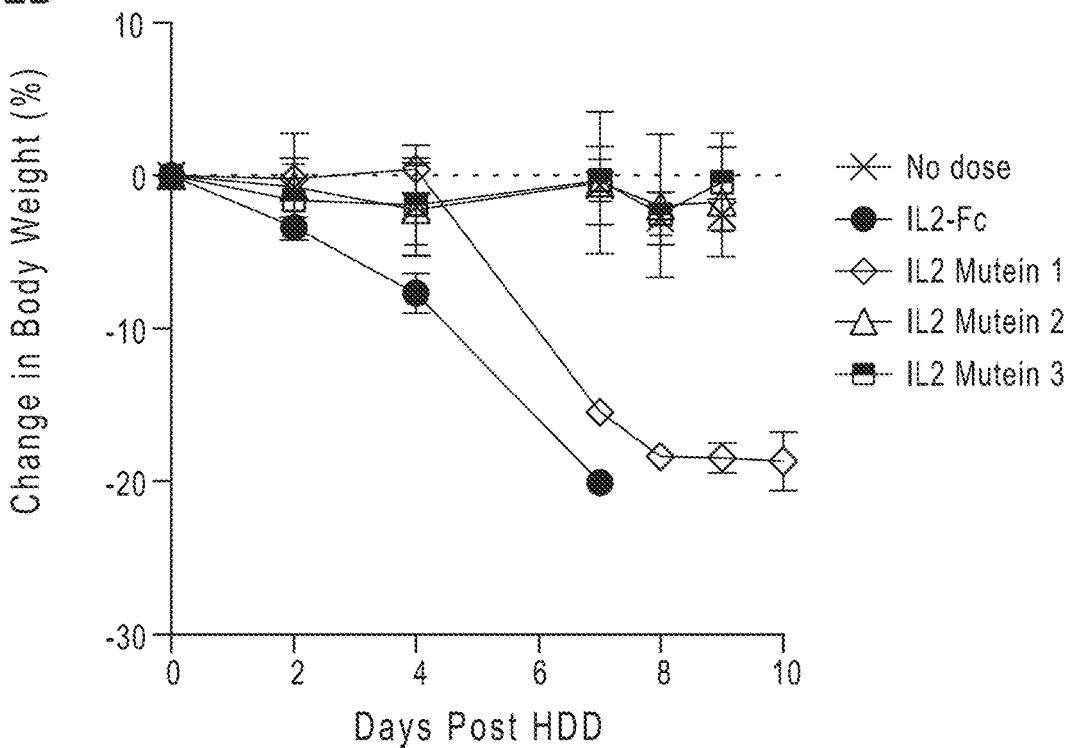

FIGS. 12A-12D show that IL2M2 and IL2M3 exhibit attenuated activity across multiple lymphocyte populations in human PBMCs (FIG. 12A-FIG. 12C) and reduced in vivo toxicity (FIG. 12D). The results in FIG. 12A through FIG. 12C are obtained with IL2M2 and IL2M3 protein and in FIG. 12D are based on in vivo administration of IL2M2 and IL2M3 encoding nucleic acids by hydrodynamic DNA delivery ("HDD").

Figure 13A:
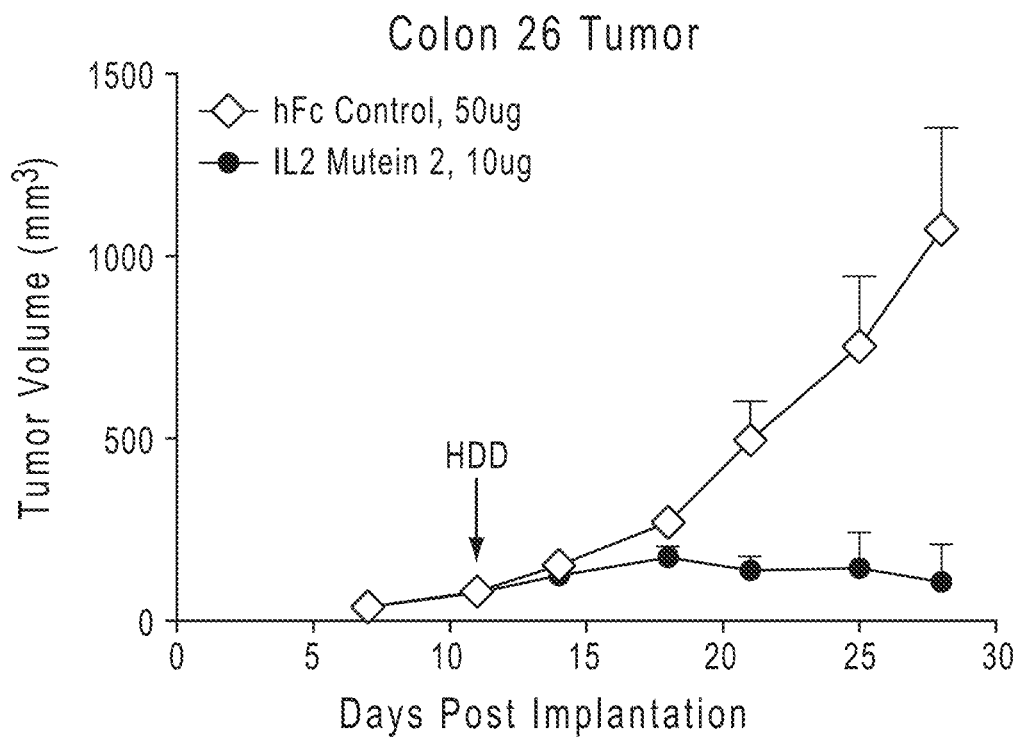
Figure 13B:
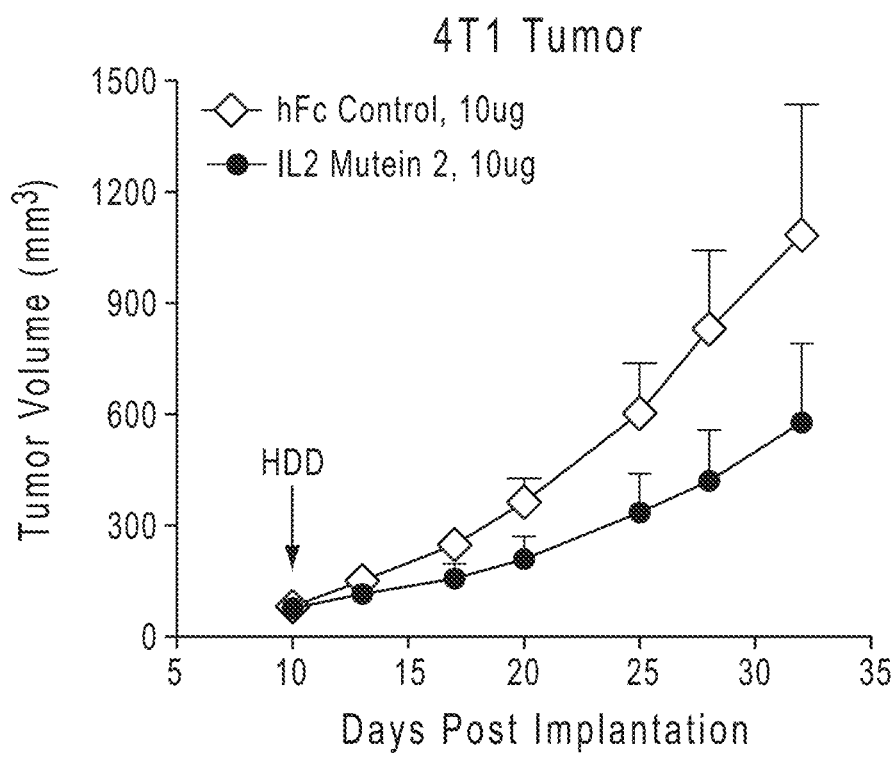
Figure 13C:
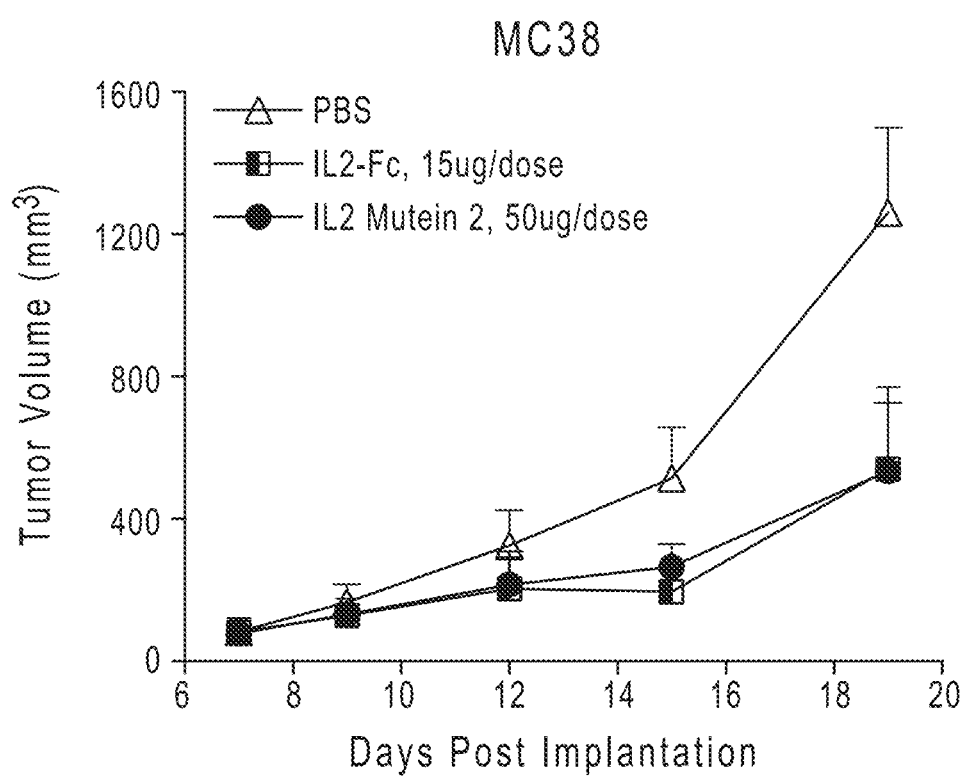

FIGS. 13A-13C show that IL2M2 displays anti-tumor efficacy as a single agent in multiple syngeneic mouse tumor models. IL2M2 was delivered via hydrodynamic DNA delivery (HDD) (FIGS. 13A and 13B) or as purified protein (FIG. 13C).

Figure 14A:
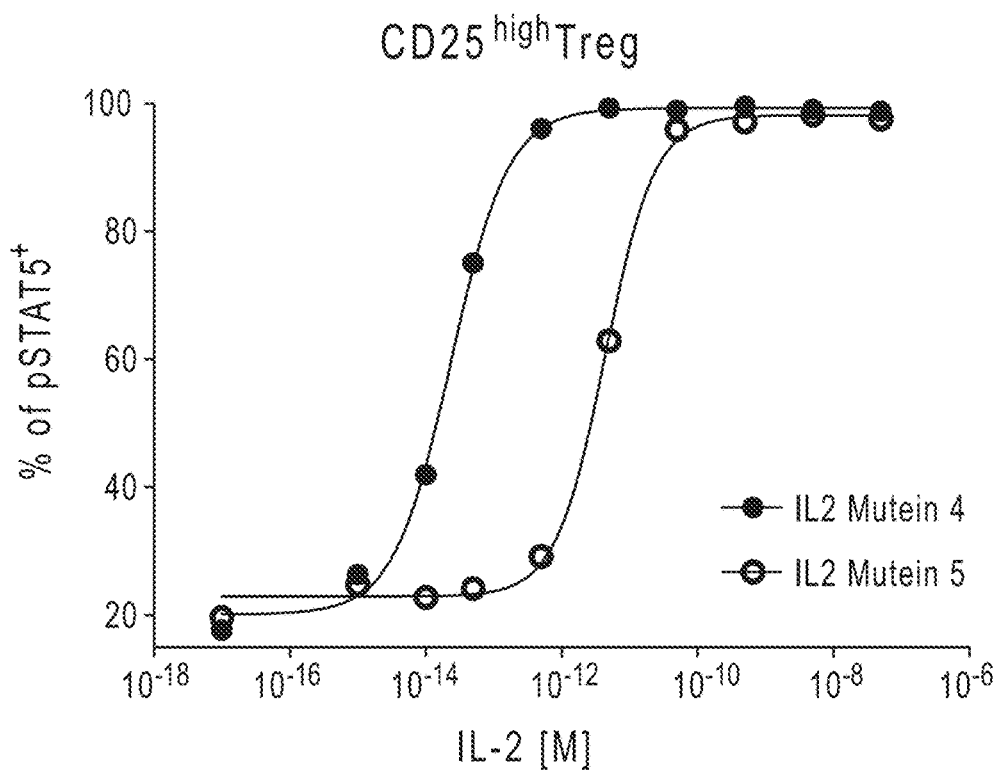
Figure 14B:
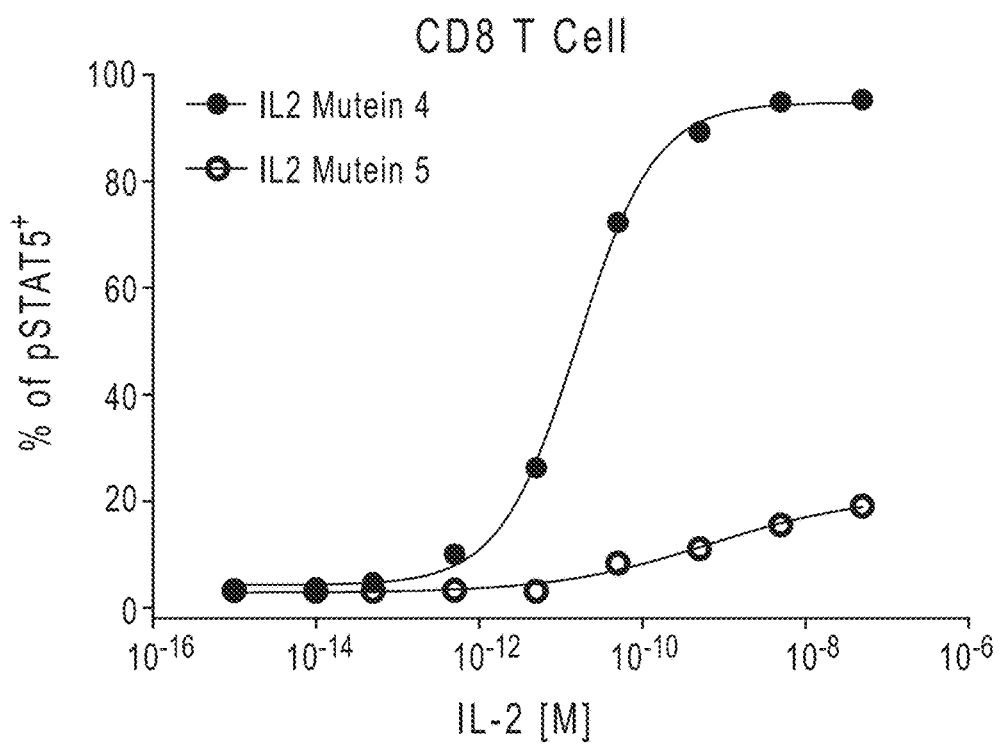
Figure 14C:
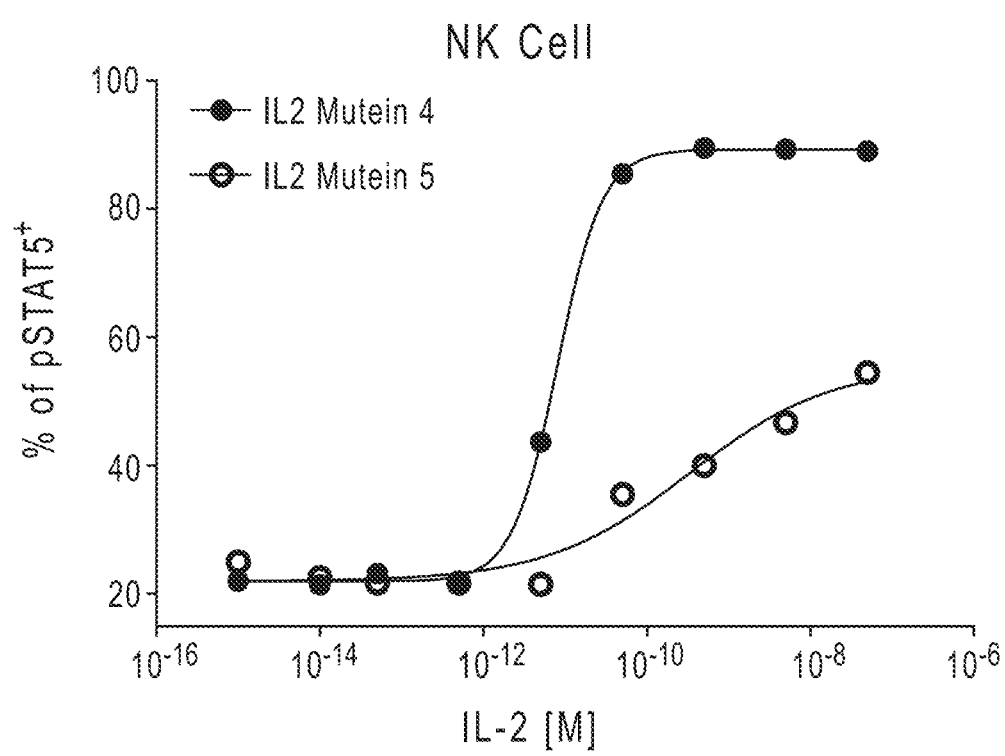

FIGS. 14A-14C show activity of IL2M4 and IL2M5 on different lymphocyte populations of human PBMC.

FIGS. 15A-15D show antitumor efficacy of IL2M5.

Figure 16A:
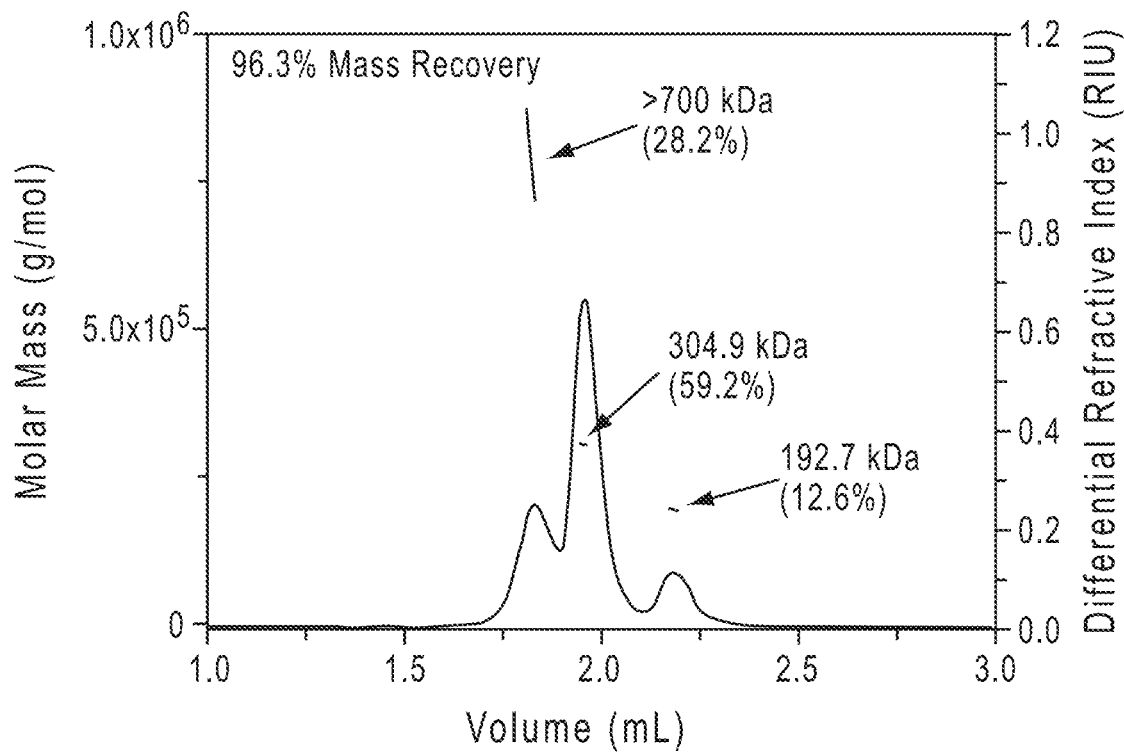
Figure 16B:
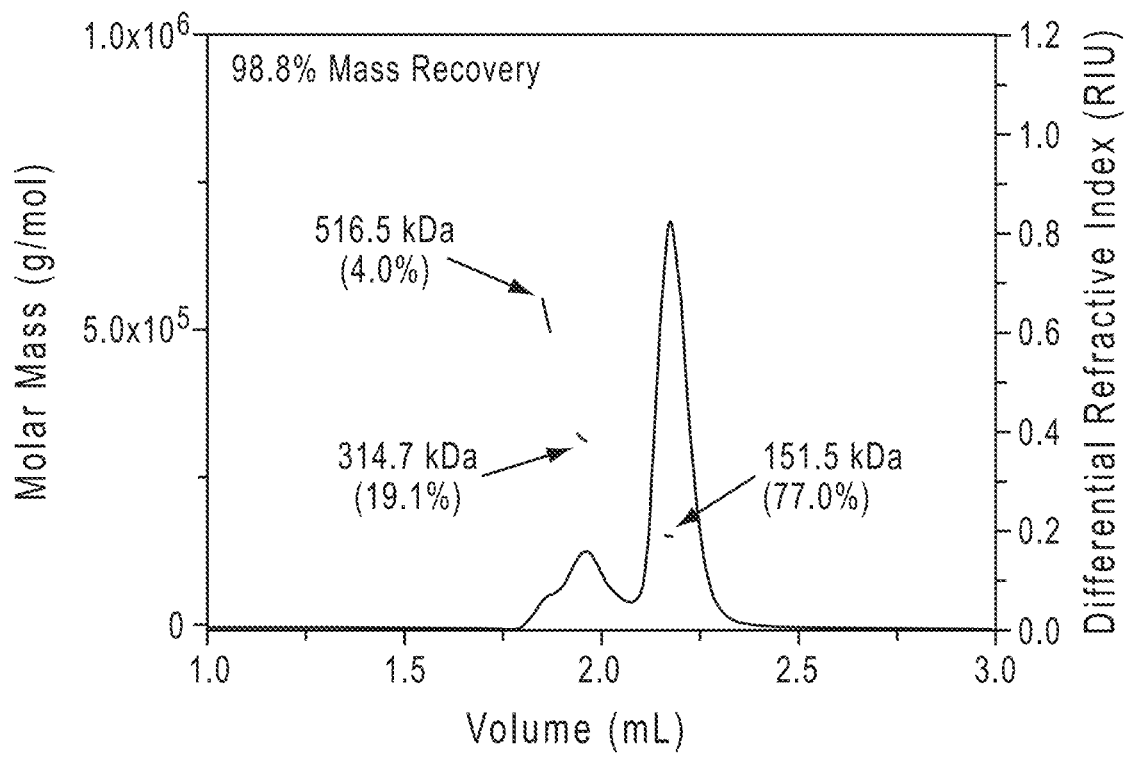

FIGS. 16A-16B show the results of SEC-MALS studies of IL2M2 (FIG. 16A), which primarily consists of higher order oligomers, vs. IL2M3 (FIG. 16B), which predominantly exists as a Fc homodimer, believed to be a result of the orientation of the IL2 domain relative to the Fc domain and/or length of the linker connecting the domains.

Figure 17:
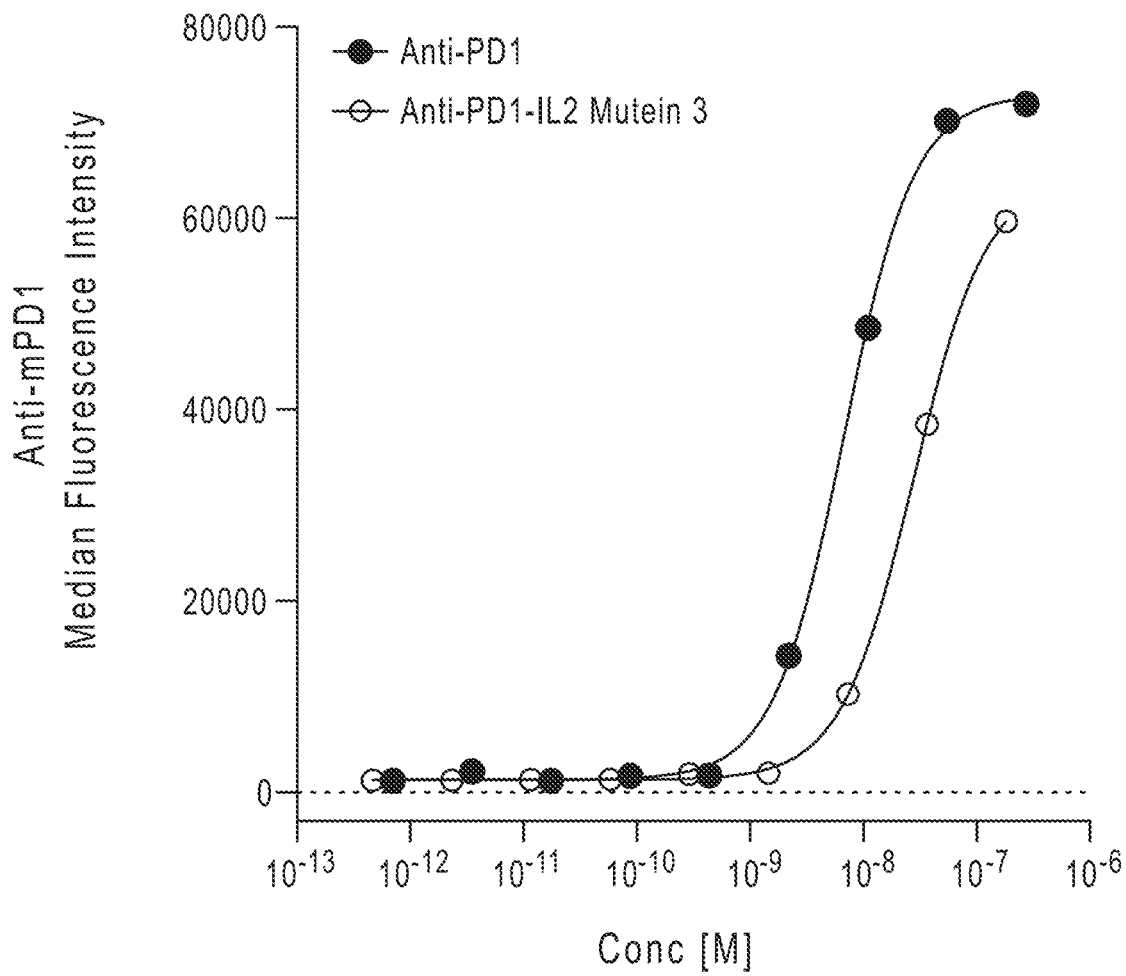

FIG. 17 shows results of FACS binding of anti-PD1 and T1-IL2M3 to HEK293-mPD1 cells.

Figure 18A:
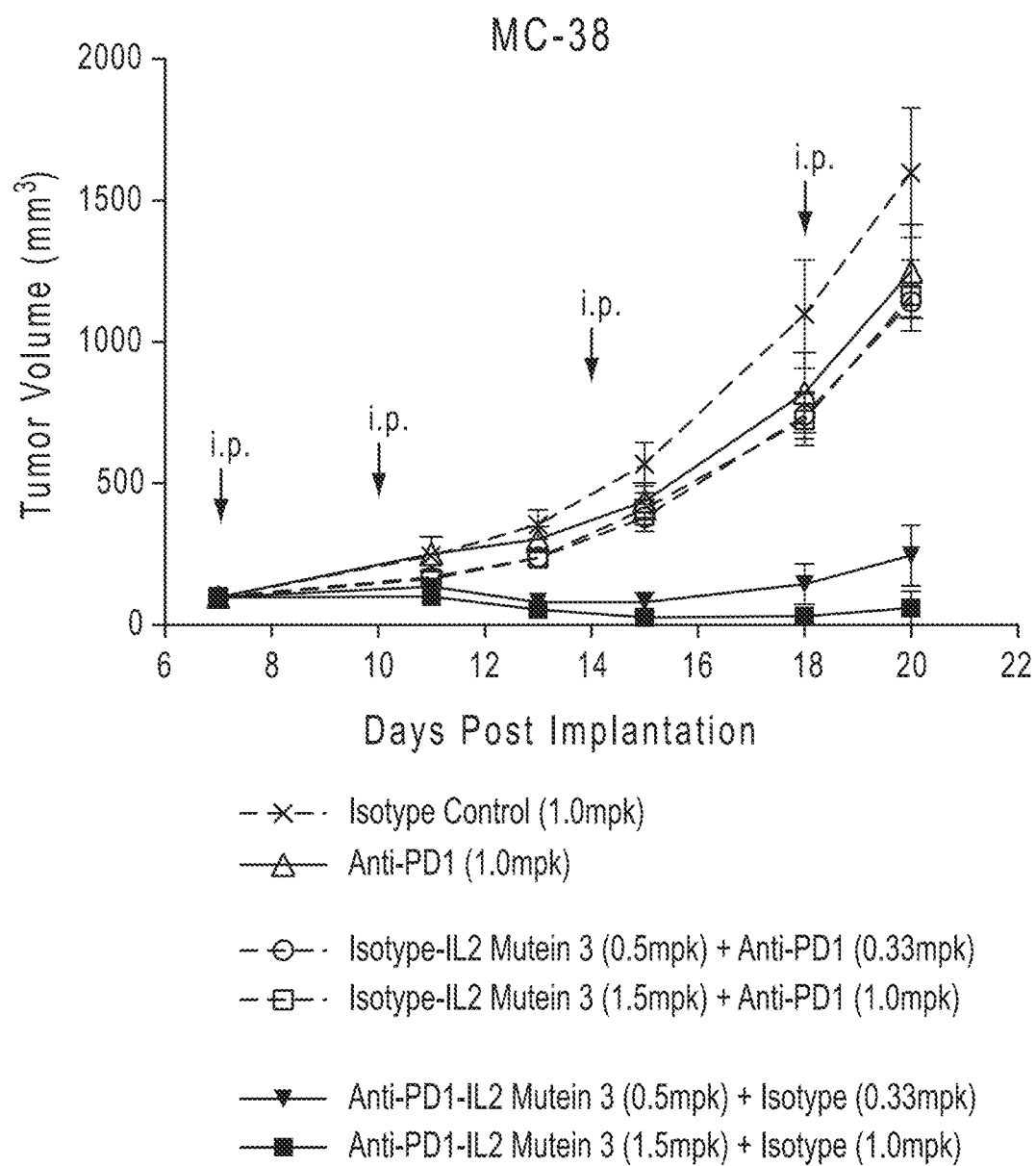

FIGS. 18A-18E.2 show superior anti-tumor efficacy of T1-IL2M3 to the combination of anti-PD1 and non-targeted IL2M3 (FIGS. 18A-18B.4), and that T1-IL2M3 expands effector CD8+ T cells that are PD1+ while causes less expansion of Tregs than non-targeted IL2M3 (FIGS. 18C.1-18E.2).

Figure 19:
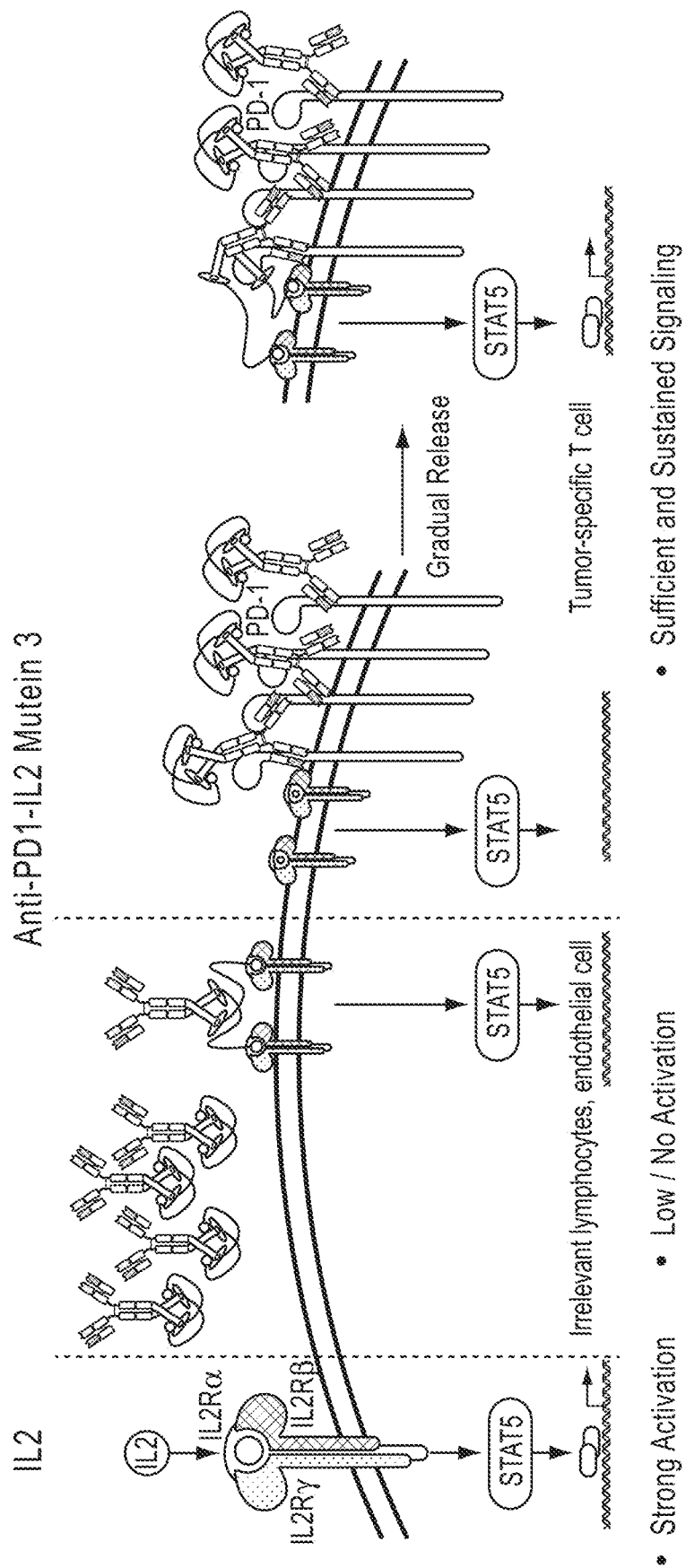

FIG. 19 shows a schematic of (a) IL2 binding by the IL-2Rαβγ complex, resulting in signal transduction through STAT5 and strong cell activation (left portion of figure) (b) low level binding of an anti-PD1-IL2 Mutein 3 fusion to the IL-2Rαβγ complex on lymphocytes and endothelial cells in the absence of cell surface expressed PD-1, resulting in low or no activation of those cells (middle portion of the figure between the two dotted lines), and (c) binding of an anti-PD1-IL2 Mutein 3 fusion to the IL-2Rαβγ complex on tumor specific T-cells with cell surface expressed PD-1, resulting in sustained signaling and T-cell activation.

Figures 20A, 20B:
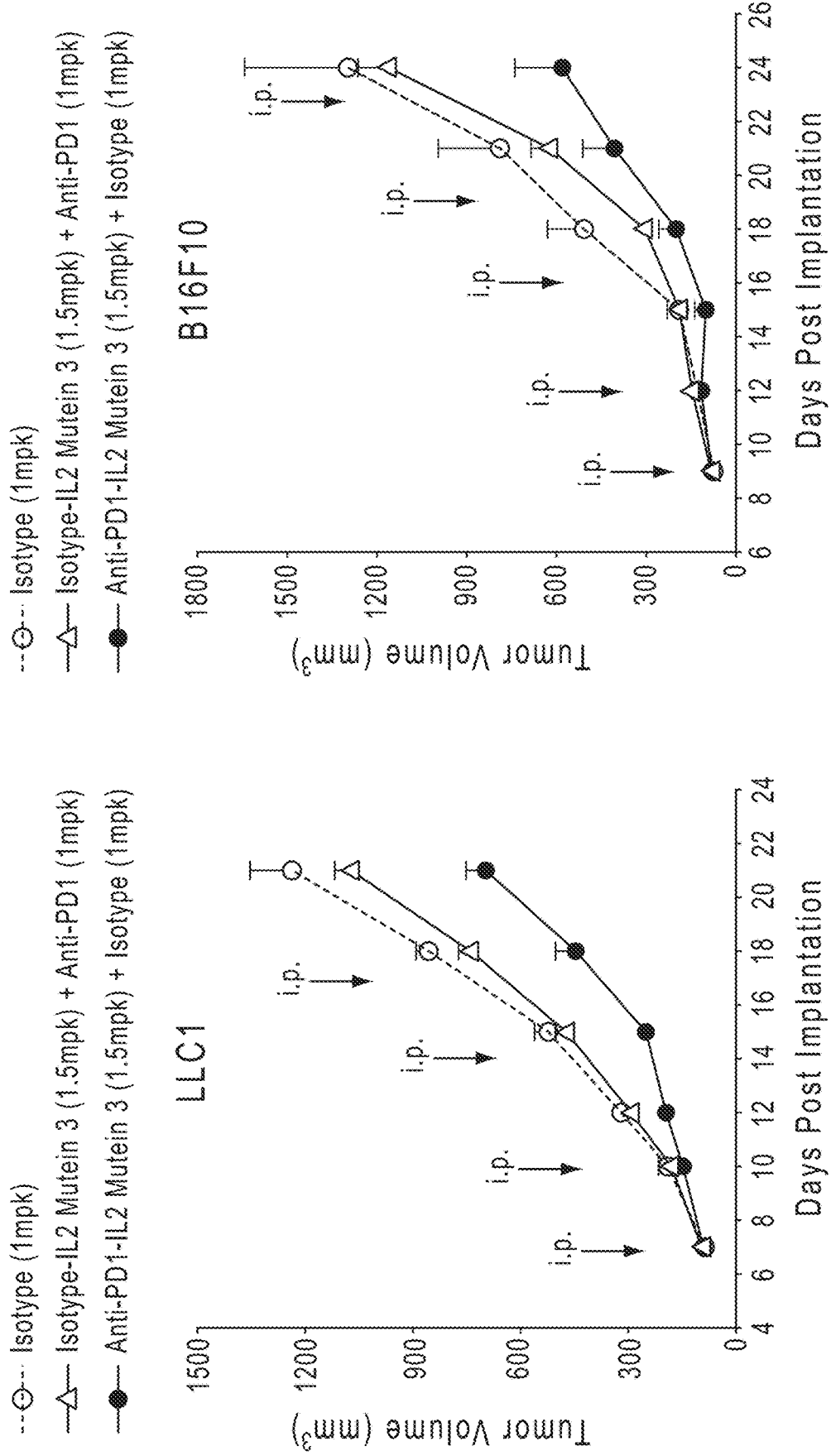
Figure 20C:
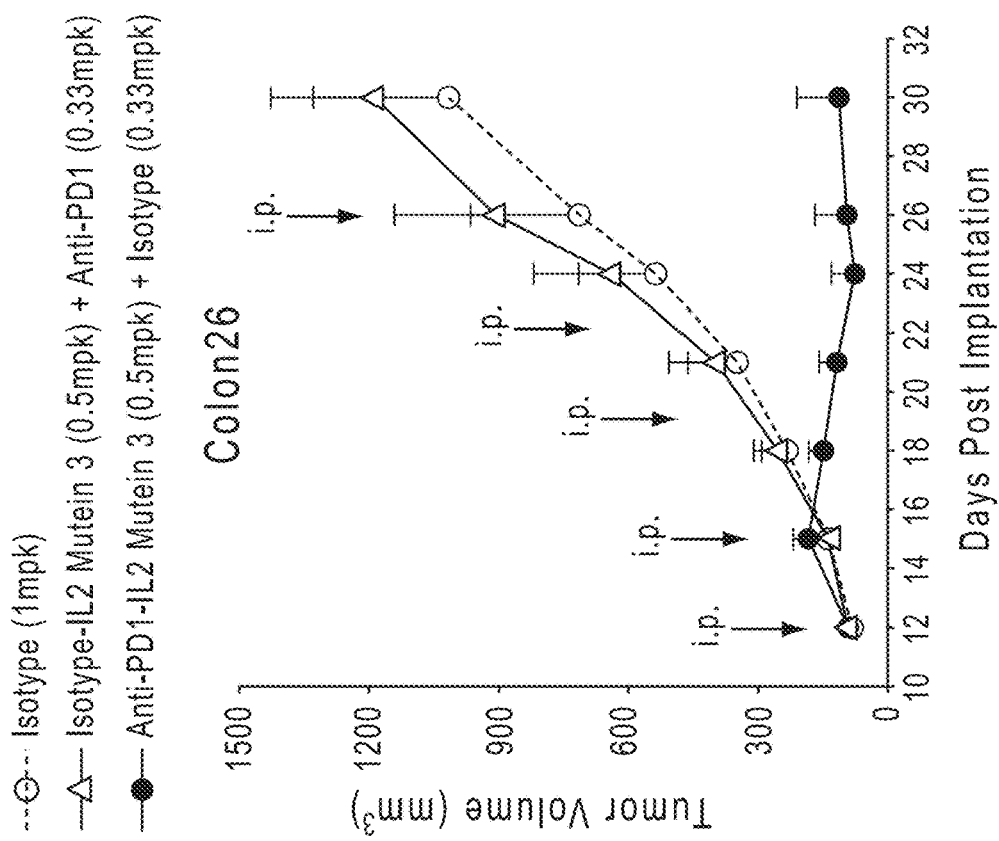
Figure 20D:
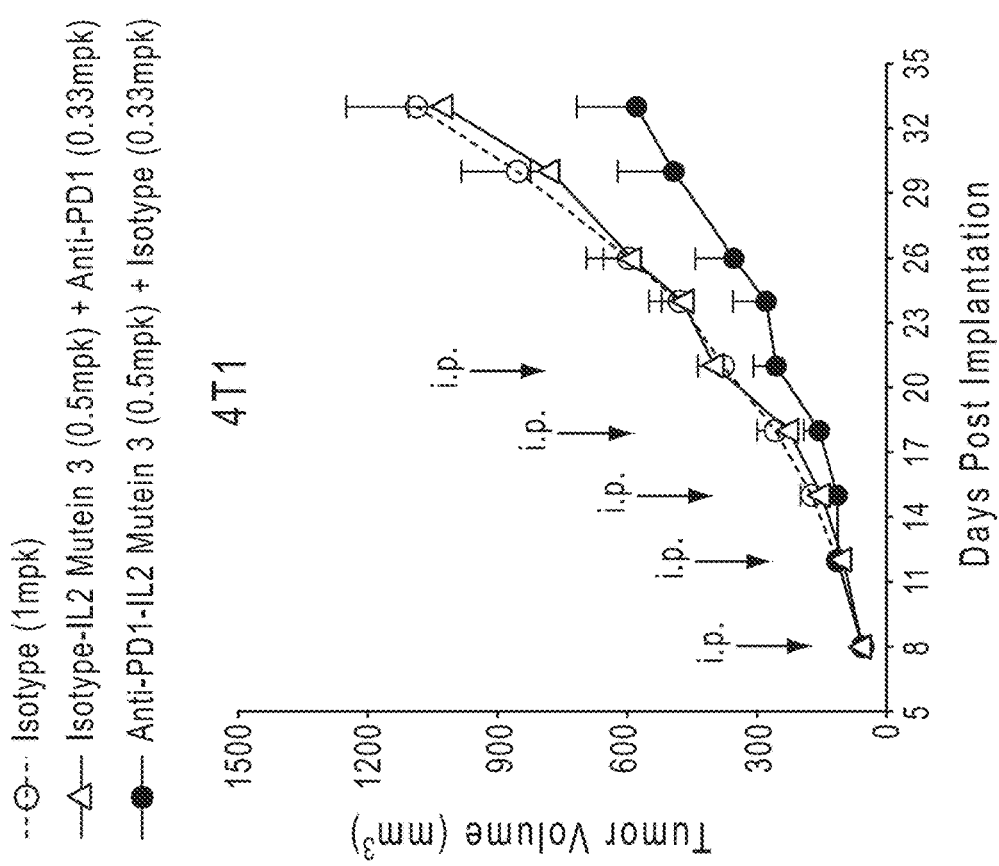

FIGS. 20A-20D show anti-tumor efficacy of an anti-mPD1-IL2 mutein 3 fusion in murine syngeneic tumor models: lung (FIG. 20A); skin (FIG. 20B); breast (FIG. 20C); and colon (FIG. 20D).

Figures 21A, 21B:
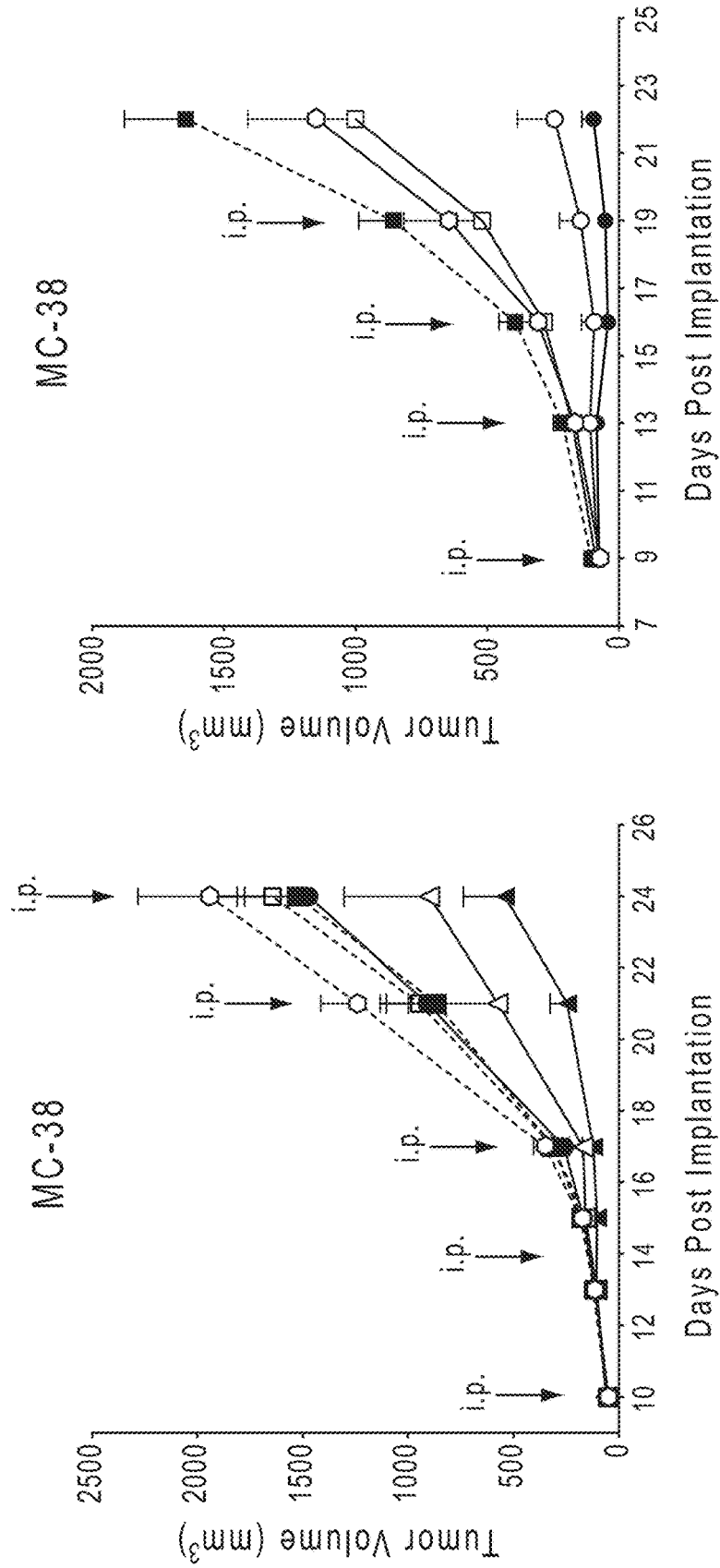

FIGS. 21A-21B show anti-tumor efficacy of an anti-LAG3-IL2 Mutein 3 fusion (FIG. 21A) and anti-tumor efficacy of an anti-LAG3-IL2 Mutein 3 fusion in combination with anti-mPD1 antibody (FIG. 21B).

FIGS. 22A.1-22B show homodimeric and heterodimeric embodiments of single chain peptide-MHC-targeted IL2 muteins (FIGS. 22A.1-22A.2) and results from a study demonstrating that a single chain peptide-MHC-targeted IL2 mutein fusion allows selective stimulation of antigen-specific mouse CD8+ T cells (FIG. 22B).

Figure 23A:
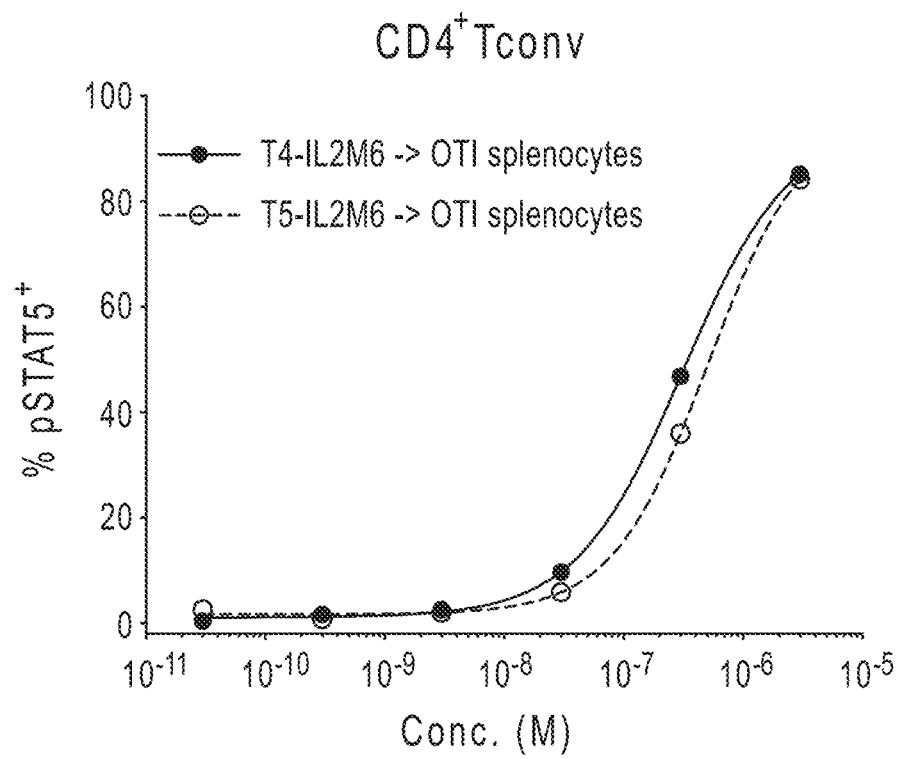
Figure 23B:
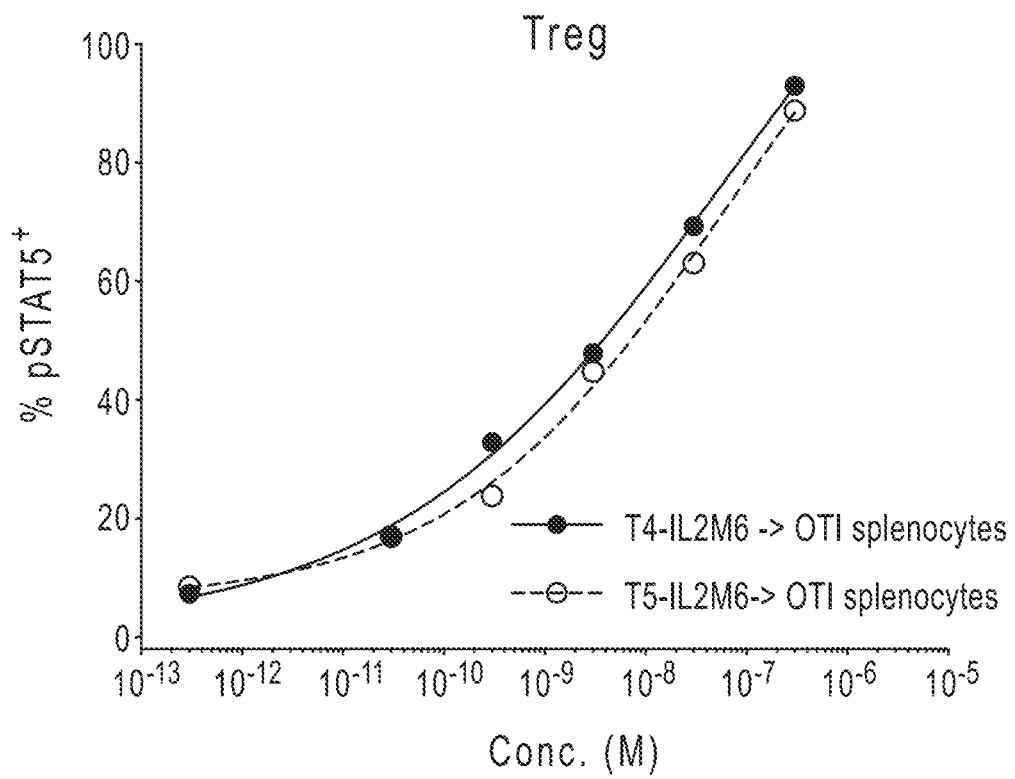

FIGS. 23A-23B show the activity of single chain peptide-MHC targeted IL2 muteins on non-CD8+ T cells that do not express antigen-specific TCR. The different muteins show indistinguishable activities.

Figure 24:
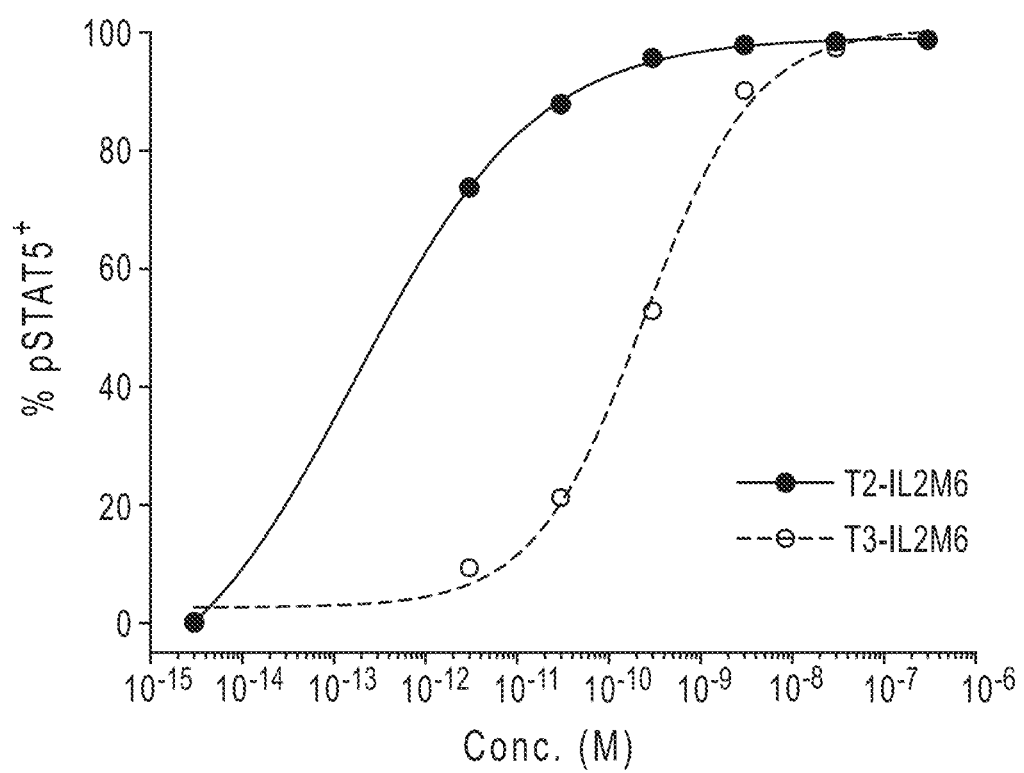

FIG. 24 shows selective stimulation of CMV antigen-specific human CD8+ T cells by a single chain IL2 mutein with a peptide-MHC targeting moiety.

FIGS. 25A-25C show a schematic of a chimeric antigen receptor (CAR) comprising a VL-VH scFv recognizing the peptide-MHC targeting moiety referred to herein as T3, a human CD8a hinge and transmembrane (TM) domain, a 4-1 BB costimulatory domain, a CD3z signaling domain, and a P2A:eGFP sequence for tracking CAR-transduced T cells (FIG. 25A) and the frequency and composition of viable CAR-T cells post-expansion (FIGS. 25B-25C).

Figure 26A:
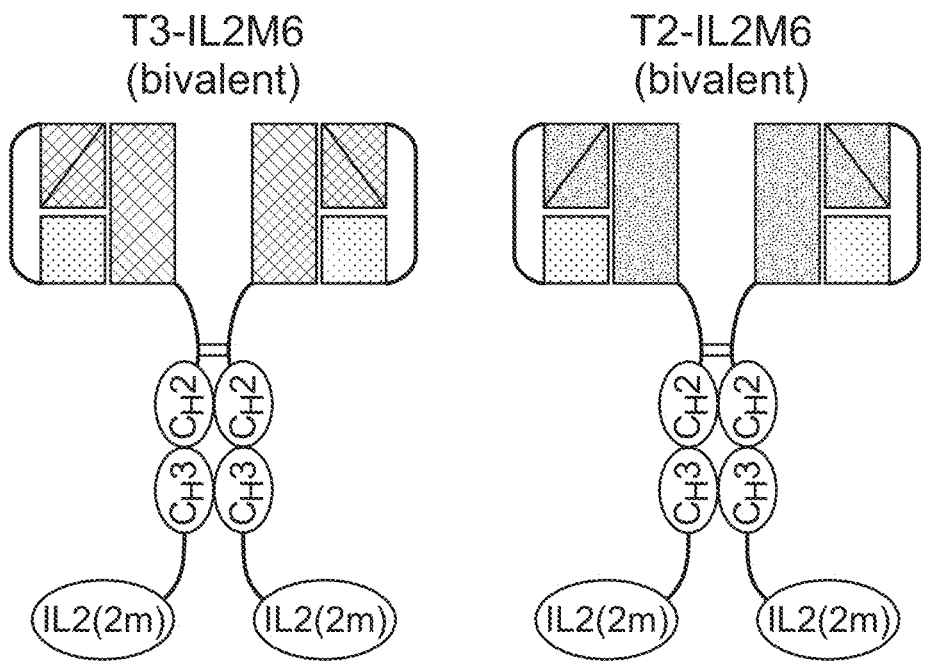
Figure 26B:
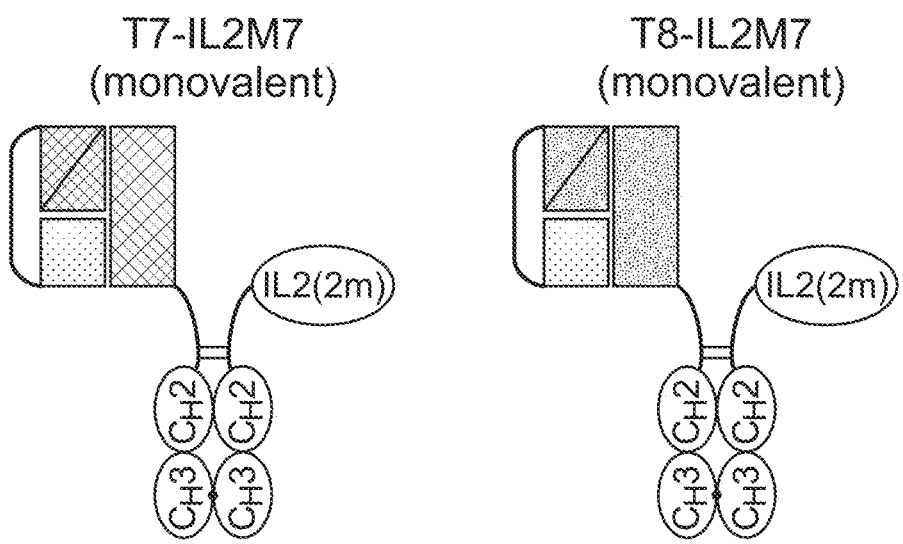

FIGS. 26A-26B illustrate the structures of the bivalent targeted IL2 muteins T2-IL2M6 and T3-IL2M6 (FIG. 26A) and the monovalent targeted IL2 muteins T7-IL2M7 and T8-IL2M7 (FIG. 26B), both with peptide-MHC targeting moieties.

Figure 27A:
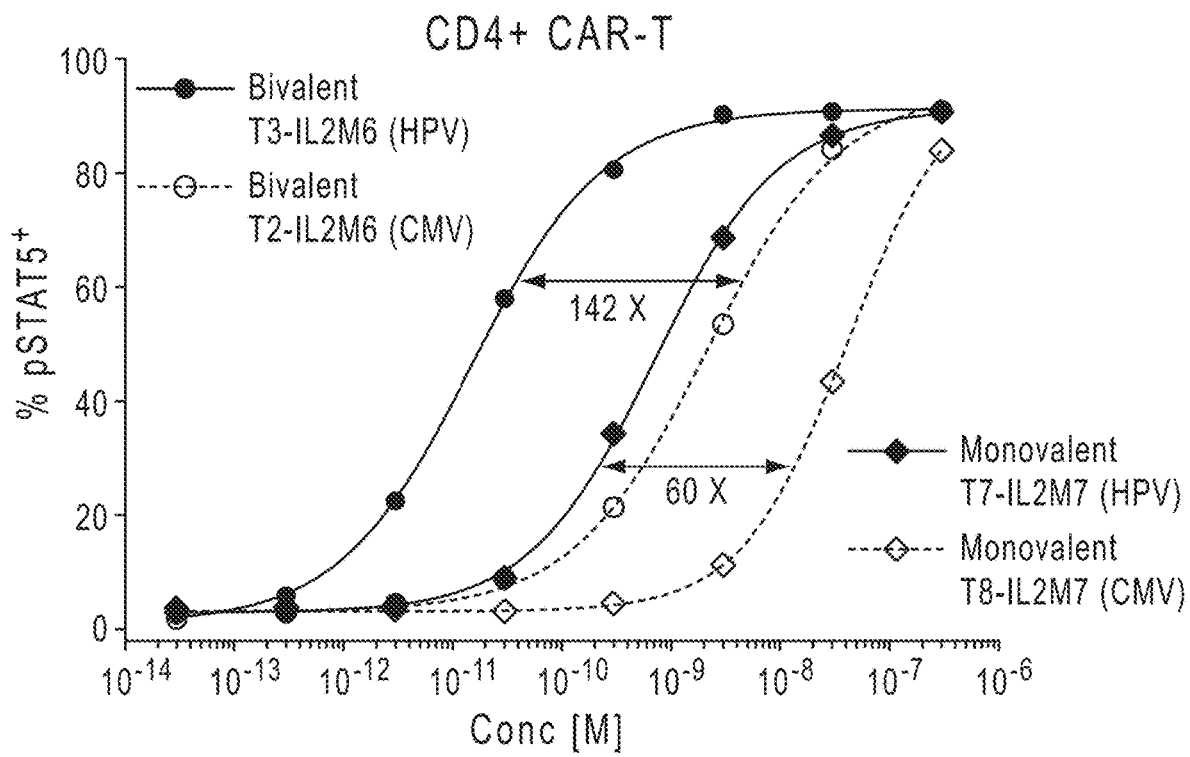
Figure 27B:
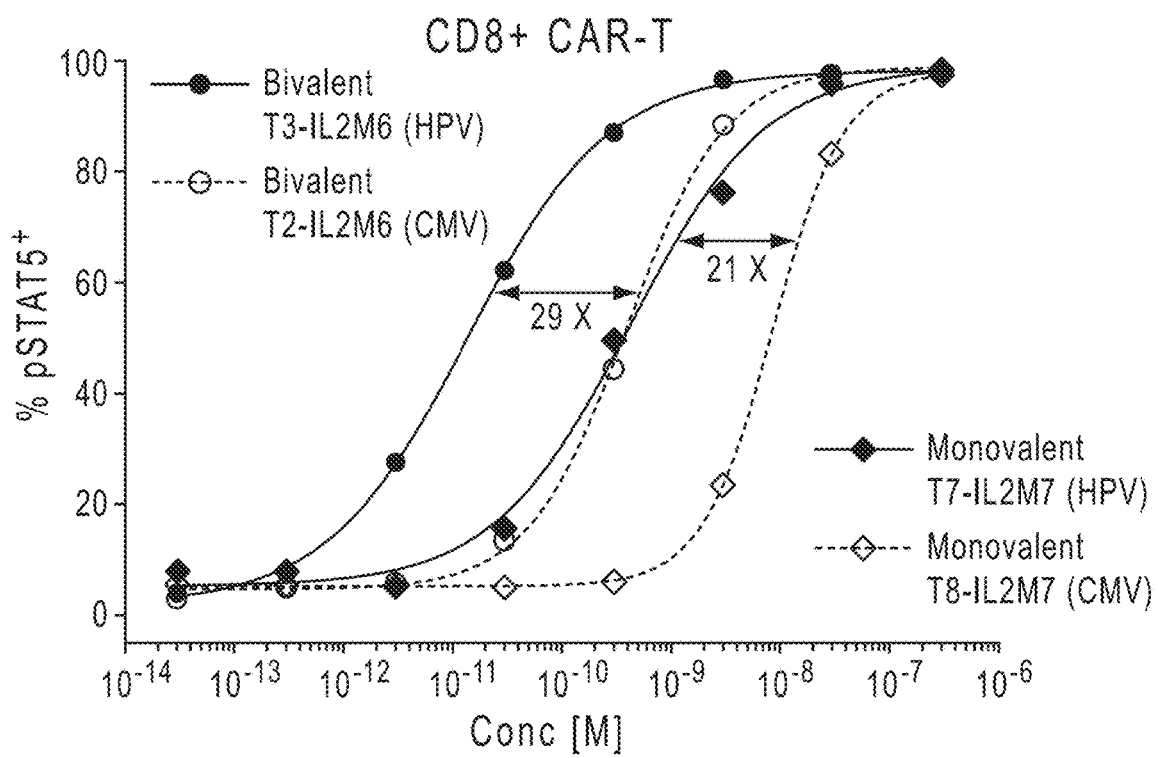

FIGS. 27A-27B show STAT5 stimulation of CAR-expressing CD4+ (FIG. 27A) and CD8+ (FIG. 27B) T cells by the peptide-MHC targeted IL2 muteins illustrated in FIGS. 26A and 26B.

Figure 28C:
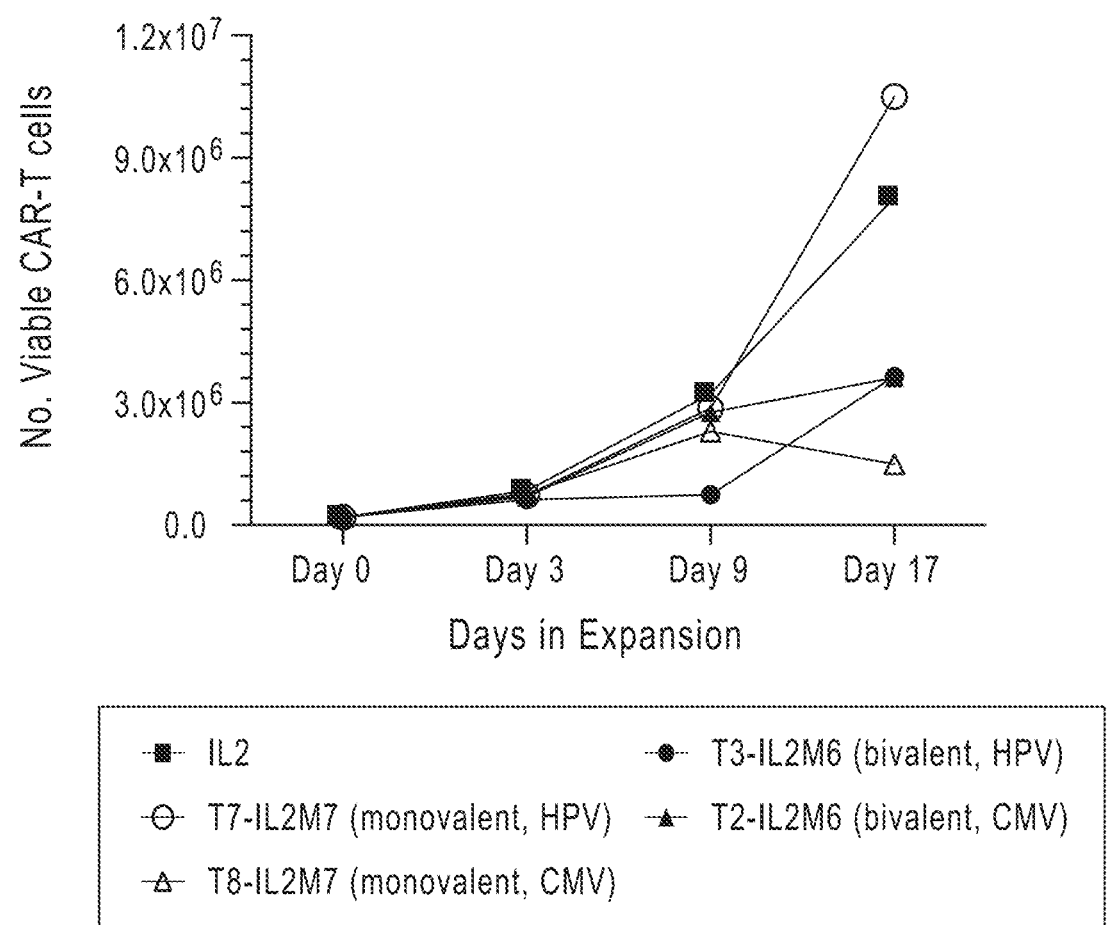

FIGS. 28A.1-28C show selective enrichment of CAR-T by a monovalent IL2 mutein with a targeting moiety recognized by the scFV of the CAR. FIGS. 28A.1-28A.16 shows the frequency of CAR-T cells is enriched during expansion in response to monovalent single chain peptide loaded HLA-A2 as determined by flow cytometry. All biologics were maintained at a concentration of $3.3 \times 10^{-10}$M. FIGS. 28B.1-28B.4 shows that the $CAR^{Pos}/CAR^{Neg}$ ratio selectively increases during expansion in response to monovalent single chain peptide loaded HLA-A2 fused to attenuated IL(2m) (open circle). Recombinant IL2 (Aldesleukin) yields the largest number of total T cells yet the degree of CAR-T enrichment is lesser relative to single chain peptide loaded HLA-A2 fused to attenuated IL2(2m). FIG. 28C shows the expansion of CAR-T using single chain peptide loaded HLA-A2 fused to attenuated IL2(2m) (open circle) yields the greatest number of viable CAR-T.

Figure 29:
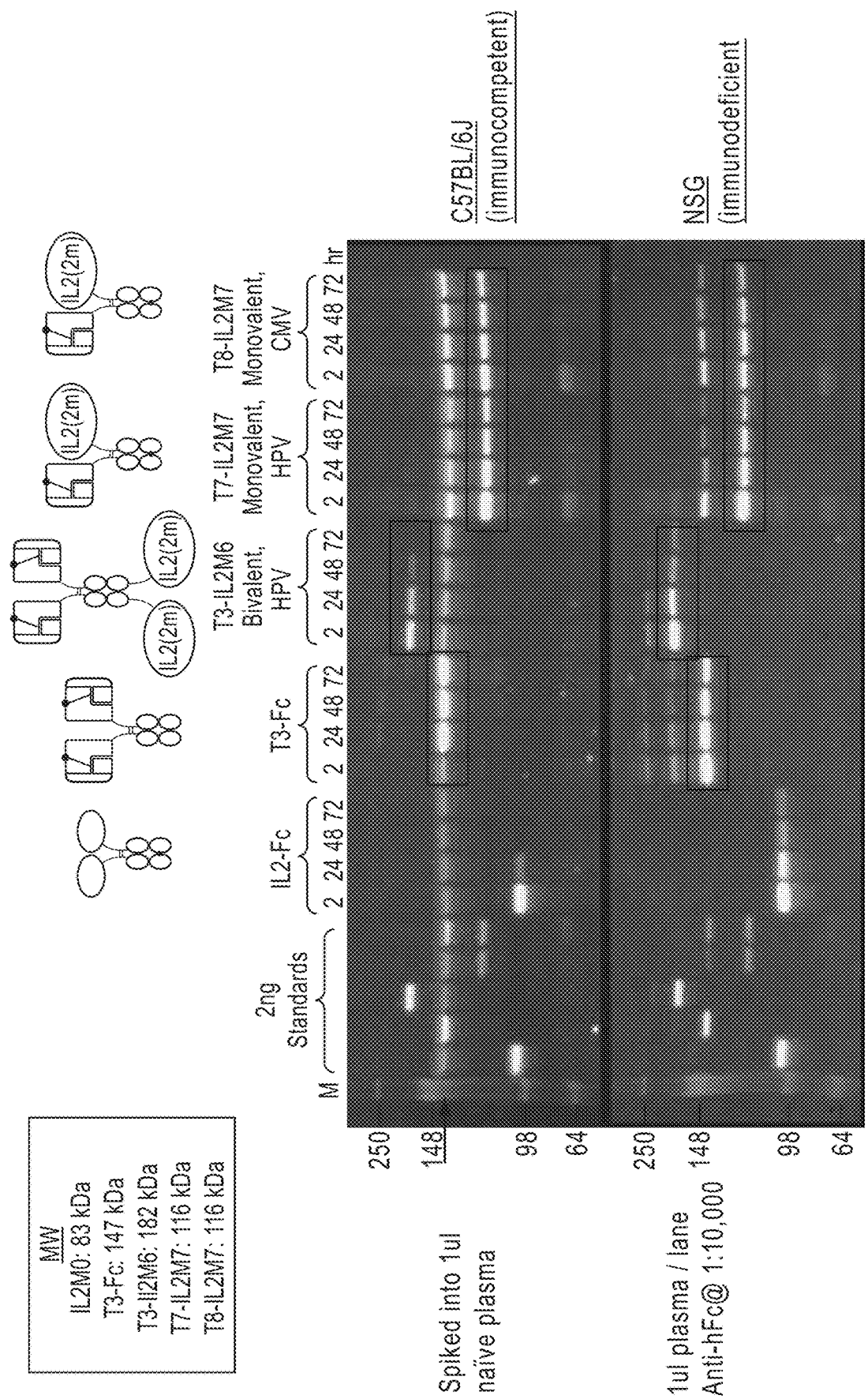

FIG. 29 shows the results of an in vivo PK assessment of monovalent and bivalent targeted attenuated IL2 muteins in immunocompetent (C57BL/6J) and immunodeficient (NOD.Scid.IL2Rgnull) mice. Both bivalent and monovalent muteins show delayed clearance relative to hIL2 fused to Fc (IL2-Fc). Mice were injected with each biologic and blood samples were collected at 2, 24, 48, and 72 hr after dosing. Pharmacokinetics of Fc fusion proteins in plasma was investigated by Western blot. The proteins of interest are denoted by the black boxes.

6. DETAILED DESCRIPTION

6.1. Definitions

About, Approximately: The terms "about", "approximately" and the like are used throughout the specification in front of a number to show that the number is not necessarily exact (e.g., to account for fractions, variations in measurement accuracy and/or precision, timing, etc.). It should be understood that a disclosure of "about X" or "approximately X" where X is a number is also a disclosure of "X." Thus, for example, a disclosure of an embodiment in which one sequence has "about X % sequence identity" to another sequence is also a disclosure of an embodiment in which the sequence has "X % sequence identity" to the other sequence.

And, or: Unless indicated otherwise, an "or" conjunction is intended to be used in its correct sense as a Boolean logical operator, encompassing both the selection of features in the alternative (A or B, where the selection of A is mutually exclusive from B) and the selection of features in conjunction (A or B, where both A and B are selected). In some places in the text, the term "and/or" is used for the same purpose, which shall not be construed to imply that "or" is used with reference to mutually exclusive alternatives.

Antigen Binding Domain or ABD: The term "antigen binding domain" or "ABD" as used herein refers to the portion of a targeting moiety that is capable of specific, non-covalent, and reversible binding to a target molecule.

Associated: The term "associated" in the context of an IL2 agonist or a component thereof (e.g., a targeting moiety such as an antibody) refers to a functional relationship between two or more polypeptide chains. In particular, the term "associated" means that two or more polypeptides are associated with one another, e.g., non-covalently through molecular interactions or covalently through one or more disulfide bridges or chemical cross-linkages, so as to produce a functional IL2 agonist. Examples of associations that might be present in an IL2 agonist of the disclosure include (but are not limited to) associations between homodimeric or heterodimeric Fc domains in an Fc region, associations between VH and VL regions in a Fab or scFv, associations between CH1 and CL in a Fab, and associations between CH3 and CH3 in a domain substituted Fab.

Bivalent: The term "bivalent" as used herein in reference to an IL2 moiety and/or a targeting moiety in an IL2 agonist means an IL2 agonist that has two IL2 moieties and/or targeting moieties, respectively. Typically, IL2 agonists that are bivalent for an IL2 moiety and/or a targeting moiety are dimeric (either homodimeric or heterodimeric).

Cancer: The term "cancer" refers to a disease characterized by the uncontrolled (and often rapid) growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, adrenal gland cancer, autonomic ganglial cancer, biliary tract cancer, bone cancer, endometrial cancer, eye cancer, fallopian tube cancer, genital tract cancers, large intestinal cancer, cancer of the meninges, oesophageal cancer, peritoneal cancer, pituitary cancer, penile cancer, placental cancer, pleura cancer, salivary gland cancer, small intestinal cancer, stomach cancer, testicular cancer, thymus cancer, thyroid cancer, upper aerodigestive cancers, urinary tract cancer, vaginal cancer, vulva cancer, lymphoma, leukemia, lung cancer and the like.

Complementarity Determining Region or CDR: The terms "complementarity determining region" or "CDR," as used herein, refer to the sequences of amino acids within antibody variable regions which confer antigen specificity and binding affinity. In general, there are three CDRs in each heavy chain variable region (CDR-H1, CDR-H2, HCDR-H3) and three CDRs in each light chain variable region (CDR1-L1, CDR-L2, CDR-L3). Exemplary conventions that can be used to identify the boundaries of CDRs include, e.g., the Kabat definition, the Chothia definition, the ABM definition and the IMGT definition. See, e.g., Kabat, 1991, "Sequences of Proteins of Immunological Interest," National Institutes of Health, Bethesda, Md. (Kabat numbering scheme); Al-Lazikani et al., 1997, J. Mol. Biol. 273:927-948 (Chothia numbering scheme); Martin et al., 1989, Proc. Natl. Acad. Sci. USA 86:9268-9272 (ABM numbering scheme); and Lefranc et al., 2003, Dev. Comp. Immunol. 27:55-77 (IMGT numbering scheme). Public databases are also available for identifying CDR sequences within an antibody.

EC50: The term "EC50" refers to the half maximal effective concentration of a molecule (such as an IL2 agonist) which induces a response halfway between the baseline and maximum after a specified exposure time. The EC50 essentially represents the concentration of an antibody or IL2 agonist where 50% of its maximal effect is observed. In certain embodiments, the EC50 value equals the concentration of an IL2 agonist that gives half-maximal STAT5 activation in an assay as described in Section 7.1.2.

Epitope: An epitope, or antigenic determinant, is a portion of an antigen (e.g., target molecule) recognized by an antibody or other antigen-binding moiety as described herein. An epitope can be linear or conformational.

Fab: The term "Fab" in the context of a targeting moiety of the disclosure refers to a pair of polypeptide chains, the first comprising a variable heavy (VH) domain of an antibody N-terminal to a first constant domain (referred to herein as C1), and the second comprising variable light (VL) domain of an antibody N-terminal to a second constant domain (referred to herein as C2) capable of pairing with the first constant domain. In a native antibody, the VH is N-terminal to the first constant domain (CH1) of the heavy chain and the VL is N-terminal to the constant domain of the light chain (CL). The Fabs of the disclosure can be arranged according to the native orientation or include domain substitutions or swaps on that facilitate correct VH and VL pairings. For example, it is possible to replace the CH1 and CL domain pair in a Fab with a CH3-domain pair to facilitate correct modified Fab-chain pairing in heterodimeric molecules. It is also possible to reverse CH1 and CL, so that the CH1 is attached to VL and CL is attached to the VH, a configuration generally known as Crossmab.

Fc Domain and Fc Region: The term "Fc domain" refers to a portion of the heavy chain that pairs with the corresponding portion of another heavy chain. The term "Fc region" refers to the region of antibody-based binding molecules formed by association of two heavy chain Fc domains. The two Fc domains within the Fc region may be the same or different from one another. In a native antibody the Fc domains are typically identical, but one or both Fc domains might advantageously be modified to allow for heterodimerization, e.g., via a knob-in-hole interaction.

Host cell: The term "host cell" as used herein refers to cells into which a nucleic acid of the disclosure has been introduced. The terms "host cell" and "recombinant host cell" are used interchangeably herein. It is understood that such terms refer to the particular subject cell and to the progeny or potential progeny of such a cell. Because certain modifications may occur in succeeding generations due to either mutation or environmental influences, such progeny may not, in fact, be identical to the parent cell, but are still included within the scope of the term as used herein. Typical host cells are eukaryotic host cells, such as mammalian host cells.

Exemplary eukaryotic host cells include yeast and mammalian cells, for example vertebrate cells such as a mouse, rat, monkey or human cell line, for example HKB11 cells, PER.C6 cells, HEK cells or CHO cells.

IL2 Mutein: Is a variant IL2 molecule that has IL2 activity. The variant can be an IL2 fusion protein (e.g., an IL2 fused to IL-2Rα) and/or a mutant IL2, e.g., with one or more amino acid substitutions compared to wild type IL2. An IL2 mutein can have altered function (e.g., receptor binding, affinity, cytokine activity) and/or altered pharmacokinetics as compared to wild type IL2. While in the context of the IL2 agonists of the disclosure, the term "IL2 mutein" sometimes refers to the non-targeting components of the an IL2 molecule (and associated linker moieties), and it is to be understood that the term "IL2 mutein" encompass IL2 molecules with or without a targeting moiety and with or without a multimerization moiety unless the context dictates otherwise.

Major histocompatibility complex and MHC: These terms refer to naturally occurring MHC molecules, individual chains of MHC molecules (e.g., MHC class I α (heavy) chain, β2 microglobulin, MHC class II α chain, and MHC class II β chain), individual subunits of such chains of MHC molecules (e.g., α1, α2, and/or α3 subunits of MHC class I α chain, α1-α2 subunits of MHC class II α chain, β1-β2 subunits of MHC class II @ chain) as well as portions (e.g., the peptide-binding portions, e.g., the peptide-binding grooves), mutants and various derivatives thereof (including fusions proteins), wherein such portion, mutants and derivatives retain the ability to display an antigenic peptide for recognition by a T-cell receptor (TCR), e.g., an antigen-specific TCR. An MHC class I molecule comprises a peptide binding groove formed by the α1 and α2 domains of the heavy α chain that can stow a peptide of around 8-10 amino acids. Despite the fact that both classes of MHC bind a core of about 9 amino acids (e.g., 5 to 17 amino acids) within peptides, the open-ended nature of MHC class II peptide binding groove (the α1 domain of a class II MHC a polypeptide in association with the β1 domain of a class II MHC β polypeptide) allows for a wider range of peptide lengths. Peptides binding MHC class II usually vary between 13 and 17 amino acids in length, though shorter or longer lengths are not uncommon. As a result, peptides may shift within the MHC class II peptide binding groove, changing which 9-mer sits directly within the groove at any given time. Conventional identifications of particular MHC variants are used herein. The terms encompass "human leukocyte antigen" or "HLA".

Monovalent: The term "monovalent" as used herein in reference to an IL2 moiety and/or a targeting moiety in an IL2 agonist means an IL2 agonist that has only a single IL2 moiety and/or targeting moiety, respectively. Typically, IL2 agonists that are monovalent for the IL2 moiety and/or targeting moiety are monomeric or heterodimeric.

Operably linked: The term "operably linked" as used herein refers to a functional relationship between two or more regions of a polypeptide chain in which the two or more regions are linked so as to produce a functional polypeptide, or two or more nucleic acid sequences, e.g., to produce an in-frame fusion of two polypeptide components or to link a regulatory sequence to a coding sequence.

Peptide-MHC complex, pMHC complex, peptide-in-groove: An (i) an MHC domain (e.g., a human MHC molecule or portion thereof (e.g., the peptide-binding groove thereof and e.g., the extracellular portion thereof), (ii) an antigenic peptide, and, optionally, (iii) a β2 microglobulin domain (e.g., a human β2 microglobulin or portion thereof), where the MHC domain, the antigenic peptide and optional β2 microglobulin domain are complexed in such a manner that permits specific binding to a T-cell receptor. In some embodiments, a pMHC complex comprises at least the extracellular domains of a human HLA class I/human β2 microglobulin molecule and/or a human HLA class II molecule.

Single Chain Fv or scFv: The term "single chain Fv" or "scFv" as used herein refers to a polypeptide chain comprising the VH and VL domains of antibody, where these domains are present in a single polypeptide chain.

Specifically (or selectively) binds: The term "specifically (or selectively) binds" as used herein means that a targeting moiety, e.g., an antibody, or antigen binding domain ("ABD") thereof, forms a complex with a target molecule that is relatively stable under physiologic conditions. Specific binding can be characterized by a $K_D$ of about $5 \times 10^{-2}$M or less (e.g., less than $5 \times 10^{-2}$M, less than $10^{-2}$M, less than $5 \times 10^{-3}$M, less than $10^{-3}$M, less than $5 \times 10^{-4}$M, less than $10^{-4}$M, less than $5 \times 10^{-5}$M, less than $10^{-5}$M, less than $5 \times 10^{-6}$M, less than $10^{-6}$M, less than $5 \times 10^{-7}$M, less than $10^{-7}$M, less than $5 \times 10^{-8}$M, less than $10^{-8}$M, less than $5 \times 10^{-9}$M, less than $10^{-9}$M, or less than $10^{-10}$M). Methods for determining the binding affinity of an antibody or an antibody fragment, e.g., an IL2 agonist or a component targeting moiety, to a target molecule are well known in the art and include, for example, equilibrium dialysis, surface plasmon resonance (e.g., BIACORE assays), fluorescent-activated cell sorting (FACS) binding assays and the like. An IL2 agonist of the disclosure comprising a targeting moiety or an ABD thereof that specifically binds a target molecule from one species can, however, have cross-reactivity to the target molecule from one or more other species.

Subject: The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

Target Molecule: The term "target molecule" as used herein refers to any biological molecule (e.g., protein, carbohydrate, lipid or combination thereof) expressed on a cell surface or in the extracellular matrix that can be specifically bound by a targeting moiety in an IL2 agonist of the disclosure.

Targeting Moiety: The term "targeting moiety" as used herein refers to any molecule or binding portion (e.g., an immunoglobulin or an antigen binding fragment) thereof that can bind to a cell surface or extracellular matrix molecule at a site to which an IL2 agonist of the disclosure is to be localized, for example on tumor cells or on lymphocytes in the tumor microenvironment. The targeting moiety can also have a functional activity in addition to localizing an IL2 agonist to a particular site. For example, a targeting moiety that is an anti-PD1 antibody or an antigen binding portion thereof can also exhibit anti-tumor activity or enhance the anti-tumor activity by an IL2 mutein by inhibiting PD1 signaling.

Treat, Treatment, Treating: As used herein, the terms "treat", "treatment" and "treating" refer to the reduction or amelioration of the progression, severity and/or duration of a proliferative disorder, or the amelioration of one or more symptoms (preferably, one or more discernible symptoms) of a proliferative disorder resulting from the administration of one or more IL2 agonists of the disclosure. In specific embodiments, the terms "treat", "treatment" and "treating" refer to the amelioration of at least one measurable physical parameter of a proliferative disorder, such as growth of a tumor, not necessarily discernible by the patient. In other embodiments the terms "treat", "treatment" and "treating" refer to the inhibition of the progression of a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

Tumor: The term "tumor" is used interchangeably with the term "cancer" herein, e.g., both terms encompass solid and liquid, e.g., diffuse or circulating, tumors. As used herein, the term "cancer" or "tumor" includes premalignant, as well as malignant cancers and tumors.

Tumor-Associated Antigen: The term "tumor-associated antigen" or "TAA" refers to a molecule (typically a protein, carbohydrate, lipid or some combination thereof) that is expressed on the surface of a cancer cell, either entirely or as a fragment (e.g., MHC/peptide), and which is useful for the preferential targeting of a pharmacological agent to the cancer cell. In some embodiments, a TAA is a marker expressed by both normal cells and cancer cells, e.g., a lineage marker, e.g., CD19 on B cells. In some embodiments, a TAA is a cell surface molecule that is overexpressed in a cancer cell in comparison to a normal cell, for instance, 1-fold over expression, 2-fold overexpression, 3-fold overexpression or more in comparison to a normal cell. In some embodiments, a TAA is a cell surface molecule that is inappropriately synthesized in the cancer cell, for instance, a molecule that contains deletions, additions or mutations in comparison to the molecule expressed on a normal cell. In some embodiments, a TAA will be expressed exclusively on the cell surface of a cancer cell, entirely or as a fragment (e.g., MHC/peptide), and not synthesized or expressed on the surface of a normal cell. Accordingly, the term "TAA" encompasses antigens that are specific to cancer cells, sometimes known in the art as tumor-specific antigens ("TSAs").

Universal Light Chain: The term "universal light chain" as used herein in the context of a targeting moiety refers to a light chain polypeptide capable of pairing with the heavy chain region of the targeting moiety and also capable of pairing with other heavy chain regions.

Universal light chains are also known as "common light chains."

VH: The term "VH" refers to the variable region of an immunoglobulin heavy chain of an antibody, including the heavy chain of an scFv or a Fab.

VL: The term "VL" refers to the variable region of an immunoglobulin light chain, including the light chain of an scFv or a Fab.

6.2. IL2 Agonists

The present disclosure provides IL2 agonists comprising an IL2 moiety, an optional multimerization moiety, and an optional targeting moiety.

The IL2 agonists of the disclosure can be monomers or multimers, e.g., dimers (homo dimers or heterodimers) or high order complexes. For convenience, IL2 agonists that are homodimers (or higher order multimers of the same polypeptide) are described by their constituent monomers; however, upon recombinant expression of the component monomers in a suitable cell line a homodimeric (or higher order multimer) molecule can be produced.

In various embodiments, the IL2 agonists are (a) monovalent or bivalent for the IL2 moiety and/or (b) monovalent or bivalent for a targeting moiety (if present).

The IL2 agonists of the disclosure and/or the IL2 muteins in the IL2 agonists of the disclosure are typically not CD122 directed, e.g., they do not have amino acid substitutions or other modifications (e.g., pegylation) in the IL2 moiety that make them preferentially bind to IL-2Rβ as compared to IL-2Rα, relative to wild type IL2. However, in certain embodiments, the IL2 agonists of the disclosure can be CD122 directed, for example where the IL2 agonists are pMHC-targeted (e.g., as described in Section 6.4.3) and/or used in combination with CAR Treg therapy of autoimmune disease, for example as described in Sections 6.11.1 and 6.11.1.4. In some embodiments, such IL2 agonists can have up to a 1000 fold reduction in binding affinity for IL-2Rα and up to a 50 fold reduction in binding affinity to IL-2Rβ.

The IL2 agonists of the disclosure and/or the IL2 muteins in the IL2 agonists of the disclosure can be CD25 directed, e.g., they have one or more amino acid substitutions or other modifications in the IL2 moiety that make them preferentially bind to the IL-2Rα as compared to IL-2Rβ as compared to wild type IL2.

Thus, the IL2 agonists of the disclosure and/or the IL2 muteins in the IL2 agonists of the disclosure can have amino acid modifications that result in a reduction in IL-2Rβ and/or IL-2Rα binding affinity.

Overall, the IL2 agonists of the disclosure and/or the IL2 muteins in the IL2 agonists of the disclosure can have normal or attenuated binding (i.e., reduced affinity) to the intermediate and/or high affinity IL2 receptors (e.g., by up to 10-fold, by up to 50-fold, by up to 100-fold, by up to-200 fold, by up to 500-fold, by up to 1,000-fold or by up to 5,000-fold). In some embodiments, the binding is attenuated but the preference for intermediate versus high affinity IL2 receptors is similar to wild type IL2.

Preferential binding to one receptor vs the other can be evaluated by measuring the difference in binding affinity to high affinity receptor (IL-2Rαβγ) expressing cells and intermediate affinity receptor (IL-2Rβγ) expressing cells, and comparing the ratio to the corresponding ratio for wild type IL2.

In certain embodiments, the IL2 agonists of the disclosure have one or more amino acid substitutions in the IL2 moiety that reduce binding to IL-2Rβ. For example, in some embodiments, the IL2 moiety can have up to 100-fold to 1,000-fold attenuated binding to human IL-2Rβ as compared to wild-type human IL2.

The IL2 moiety with reduced binding to IL-2Rβ can retain its affinity to IL-2Rα, or have reduced binding to IL-2Rα. For example, in some embodiments, the IL2 moiety can have up to 50-fold, up to 100-fold, up to 500-fold, up to 1,000-fold or up to 5,000 fold attenuated binding to human IL2-Rα as compared to wild-type human IL2.

Binding affinity to IL-2Rα, IL-2Rβ, the intermediate affinity receptor and the high affinity receptor can be assayed by surface plasmon resonance (SPR) techniques (analyzed on a BIAcore instrument) (Liljeblad et al., 2000, Glyco J 17:323-329).

Exemplary IL2 moieties suitable for use in the IL2 agonists of the disclosure are described in Section 6.2.

The IL2 agonist can be a fusion protein comprising the IL2 moiety and a multimerization moiety and/or a targeting moiety. Exemplary multimerization moieties are described in Section 6.5 and include Fc domains that confer homodimerization or heterodimerization capability to the IL2 agonist. Free IL2 has very poor pharmacokinetics (a serum half-life of <10 min) and, without being bound by theory, it is believed that the inclusion of a multimerization domain, such as an Fc domain, improves serum stability and the pharmacokinetic profile of an IL2 agonist. Thus, the Fc domain can be a dual purpose domain, conferring stabilization properties of a stabilization moiety as described in Section 6.6.

Sometimes, for convenience, the IL2 moiety and optional multimerization and/or stabilization moiety are referred to herein as an IL2 mutein, although the term "mutein" also encompasses molecules with a targeting moiety. Exemplary targeting moieties are described in Section 6.4 and include an antigen binding domain (e.g., a scFv or Fab) that binds to a tumor associated antigen, binds to a tumor microenvironment antigen, or binds to tumor lymphocytes, as well as a peptide-MHC complex that recognizes tumor lymphocytes.

Further, each of the IL2 moiety, multimerization moiety, and targeting moiety can itself be a fusion protein. For example, the IL2 moiety can comprise an IL2 or IL2 variant domain and an IL-2Rα domain.

In various embodiments, the IL2 agonist does not comprise (a) a cytokine other than IL2; (b) an anti-IL2 antibody or antibody fragment; (c) an anti-DNA antibody or antibody fragment; (b) a non-binding antibody variable domain; any combination two, three or all four of the above.

The IL2 agonist can include one or more linker sequences connecting the various components of the molecule, for example the different domains present in a fusion protein.

Exemplary linkers are described in Section 6.7.

In certain aspects, the IL2 agonists of the disclosure, following administration to a subject (e.g., a patient with cancer or a tumor-bearing mouse), increase ratio $CD8^+$ T cells to Treg cells within a tumor.

Below are some illustrative orientations of IL2 muteins and agonists of the disclosure, in an N-to-C terminal orientation:

(1) Orientation 1: IL2 moiety-optional linker-multimerization and/or stabilization moiety.

(2) Orientation 2: Multimerization and/or stabilization moiety-optional linker-IL2 moiety.

(3) Orientation 3: Targeting moiety-optional linker-multimerization and/or stabilization moiety-optional linker-IL2 moiety.

(4) Orientation 4: A heterodimer comprising two polypeptides, A and B:

Polypeptide A: IL2 moiety-optional linker-multimerization moiety; and

Polypeptide B: Targeting moiety-optional linker-multimerization moiety.

In the IL2 agonists of the disclosure, when the targeting moiety is an antigen binding domain ("ABD") of an antibody, each IL2 molecule can be composed of two polypeptide chains, one polypeptide chain bearing the heavy chain variable region and the other polypeptide chain bearing the light chain variable region. Thus, in Orientation 3 and Orientation 4, the targeting moiety itself can comprise heavy and light chain variable domains on separate polypeptide chains. For example, with respect an Orientation 4 IL2 agonist, Polypeptide B can be composed of two polypeptide chains, B-1 and B-2. Polypeptide chain B-1 can contain the heavy chain variable domain of a targeting moiety-optional linker-multimerization moiety, and polypeptide chain B-2 can comprise the light chain variable domain of a targeting moiety. The Polypeptide A-Polypeptide B heterodimer can be associated through the pairing of Fc heterodimerization variants as described in Section 6.5.1.2.

Alternatively, an scFv can be used in which the heavy and light chain variable regions are fused to one another in a single polypeptide.

An exemplary embodiment of Orientation 1 IL2 agonist comprises, in an N- to C-terminal orientation:
a) IL2 moiety comprising:
i) IL2 or IL2 variant (e.g., IL2 N88D) domain, with or without a substitution at C125 that reduces aggregation (e.g., C125S or C125A or C125V);
ii) Linker (e.g., as described in Section 6.7); and
iii) IL2 binding portion of IL-2Rα;
b) Linker (e.g., as described in Section 6.7); and
c) Fc domain (e.g., IgG1 or IgG4, with or without substitutions that reduce glycosylation and/or effector function as described in Section 6.5.1 and subsections thereof).

The IL2 agonists referred to as IL2M0 and IL2M2 in Section 7 are particular embodiments of Orientation 1 IL2 agonists.

An exemplary embodiment of an Orientation 2 IL2 agonist comprises, in an N- to C-terminal orientation:
a) Fc domain (e.g., IgG1 or IgG4, with or without substitutions that reduce glycosylation and/or effector function as described in Section 6.5.1 and subsections thereof);
b) Linker (e.g., as described in Section 6.7); and
c) IL2 or IL2 variant (e.g., IL2 N88D) domain, with or without a substitution at C125 that reduces aggregation (e.g., C125S or C125A or C125V).

The IL2 agonist referred to as IL2M4 and IL2M5 are particular embodiments of these Orientation 2 IL2 agonists.

Another exemplary embodiment of an Orientation 2 IL2 agonist comprises, in an N- to C-terminal orientation:
a) Fc domain (e.g., IgG1 or IgG4, with or without substitutions that reduce glycosylation and/or effector function as described in Section 6.5.1 and subsections thereof);
b) Linker (e.g., as described in Section 6.7); and
c) IL2 moiety comprising:
i) IL2 or IL2 variant (e.g., IL2 N88D) domain, with or without a substitution at C125 that reduces aggregation (e.g., C125S or C125A or C125V);
ii) Linker (e.g., as described in Section 6.7); and
iii) IL2 binding portion of IL-2Rα.

The IL2 agonist referred to as IL2M3 in Section 7 is a particular embodiment of this Orientation 2 IL2 agonist.

An exemplary embodiment of an Orientation 3 IL2 agonist comprises, in an N- to C-terminal orientation:
a) scFv or a heavy chain variable region of a Fab (associated with a corresponding light chain variable region on a separate polypeptide) (e.g., as described in Section 6.4.2 and subsections thereof);
b) Linker (e.g., as described in Section 6.7);
c) Fc domain (e.g., IgG1 or IgG4, with or without substitutions that reduce glycosylation and/or effector function as described in Section 6.5.1 and subsections thereof);
d) Linker (e.g., as described in Section 6.7); and
e) An IL2 moiety comprising:
i) IL2 or IL2 variant (e.g., IL2 N88D) domain, with or without a substitution at C125 that reduces aggregation (e.g., C125S or C125A or C125V);
ii) Linker (e.g., as described in Section 6.7); and
iii) IL2 binding portion of IL-2Rα (e.g., as described in Section 6.3).

The T1 targeted version of the IL2 agonist referred to as IL2M3 in Section 7 is a particular embodiment of this Orientation 3 IL2 agonist.

Another exemplary embodiment of an Orientation 3 IL2 agonist comprises, in an N- to C-terminal orientation:
a) Peptide-MHC complex (e.g., as described in Section 6.4.3) comprising:
i) MHC peptide;
ii) Linker (e.g., as described in Section 6.7 or subsections thereof, for example in Section 6.7.1);
iii) Optional β2-microglobulin (β2m);
iv) Optional linker (e.g., as described in Section 6.7 or subsections thereof, for example in Section 6.7.1); and
v) MHC;
b) Optional linker (e.g., as described in Section 6.7);
c) Fc domain (e.g., IgG1 or IgG4, with or without substitutions that reduce glycosylation and/or effector function as described in Section 6.5.1 and subsections thereof);

d) Linker (e.g., as described in Section 6.7);
e) IL2 moiety comprising:
  i) IL2 or IL2 variant (e.g., IL2 N88D) domain, with or without a substitution at C125 that reduces aggregation (e.g., C125S, C125A or C125V);
  ii) Linker (e.g., as described in Section 6.7); and
  iii) IL2 binding portion of IL-2Rα (e.g., as described in Section 6.3).

The T2 and T3 targeted versions of the IL2 agonist referred to as IL2M3 in Section 7 are particular embodiments of this Orientation 3 IL2 agonist.

In an exemplary embodiment, an Orientation 4 IL2 agonist comprises two polypeptides, A and B, comprising, in an N- to C-terminal orientation:

In certain aspects, an Orientation 4 IL2 agonist comprises two polypeptides, A and B, comprising, in an N- to C-terminal orientation:

Polypeptide A:
  a) Targeting moiety, e.g., peptide-MHC complex (e.g., as described in Section 6.4.3), Fab domain (e.g., as described in Section 6.4.2.2) (e.g., a heavy chain of a Fab on polypeptide A associated with a third polypeptide, polypeptide C, comprising the light chain of the Fab), or scFv domain (e.g., as described in Section 6.4.2.1);
  b) Optional linker (e.g., as described in Section 6.7); and
  c) A first Fc domain.

Polypeptide B:
  d) IL2 moiety comprising an IL2 or IL2 variant domain (e.g., an IL2 domain with the substitutions H16A, F42A, also referred to as IL2(2m)), with or without a substitution at C125 that reduces aggregation (e.g., C125S, C125A or C125V);
  e) An optional linker (e.g., as described in Section 6.7); and
  f) A second Fc domain that is not identical to, but can heterodimerize with, the first Fc domain (e.g., as described in Section 6.5.1.2).

In some embodiments, the IL2 agonist is a heterodimer that is monovalent for the targeting moiety and monovalent for the IL2 moiety.

A particular embodiment of this Orientation 4 IL2 agonist comprises:

Polypeptide A:
  a) Peptide-MHC complex (e.g., as described in Section 6.4.3) comprising:
    i) MHC peptide;
    ii) Linker (e.g., as described in Section 6.7);
    iii) Optional β2-microglobulin (β2m);
    iv) Optional linker (e.g., as described in Section 6.7); and
    v) MHC;
  b) Optional linker (e.g., as described in Section 6.7); and
  c) A first Fc domain.

Polypeptide B:
  d) IL2 moiety comprising an IL2 or IL2 variant (e.g., IL2 H16A, F42A, also referred to as IL2(2m)) domain, with or without a substitution at C125 that reduces aggregation (e.g., C125S, C125A or C125V);
  e) An optional linker (e.g., as described in Section 6.7); and
  f) A second Fc domain that is not identical to, but can heterodimerize with, the first Fc domain (e.g., as described in Section 6.5.1.2).

The first and second Fc domains can be e.g., IgG1 or IgG4 Fc domains, with or without substitutions that reduce glycosylation and/or effector function as described in Section 6.5.1 and subsections thereof.

An exemplary Orientation 4 IL2 agonist is illustrated in FIG. 22A.2.

The inclusion of a β2 microglobulin in a peptide-MHC complex, for example in the exemplary Orientation 3 and Orientation 4 agonists described above, is believed to stabilize human cell surface MHC I molecules and facilitate their loading with exogenous peptides. See, e.g., Shields et al., 1998, J Biol Chem. 273(43):28010-8; Obermann et al., 2007, Immunology 122(1):90-7.

In certain aspects, the IL2 agonist comprises an IL2 mutein which has the configuration of IL2M0, IL2M1, IL2M2, IL2M3, IL2M4, IL2M5, IL2M6, or IL2M7, with an optional targeting moiety and an optional linker, e.g., at the N-terminus. In some embodiments, the IL2 agonist comprises an IL2 mutein which has the amino acid sequence of IL2M0, IL2M1, IL2M2, IL2M3, IL2M4, IL2M5, IL2M6, or IL2M7, with an optional targeting moiety and an optional linker, e.g., at the N-terminus.

The IL2 agonists of the disclosure generally have improved therapeutic indices. In certain aspects, the therapeutic index can be measured as a ratio of the dose causing toxicity (e.g., loss of body weight) in tumor bearing mice vs. the minimum effective anti-tumor dose, of the IL2 agonist as a whole or of a non-targeting component thereof (e.g., a molecule comprising the IL2 moiety and the multimerization moiety, for convenience referred to herein the "IL2 mutein" or "IL2M" component) as exemplified in Section 7. The data in Section 7 shows the following therapeutic indices:

|  | IL2M0 | IL2M1 | IL15M1 |
| --- | --- | --- | --- |
| Efficacious dose | >5 µg | >75 µg | >20 µg |
| Toxic dose | >30 µg | >40 µg | >10 µg |
| Therapeutic index | 6 | 0.53 | 0.5 |

In certain aspects, an IL2 agonist of the disclosure, or of an IL2M component thereof, has a therapeutic index of greater than 1, and preferably greater than 2, and even more preferably greater than 10. In particular embodiments, the therapeutic index is about 10, about 20, about 100, or about 200.

Further details of the components of the IL2 agonists of the disclosure are presented below.

6.3. The IL2 Moiety

The IL2 moiety of the IL2 antagonists of the disclosure comprises a wild type or variant IL2 domain, which is optionally fused to an IL2 binding domain of IL-2Rα, optionally via a linker (e.g., as described in Section 6.7). When present, the IL2 binding domain of IL-2Rα can be N-terminal or C-terminal to the wild type or variant IL2 domain.

In eukaryotic cells human IL2 is synthesized as a precursor polypeptide of 153 amino acids, from which 20 amino acids are removed to generate mature secreted IL2 (Taniguchi et al., 1983, Nature 302(5906):305-10). Mature human IL2 has the following amino acid sequence:

(SEQ ID NO: 2)
APTSSSTKKTQLQLEHLLLDLQMILNGINNYKNPKLTRMLTFKFYMPKKA
TELKHLQCLEEELKPLEEVLNLAQSKNFHLRPRDLISNINVIVLELKGSE
TTFMCEYADETATIVEFLNRWITFCQSIISTLT

The IL2 moieties of the disclosure are typically not CD122 directed, e.g., they do not have amino acid substitutions in the IL2 domain that make them preferentially bind to IL-2Rβ as compared to IL-2Rα.

The IL2 moieties of the disclosure can be CD25 directed, e.g., they have one or more amino acid substitutions in the IL2 domain that make them preferentially bind to IL-2Rα as compared to IL-2Rβ.

In certain embodiments, the IL2 agonists of the disclosure have one or more amino acid substitutions in the IL2 moiety that reduce binding to IL-2Rβ. For example, in some embodiments, the IL2 moiety can have up to 50-fold (and in some embodiments up to 100-fold) to 1,000-fold attenuated binding to human IL-2Rβ as compared to wild-type human IL2.

The IL2 moiety with reduced binding to IL-2Rβ can retain its affinity to IL-2Rα, or have reduced binding to IL-2Rα. For example, in some embodiments, the IL2 moiety can have up to 50-fold attenuated binding to human IL2-Rα as compared to wild-type human IL2.

Other characteristics of useful IL2 variants may include the ability to induce proliferation of IL-2Rα-bearing CD8+ T cells in tumors, the ability to induce IL2 signaling in IL-2Rα-bearing CD8+ T cells in tumors, and an improved therapeutic index.

In one embodiment, the IL2 moiety comprises one or more amino acid substitutions that reduce affinity to IL-2Rβ and preserve affinity to IL2-Rα. An exemplary amino acid substitution is N88D. Other amino acid substitutions that reduce or abolish the affinity of IL2 to IL-2Rβ are D20T, N88R, N88D or Q126D (see e.g., US Patent Publication No. US 2007/0036752).

In one embodiment, the IL2 moiety comprises one or more amino acid substitutions that reduce affinity to IL2-Rα and β reserve, or reduces affinity to a lesser degree, to IL-2Rβ, resulting in CD122 directed IL2 moieties. Such IL2 moieties are particularly useful to be incorporated into IL2 agonists with peptide-MHC targeting moieties and/or used as adjunct therapy for CAR Treg therapy, as disclosed in Section 6.11.1.4. Exemplary CD122 directed IL2 moieties are those comprising both H16A and F42A substitutions, as exemplified in IL2M6 and IL2M7. Accordingly, in some embodiments, the IL2 moiety comprises the amino acid sequence of human IL2 with H16A and F42A substitutions, as shown below:

(SEQ ID NO: 124)
SAPTSSSTKKTQLQLEALLLDLQMILNGINNYKNPKLTRMLTAKFYMPKK
ATELKHLQCLEEELKPLEEVLNLAQSKNFHLRPRDLISNINVIVLELKGS
ETTFMCEYADETATIVEFLNRWITFCQSIISTLT

In certain embodiments, the IL2 moiety comprises an amino acid substitution which eliminates the O-glycosylation site of IL2 at a position corresponding to residue 3 of human IL2.

Exemplary amino acid substitutions at T3 are T3A, T3G, T3Q, T3E, T3N, T3D, T3R, T3K, and T3P. In a specific embodiment, the substitution is T3A.

The IL2 moiety is preferably essentially a full-length IL2 molecule, e.g., a human IL2 molecule. In certain embodiments the IL2 moiety is a human IL-2 molecule.

C125 can be substituted with S, V, or A to reduce protein aggregation, as described in U.S. Pat. No. 4,518,584.

As described therein, one may also delete the N-terminal alanine residue of IL2, resulting in des-A1 IL2.

Further, the IL2 moiety may include a substitution of methionine 104 with a neutral amino acid such as alanine, as described in U.S. Pat. No. 5,206,344.

Accordingly, the IL2 moieties of the disclosure can have amino acid deletions and/or substitutions selected from des-A1 M104A IL2, des-A1 M104A C125S IL2, M104A IL2, M104A C125A IL2, des-A1 M104A C125A IL2, or M104A C125S IL2, in addition to other variations alter the binding of IL2 to its receptor. These and other mutants may be found in U.S. Pat. No. 5,116,943 and in Weiger et al., 1989, Eur J Biochem 180:295-300.

In various aspects, any of the foregoing IL2 moieties comprises an amino acid sequence having at least about 90%, at least about 91%, at least about 92%, about at least 93%, at least about 94%, at eat least about 95%, at least about 96%, at least about 97%, at least about 98%, at least about 99% or 100% sequence identity to mature human IL2.

The IL2 moieties of the disclosure can further include an IL2 binding domain of IL-2Rα (referred to as the "IL2-Ra domain" for convenience), e.g., the extracellular domain of an IL-2Rα, fused at the C-terminus or the N-terminus of IL2, optionally via a linker as described in Section 6.7. The sequence of the mature human IL-2Rα extracellular domain (corresponding to amino acids 22-272 of human IL-Ra) is:

(SEQ ID NO: 3)
Glu Leu Cys Asp Asp Asp Pro Pro Glu Ile Pro His

Ala Thr Phe Lys Ala Met Ala Tyr Lys Glu Gly Thr

Met Leu Asn Cys Glu Cys Lys Arg Gly Phe Arg Arg

Ile Lys Ser Gly Ser Leu Tyr Met Leu Cys Thr Gly

Asn Ser Ser His Ser Ser Trp Asp Asn Gln Cys Gln

Cys Thr Ser Ser Ala Thr Arg Asn Thr Thr Lys Gln

Val Thr Pro Gln Pro Glu Glu Gln Lys Glu Arg Lys

Thr Thr Glu Met Gln Ser Pro Met Gln Pro Val Asp

Gln Ala Ser Leu Pro Gly His Cys Arg Glu Pro Pro

Pro Trp Glu Asn Glu Ala Thr Glu Arg Ile Tyr His

Phe Val Val Gly Gln Met Val Tyr Tyr Gln Cys Val

Gln Gly Tyr Arg Ala Leu His Arg Gly Pro Ala Glu

Ser Val Cys Lys Met Thr His Gly Lys Thr Arg Trp

Thr Gln Pro Gln Leu Ile Cys Thr Gly Glu Met Glu

Thr Ser Gln Phe Pro Gly Glu Glu Lys Pro Gln Ala

Ser Pro Glu Gly Arg Pro Glu Ser Glu Thr Ser Cys

Leu Val Thr Thr Thr Asp Phe Gln Ile Gln Thr Glu

```
Met Ala Ala Thr Met Glu Thr Ser Ile Phe Thr Thr

Glu Tyr Gln Val Ala Val Ala Gly Cys Val Phe Leu

Leu Ile Ser Val Leu Leu Leu Ser Gly Leu Thr Trp

Gln Arg Arg Gln Arg Lys Ser Arg Arg Thr Ile
```

The sequence of an IL2 binding portion of the human IL-2Rα extracellular domain (comprising the two "sushi" domains, which corresponds to amino acids 22-186 of human IL-2Rα) is:

```
                                    (SEQ ID NO: 4)
Glu Leu Cys Asp Asp Asp Pro Pro Glu Ile Pro His

Ala Thr Phe Lys Ala Met Ala Tyr Lys Glu Gly Thr

Met Leu Asn Cys Glu Cys Lys Arg Gly Phe Arg Arg

Ile Lys Ser Gly Ser Leu Tyr Met Leu Cys Thr Gly

Asn Ser Ser His Ser Ser Trp Asp Asn Gln Cys Gln

Cys Thr Ser Ser Ala Thr Arg Asn Thr Thr Lys Gln

Val Thr Pro Gln Pro Glu Glu Gln Lys Glu Arg Lys

Thr Thr Glu Met Gln Ser Pro Met Gln Pro Val Asp

Gln Ala Ser Leu Pro Gly His Cys Arg Glu Pro Pro

Pro Trp Glu Asn Glu Ala Thr Glu Arg Ile Tyr His

Phe Val Val Gly Gln Met Val Tyr Tyr Gln Cys Val

Gln Gly Tyr Arg Ala Leu His Arg Gly Pro Ala Glu

Ser Val Cys Lys Met Thr His Gly Lys Thr Arg Trp

Thr Gln Pro Gln Leu Ile Cys Thr Gly
```

The sequence of an alternative IL2 binding portion of the human IL-2Rα extracellular domain, which corresponds to amino acids 22-240 of human IL-2Rα, is:

```
                                    (SEQ ID NO: 5)
Glu Leu Cys Asp Asp Asp Pro Pro Glu Ile Pro His

Ala Thr Phe Lys Ala Met Ala Tyr Lys Glu Gly Thr

Met Leu Asn Cys Glu Cys Lys Arg Gly Phe Arg Arg

Ile Lys Ser Gly Ser Leu Tyr Met Leu Cys Thr Gly

Asn Ser Ser His Ser Ser Trp Asp Asn Gln Cys Gln

Cys Thr Ser Ser Ala Thr Arg Asn Thr Thr Lys Gln

Val Thr Pro Gln Pro Glu Glu Gln Lys Glu Arg Lys

Thr Thr Glu Met Gln Ser Pro Met Gln Pro Val Asp

Gln Ala Ser Leu Pro Gly His Cys Arg Glu Pro Pro

Pro Trp Glu Asn Glu Ala Thr Glu Arg Ile Tyr His

Phe Val Val Gly Gln Met Val Tyr Tyr Gln Cys Val

Gln Gly Tyr Arg Ala Leu His Arg Gly Pro Ala Glu

Ser Val Cys Lys Met Thr His Gly Lys Thr Arg Trp

Thr Gln Pro Gln Leu Ile Cys Thr Gly Glu Met Glu

Thr Ser Gln Phe Pro Gly Glu Glu Lys Pro Gln Ala
```

-continued

```
Ser Pro Glu Gly Arg Pro Glu Ser Glu Thr Ser Cys

Leu Val Thr Thr Thr Asp Phe Gln Ile Gln Thr Glu

Met Ala Ala Thr Met Glu Thr Ser Ile Phe Thr Thr

Glu Tyr Gln
```

The IL2-Rα domain or the IL2 binding portion of the IL-2Rα extracellular domain preferably has an amino acid sequence with at least about 90%, at least about 95%, at least about 96%, at least about 97%, at least about 98%, at least about 99% or 100% sequence identity to any of the sequences above, i.e., any one of amino acids 22-186 of IL-2Rα, amino acids 22-240 of IL-2Rα, or amino acids 22-272 of IL-2Rα, or any IL2 binding portion thereof.

In certain aspects, the IL2-Rα domain or the IL2 binding portion can comprise or consist of an amino acid sequence having at least about 90%, at least about 95%, at least about 96%, at least about 97%, at least about 98%, at least about 99% or 100% sequence identity to an IL2 binding portion of human IL-2Rα, optionally wherein the binding portion has an amino acid sequence of (a) at least 160 amino acids, at least 161 amino acids, at least 162 amino acids, at least 164 amino acids or at least 165 amino acids and/or (b) up to 251, up to 240, up to 230, up to 220, up to 210, up to 200, up to 190, up to 180 or up to 170 amino acids of the extracellular domain of human IL2-Rα. In particular embodiments, the portion of human IL-2Rα is bounded by any one of (a) and (b) in the preceding sentence, e.g., at least 160 and up to 180 amino acids from human IL-2Rα, at least 162 and up to 200 amino acids from human IL-2Rα, at least 160 and up to 220 amino acids from human IL-2Rα, at least 164 and up to 190 amino acids from human IL-2Rα, and so on and so forth.

In some embodiments, the IL2-Rα domain or the IL2 binding portion comprises or consists of an amino acid sequence having at least about 90%, at least about 95%, at least about 96%, at least about 97%, at least about 98%, at least about 99% or 100% sequence identity to amino acids 22-186, with or without an additional up to 5 amino acids, up to 10 amino acids, up to 15 amino acids, up to 20 amino acids, up to 30 amino acids, or up to 40 amino acids C-terminal to amino acid residue 186, of IL2-Rα.

As illustrated in FIGS. 3A-3B, the fusion of IL2 to the C-terminus of the IL2 binding portion of IL-2Rα, with an N-terminal Fc domain, results in IL2 agonists that do not form higher order structures as with an IL2 agonist comprising, in an N-to-C direction, IL2-IL-2Rα extracellular domain-Fc. Accordingly, the IL-2Rα-containing IL2 muteins of the disclosure preferably have the IL-2Rα extracellular domain at the N-terminus of IL2. An exemplary mutein with this orientation is IL2M3.

In certain embodiments, the IL2-Rα domain or the IL-2Rα extracellular domain has at least one fewer O-glycosylation and/or N-glycosylation compared to the extracellular domain of native IL-2Rα, for example by a substitution at one or more of amino acid N49, amino acid N68, amino acid T74, amino acid T85, amino acid T197, amino acid T203, amino acid T208, and amino acid T216. In some embodiments, the one or more substitutions are from asparagine to an amino acid selected from the group consisting of alanine, threonine, serine, arginine, aspartic acid, glutamine, glutamic acid, glycine, histidine, isoleucine, leucine, lysine, methionine, phenylalanine, proline, tryptophan, tyrosine, and valine. In some embodiments, the one or more substitutions are from threonine to an amino acid selected from the group consisting of alanine, arginine, asparagine, aspartic acid, cysteine, glutamine, glutamic acid, glycine, histidine, isoleucine, leucine, lysine, methionine, phenylalanine, proline, serine, tryptophan, tyrosine, and valine. In some embodiments, the one or more substitutions are at amino acid S50 (e.g., S50P), amino acid S51 (e.g., S51R, S51N, S51D, S51C, S51Q, S51E, S51G, S51H, S511, S51L, S51K, S51M, S51F, S51P, S51W, S51Y, or S51V), amino acid T69 (e.g., T69P), amino acid T70 (e.g., T70R, T70N, T70D, T70C, T70Q, T70E, T70G, T70H, T70I, T70L, T70K, T70M, T70F, T70P, T70W, T70Y, or T70V, amino acid C192 (e.g., C192R, C192N, C192D, C192Q, C192E, C192G, C192H, C1921, C192L, C192K, C192M, C192F, C192P, C192W, C192Y, or C192V), or any combination thereof.

6.4. The Targeting Moiety

The incorporation of targeting moieties in the IL2 agonists of the disclosure permits the delivery of high concentrations of IL2 into the tumor microenvironment or to tumor reactive lymphocytes (including CART lymphocytes) with a concomitant reduction of systemic exposure, resulting in fewer side effects than obtained with wild type IL2.

Suitable targeting moiety formats are described in Section 6.4.2. The targeting moiety is preferably an antigen binding moiety, for example an antibody or an antigen-binding portion of an antibody, e.g., an scFv, as described in Section 6.4.2.1, or a Fab, as described in Section 6.4.2.2.

The antibodies and antigen-binding portions generally bind to specific antigenic determinants and are able to direct the IL2 agonist to a target site, for example to a specific type of tumor cell or tumor stroma that bears the antigenic determinant. Exemplary target molecules recognized by the targeting moieties of the disclosure are described in Section 6.4.1.

In other embodiments, the targeting moiety is a peptide-MHC complex, as described in 6.4.3, e.g., a peptide-MHC complex that is recognized by tumor lymphocytes.

In some embodiments, the targeting moiety is in the form of an Fc fusion protein, for example as exemplified in the structures referred to in the Examples as T7 and T8. The Fc portion of the targeting moiety polypeptide can be used to multimerize with an Fc domain in a separate polypeptide chain containing an IL2 moiety.

6.4.1. Target Molecules

The target molecules recognized by the targeting moieties of the IL2 agonists of the disclosure are generally found, for example, on the surfaces of activated T cells, on the surfaces of tumor cells, on the surfaces of virus-infected cells, on the surfaces of other diseased cells, free in blood serum, in the extracellular matrix (ECM), or immune cells present in the target site, e.g., tumor reactive lymphocytes. Where the immune cells are exogenously administered (e.g., chimeric antigen receptor ("CAR") expressing T cells), the targeting moiety can recognize the chimeric antigen receptor (CAR) or another molecule found on the surface of the CAR T cells. In various embodients, the CAR is comprises CDRs or VH and VL sequences (e.g., in the format of an scFv) that specifically recognize a TAA or a pMHC complex.

Exemplary target molecules are Fibroblast Activation Protein (FAP), the A1 domain of Tenascin-C (TNC A1), the A2 domain of Tenascin-C(TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (ADAbp), cyclophilin b, colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22 (B-cell receptor), CD23 (low affinity IgE receptor), CD30 (cytokine receptor), CD33 (myeloid cell surface antigen), CD40 (tumor necrosis factor receptor), IL-6R-(IL6 receptor), CD20, MCSP, PDGFβR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, the extra domain A (EDA) and extra domain B (EDB) of fibronectin and the A1 domain of tenascin-C(TnC A1).

Non-limiting examples of viral antigens include an EBV antigen (e.g., Epstein-Barr virus LMP-1), a hepatitis C virus antigen (e.g., hepatitis C virus E2 glycoprotein), an HIV antigen (e.g., HIV gp160, and HIV gp120); a CMV antigen; a HPV-specific antigen, or an influenza virus antigen (e.g., influenza virus hemagglutinin).

Non-limiting examples of ECM antigens include syndecan, heparanase, integrins, osteopontin, link, cadherins, laminin, laminin type EGF, lectin, fibronectin, notch, tenascin, collagen and matrixin.

Other target molecules are cell surface molecules of tumor or viral lymphocytes, for example T-cell co-stimulatory proteins such as CD27, CD28, 4-1BB (CD137), OX40, CD30, CD40, ICOS, lymphocyte function-associated antigen-1 (LFA-1), CD2, CD7, LIGHT, NKG2C, and B7-H3.

In particular embodiments, the target molecules are checkpoint inhibitors, for example CTLA-4, PD1, PDL1, PDL2, B7-H3, B7-H4, BTLA, HVEM, TIM3, GAL9, LAG3, VISTA, KIR, 2B4, CD160, CGEN-15049, CHK1, CHK2. In particular embodiments, the target molecule is PD1. In other embodiments, the target molecule is LAG3.

6.4.2. Targeting Moiety Format

In certain aspects, the targeting moiety can be any type of antibody or fragment thereof that retains specific binding to an antigenic determinant. In one embodiment the antigen binding moiety is a full-length antibody. In one embodiment the antigen binding moiety is an immunoglobulin molecule, particularly an IgG class immunoglobulin molecule, more particularly an $IgG_1$ or $IgG_4$ immunoglobulin molecule. Antibody fragments include, but are not limited to, VH (or $V_H$) fragments, VL (or $V_L$) fragments, Fab fragments, F(ab')$_2$ fragments, scFv fragments, Fv fragments, minibodies, diabodies, triabodies, and tetrabodies.

6.4.2.1. scFv

Single chain Fv or "scFv" antibody fragments comprise the VH and VL domains of an antibody in a single polypeptide chain, are capable of being expressed as a single chain polypeptide, and retain the specificity of the intact antibodies from which they are derived. Generally, the scFv polypeptide further comprises a polypeptide linker between the VH and VL domain that enables the scFv to form the desired structure for target binding. Examples of linkers suitable for connecting the VH and VL chains of an scFv are the linkers identified in Section 6.4.3.

Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

The scFv can comprise VH and VL sequences from any suitable species, such as murine, human or humanized VH and VL sequences.

To create an scFv-encoding nucleic acid, the VH and VL-encoding DNA fragments are operably linked to another fragment encoding a linker, e.g., encoding any of the linkers described in Section 6.4.3 (typically a repeat of a sequence containing the amino acids glycine and serine, such as the amino acid sequence (Gly4-Ser)$_3$ (SEQ ID NO:6), such that the VH and VL sequences can be expressed as a contiguous single-chain protein, with the VL and VH regions joined by the flexible linker (see, e.g., Bird et al., 1988, Science 242:423-426; Huston et al., 1988, Proc. Natl. Acad. Sci. USA 85:5879-5883; McCafferty et al., 1990, Nature 348: 552-554).

6.4.2.2. Fab

Fab domains were traditionally produced from by proteolytic cleavage of immunoglobulin molecules using enzymes such as papain. In the IL2 agonists of the disclosure, the Fab domains are typically recombinantly expressed as part of the IL2 agonist.

The Fab domains can comprise constant domain and variable region sequences from any suitable species, and thus can be murine, chimeric, human or humanized.

Fab domains typically comprise a CH1 domain attached to a VH domain which pairs with a CL domain attached to a VL domain. In a wild-type immunoglobulin, the VH domain is paired with the VL domain to constitute the Fv region, and the CH1 domain is paired with the CL domain to further stabilize the binding module. A disulfide bond between the two constant domains can further stabilize the Fab domain.

For the IL2 agonists of the disclosure, particularly when the light chain is not a common or universal light chain, it is advantageous to use Fab heterodimerization strategies to permit the correct association of Fab domains belonging to the same ABD and minimize aberrant pairing of Fab domains belonging to different ABDs. For example, the Fab heterodimerization strategies shown in Table 1 below can be used:

TABLE 1

| Fab Heterodimerization Strategies | | | | | |
|---|---|---|---|---|---|
| STRATEGY | VH | CH1 | VL | CL | REFERENCE |
| CrossMabCH1-CL | WT | CL domain | WT | CH1 domain | Schaefer et al., 2011, Cancer Cell 2011; 20: 472-86; PMID: 22014573. |
| orthogonal Fab VHVRD1CH1CRD2-VLVRD1CλCRD2 | 39K, 62E | H172A, F174G | 1R, 38D, (36F) | L135Y, S176W | Lewis et al., 2014, Nat Biotechnol 32: 191-8 |
| orthogonal Fab VHVRD2CH1wt-VLVRD2Cλwt | 39Y | WT | 38R | WT | Lewis et al., 2014, Nat Biotechnol 32: 191-8 |
| TCR CαCβ | 39K | TCR Cα | 38D | TCR Cβ | Wu et al., 2015, MAbs 7: 364-76 |
| CR3 | WT | T192E | WT | N137K, S114A | Golay at al., 2016, J Immunol 196: 3199-211. |
| MUT4 | WT | L143Q, S188V | WT | V133T, S176V | Golay at al., 2016, J Immunol 196: 3199-211. |
| DuetMab | WT | F126C | WT | S121C | Mazor et al., 2015, MAbs 7: 377-89; Mazor et al., 2015, MAbs 7: 461-669. |
| Domain exchanged | WT | CH3 + knob or hole mutation | WT | CH3 + hole or knob mutation | Wozniak-Knopp et al., 2018, PLoSONE13(4): e0195442 |

Accordingly, in certain embodiments, correct association between the two polypeptides of a Fab is promoted by exchanging the VL and VH domains of the Fab for each other or exchanging the CH1 and CL domains for each other, e.g., as described in WO 2009/080251.

Correct Fab pairing can also be promoted by introducing one or more amino acid modifications in the CH1 domain and one or more amino acid modifications in the CL domain of the Fab and/or one or more amino acid modifications in the VH domain and one or more amino acid modifications in the VL domain. The amino acids that are modified are typically part of the VH:VL and CH1:CL interface such that the Fab components preferentially pair with each other rather than with components of other Fabs.

In one embodiment, the one or more amino acid modifications are limited to the conserved framework residues of the variable (VH, VL) and constant (CH1, CL) domains as indicated by the Kabat numbering of residues. Almagro, 2008, Frontiers In Bioscience 13:1619-1633 provides a definition of the framework residues on the basis of Kabat, Chothia, and IMGT numbering schemes.

In one embodiment, the modifications introduced in the VH and CH1 and/or VL and CL domains are complementary to each other. Complementarity at the heavy and light chain interface can be achieved on the basis of steric and hydrophobic contacts, electrostatic/charge interactions or a combination of the variety of interactions. The complementarity between protein surfaces is broadly described in the literature in terms of lock and key fit, knob into hole, protrusion and cavity, donor and acceptor etc., all implying the nature of structural and chemical match between the two interacting surfaces.

In one embodiment, the one or more introduced modifications introduce a new hydrogen bond across the interface of the Fab components. In one embodiment, the one or more introduced modifications introduce a new salt bridge across the interface of the Fab components. Exemplary substitutions are described in WO 2014/150973 and WO 2014/082179, the contents of which are hereby incorporated by reference.

In some embodiments, the Fab domain comprises a 192E substitution in the CH1 domain and 114A and 137K substitutions in the CL domain, which introduces a salt-bridge between the CH1 and CL domains (see, e.g., Golay et al., 2016, J Immunol 196:3199-211).

In some embodiments, the Fab domain comprises a 143Q and 188V substitutions in the CH1 domain and 113T and 176V substitutions in the CL domain, which serves to swap hydrophobic and polar regions of contact between the CH1 and CL domain (see, e.g., Golay et al., 2016, J Immunol 196:3199-211).

In some embodiments, the Fab domain can comprise modifications in some or all of the VH, CH1, VL, CL domains to introduce orthogonal Fab interfaces which promote correct assembly of Fab domains (Lewis et al., 2014 Nature Biotechnology 32:191-198). In an embodiment, 39K, 62E modifications are introduced in the VH domain, H172A, F174G modifications are introduced in the CH1 domain, 1R, 38D, (36F) modifications are introduced in the VL domain, and L135Y, S176W modifications are introduced in the CL domain. In another embodiment, a 39Y modification is introduced in the VH domain and a 38R modification is introduced in the VL domain.

Fab domains can also be modified to replace the native CH1:CL disulfide bond with an engineered disulfide bond, thereby increasing the efficiency of Fab component pairing. For example, an engineered disulfide bond can be introduced by introducing a 126C in the CH1 domain and a 121 C in the CL domain (see, e.g., Mazor et al., 2015, MAbs 7:377-89).

Fab domains can also be modified by replacing the CH1 domain and CL domain with alternative domains that promote correct assembly. For example, Wu et al., 2015, MAbs 7:364-76, describes substituting the CH1 domain with the constant domain of the a T cell receptor and substituting the CL domain with the b domain of the T cell receptor, and pairing these domain replacements with an additional charge-charge interaction between the VL and VH domains by introducing a 38D modification in the VL domain and a 39K modification in the VH domain.

In lieu of, or in addition to, the use of Fab heterodimerization strategies to promote correct VH-VL pairings, the VL of common light chain (also referred to as a universal light chain) can be used for each Fab VL region of an IL2 agonist of the disclosure. In various embodiments, employing a common light chain as described herein reduces the number of inappropriate species of IL2 agonists as compared to employing original cognate VLs. In various embodiments, the VL domains of the IL2 agonists are identified from monospecific antibodies comprising a common light chain. In various embodiments, the VH regions of the IL2 agonists comprise human heavy chain variable gene segments that are rearranged in vivo within mouse B cells that have been previously engineered to express a limited human light chain repertoire, or a single human light chain, cognate with human heavy chains and, in response to exposure with an antigen of interest, generate an antibody repertoire containing a plurality of human VHs that are cognate with one or one of two possible human VLs, wherein the antibody repertoire specific for the antigen of interest. Common light chains are those derived from a rearranged human Vκ1-39Jκ5 sequence or a rearranged human Vκ3-20Jκ1 sequence, and include somatically mutated (e.g., affinity matured) versions. See, for example, U.S. Pat. No. 10,412,940.

6.4.3. MHC-Peptide Fusions

The targeting moiety of an IL2 agonist of the disclosure can be a peptide-MHC complex (a "pMHC compex"), e.g., a peptide complexed with an MHC class I domain or a peptide complexed with an MHC class II domain, optionally with a β2 microglobulin domain.

Naturally-occurring MHCs are encoded by a cluster of genes on human chromosome 6. MHCs include, but are not limited to, HLA specificities such as A (e.g., A1-A74), B (e.g., B1-B77), C (e.g., C1-C11), D (e.g., D1-D26), DR (e.g., DR1-DR8), DQ (e.g., DQ1-DQ9) and DP (e.g., DP1-DP6). HLA specificities include A1, A2, A3, A11, A23, A24, A28, A30, A33, B7, B8, B35, B44, B53, B60, B62, DR1, DR2, DR3, DR4, DR7, DR8, and DR11.

Figure 3A:
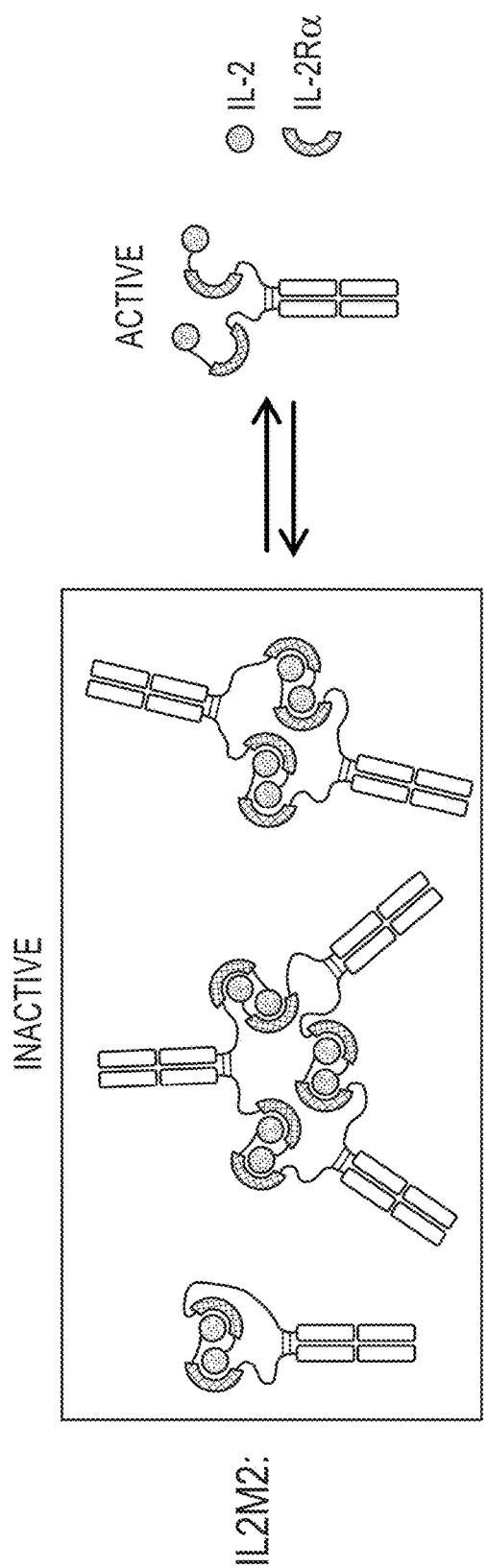
FIGS. 3A-3B show the equilibrium between different structures formed from two different species of IL-2Rα-containing IL2 muteins.

Naturally occurring MHC class I molecules bind peptides derived from proteolytically degraded proteins. Small peptides obtained accordingly are transported into the endoplasmic reticulum where they associate with nascent MHC class I molecules before being routed through the Golgi apparatus and displayed on the cell surface for recognition by cytotoxic T lymphocytes, as illustrated in FIG. 3A.

Naturally occurring MHC class I molecules consist of an a (heavy) chain associated with β2 microglobulin. The heavy chain consists of subunits α1-α3. The β2 microglobulin protein and α3 subunit of the heavy chain are associated. In certain embodiments, β2 microglobulin and α3 subunit are associated by covalent binding. In certain embodiments, β2 microglobulin and α3 subunit are associated non-covalently. The α1 and α2 subunits of the heavy chain fold to form a groove for a peptide, e.g., antigenic determinant, to be displayed and recognized by TCR.

Class I molecules generally associate with, e.g., bind, peptides of about 8-9 amino acids (e.g., 7-11 amino acids) in length. All humans have between three and six different class I molecules, which can each bind many different types of peptides. In one specific embodiment, the class I MHC polypeptide is a human class I MHC polypeptide selected from the group consisting of HLA-A, HLA-B, HLA-C, HLA-E, HLA-F, and HLA-G.

In some embodiments, the targeting moiety comprises an MHC class I α heavy chain extracellular domain (human α1, α2, and/or α3 domains) without a transmembrane domain.

In some embodiments, the class I α heavy chain polypeptide is HLA-A, HLA-B, HLA-C, HLA-E, HLA-F, HLA-G, HLA-K, or HLA-L. In some embodiments, the HLA-A sequence can be an HLA-A*0201 sequence.

The peptide in the pMHC complex can have the amino acid sequence of a peptide which can be associated with, e.g., presented by, an MHC class I molecule. In certain embodiments, the sequence can comprise from 6 to 20 contiguous amino acids. In certain embodiments, a peptide sequence can be that of a protein fragment, wherein the protein is a derived from, e.g., a portion of, a cellular protein, such as, for example, a protein associated with cancer or cancer neoantigen, and wherein the peptide can be bound to the MHC class I heavy chain.

In some embodiments, a pMHC complex targeting moiety comprises (i) an antigenic peptide; (ii) a class I MHC polypeptide or a fragment, mutant or derivative thereof (e.g., the extracellular domain), and optionally, (iii) a β2 microglobulin polypeptide or a fragment, mutant or derivative thereof. For example, the pMHC complex can comprise, from the N- to C-terminus, (i) an antigenic peptide, (ii) a β2M sequence, and (iii) a class I α (heavy) chain sequence. Alternatively, the pMHC complex can comprise, from the N- to C-terminus, (i) an antigenic peptide, (ii) a class I α (heavy) chain sequence, and (iii) a β2M sequence.

In one specific embodiment, the antigenic peptide and the MHC sequence and/or the MHC sequence and the β2M domain are linked to one another via a peptide linker, e.g., as described in Section 6.7. In some embodiments, a single-chain pMHC complex can comprise a first flexible linker between the peptide segment and the β2 microglobulin segment. For example, linkers can extend from and connect the carboxy terminal of the peptide to the amino terminal of the β2 microglobulin segment. In some embodiments, the linkers are structured to allow the peptide to fold into the binding groove resulting in a functional pMHC complex. In some embodiments, this linker can comprise at least 3 amino acids, up to about 15 amino acids (e.g., 20 amino acids). The pMHC linker can comprise a second flexible linker inserted between the β2 microglobulin and MHC I heavy chain segment. For example, linkers can extend from and connect the carboxy terminal of the β2 microglobulin segment to the amino terminal of the MHC I heavy chain segment. In certain embodiments, the β2 microglobulin and the MHC I heavy chain can fold into the binding groove resulting in a molecule which can function in promoting T cell expansion.

When β2M is present, the pMHC complex can include mutations in β2M and in the MHC class I α heavy chain domain such that a disulfide bond may form between them. Exemplary amino acid pairs that can be substituted with cysteines to allow for disulfide bonding between the two domains are identified in Table 2 below or as described in PCT Pub. WO 2015/195531, incorporated herein by reference in its entirety:

TABLE 2

| β2M Domain | MHC Domain |
|---|---|
| 12 | 236 |
| 12 | 237 |
| 8 | 234 |
| 10 | 235 |
| 24 | 236 |
| 28 | 232 |
| 98 | 192 |
| 99 | 234 |
| 3 | 120 |

TABLE 2-continued

| β2M Domain | MHC Domain |
|---|---|
| 31 | 96 |
| 53 | 35 |
| 60 | 96 |
| 60 | 122 |
| 63 | 27 |
| R3 | G120 |
| H31 | Q96 |
| D53 | R35 |
| W60 | Q96 |
| W60 | D122 |
| Y63 | Y27 |
| K6 | E232 |
| Q8 | R234 |
| Y10 | P235 |
| S11 | Q242 |
| N24 | A236 |
| S28 | E232 |
| D98 | H192 |
| M99 | R234 |
| R12 | G237 |

In further embodiments, the single-chain pMHC complex can comprise a peptide covalently attached to an MHC class I α (heavy) chain via a disulfide bridge (i.e., a disulfide bond between two cysteines). See, e.g., U.S. Pat. Nos. 8,992,937 and 8,895,020, each of which is incorporated in its entirety by reference. In certain embodiments, the disulfide bond comprises a first cysteine, that is positioned within a linker extending from the carboxy terminal of the peptide, and a second cysteine that is positioned within an MHC class I heavy (e.g., an MHC class I α (heavy) chain which has a non-covalent binding site for the antigen peptide). In certain embodiments, the second cysteine can be a mutation (addition or substitution) in the MHC class I α (heavy) chain. Preferably, the pMHC complex can comprise one contiguous polypeptide chain as well as a disulfide bridge. Alternatively, the pMHC complex can comprise two contiguous polypeptide chains which are attached via the disulfide bridge as the only covalent linkage. In some embodiments, the linking sequences can comprise at least one amino acid in addition to the cysteine, including one or more glycines, one or more, alanines, and/or one or more serines. In some embodiments, the single-chain molecule comprises from N-terminus to C-terminus an MHC class I peptide (e.g., an antigenic peptide), a first linker that comprises a first cysteine, a β2-microglobulin sequence, a second linker, and a MHC class I heavy chain sequence comprising a second cysteine, wherein the first cysteine and the second cysteine comprise a disulfide bridge. In some embodiments, the second cysteine is a substitution of an amino acid of the MHC class I heavy chain selected from the group consisting of T80C, Y84C and N86C (Y84C refers to a mutation at position 108 in a mature protein, where the mature protein lacks a signal sequence. Alternatively, when the protein still includes a 24 mer signal sequence, the position is instead referred to as Y108C).

In certain embodiments, the disulfide bridge can link a peptide in the class I groove of the pMHC complex if the pMHC complex comprises a first cysteine in a Gly-Ser linker extending between the C-terminus of the peptide and the β2 microglobulin, and a second cysteine in a proximal heavy chain position.

When present, the β2 microglobulin sequence can comprise a full-length (human or non-human) β2 microglobulin sequence. In certain embodiments, the β2 microglobulin sequence lacks the leader peptide sequence. As such, the β2 microglobulin sequence can comprise about 99 amino acids.

An exemplary human β2 microglobulin sequence is Genbank accession no. AF072097.1.

As an alternative to type I MHC-based pMHC complexes, the IL2 agonists of the disclosure can include a class II MHC-based pMHC complexes as targeting moieties. A class II MHC-based pMHC complex generally includes a class I MHC polypeptide or a fragment, mutant or derivative thereof. In one specific embodiment, the MHC comprises α and β polypeptides of a class II MHC molecule or a fragment, mutant or derivative thereof. In one specific embodiment, the α and β polypeptides are linked by a peptide linker. In one specific embodiment, the MHC comprises α and β polypeptides of a human class II MHC molecule selected from the group consisting of HLA-DP, HLA-DR, HLA-DQ, HLA-DM and HLA-DO.

MHC class II molecules generally consist of two polypeptide chains, α and β. The chains may come from the DP, DQ, or DR gene groups. There are about 40 known different human MHC class II molecules. All have the same basic structure but vary subtly in their molecular structure. MHC class II molecules bind peptides of 13-18 amino acids in length.

In some embodiments, the pMHC complex comprises one or more MHC class II α chains or an extracellular portion thereof. In some embodiments, the class II α chain is HLA-DMA, HLA-DOA, HLA-DPA, HLA-DQA or HLA-DRA.

In other embodiments, the pMHC complex comprises one or more MHC class II β chains or an extracellular portion thereof. In some embodiments, the class II β chain is HLA-DMB, HLA-DOB, HLA-DPB, HLA-DQB or HLA-DRB.

The peptide in a pMHC complex can be any peptide that is capable of binding to an MHC protein in a manner such that the pMHC complex can bind to a TCR, e.g., in a specific manner.

Examples include peptides produced by hydrolysis and most typically, synthetically produced peptides, including randomly generated peptides, specifically designed peptides, and peptides where at least some of the amino acid positions are conserved among several peptides and the remaining positions are random.

In nature, peptides that are produced by hydrolysis undergo hydrolysis prior to binding of the antigen to an MHC protein. Class I MHC typically present peptides derived from proteins actively synthesized in the cytoplasm of the cell. In contrast, class MHC typically present peptides derived either from exogenous proteins that enter a cell's endocytic pathway or from proteins synthesized in the ER. Intracellular trafficking permits a peptide to become associated with an MHC protein.

The binding of a peptide to an MHC peptide binding groove can control the spatial arrangement of MHC and/or peptide amino acid residues recognized by a TCR, or pMHC-binding protein produced by an animal genetically modified as disclosed herein. Such spatial control is due in part to hydrogen bonds formed between a peptide and an MHC protein. Based on the knowledge on how peptides bind to various MHCs, the major MHC anchor amino acids and the surface exposed amino acids that are varied among different peptides can be determined. In some embodiments, the length of an MHC-binding peptide is from 5 to 40 amino acid residues, e.g., from 6 to 30 amino acid residues, e.g., from 8 to 20 amino acid residues, e.g., between 9 and 11 amino acid residues, including any size peptide between 5 and 40 amino acids in length, in whole integer increments (i.e., 5, 6, 7, 8, 9 . . . 40). While naturally MHC Class II-bound peptides vary from about 9-40 amino acids, in nearly all cases the peptide can be truncated to a 9-11 amino acid core without loss of MHC binding activity or T-cell recognition.

The peptides in the pMHC complexes of the disclosure typically at least a portion, e.g., an antigenic determinant, of proteins of infectious agents (e.g., bacterial, viral or parasitic organisms), allergens, and tumor associated proteins. Preferably, the pMHC complexes comprise an antigenic determinant of cancer cells. Exemplary antigenic determinants of cancer cells include LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYES1 (157-165, C165A), NYES1 (157-165, C165V), p54 WT (264-272), PAP-3 (136-143), PSMA (4-12), PSMA (135-145), Survivin (96-014), Tyrosinase (369-377, 3710), and WT (126-134). An exemplary HPV E7 (11-19) peptide sequence is YMLDLQPET (SEQ ID NO:7), SEQ ID NO:537 of International Patent Publication WO 2019/005897. An exemplary HPV E7 (82-90) peptide sequence is LLMGTLGIV (SEQ ID NO:8), SEQ ID NO:538 of International Patent Publication WO 2019/005897. The contents of International Patent Publication WO 2019/005897 are incorporated by reference in their entirety herein.

Other antigenic determinants of cancer cells suitable for incorporation into the pMHC targeting moieties of the disclosure are cancer neoantigens listed in Table 3 below and their corresponding HLA allele. The neoantigens contain either mutations relative to a wild type allele or result from the expression of a new open reading frame in cancer cells, as shown in Table 1 of Fritsch et al., 2014, Cancer Immunol Res 2:522-529 and incorporated by reference herein in its entirety.

TABLE 3

| Gene | HLA allele | Neoantigen | SEQ ID NO: |
|---|---|---|---|
| ECGF-1 | B 07:02 | RPHAIRRPLAL | 9 |
| ME-1 | A 02:01 | FLDEFMEGV | 10 |
| PLEKHM2 | A 01:01 | LTDDRLFTCY | 11 |
| FNDC3B | A 02:01 | VVMSWAPPV | 12 |
| PRDX5 | A 02:01 | LLLDDLLVSI | 13 |
| MATN2 | A 11:01 | KTLTSVFQK | 14 |
| DDX21 | A 68:01 | EAFIQPITR | 15 |
| RBAF | B 07:02 | RPHVPESAF | 16 |
| GAS7 | A 02:01 | SLADEAEVYL | 17 |
| ATR | A 03:01 | KLYEEPLLK | 18 |
| SIRT2 | A 03:01 | KIFSEVTLK | 19 |
| EF2 | A 68:02 | ETVSEQSNV | 20 |
| KIAA0223 | A 02:01 | VLHDDLLEA | 21 |
| GAPDH | A 02:01 | GIVEGLITTV | 22 |
| BCL2A1 | A 24:02 | DYLQYVLQI | 23 |
| HSP70 | A 02:01 | SLFEGIDIYT | 24 |

TABLE 3-continued

| Gene | HLA allele | Neoantigen | SEQ ID NO: |
|---|---|---|---|
| ACTININ | A 02:01 | FIASNGVKLV | 25 |
| CDK12 | A 11:01 | CILGKLFTK | 26 |
| KIAA1440 | A 01:01 | QTACEVLDY | 27 |
| HAUS3 | A 02:01 | ILNAMIAKI | 28 |
| BCL2A1 | B 44:03 | KEFEDDIINW | 29 |
| PPP1R3B | A 01:01 | YTDFHCQYV | 30 |
| HB-1 | B 44:03 | EEKRGSLHVW | 31 |
| MUM-2 | B 44:02 | SELFRSGLDSY | 32 |
| KIAA0205 | B 44:03 | AEPIDIQTW | 33 |
| GPNMB | A 03:01 | TLDWLLQTPK | 34 |
| CSNK1A1 | A 02:01 | GLFGDIYLAI | 35 |
| CLPP | A 02:01 | ILDKVLVHL | 36 |
| CTNNB1 | A 24:02 | SYLDSGIHF | 37 |
| SNRP116 | A 03:01 | KILDAVVAQK | 38 |
| OS9 | B 44:03 | KELEGILLL | 39 |
| MYH2 | A 03:01 | KINKNPKYK | 40 |
| MART-2 | A 01:01 | FLEGNEVGKTY | 41 |
| NFYC | B 52:01 | AQQITKTEV | 42 |
| CDK4 | A 02:01 | ACDPHSGHFV | 43 |
| pARF14-ORF3 | A 11:01 | AVCPWTWLR | 44 |
| HMSD-n | B 44:03 | MEIFIEVFSHF | 45 |
| PANE-1 | A 03:01 | RVWDLPGVLK | 46 |
| MUM1 | B 44:02 | EEKLIVVLF | 47 |
| P2x5 | B 07:02 | TPNQRQNVC | 48 |

6.5. The Multimerization Moiety

6.5.1. Fc Domains

The IL2 agonists of the disclosure can include an Fc region derived from any suitable species. In one embodiment the Fc region is derived from a human Fc domain. In preferred embodiments, the IL2 domain is fused to an IgG Fc molecule.

The IL2 domain may be fused to the N-terminus or the C-terminus of the IgG Fc region. As shown in the Examples, fusion to the C-terminus of the IgG Fc region maintains the IL2 domain activity to a greater extent than when fused to the N-terminus of the IgG Fc.

One embodiment of the present disclosure is directed to a dimer comprising two Fc-fusion polypeptides created by fusing an IL2 domain to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain bonds form between the Fc moieties to yield the dimer.

The Fc domain can be derived from any suitable class of antibody, including IgA (including subclasses IgA1 and IgA2), IgD, IgE, IgG (including subclasses IgG1, IgG2, IgG3 and IgG4), and IgM. In one embodiment, the Fc domain is derived from IgG1, IgG2, IgG3 or IgG4. In one embodiment the Fc domain is derived from IgG1. In one embodiment the Fc domain is derived from IgG4.

The two Fc domains within the Fc region can be the same or different from one another. In a native antibody the Fc domains are typically identical, but for the purpose of producing multispecific binding molecules, e.g., the IL2 agonists of the disclosure, the Fc domains might advantageously be different to allow for heterodimerization, as described in Section 6.5.1.2 below.

In native antibodies, the heavy chain Fc domain of IgA, IgD and IgG is composed of two heavy chain constant domains (CH2 and CH3) and that of IgE and IgM is composed of three heavy chain constant domains (CH2, CH3 and CH4). These dimerize to create an Fc region.

In IL2 agonists of the present disclosure, the Fc region, and/or the Fc domains within it can comprise heavy chain constant domains from one or more different classes of antibody, for example one, two or three different classes.

In one embodiment the Fc region comprises CH2 and CH3 domains derived from IgG1.

In one embodiment the Fc region comprises CH2 and CH3 domains derived from IgG2.

In one embodiment the Fc region comprises CH2 and CH3 domains derived from IgG3.

In one embodiment the Fc region comprises CH2 and CH3 domains derived from IgG4.

In one embodiment the Fc region comprises a CH4 domain from IgM. The IgM CH4 domain is typically located at the C-terminus of the CH3 domain.

In one embodiment the Fc region comprises CH2 and CH3 domains derived from IgG and a CH4 domain derived from IgM.

It will be appreciated that the heavy chain constant domains for use in producing an Fc region for the IL2 agonists of the present disclosure may include variants of the naturally occurring constant domains described above. Such variants may comprise one or more amino acid variations compared to wild type constant domains. In one example the Fc region of the present disclosure comprises at least one constant domain that varies in sequence from the wild type constant domain. It will be appreciated that the variant constant domains may be longer or shorter than the wild type constant domain. Preferably the variant constant domains are at least 60% identical or similar to a wild type constant domain. In another example the variant constant domains are at least 70% identical or similar. In another example the variant constant domains are at least 80% identical or similar. In another example the variant constant domains are at least 90% identical or similar. In another example the variant constant domains are at least 95% identical or similar.

IgM and IgA occur naturally in humans as covalent multimers of the common H2L2 antibody unit. IgM occurs as a pentamer when it has incorporated a J-chain, or as a hexamer when it lacks a J-chain. IgA occurs as monomer and dimer forms. The heavy chains of IgM and IgA possess an 18 amino acid extension to the C-terminal constant domain, known as a tailpiece. The tailpiece includes a cysteine residue that forms a disulfide bond between heavy chains in the polymer, and is believed to have an important role in polymerization. The tailpiece also contains a glycosylation site. In certain embodiments, the IL2 agonists of the present disclosure do not comprise a tailpiece.

The Fc domains that are incorporated into the IL2 agonists of the present disclosure may comprise one or more modifications that alter the functional properties of the proteins, for example, binding to Fc-receptors such as FcRn or leukocyte receptors, binding to complement, modified disulfide bond architecture, or altered glycosylation patterns. Exemplary Fc modifications that alter effector function are described in Section 6.5.1.1

The Fc domains can also be altered to include modifications that improve manufacturability of asymmetric IL2 agonists, for example by allowing heterodimerization, which is the preferential pairing of non-identical Fc domains over identical Fc domains.

Heterodimerization permits the production of IL2 agonists in which different polypeptide components are connected to one another by an Fc region containing Fc domains that differ in sequence. Examples of heterodimerization strategies are exemplified in Section 6.5.1.2.

It will be appreciated that any of the modifications mentioned above can be combined in any suitable manner to achieve the desired functional properties and/or combined with other modifications to alter the properties of the IL2 agonists.

6.5.1.1. Fc Domains with Altered Effector Function

In some embodiments, the Fc domain comprises one or more amino acid substitutions that reduces binding to an Fc receptor and/or effector function.

In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of complement dependent cytotoxicity (CDC), antibody-dependent cell-mediated cytotoxicity (ADCC), antibody-dependent cellular phagocytosis (ADCP), and cytokine secretion. In a particular embodiment, the effector function is ADCC.

In one embodiment, the Fc region comprises an amino acid substitution at a position selected from the group of E233, L234, L235, N297, P331 and P329 (numberings according to Kabat EU index). In a more specific embodiment, the Fc region comprises an amino acid substitution at a position selected from the group of L234, L235 and P329 (numberings according to Kabat EU index). In some embodiments, the Fc region comprises the amino acid substitutions L234A and L235A (numberings according to Kabat EU index). In one such embodiment, the Fc region is an IgD Fc region, particularly a human IgD Fc region. In one embodiment, the Fc region comprises an amino acid substitution at position P329. In a more specific embodiment, the amino acid substitution is P329A or P329G, particularly P329G (numberings according to Kabat EU index). In one embodiment, the Fc region comprises an amino acid substitution at position P329 and a further amino acid substitution at a position selected from E233, L234, L235, N297 and P331 (numberings according to Kabat EU index). In a more specific embodiment, the further amino acid substitution is E233P, L234A, L235A, L235E, N297A, N297D or P331S. In particular embodiments, the Fc region comprises amino acid substitutions at positions P329, L234 and L235 (numberings according to Kabat EU index). In more particular embodiments, the Fc region comprises the amino acid mutations L234A, L235A and P329G ("P329G LALA", "PGLALA" or "LALAPG").

Typically, the same one or more amino acid substitution is present in each of the two Fc domains of an Fc region. Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one embodiment, the Fc domain is an IgG1 Fc domain, particularly a human IgG1 Fc domain.

Typically, the same one or more amino acid substitution is present in each of the two Fc domains of an Fc region. Thus, in a particular embodiment, each Fc domain of the Fc region comprises the amino acid substitutions L234A, L235A and P329G (Kabat EU index numbering), i.e. in each of the first and the second Fc domains in the Fc region the leucine residue at position 234 is replaced with an alanine residue (L234A), the leucine residue at position 235 is replaced with an alanine residue (L235A) and the proline residue at position 329 is replaced by a glycine residue (P329G) (numbering according to Kabat EU index).

In one embodiment, the Fc domain is an IgG1 Fc domain, particularly a human IgG1 Fc domain. In some embodiments, the IgG1 Fc domain is a variant IgG1 comprising D265A, N297A mutations (EU numbering) to reduce effector function.

In another embodiment, the Fc domain is an IgG4 Fc domain with reduced binding to Fc receptors. Exemplary IgG4 Fc domains with reduced binding to Fc receptors may comprise an amino acid sequence selected from Table 4 below: In some embodiments, the Fc domain includes only the bolded portion of the sequences shown below:

TABLE 4

| Fc Domain | Sequence | SEQ ID NO: |
|---|---|---|
| SEQ ID NO: 1 of WO2014/121087 | Asp Lys Arg Val Glu Ser Lys Tyr Gly Pro Pro Cys Pro Pro Cys<br>Pro Ala Pro Pro Val Ala Gly Pro Ser Val Phe Leu Phe Pro Pro<br>Lys Pro Lys Asp Thr Leu Met Ile Ser Arg Thr Pro Glu Val Thr<br>Cys Val Val Val Asp Val Ser Gln Glu Asp Pro Glu Val Gln Phe<br>Asn Trp Tyr Val Asp Gly Val Glu Val His Asn Ala Lys Thr Lys<br>Pro Arg Glu Glu Gln Phe Asn Ser Thr Tyr Arg Val Val Ser Val<br>Leu Thr Val Leu His Gln Asp Trp Leu Asn Gly Lys Glu Tyr Lys<br>Cys Lys Val Ser Asn Lys Gly Leu Pro Ser Ser Ile Glu Lys Thr<br>Ile Ser Lys Ala Lys Gly Gln Pro Arg Glu Pro Gln Val Tyr Thr<br>Leu Pro Pro Ser Gln Glu Glu Met Thr Lys Asn Gln Val Ser Leu<br>Thr Cys Leu Val Lys Gly Phe Tyr Pro Ser Asp Ile Ala Val Glu | 49 |

TABLE 4-continued

| Fc Domain | Sequence | SEQ ID NO: |
|---|---|---|
|  | Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys |  |
| SEQ ID NO: 2 of WO2014/121087 | Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys | 50 |
| SEQ ID NO: 30 of WO2014/121087 | Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Arg Asp Glu Leu Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly Lys | 51 |
| SEQ ID NO: 31 of WO2014/121087 | Ala Ser Thr Lys Gly Pro Ser Val Phe Pro Leu Ala Pro Cys Ser Arg Ser Thr Ser Glu Ser Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Lys Thr Tyr Thr Cys Asn Val Asp His Lys Pro Ser Asn Thr Lys Val Asp Lys Arg Val Glu Ser Lys Tyr Gly Pro Pro Cys Pro Pro Cys Pro Ala Pro Pro Val Ala Gly Pro Ser Val Phe Leu Phe Pro Pro Lys Pro Lys Asp Thr Leu Met Ile Ser Arg Thr Pro Glu Val Thr Cys Val Val Val Asp Val Ser Gln Glu Asp Pro Glu Val Gln Phe Asn Trp Tyr Val Asp Gly Val Glu Val His Asn Ala Lys Thr Lys Pro Arg Glu Glu Gln Phe Asn Ser Thr Tyr Arg Val Val Ser Val Leu Thr Val Leu His Gln Asp Trp Leu Asn Gly Lys Glu Tyr Lys Cys Lys Val Ser Asn Lys Gly Leu Pro Ser Ser Ile Glu Lys Thr Ile Ser Lys Ala Lys Gly Gln Pro Arg Glu Pro Gln Val Tyr Thr Leu Pro Pro Ser Gln Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Arg Leu Thr Val Asp Lys Ser Arg Trp Gln Glu Gly Asn Val Phe Ser Cys Ser Val Met His Glu Ala Leu His Asn His Tyr Thr Gln Lys Ser Leu Ser Leu Ser Leu Gly Lys | 52 |
| SEQ ID NO: 37 of WO2014/121087 | Ala Ser Thr Lys Gly Pro Ser Val Phe Pro Leu Ala Pro Ser Ser Lys Ser Thr Ser Gly Gly Thr Ala Ala Leu Gly Cys Leu Val Lys Asp Tyr Phe Pro Glu Pro Val Thr Val Ser Trp Asn Ser Gly Ala Leu Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Lys Val Glu Pro Lys Ser Cys Asp Lys Thr His Thr Cys Pro Pro Cys Pro Ala Pro Pro Val Ala Gly Pro | 53 |

TABLE 4-continued

| Fc Domain | Sequence | SEQ ID NO: |
|---|---|---|
| | Ser Val Phe Leu Phe Pro Pro Lys Pro Lys Asp Thr Leu Met Ile<br>Ser Arg Thr Pro Glu Val Thr Cys Val Val Val Asp Val Ser Gln<br>Glu Asp Pro Glu Val Gln Phe Asn Trp Tyr Val Asp Gly Val Glu<br>Val His Asn Ala Lys Thr Lys Pro Arg Glu Glu Gln Phe Asn Ser<br>Thr Tyr Arg Val Val Ser Val Leu Thr Val Leu His Gln Asp Trp<br>Leu Asn Gly Lys Glu Tyr Lys Cys Lys Val Ser Asn Lys Gly Leu<br>Pro Ser Ser Ile Glu Lys Thr Ile Ser Lys Ala Lys Gly Gln Pro<br>Arg Glu Pro Gln Val Tyr Thr Leu Pro Pro Ser Arg Asp Glu Leu<br>Thr Lys Asn Gln Val Ser Leu Thr Cys Leu Val Lys Gly Phe Tyr<br>Pro Ser Asp Ile Ala Val Glu Trp Glu Ser Asn Gly Gln Pro Glu<br>Asn Asn Tyr Lys Thr Thr Pro Pro Val Leu Asp Ser Asp Gly Ser<br>Phe Phe Leu Tyr Ser Lys Leu Thr Val Asp Lys Ser Arg Trp Gln<br>Gln Gly Asn Val Phe Ser Cys Ser Val Met His Glu Ala Leu His<br>Asn Arg Phe Thr Gln Lys Ser Leu Ser Leu Ser Pro Gly Lys | |
| SEQ ID NO: 38 of WO2014/121087 | Ala Ser Thr Lys Gly Pro Ser Val Phe Pro Leu Ala Pro Cys Ser<br>Arg Ser Thr Ser Glu Ser Thr Ala Ala Leu Gly Cys Leu Val Lys<br>Asp Tyr Phe Pro Glu Pro Val Thr Val Ser Trp Asn Ser Gly Ala<br>Leu Thr Ser Gly Val His Thr Phe Pro Ala Val Leu Gln Ser Ser<br>Gly Leu Tyr Ser Leu Ser Ser Val Val Thr Val Pro Ser Ser Ser<br>Leu Gly Thr Lys Thr Tyr Thr Cys Asn Val Asp His Lys Pro Ser<br>Asn Thr Lys Val Asp Lys Arg Val Glu Ser Lys Tyr Gly Pro Pro<br>Cys Pro Pro Cys Pro Ala Pro Pro Val Ala Gly Pro Ser Val Phe<br>Leu Phe Pro Pro Lys Pro Lys Asp Thr Leu Met Ile Ser Arg Thr<br>Pro Glu Val Thr Cys Val Val Val Asp Val Ser Gln Glu Asp Pro<br>Glu Val Gln Phe Asn Trp Tyr Val Asp Gly Val Glu Val His Asn<br>Ala Lys Thr Lys Pro Arg Glu Glu Gln Phe Asn Ser Thr Tyr Arg<br>Val Val Ser Val Leu Thr Val Leu His Gln Asp Trp Leu Asn Gly<br>Lys Glu Tyr Lys Cys Lys Val Ser Asn Lys Gly Leu Pro Ser Ser<br>Ile Glu Lys Thr Ile Ser Lys Ala Lys Gly Gln Pro Arg Glu Pro<br>Gln Val Tyr Thr Leu Pro Pro Ser Gln Glu Met Thr Lys Asn<br>Gln Val Ser Leu Thr Cys Leu Val Lys Gly Phe Tyr Pro Ser Asp<br>Ile Ala Val Glu Trp Glu Ser Asn Gly Gln Pro Glu Asn Asn Tyr<br>Lys Thr Thr Pro Pro Val Leu Asp Ser Asp Gly Ser Phe Phe Leu<br>Tyr Ser Arg Leu Thr Val Asp Lys Ser Arg Trp Gln Glu Gly Asn<br>Val Phe Ser Cys Ser Val Met His Glu Ala Leu His Asn Arg Phe<br>Thr Gln Lys Ser Leu Ser Leu Ser Leu Gly Lys | 54 |

In a particular embodiment, the IgG4 with reduced effector function comprises the bolded portion of the amino acid sequence of SEQ ID NO:31 of WO2014/121087, sometimes referred to herein as IgG4s or hIgG4s.

For heterodimeric Fc regions, it is possible to incorporate a combination of the variant IgG4 Fc sequences set forth above, for example an Fc region comprising a combination of SEQ ID NO:30 of WO2014/121087 (or the bolded portion thereof) and SEQ ID NO:37 of WO2014/121087 (or the bolded portion thereof) or an Fc region comprising a combination of SEQ ID NO:31 of WO2014/121087 (or the bolded portion thereof) and SEQ ID NO:38 of WO2014/121087 (or the bolded portion thereof).

6.5.1.2. Fc Heterodimerization Variants

Certain IL2 agonists entail dimerization between two Fc domains that, unlike a native immunoglobulin, are operably linked to non-identical N-terminal regions, e.g., one Fc domain connected to a Fab and the other Fc domain connected to an IL2 moiety. Inadequate heterodimerization of two Fc regions to form an Fc domain has can be an obstacle for increasing the yield of desired heterodimeric molecules and represents challenges for purification. A variety of approaches available in the art can be used in for enhancing dimerization of Fc domains that might be present in the IL2 agonists of the disclosure, for example as disclosed in EP 1870459A1; U.S. Pat. Nos. 5,582,996; 5,731,168; 5,910,573; 5,932,448; 6,833,441; 7,183,076; U.S. Patent Application Publication No. 2006204493A1; and PCT Publication No. WO 2009/089004A1.

The present disclosure provides IL2 agonists comprising Fc heterodimers, i.e., Fc regions comprising heterologous, non-identical Fc domains. Typically, each Fc domain in the Fc heterodimer comprises a CH3 domain of an antibody. The CH3 domains are derived from the constant region of an antibody of any isotype, class or subclass, and preferably of IgG (IgG1, IgG2, IgG3 and IgG4) class, as described in the preceding section.

Heterodimerization of the two different heavy chains at CH3 domains give rise to the desired IL2 agonist, while homodimerization of identical heavy chains will reduce yield of the desired IL2 agonist. Thus, in a preferred embodiment, the polypeptides that associate to form an IL2 agonist of the disclosure will contain CH3 domains with modifications that favor heterodimeric association relative to unmodified Fc domains.

In a specific embodiment said modification promoting the formation of Fc heterodimers is a so-called "knob-into-hole" or "knob-in-hole" modification, comprising a "knob" modification in one of the Fc domains and a "hole" modification in the other Fc domain. The knob-into-hole technology is described e.g., in U.S. Pat. Nos. 5,731,168; 7,695,936; Ridgway et al., 1996, Prot Eng 9:617-621, and Carter, 2001, Immunol Meth 248:7-15. Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in some embodiments, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable. Preferably said amino acid residue having a larger side chain volume is selected from the group consisting of arginine (R), phenylalanine (F), tyrosine (Y), and tryptophan (W). Preferably said amino acid residue having a smaller side chain volume is selected from the group consisting of alanine (A), serine (S), threonine (T), and valine (V). The protuberance and cavity can be made by altering the nucleic acid encoding the polypeptides, e.g., by site-specific mutagenesis, or by peptide synthesis. An exemplary substitution is Y470T.

In a specific such embodiment, in the first Fc domain the threonine residue at position 366 is replaced with a tryptophan residue (T366W), and in the Fc domain the tyrosine residue at position 407 is replaced with a valine residue (Y407V) and optionally the threonine residue at position 366 is replaced with a serine residue (T366S) and the leucine residue at position 368 is replaced with an alanine residue (L368A) (numbering according to Kabat EU index). In a further embodiment, in the first Fc domain additionally the serine residue at position 354 is replaced with a cysteine residue (S354C) or the glutamic acid residue at position 356 is replaced with a cysteine residue (E356C) (particularly the serine residue at position 354 is replaced with a cysteine residue), and in the second Fc domain additionally the tyrosine residue at position 349 is replaced by a cysteine residue (Y349C) (numbering according to Kabat EU index). In a particular embodiment, the first Fc domain comprises the amino acid substitutions S354C and T366W, and the second Fc domain comprises the amino acid substitutions Y349C, T366S, L368A and Y407V (numbering according to Kabat EU index).

In some embodiments, electrostatic steering (e.g., as described in Gunasekaran et al., 2010, J Biol Chem 285(25):19637-46) can be used to promote the association of the first and the second Fc domain of the Fc region.

As an alternative, or in addition, to the use of Fc domains that are modified to promote heterodimerization, an Fc domain can be modified to allow a purification strategy that enables selections of Fc heterodimers. In one such embodiment, one polypeptide comprises a modified Fc domain that abrogates its binding to Protein A, thus enabling a purification method that yields a heterodimeric protein. See, for example, U.S. Pat. No. 8,586,713. As such, the IL2 agonists comprise a first CH3 domain and a second Ig CH3 domain, wherein the first and second Ig CH3 domains differ from one another by at least one amino acid, and wherein at least one amino acid difference reduces binding of the IL2 agonist to Protein A as compared to a corresponding IL2 agonist lacking the amino acid difference. In one embodiment, the first CH3 domain binds Protein A and the second CH3 domain contains a mutation/modification that reduces or abolishes Protein A binding such as an H95R modification (by IMGT exon numbering; H435R by EU numbering). The second CH3 may further comprise a Y96F modification (by IMGT; Y436F by EU). This class of modifications is referred to herein as "star" mutations.

In some embodiments, the Fc can contain one or more mutations (e.g., knob and hole mutations) to facilitate heterodimerization as well as star mutations to facilitate purification.

6.6. Stabilization Moieties

The IL2 agonists of the disclosure can comprise a stabilization moiety that can extend the molecule's serum half-life in vivo. Serum half-life is often divided into an alpha phase and a beta phase. Either or both phases may be improved significantly by addition of an appropriate stabilization moiety. For example, the stabilization moiety can increase the serum half-life of the IL2 agonist by more than 5, 10, 20, 30, 40, 50, 60, 70, 80, 90, 100, 120, 150, 200, 400, 600, 800, 1000% or more relative to a corresponding IL2 agonist not containing the stabilization moiety. For the purpose of this disclosure, serum half-life can refer to the half-life in humans or other mammals (e.g., mice or non-human primates).

Wild type IL2 has a serum half-life of less than 10 minutes. The IL2 agonists of the disclosure have preferably a serum half-life in humans and/or mice of at least about 2 hours, at least about 4 hours, at least about 6 hours, or at least about 8 hours. In some embodiments, the IL2 agonists of the disclosure have a serum half-life of at least 10 hours, at least 12 hours, at least 15 hours, at least 18 hours, at least 24 hours, at least 36 hours, at least 48 hours, at least 60 hours, or at least 72 hours.

Stabilization moieties, include polyoxyalkylene moieties (e.g., polyethylene glycol), sugars (e.g., sialic acid), and well-tolerated protein moieties (e.g., Fc and fragments and variants thereof, transferrin, or serum albumin).

Other stabilization moieties that can be used in the IL2 agonists of the disclosure include those described in Kontermann et al., 2011, Current Opinion in Biotechnology 22:868-76. Such Stabilization moieties include, but are not limited to, human serum albumin fusions, human serum albumin conjugates, human serum albumin binders (e.g., Adnectin PKE, AlbudAb, ABD), XTEN fusions, PAS fusions (i.e., recombinant PEG mimetics based on the three amino acids proline, alanine, and serine), carbohydrate conjugates (e.g., hydroxyethyl starch (HES)), glycosylation, polysialic acid conjugates, and fatty acid conjugates.

Accordingly, in some embodiments the disclosure provides an IL2 agonist comprising a stabilization moiety that is a polymeric sugar.

Serum albumin can also be engaged in half-life extension through modules with the capacity to non-covalently interact with albumin. Accordingly, the IL2 agonists of the disclosure can include as a stabilization moiety an albumin-binding protein. The albumin-binding protein can be either conjugated or genetically fused to one or more other components of the IL2 agonist of the disclosure. Proteins with albumin-binding activity are known from certain bacteria. For example, streptococcal protein G contains several small albumin-binding domains composed of roughly 50 amino acid residues (6 kDa). Additional examples of serum albumin binding proteins such as those described in U.S. Publication Nos. 2007/0178082 and 2007/0269422. Fusion of an albumin binding domain to a protein results in a strongly extended half-life (see Kontermann et al., 2011, Current Opinion in Biotechnology 22:868-76).

In other embodiments the stabilization moiety is human serum albumin. In other embodiments, the stabilization moiety is transferrin.

In some embodiments, the stabilization moiety is an Fc domain, for example any of the Fc domains described in Section 6.5.1 and subsections thereof, incorporated by reference herein. The Fc domains described in Section 6.5.1 are generally capable of dimerization.

However, for the purpose of stabilization the Fc domain can be a soluble monomeric Fc domain that has a reduced ability to self-associate. See, e.g., Helm et al., 1996, J. Biol. Chem. 271: 7494-7500 and Ying et al., 2012, J Biol Chem. 287(23):19399-19408. An example of a soluble monomeric Fc domain comprises amino acid substitutions in the positions corresponding to T366 and/or Y407 in CH3, as described in U.S. Patent Publication No. 2019/0367611. The monomeric Fc domains can be of any Ig subtype and can include additional substitutions that reduce effector function, as described in Section 6.5.1 and subsections thereof.

In yet other embodiments, the stabilization moiety is a polyethylene glycol moiety or another polymer, as described in Section 6.6.1 below.

The stabilization moiety can be connected to one or more other components of the IL2 agonists of the disclosure via a linker, for example as described in Section 6.7 below.

6.6.1. Polyethylene Glycol

In some embodiments, the IL2 agonist comprises polyethylene glycol (PEG) or another hydrophilic polymer as a stabilization moiety, for example a copolymer of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), dextran or poly(n-vinyl pyrrolidone)polyethylene glycol, a propropylene glycol homopolymer, a prolypropylene oxide/ethylene oxide co-polymer, a polyoxyethylated polyol (e.g., glycerol), polyvinyl alcohol, and mixtures thereof. The polymer may be of any molecular weight, and may be branched or unbranched.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O(CH$_2$CH$_2$O)$_n$–1CH$_2$CH$_2$OH, where n is 20 to 2300 and X is H or a terminal modification, e.g., a C$_{1-4}$ alkyl. PEG can contain further chemical groups which are necessary for binding reactions, which result from the chemical synthesis of the molecule; or which act as a spacer for optimal distance of parts of the molecule. In addition, such a PEG can consist of one or more PEG side-chains which are linked together. PEGs with more than one PEG chain are called multiarmed or branched PEGs. Branched PEGs are described in, for example, European Application No. 473084A and U.S. Pat. No. 5,932,462.

One or more PEG molecules can be attached at different positions on the IL2 agonist, and such attachment may be achieved by reaction with amines, thiols or other suitable reactive groups. The amine moiety may be, for example, a primary amine found at the N-terminus of the IL2 agonist (or a component thereof) or an amine group present in an amino acid, such as lysine or arginine. In some embodiments, the PEG moiety is attached at a position on the IL2 agonist at a) the N-terminus; b) between the N-terminus and the most N-terminal alpha helix; c) a loop positioned on the face of IL2 that binds to IL2-Rβ; d) between the C-terminus and the most C-terminal alpha helix; e) a loop connecting two alpha helices; and/or f) at the C-terminus.

PEGylation can be achieved by site-directed PEGylation, wherein a suitable reactive group is introduced into the protein to create a site where PEGylation preferentially occurs. In some embodiments, the IL2 agonist is modified to introduce a cysteine residue at a desired position, permitting site-directed PEGylation on the cysteine. Mutations can be introduced into the coding sequence of an IL2 agonist of the disclosure to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or three dimensional structure. The three dimensional structure of IL2 is described in, e.g., Wang et al., 2005, Science 310(5751): 1159-63, and can be used to identify surface-exposed residues that can be mutated to cysteine. The mutations can be chosen to avoid disrupting the interaction between IL2 and one or more of its receptors, although in some embodiments (e.g., where biased binding to a receptor is desired) the substitution of an amino acid with cysteine and subsequent pegylation is designed to reduce binding to one or more of the receptors, e.g., IL2-Rα or IL2-Rβ. PEGylation of cysteine residues may be carried out using, for example, PEG-maleimide, PEG-vinylsulfone, PEG-iodoacetamide, or PEG-orthopyridyl disulfide.

The PEG is typically activated with a suitable activating group appropriate for coupling to a desired site on the polypeptide. PEGylation methods are well-known in the art and further described in Zalipsky et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992), and in Zalipsky, 1995, Advanced Drug Reviews 16: 157-182.

PEG moieties may vary widely in molecular weight and may be branched or linear. Typically, the weight-average molecular weight of PEG is from about 100 Daltons to about 150,000 Daltons. Exemplary weight-average molecular weights for PEG include about 20,000 Daltons, about 40,000 Daltons, about 60,000 Daltons and about 80,000 Daltons. In certain embodiments, the molecular weight of PEG is 40,000 Daltons. Branched versions of PEG having a total molecular weight of any of the foregoing can also be used. In some embodiments, the PEG has two branches. In other embodiments, the PEG has four branches. In another embodiment, the PEG is a bis-PEG (NOF Corporation, DE-200MA), in which two IL2-containing polypeptide chains are conjugated.

Conventional separation and purification techniques known in the art can be used to purify PEGylated IL2 agonists, such as size exclusion (e.g., gel filtration) and ion exchange chromatography. Products can also be separated using SDS-PAGE. Products that can be separated include mono-, di-, tri-, poly- and un-PEGylated IL2 agonists, as well as free PEG. The percentage of mono-PEG conjugates can be controlled by pooling broader fractions around the elution peak to increase the percentage of mono-PEG in the composition. About 90% mono-PEG conjugates represent a good balance of yield and activity.

In some embodiments, the PEGylated IL2 agonists will preferably retain at least about 25%, 50%, 60%, 70%, 80%, 85%, 90%, 95% or 100% of the biological activity associated with the unmodified IL2 agonist. In some embodiments, biological activity refers to its ability to bind to the high or intermediate affinity IL2 receptor, as assessed by $K_D$, $k_{on}$, or $k_{off}$.

6.7. Linkers

In certain aspects, the present disclosure provides IL2 agonists in which two or more components of an IL2 agonist are connected to one another by a peptide linker. By way of example and not limitation, linkers can be used to connect (a) an IL2 moiety and a multimerization moiety; (b) an IL2 moiety and a targeting moiety; (c) a targeting moiety and a multimerization moiety (e.g., a Fab domain and an Fc domain); (d) different domains within an IL2 moiety (e.g., an IL2 domain and an IL-Ra domain); or (e) different domains within a targeting moiety (e.g., different components of a peptide-MHC complex or the VH and VL domains in a scFv).

A peptide linker can range from 2 amino acids to 60 or more amino acids, and in certain aspects a peptide linker ranges from 3 amino acids to 50 amino acids, from 4 to 30 amino acids, from 5 to 25 amino acids, from 10 to 25 amino acids, 10 amino acids to 60 amino acids, from 12 amino acids to 20 amino acids, from 20 amino acids to 50 amino acids, or from 25 amino acids to 35 amino acids in length.

In particular aspects, a peptide linker is at least 5 amino acids, at least 6 amino acids or at least 7 amino acids in length and optionally is up to 30 amino acids, up to 40 amino acids, up to 50 amino acids or up to 60 amino acids in length.

In some embodiments of the foregoing, the linker ranges from 5 amino acids to 50 amino acids in length, e.g., ranges from 5 to 50, from 5 to 45, from 5 to 40, from 5 to 35, from 5 to 30, from 5 to 25, or from 5 to 20 amino acids in length. In other embodiments of the foregoing, the linker ranges from 6 amino acids to 50 amino acids in length, e.g., ranges from 6 to 50, from 6 to 45, from 6 to 40, from 6 to 35, from 6 to 30, from 6 to 25, or from 6 to 20 amino acids in length. In yet other embodiments of the foregoing, the linker ranges from 7 amino acids to 50 amino acids in length, e.g., ranges from 7 to 50, from 7 to 45, from 7 to 40, from 7 to 35, from 7 to 30, from 7 to 25, or from 7 to 20 amino acids in length.

Charged (e.g., charged hydrophilic linkers) and/or flexible linkers are particularly preferred.

Examples of flexible linkers that can be used in the IL2 agonists of the disclosure include those disclosed by Chen et al., 2013, Adv Drug Deliv Rev. 65(10): 1357-1369 and Klein et al., 2014, Protein Engineering, Design & Selection 27(10): 325-330. Particularly useful flexible linkers are or comprise repeats of glycines and serines, e.g., a monomer or multimer of $G_nS$ (SEQ ID NO:55) or $SG_n$ (SEQ ID NO:56), where n is an integer from 1 to 10, e.g., 1 2, 3, 4, 5, 6, 7, 8, 9 or 10. In one embodiment, the linker is or comprises a monomer or multimer of repeat of $G_4S$ e.g., $(GGGGS)_n$ (SEQ ID NO:57).

Polyglycine linkers can suitably be used in the IL2 agonists of the disclosure. In some embodiments, a peptide linker comprises two consecutive glycines (2Gly), three consecutive glycines (3Gly), four consecutive glycines (4Gly) (SEQ ID NO:58), five consecutive glycines (5Gly) (SEQ ID NO:59), six consecutive glycines (6Gly) (SEQ ID NO:60), seven consecutive glycines (7Gly) (SEQ ID NO:61), eight consecutive glycines (8Gly) (SEQ ID NO:62) or nine consecutive glycines (9Gly) (SEQ ID NO:63).

6.7.1. pMHC Linkers

For pMHC complexes, suitable linkers can range from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. In addition to the linkers above, pMHC linkers include glycine polymers (G)n, glycine-serine polymers (including, for example, (GS)n, (GSGGS)n (SEQ ID NO:64) and (GGGS)n (SEQ ID NO:65), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see Scheraga, 1992, Rev. Computational Chem. 1 1173-142, incorporated herein in its entirety by reference). Exemplary linkers can comprise amino acid sequences including, but not limited to, GGSG (SEQ ID NO:66), GGSGG (SEQ ID NO:67), GSGSG (SEQ ID NO:68), GSGGG (SEQ ID NO:69), GGGSG (SEQ ID NO:70), GSSSG (SEQ ID NO:71), GCGASGGGGSGGGGS (SEQ ID NO:72), GGGGSGGGGS (SEQ ID NO:73), GGGASGGGGSGGGGS (SEQ ID NO:74), GGGGSGGGGSGGGGS (SEQ ID NO:6), GGGASGGGGS (SEQ ID NO:75), GGGGSGGGGSGGGGSGGGGS (SEQ ID NO:76), GCGGS (SEQ ID NO:77) and the like. In some embodiments, a linker polypeptide includes a cysteine residue that can form a disulfide bond with a cysteine residue present in another portion of the pMHC complex. In certain embodiments, the linker comprises the amino acid sequence GCGGS (SEQ ID NO:77). The substitution of a glycine in the $G_4S$ linker (SEQ ID NO:57) with cysteine can result in the formation of a disulfide bond, for example an MHC targeting moiety with a corresponding cysteine substitution in HLA.A2 that stabilizes the MHC peptide within the MHC complex.

6.7.2. Hinge Sequences

In other embodiments, the IL2 agonists of the disclosure comprise a linker that is a hinge region. In particular, where an IL2 agonist contains an immunoglobulin-based targeting moiety, the hinge can be used to connect the targeting moiety, e.g., a Fab domain, to a multimerization domain, e.g., an Fc domain. The hinge region can be a native or a modified hinge region. Hinge regions are typically found at the N-termini of Fc regions. The term "hinge region", unless the context dictates otherwise, refers to a naturally or non-naturally occurring hinge sequence that in the context of a single or monomeric polypeptide chain is a monomeric hinge domain and in the context of a dimeric polypeptide (e.g., a homodimeric or heterodimeric IL2 agonist formed by the association of two Fc domains) can comprise two associated hinge sequences on separate polypeptide chains.

A native hinge region is the hinge region that would normally be found between Fab and Fc domains in a naturally occurring antibody. A modified hinge region is any hinge that differs in length and/or composition from the native hinge region. Such hinges can include hinge regions from other species, such as human, mouse, rat, rabbit, shark, pig, hamster, camel, llama or goat hinge regions. Other modified hinge regions may comprise a complete hinge region derived from an antibody of a different class or subclass from that of the heavy chain Fc region. Alternatively, the modified hinge region may comprise part of a natural hinge or a repeating unit in which each unit in the repeat is derived from a natural hinge region. In a further alternative, the natural hinge region may be altered by converting one or more cysteine or other residues into neutral residues, such as serine or alanine, or by converting suitably placed residues into cysteine residues. By such means the number of cysteine residues in the hinge region may be increased or decreased. Other modified hinge regions may be entirely synthetic and may be designed to possess desired properties such as length, cysteine composition and flexibility.

A number of modified hinge regions have already been described for example, in U.S. Pat. No. 5,677,425, WO 99/15549, WO 2005/003170, WO 2005/003169, WO 2005/003170, WO 98/25971 and WO 2005/003171 and these are incorporated herein by reference.

In one embodiment, an IL2 agonist of the disclosure comprises an Fc region in which one or both Fc domains possesses an intact hinge region at its N-terminus.

In various embodiments, positions 233-236 within a hinge region may be G, G, G and unoccupied; G, G, unoccupied, and unoccupied; G, unoccupied, unoccupied, and unoccupied; or all unoccupied, with positions numbered by EU numbering.

In some embodiments, the IL2 agonists of the disclosure comprise a modified hinge region that reduces binding affinity for an Fcγ receptor relative to a wild-type hinge region of the same isotype (e.g., human IgG1 or human IgG4).

In one embodiment, the IL2 agonists of the disclosure comprise an Fc region in which each Fc domain possesses an intact hinge region at its N-terminus, where each Fc domain and hinge region is derived from IgG4 and each hinge region comprise the modified sequence CPPC (SEQ ID NO:78). The core hinge region of human IgG4 contains the sequence CPSC (SEQ ID NO:79) compared to IgG1 that contains the sequence CPPC (SEQ ID NO:78). The serine residue present in the IgG4 sequence leads to increased flexibility in this region, and therefore a proportion of molecules form disulfide bonds within the same protein chain (an intrachain disulfide) rather than bridging to the other heavy chain in the IgG molecule to form the interchain disulfide. (Angel et al., 1993, Mol Immunol 30(1):105-108). Changing the serine residue to a proline to give the same core sequence as IgG1 allows complete formation of interchain disulfides in the IgG4 hinge region, thus reducing heterogeneity in the purified product. This altered isotype is termed IgG4P.

6.7.2.1. Chimeric Hinge Sequences

The hinge region can be a chimeric hinge region.

For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region.

In particular embodiments, a chimeric hinge region comprises the amino acid sequence EPKSCDKTHTCPPCPAPPVA (SEQ ID NO:80) (previously disclosed as SEQ ID NO:8 of WO2014/121087, which is incorporated by reference in its entirety herein) or ESKYGPPCPPCPAPPVA (SEQ ID NO:81) (previously disclosed as SEQ ID NO:9 of WO2014/121087). Such chimeric hinge sequences can be suitably linked to an IgG4 CH2 region (for example by incorporation into an IgG4 Fc domain, for example a human or murine Fc domain, which can be further modified in the CH2 and/or CH3 domain to reduce effector function, for example as described in Section 6.5.1.1).

6.7.2.2. Hinge Sequences with Reduced Effector Function

Figure 1:
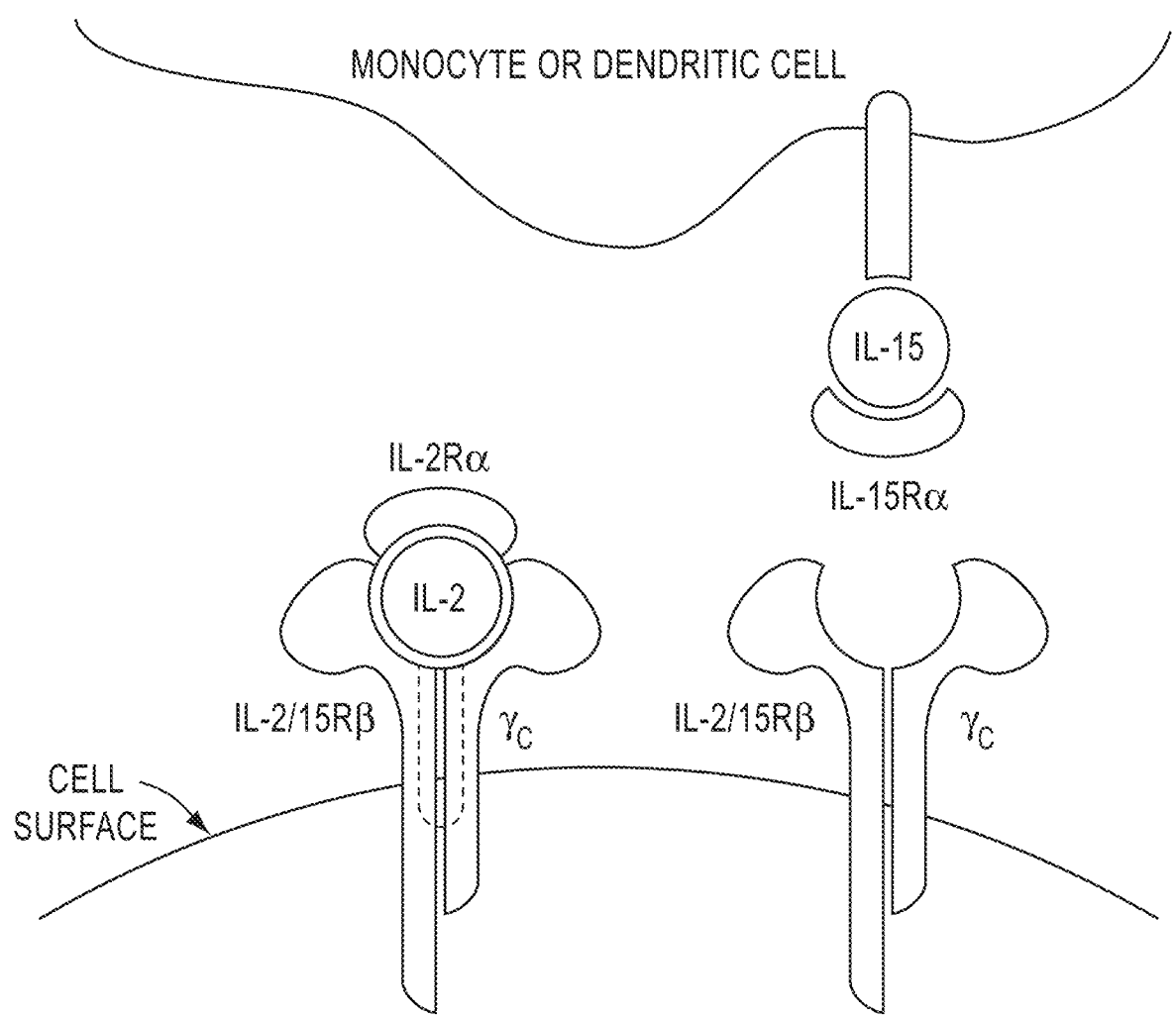
FIG. 1 illustrates the IL2 and IL15 signaling pathways, which have unique receptor subunits but share common β/γ receptor subunits.
Figure 2B:
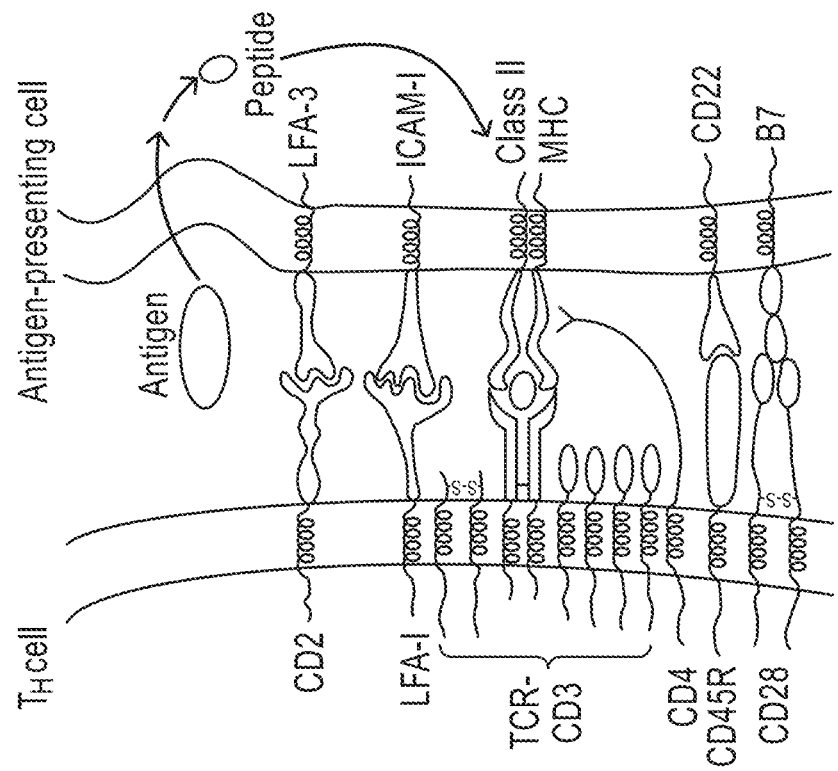
FIGS. 2A-2D illustrate presentation of antigens by antigen-presenting cells to T cells via the class I (FIG. 2A) and class II (FIG. 2B) MHC complexes, and activation of the T cell receptor complexes by MHC-peptide complexes (FIGS. 2C-2D).
Figure 2A:
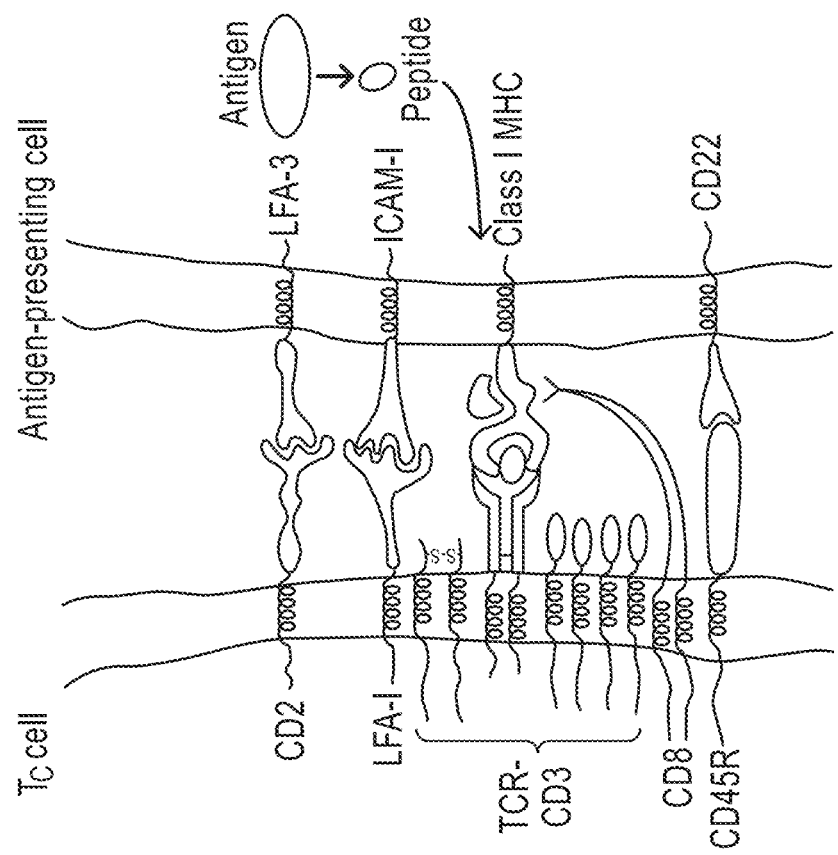
Figure 2D:
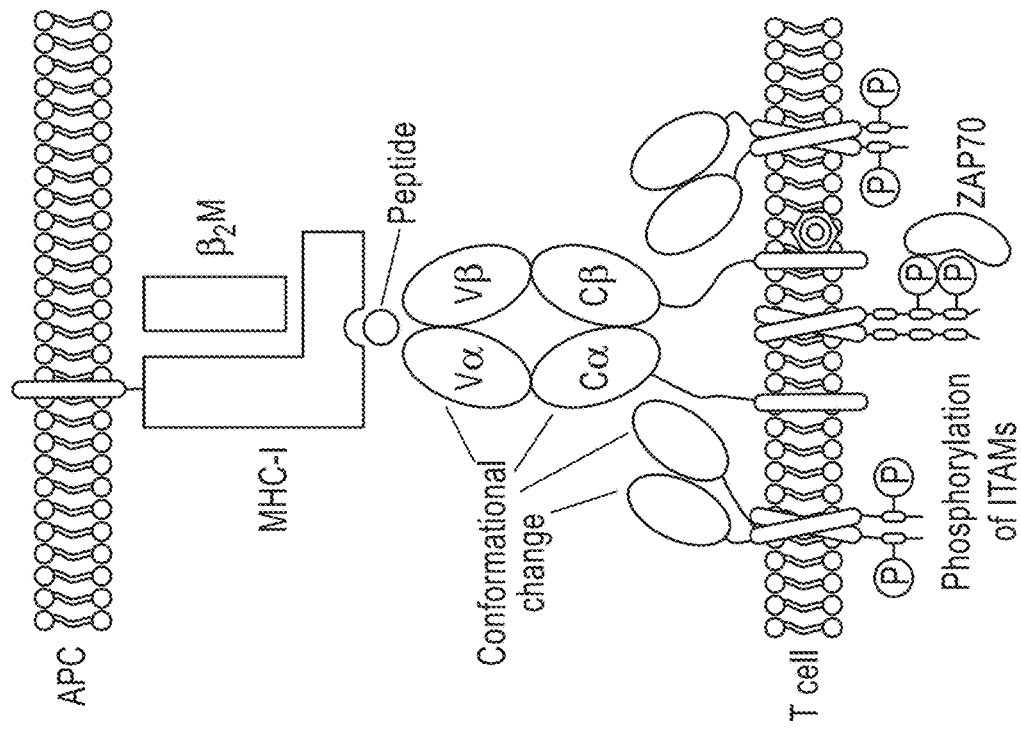
Figure 2C:
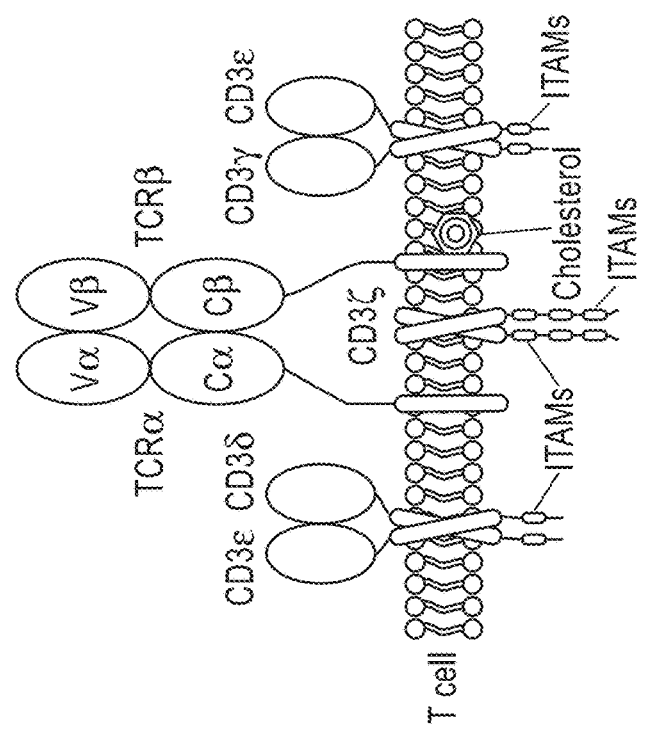

In further embodiments, the hinge region can be modified to reduce effector function, for example as described in WO2016161010A2, which is incorporated by reference in its entirety herein. In various embodiments, the positions 233-236 of the modified hinge region are G, G, G and unoccupied; G, G, unoccupied, and unoccupied; G, unoccupied, unoccupied, and unoccupied; or all unoccupied, with positions numbered by EU numbering (as shown in FIG. 1 of WO2016161010A2). These segments can be represented as GGG-, GG--, G--- or ---- with "-" representing an unoccupied position.

Position 236 is unoccupied in canonical human IgG2 but is occupied by in other canonical human IgG isotypes. Positions 233-235 are occupied by residues other than G in all four human isotypes (as shown in FIG. 1 of WO2016161010A2).

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies. Preferably positions 226-229 are occupied by C, P, P and C respectively.

Exemplary hinge regions have residues 226-236, sometimes referred to as middle (or core) and lower hinge, occupied by the modified hinge sequences designated GGG-(233-236), GG--(233-236), G---(233-236) and no G (233-236). Optionally, the hinge domain amino acid sequence comprises CPPCPAPGGG-GPSVF (SEQ ID NO:82) (previously disclosed as SEQ ID NO:1 of WO2016161010A2), CPPCPAPGG--GPSVF (SEQ ID NO:83) (previously disclosed as SEQ ID NO:2 of WO2016161010A2), CPPCPAPG---GPSVF (SEQ ID NO:84) (previously disclosed as SEQ ID NO:3 of WO2016161010A2), or CPPCPAP----GPSVF (SEQ ID NO:85) (previously disclosed as SEQ ID NO:4 of WO2016161010A2).

The modified hinge regions described above can be incorporated into a heavy chain constant region, which typically include CH2 and CH3 domains, and which may have an additional hinge segment (e.g., an upper hinge) flanking the designated region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4 of WO2016161010A2.

In specific embodiments, the modified hinge sequences can be linked to an IgG4 CH2 region (for example by incorporation into an IgG4 Fc domain, for example a human or murine Fc domain, which can be further modified in the CH2 and/or CH3 domain to reduce effector function, for example as described in Section 6.5.1.1).

6.8. Nucleic Acids and Host Cells

In another aspect, the disclosure provides nucleic acids encoding the IL2 agonists of the disclosure. In some embodiments, the IL2 agonists are encoded by a single nucleic acid. In other embodiments, for example in the case of a heterodimeric molecule or a molecule comprising a targeting moiety composed of more than one polypeptide chain, the IL2 agonists can be encoded by a plurality (e.g., two, three, four or more) nucleic acids.

A single nucleic acid can encode an IL2 agonist that comprises a single polypeptide chain, an IL2 agonist that comprises two or more polypeptide chains, or a portion of an IL2 agonist that comprises more than two polypeptide chains (for example, a single nucleic acid can encode two polypeptide chains of an IL2 agonist comprising three, four or more polypeptide chains, or three polypeptide chains of an IL2 agonist comprising four or more polypeptide chains). For separate control of expression, the open reading frames encoding two or more polypeptide chains can be under the control of separate transcriptional regulatory elements (e.g., promoters and/or enhancers). The open reading frames encoding two or more polypeptides can also be controlled by the same transcriptional regulatory elements, and separated by internal ribosome entry site (IRES) sequences allowing for translation into separate polypeptides.

In some embodiments, an IL2 agonist comprising two or more polypeptide chains is encoded by two or more nucleic acids. The number of nucleic acids encoding an IL2 agonist can be equal to or less than the number of polypeptide chains in the IL2 agonist (for example, when more than one polypeptide chains are encoded by a single nucleic acid).

The nucleic acids of the disclosure can be DNA or RNA (e.g., mRNA).

In another aspect, the disclosure provides host cells and vectors containing the nucleic acids of the disclosure. The nucleic acids may be present in a single vector or separate vectors present in the same host cell or separate host cell, as described in more detail herein below.

6.8.1. Vectors

The disclosure provides vectors comprising nucleotide sequences encoding an IL2 agonist or an IL2 agonist component described herein, for example one or two of the polypeptide chains of a half antibody. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes can be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by co-transformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors can be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. Methods and conditions for culturing the resulting transfected cells and for recovering the expressed polypeptides are known to those skilled in the art, and may be varied or optimized depending upon the specific expression vector and mammalian host cell employed, based upon the present description.

6.8.2. Cells

The disclosure also provides host cells comprising a nucleic acid of the disclosure.

In one embodiment, the host cells are genetically engineered to comprise one or more nucleic acids described herein.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The disclosure also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

6.9. Pharmaceutical Compositions 6.9.1. Pharmaceutical Compositions Comprising IL2 Agonist Polypeptide The IL2 agonists of the disclosure may be in the form of compositions comprising the IL2 agonist and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the IL2 agonist and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an IL2 agonist of the disclosure per dose. The quantity of IL2 agonist included in a unit dose will depend on the disease being treated, as well as other factors as are well known in the art. Such unit dosages may be in the form of a lyophilized dry powder containing an amount of IL2 agonist suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of IL2 agonist suitable for a single administration.

The pharmaceutical compositions may also be supplied in bulk from containing quantities of IL2 agonist suitable for multiple administrations.

Pharmaceutical compositions may be prepared for storage as lyophilized formulations or aqueous solutions by mixing an IL2 agonist having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 wt % per wt of IL2 agonist.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

6.9.2. Pharmaceutical Compositions For Delivery of IL2 Agonist Encoding Nucleic Acids An IL2 agonist of the disclosure can be delivered by any method useful for gene therapy, for example as mRNA or through viral vectors encoding the IL2 agonist under the control of a suitable promoter.

Exemplary gene therapy vectors include adenovirus- or AAV-based therapeutics. Non-limiting examples of adenovirus-based or AAV-based therapeutics for use in the methods, uses or compositions herein include, but are not limited to: rAd-p53, which is a recombinant adenoviral vector encoding the wild-type human tumor suppressor protein p53, for example, for the use in treating a cancer (also known as Gendicine®, Genkaxin®, Qi et al., 2006, Modern Oncology, 14:1295-1297); Ad5_d11520, which is an adenovirus lacking the E1B gene for inactivating host p53 (also called H101 or ONYX-015; see, e.g., Russell et al., 2012, Nature Biotechnology 30:658-670); AD5-D24-GM-CSF, an adenovirus containing the cytokine GM-CSF, for example, for the use in treating a cancer (Cerullo et al., 2010, Cancer Res. 70:4297); rAd-HSVtk, a replication deficient adenovirus with HSV thymidine kinase gene, for example, for the treatment of cancer (developed as Cerepro®, Ark Therapeutics, see e.g. U.S. Pat. No. 6,579,855; developed as ProstAtak™ by Advantagene; International PCT Appl. No. WO2005/049094); rAd-TNFα, a replication-deficient adenoviral vector expressing human tumor necrosis factor alpha (TNFα) under the control of the chemoradiation-inducible EGR-1 promoter, for example, for the treatment of cancer (TNFerade™, GenVec; Rasmussen et al., 2002, Cancer Gene Ther. 9:951-7; Ad-IFNβ, an adenovirus serotype 5 vector from which the E1 and E3 genes have been deleted expressing the human interferon-beta gene under the direction of the cytomegalovirus (CMV) immediate-early promoter, for example for treating cancers (BG00001 and H5.110CMVhIFN-β, Biogen; Sterman et al., 2010, Mol. Ther. 18:852-860).

The nucleic acid molecule (e.g., mRNA) or virus can be formulated as the sole pharmaceutically active ingredient in a pharmaceutical composition or can be combined with other active agents for the particular disorder treated. Optionally, other medicinal agents, pharmaceutical agents, carriers, adjuvants, diluents can be included in the compositions provided herein. For example, any one or more of a wetting agents, emulsifiers and lubricants, such as sodium lauryl sulfate and magnesium stearate, as well as coloring agents, release agents, coating agents, sweetening, flavoring and perfuming agents, preservatives, antioxidants, chelating agents and inert gases also can be present in the compositions. Exemplary other agents and excipients that can be included in the compositions include, for example, water soluble antioxidants, such as ascorbic acid, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, α-tocopherol; and metal chelating agents, such as citric acid, ethylenediamine tetraacetic acid (EDTA), sorbitol, tartaric acid and phosphoric acid.

When used as adjunct therapy for adoptive cell transfer therapies, e.g., CAR-expressing cell therapies as described in Section 6.11.1, the cell therapies, e.g., CAR-expressing cells, can be engineered to express the IL2 agonists of the disclosure. The IL2 agonist can be targeted to a specific genomic locus, e.g., the endogenous IL2 locus or another locus that is active in activated or dysfunctional lymphocytes, e.g., the PD-1 locus, or inserted into a non-specific genomic locus. Targeting a specific genomic locus can be achieved through gene editing, e.g., using zinc finger proteins, the CRISPR/Cas9 system, and the like.

6.10. Therapeutic Indications and Methods of Treatment

IL2 agonists of the disclosure are useful in treating disease states where stimulation of the immune system of the host is beneficial, in particular conditions where an enhanced cellular immune response is desirable. These may include disease states where the host immune response is insufficient or deficient. Disease states for which the IL2 agonists of the disclosure can be administered comprise, for example, a tumor or infection where a cellular immune response would be a critical mechanism for specific immunity. Specific disease states for which IL2 agonists of the present disclosure can be employed include cancer, for example renal cell carcinoma or melanoma; immune deficiency, specifically in HIV-positive patients, immunosuppressed patients, chronic infection and the like. The IL2 agonists of the disclosure may be administered per se or in any suitable pharmaceutical composition.

In one aspect, IL2 agonists of the disclosure for use as a medicament are provided. In further aspects, IL2 agonists of the disclosure for use in treating a disease are provided. In certain embodiments, IL2 agonists of the disclosure for use in a method of treatment are provided. In one embodiment, the disclosure provides an IL2 agonist as described herein for use in the treatment of a disease in a subject in need thereof. In certain embodiments, the disclosure provides an IL2 agonist for use in a method of treating a subject having a disease comprising administering to the individual a therapeutically effective amount of the IL2 agonist. In certain embodiments the disease to be treated is a proliferative disorder. In a preferred embodiment the disease is cancer. In certain embodiments the method further comprises administering to the individual a therapeutically effective amount of at least one additional therapeutic agent, e.g., an anti-cancer agent if the disease to be treated is cancer. In further embodiments, the disclosure provides an IL2 agonist for use in stimulating the immune system. In certain embodiments, the disclosure provides an IL2 agonist for use in a method of stimulating the immune system in a subject comprising administering to the individual an effective amount of the IL2 agonist to stimulate the immune system. An "individual" according to any of the above embodiments is a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In a further aspect, the disclosure provides for the use of an IL2 agonist of the disclosure in the manufacture or preparation of a medicament for the treatment of a disease in a subject in need thereof. In one embodiment, the medicament is for use in a method of treating a disease comprising administering to a subject having the disease a therapeutically effective amount of the medicament. In certain embodiments the disease to be treated is a proliferative disorder. In a preferred embodiment the disease is cancer. In one such embodiment, the method further comprises administering to the individual a therapeutically effective amount of at least one additional therapeutic agent, e.g., an anti-cancer agent if the disease to be treated is cancer. In a further embodiment, the medicament is for stimulating the immune system. In a further embodiment, the medicament is for use in a method of stimulating the immune system in a subject comprising administering to the individual an amount effective of the medicament to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In a further aspect, the disclosure provides a method for treating a disease in a subject, comprising administering to said individual a therapeutically effective amount of an IL2 agonist of the disclosure. In one embodiment a composition is administered to said individual, comprising the IL2 agonist of the disclosure in a pharmaceutically acceptable form. In certain embodiments the disease to be treated is a proliferative disorder. In a preferred embodiment the disease is cancer. In certain embodiments the method further comprises administering to the individual a therapeutically effective amount of at least one additional therapeutic agent, e.g., an anti-cancer agent if the disease to be treated is cancer. In a further aspect, the disclosure provides a method for stimulating the immune system in a subject, comprising administering to the individual an effective amount of an IL2 agonist to stimulate the immune system. An "individual" according to any of the above embodiments may be a mammal, preferably a human. "Stimulation of the immune system" according to any of the above embodiments may include any one or more of a general increase in immune function, an increase in T cell function, an increase in B cell function, a restoration of lymphocyte function, an increase in the expression of IL-2 receptors, an increase in T cell responsiveness, an increase in natural killer cell activity or lymphokine-activated killer (LAK) cell activity, and the like.

In certain embodiments the disease to be treated is a proliferative disorder, preferably cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using an IL2 agonist of the present disclosure include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. Similarly, other cell proliferation disorders can also be treated by the IL2 agonists of the present disclosure. Examples of such cell proliferation disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other cell proliferation disease, besides neoplasia, located in an organ system listed above. In another embodiment, the disease is related to autoimmunity, transplantation rejection, post-traumatic immune responses and infectious diseases (e.g., HIV). More specifically, the IL2 agonists may be used in eliminating cells involved in immune cell-mediated disorders, including lymphoma; autoimmunity, transplantation rejection, graft-versus-host disease, ischemia and stroke. A skilled artisan readily recognizes that in many cases the IL2 agonists may not provide a cure but may only provide partial benefit. In some embodiments, a physiological change having some benefit is also considered therapeutically beneficial. Thus, in some embodiments, an amount of IL2 agonist that provides a physiological change is considered an "effective amount" or a "therapeutically effective amount". The subject, patient, or individual in need of treatment is typically a mammal, more specifically a human.

For the prevention or treatment of disease, the appropriate dosage of an IL2 agonist of the disclosure (when used alone or in combination with one or more other additional therapeutic agents) will depend on the type of disease to be treated, the route of administration, the body weight of the patient, the particular IL2 agonist, the severity and course of the disease, whether the antibody is administered for preventive or therapeutic purposes, previous or concurrent therapeutic interventions, the patient's clinical history and response to the IL2 agonist, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

A single administration of unconjugated IL2 can range from about 50,000 IU/kg to about 1,000,000 IU/kg or more, more typically about 600,000 IU/kg of IL2. This may be repeated several times a day (e.g., 2-3 times.), for several days (e.g., about 3-5 consecutive days) and then may be repeated one or more times following a period of rest (e.g., about 7-14 days). Thus, a therapeutically effective amount may comprise only a single administration or many administrations over a period of time (e.g., about 20-30 individual administrations of about 600,000 IU/kg of IL2 each given over about a 10-20 day period).

Similarly, the IL2 agonist is suitably administered to the patient at one time or over a series of treatments. Depending on the type and severity of the disease, about 1 µg/kg to 15 mg/kg (e.g., 0.1 mg/kg-10 mg/kg) of IL2 agonist can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the IL2 agonist would be in the range from about 0.005 mg/kg to about 10 mg/kg. In other non-limiting examples, a dose may also comprise from about 1 µg/kg/body weight, about 5 µg/kg/body weight, about 10 µg/kg/body weight, about 50 µg/kg/body weight, about 100 µg/kg/body weight, about 200 µg/kg/body weight, about 350 µg/kg/body weight, about 500 µg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 µg/kg/body weight to about 500 mg/kg/body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the IL2 agonist). An initial higher loading dose, followed by one or more lower doses may be administered. However, other dosage regimens may be useful. The progress of this therapy is easily monitored by conventional techniques and assays.

The IL2 agonists of the disclosure will generally be used in an amount effective to achieve the intended purpose. For use to treat or prevent a disease condition, the IL2 agonists of the disclosure, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $EC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the IL2 agonists which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by ELISA HPLC.

In cases of local administration or selective uptake, the effective local concentration of the IL2 agonists may not be related to plasma concentration. One having skill in the art will be able to optimize therapeutically effective local dosages without undue experimentation.

A therapeutically effective dose of the IL2 agonists described herein will generally provide therapeutic benefit without causing substantial toxicity. Toxicity and therapeutic efficacy of an IL2 agonist can be determined by standard pharmaceutical procedures in cell culture or experimental animals (see, e.g., Examples 7 and 8). Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. IL2 agonists that exhibit large therapeutic indices are preferred. In one embodiment, the IL2 agonist according to the present disclosure exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition. (See, e.g., Fingl et al., 1975, In: The Pharmacological Basis of Therapeutics, Ch. 1, p. 1, incorporated herein by reference in its entirety).

The attending physician for patients treated with IL2 agonists of the disclosure would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Due to lower toxicity, the IL2 agonists of the disclosure can be have higher maximum therapeutic doses than wild type IL2, although, IL2 agonists containing a stabilization moiety are typically administered at lower doses than wild type IL2 due to the prolonged half-lives.

6.11. Combination Therapy

The IL2 agonists according to the disclosure may be administered in combination with one or more other agents in therapy. For instance, an IL2 agonist of the disclosure may be co-administered with at least one additional therapeutic agent. The term "therapeutic agent" encompasses any agent administered to treat a symptom or disease in a subject in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of IL2 agonist used, the type of disorder or treatment, and other factors discussed above. The IL2 agonists are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the IL2 agonist of the disclosure can occur prior to, simultaneously, and/or following, administration of the additional therapeutic agent and/or adjuvant. IL2 agonists of the disclosure can also be used in combination with radiation therapy.

6.11.1. Combination Therapy Using IL2 Agonist Therapy and Immunotherapy

The IL2 agonists of the disclosure can be advantageously used in combination with chimeric antigen receptor ("CAR")-expressing cells, e.g., CAR-expressing T ("CAR-T") cells, for example CAR-T in the treatment of cancer or autoimmune diseases. In some embodiments, the CAR-T cells are recognized by a targeting moiety in the IL2 agonist. The targeting moiety can recognize a T cell receptor or another cell surface molecule on the CART cells. In some embodiments, a targeting moiety in the IL2 agonist is capable of binding to an extracellular domain of the CAR, for example the antigen binding domain.

Conditioning or lymphodepletion therapy, e.g., a regimen of cyclophosphamide and fludarabine, can also be administered to a subject receiving CAR and IL2 agonist therapy. Such therapy is usually performed in the days prior to administration of the CAR-expressing cells to the subject. For example, cyclophosphamide can be administered for two days, e.g., at days −8 and −7 prior to infusion with CAR-expressing cells (the infusion day being zero) and fludarabine can be administered to the subject for five consecutive days from day −6 to day −2. In one embodiment, 60 mg/kg of cyclophosphamide is administered to the subject. In one embodiment, 25 mg/m$^2$ of fludarabine is administered to the subject. In one embodiment, there is a day of no treatment on day −1, the day immediately prior to the CAR-expressing cell infusion to the subject.

The CAR-expressing cells can be administered in an amount ranging from $10^4$ to $10^9$ cells/kg body weight, preferably $10^5$ to $10^6$ cells/kg body weight, including all integer values within those ranges. T-cell compositions may also be administered multiple times at these dosages. In some embodiments, the CAR-expressing cells are administered in doses of $1\times10^6$ to $1\times10^{11}$ cells or $1\times10^7$ to $1\times10^8$ cells.

The CAR-expressing cells can be activated with an anti-CD3 and/or anti-CD28 antibody in concert with IL2 expansion prior to administration to the human subject.

The CAR-expressing cells, e.g., T cells, are preferably autologous to the subject but can also be of allogeneic origin.

In one embodiment, the IL2 agonist is administered to the human subject by bolus infusion for four consecutive days beginning on the day of administration of the population of CAR-expressing cells.

In one embodiment, the IL2 agonist is administered to the human subject by bolus for at least five consecutive days beginning on the day of administration of the population of CAR-expressing cells.

The IL2 agonist can be administered for longer periods, for example for a week, for two weeks, for one month or longer. The dosing frequency can be reduced, e.g., after exhaustion of the CAR-expressing cells. For example, the IL2 agonist can be initially administered on a daily basis and then the dosing frequency reduced to weekly.

The initiation of IL2 therapy can begin on the same day as, or one, two, three, four, five, six days or a week after, administration of the CAR-expressing cells.

In one embodiment, the population of cells comprises T-cells obtained from the subject that have been engineered to recombinantly express the CAR.

In one embodiment, the IL2 agonist plasma level is maintained for one to two weeks following administration of the population of cells to the subject.

In one embodiment, the IL2 agonist plasma level is maintained for a month following administration of the population of cells to the subject.

6.11.1.1. CAR Components

A typical CAR comprises an extracellular region comprising antigen binding domain, e.g., an antigen binding domain of an antibody, linked to an intracellular signaling block that includes CD3 signaling domains that induce T cell activation following antigen binding (e.g., a CD3 (signaling region of a T cell receptor). The antigen binding domain can be in the form of an scFv, as described in Section 6.4.2.1.

The antigen binding domain is typically linked to the signal domain via a linker (e.g., a linker as described in Section 6.7), an optional spacer (e.g., as described in Section 6.11.1.1.1), an optional hinge (e.g., as described in Section 6.11.1.1.2), a transmembrane domain (e.g., as described in Section 6.11.1.1.3), and an intracellular signaling block (e.g., as described in Section 6.11.1.1.4).

6.11.1.1.1. Spacer Domain

In particular embodiments, the antigen binding domain of the CAR (followed by an optional linker) is followed by one or more "spacer domains," which refers to the region that moves the antigen binding domain away from the effector cell surface to enable proper cell/cell contact, antigen binding and activation (Patel et al., 1999, Gene Therapy 6:412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 domains of IgG1 or IgG4.

6.11.1.1.2. Hinge Domain

The antigen binding domain of the CAR is generally followed by one or more "hinge domains" (downstream of the optional linker and/or spacer), which play a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

An "altered hinge region" refers to (a) a naturally occurring hinge region with up to 30% amino acid changes (e.g., up to 25%, 20%, 15%, 10%, or 5% amino acid substitutions or deletions), (b) a portion of a naturally occurring hinge region that is at least 10 amino acids (e.g., at least 12, 13, 14 or 15 amino acids) in length with up to 30% amino acid changes (e.g., up to 25%, 20%, 15%, 10%, or 5% amino acid substitutions or deletions), or (c) a portion of a naturally occurring hinge region that comprises the core hinge region (which may be 4, 5, 6, 7, 8, 9, 10, 11, 12, 13, 14, or 15, or at least 4, 5, 6, 7, 8, 9, 10, 11, 12, 13, 14, or 15 amino acids in length). In certain embodiments, one or more cysteine residues in a naturally occurring immunoglobulin hinge region may be substituted by one or more other amino acid residues (e.g., one or more serine residues). An altered immunoglobulin hinge region may alternatively or additionally have a proline residue of a wild type immunoglobulin hinge region substituted by another amino acid residue (e.g., a serine residue).

Other illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8α hinge region.

6.11.1.1.3. Transmembrane (TM) Domain

The "transmembrane domain" is the portion of the CAR that fuses the extracellular binding portion and intracellular signaling domain and anchors the CAR to the plasma membrane of the immune effector cell. As used herein, the term "transmembrane domain" refers to any polypeptide structure that is thermodynamically stable in a cell membrane, preferably a eukaryotic cell membrane (e.g., a mammalian cell membrane).

The TM domain may be derived either from a natural, synthetic, semi-synthetic, or recombinant source. The TM domain may be derived from (e.g., comprise at least the transmembrane region(s) of) the alpha, beta or zeta chain of the T-cell receptor, CD3ε, CD3ζ, CD4, CD5, CD8α, CD9, CD 16, CD22, CD27, CD28, CD33, CD37, CD45, CD64, CD80, CD86, CD 134, CD137, CD152, CD 154, or PD1. In a particular embodiment, the TM domain is synthetic and predominantly comprises hydrophobic residues such as leucine and valine.

In certain embodiments, the CAR comprises a CD3ζ transmembrane domain (e.g., a transmembrane domain that comprises the amino acid sequence LCYLLDGIL-FIYGVILTALFL (SEQ ID NO:86) or LDPKLCYLLDGIL-FIYGVILTALFLRVK (SEQ ID NO:87)), a CD28 transmembrane domain (e.g., a transmembrane domain that comprises the amino acid sequence FWVLVVVGGVLA-CYSLLVTVAFIIFWV (SEQ ID NO:88)) or a CD8α transmembrane domain (e.g., a transmembrane domain that comprises the amino acid sequence KPTTTPAPRPPTPAPTIASQPLSLR PEACR-PAAGGAVHTRGLDFA (SEQ ID NO:89)).

The TM can be followed by a short linker, preferably 1, 2, 3, 4, 5, 6, 7, 8, 9, or 10 amino acids in length that links the TM domain and the intracellular signaling domain of the CAR. A glycine-serine based linker (e.g., a linker according to Section 6.7) provides a particularly suitable linker.

6.11.1.1.4. Intracellular Signaling Domain

CARs typically comprise an intracellular signaling domain. An "intracellular signaling domain," refers to the part of a CAR that participates in transducing the message of effective antigen binding into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or co-stimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and co-stimulatory signaling domains that act in an antigen-independent manner to provide a secondary or co-stimulatory signal. In preferred embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains that are of particular use in the methods of the disclosure include those derived from TCRζ, FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more co-stimulatory signaling domains. The intracellular primary signaling and co-stimulatory signaling domains may be linked in any order in tandem to the carboxyl terminus of the transmembrane domain.

CARs contemplated herein comprise one or more co-stimulatory signaling domains to enhance the efficacy and expansion of T cells expressing CAR receptors. As used herein, the term, "co-stimulatory signaling domain," or "co-stimulatory domain," refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70.

In some embodiments, the CD3 signaling region is linked to co-stimulatory endodomains of CD28, 4-1BB (also known as CD137), CD70, or OX40 (also known as CD134), or combinations thereof, or have two signaling domains of CD3ζ in tandem. These endodomains allow for robust T cell activation during TCR recognition by antigen-presenting cells (APCs), improving cytokine production and proliferation of CAR-T cells.

In another embodiment, a CAR comprises CD28 and CD137 co-stimulatory signaling domains and a CD3ζ primary signaling domain.

In yet another embodiment, a CAR comprises CD28 and CD134 co-stimulatory signaling domains and a CD3ζ primary signaling domain.

In one embodiment, a CAR comprises CD137 and CD134 co-stimulatory signaling domains and a CD3ζ primary signaling domain.

Exemplary CD3ζ signaling regions can comprise one of the following amino acid sequences:

```
                                          (SEQ ID NO: 90)
LDPKLCYLLDGILFIYGVILTALFLRVKFSRSADAPAYQQGGQNQLYNELN

LGRREEYDVLDKRRGRDPEMGGKPRRKNPQEGLYNELQKDKMAEAYSEIG

MKGERRRGKGHDGLYQGLSTATKDTYDALHMQALPPR.

(SEQ ID NO: 91)
RVKFSRSADAPAYQQGGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Exemplary CD28 signaling regions can comprise one of the following amino acid sequences:

```
                                          (SEQ ID NO: 92)
KIEVMYPPPYLDNEKSNGTIIHVKGKHLCPSPLFPGPSKPFWVLVVVGGV

LACYSLLVTVAFIIFWWRSKRSRLLHSDYMNMTPRRPGPTRKHYQPYAPP

RDFAAYRS.

(SEQ ID NO: 93)
RSKRSRLLHSDYMNMTPRRPGPTRKHYQPYAPPRDFAAYRS (SEQ ID NO: 94)
KIEVMYPPPYLDNEKSNGTIIHVKGKHLCPSPLFPGPSKP
```

-continued

FWWLVVVGGVLACYSLLVTVAFIIFW (SEQ ID NO: 88)

RSKRSRLLHSDYMNMTPRRPGPTRKHYQPYAPPRDFAAYRS (SEQ ID NO: 93)

Exemplary CD137 (41BB) signaling regions can comprise the following amino acid sequence:

KRGRKKLLYIFKQPFMRPVQTTQEEDGCSCRFPEEEEGGCEL (SEQ ID NO: 95)

6.11.1.1.5. Tag

In some embodiments, the CAR comprises a tag used for identification of the CAR, for example a V5 epitope tag is derived from a small epitope (Pk) present on the P and V proteins of the paramyxovirus of simian virus 5 (SV5). The V5 tag is usually used with all 14 amino acids (GKPIPN-PLLGLDST) (SEQ ID NO:96), although it has also been used with a shorter 9 amino acid sequence (IPNPLLGLD) (SEQ ID NO:97).

6.11.1.1.6. Signal Peptide

In some embodiments, the CAR comprises a signal peptide. Signal peptides facilitate the expression of the CAR of the cell surface. Signal peptides, including signal peptides of naturally occurring proteins or synthetic, non-naturally occurring signal peptides, that are compatible for use in the CARs described herein will be evident to those of skill in the art. In some embodiments, the signal peptide is disposed N-terminus of the antigen-binding portion of the CAR. Upon expression and processing of the CAR in a cell, e.g., a T cell, the signal peptide is cleaved and is therefore typically not present in the mature molecule.

6.11.1.2. Preparation of CART Cells

For generating CART cells ex vivo, PBMC, peripheral blood lymphocytes, or T cells enriched therefrom, can be expanded prior to and/or following introduction of a nucleic encoding the CAR into the cells, for example by viral transduction.

T cells useful for generating CART cells can be isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in one embodiment, T cells are isolated by incubation with anti-CD3/anti-CD28 (e.g., 3×28)-conjugated beads, such as DYNA-BEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this disclosure. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. T reg cells can be also be depleted by anti-C25 conjugated beads or other similar method of selection.

In certain embodiments, for example for applications involving the treatment of autoimmune disease as described in Section 6.11.1.4, it may be desirable to enrich for or positively select for regulatory T cells which typically express CD4+, CD25+, CD62L$^{hi}$, GITR$^+$, and FoxP3$^+$. T regs can also be induced by recombinant expression of FoxP3.

Whether prior to or after genetic modification of the T cells to express a desirable CAR, the T cells can be activated and expanded generally using methods known in the art, for example as described in U.S. Pat. Nos. 7,144,575; 7,067,318; 7,172,869; 7,232,566; or 7,175,843.

Generally, the T cells useful in the methods of the disclosure are expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For costimulation of an accessory molecule on the surface of the T cells, a ligand that binds the accessory molecule is used. For example, a population of T cells can be contacted with an anti-CD3 antibody and optionally an anti-CD28 antibody, for example on anti-CD3 and anti-CD28 bead, under conditions appropriate for stimulating proliferation of the T cells.

Prior to administration to the human subject the CAR-expressing cells can also be conditioned with IL12 (see, e.g., Emtage et al., 2003, J. Immunother. 16(2): 97-106, incorporated herein by reference).

6.11.1.3. Cancer Immunotherapy

Accordingly, the present disclosure provides methods of treating cancer in a human subject in need thereof, comprising administering to the subject an effective amount of an IL2 agonist of the disclosure and administering to the CAR-expressing cells, e.g., the CAR-expressing T cells (or "CART cells"). Particularly useful T cell subtypes for the treatment of cancer are T cells with robust CAR mediated cytotoxicity, e.g., CD3+CD8+ T cells, which can be prepared as described in 6.11.1.2 above.

For treatment of cancer, the extracellular domain of the CAR can target a tumor associated antigen, for example as described in Section 6.4.1. In certain embodiments, the tumor associated antigen is CD20, EGFR, FITC, CD19, CD22, CD33, PSMA, GD2, EGFR variants, ROR1, c-Met, HER2, CEA, mesothelin, GM2, CD7, CD10, CD30, CD34, CD38, CD41, CD44, CD74, CD123 CD133, CD171, MUC16, MUC1, CS1 (CD319), IL-13Ra2, BCMA, Lewis Y, IgG kappa chain, folate receptor-alpha, PSCA, or EpCAM. In particular embodiments:

the CAR is designed to target CD22 to treat diffuse large B-cell lymphoma.

the CAR is designed to target mesothelin to treat mesothelioma, pancreatic cancer, ovarian cancer, and the like.

the CAR is designed to target CD33/IL3Ra to treat acute myelogenous leukemia and the like.

the CAR is designed to target c-Met to treat triple negative breast cancer, non-small cell lung cancer, and the like.

the CAR is designed to target PSMA to treat prostate cancer and the like.

the CAR is designed to target Glycolipid F77 to treat prostate cancer and the like.

the CAR is designed to target EGFRvII to treat glioblastoma and the like.

the CAR is designed to target GD-2 to treat neuroblastoma, melanoma, and the like.

the CAR is designed to target NY-ESO-1 TCR to treat myeloma, sarcoma, melanoma, and the like.

the CAR is designed to target MAGE A3 TCR to treat myeloma, sarcoma, melanoma, and the like.

Particularly useful for CAR-IL2 agonist combination therapy are IL2 agonists comprising a targeting moiety that recognizes a cell surface antigen present on the surface of the CAR-expressing lymphocytes cells.

Where the IL2 agonist administered in combination with the CAR therapy has a peptide-MHC targeting moiety, the CAR-expressing cell is preferably a $CD4^+$ or $CD8^+$ cell whose TCR recognizes the peptide-MHC complex. For example, the CAR-expressing cells can be T lymphocytes whose TCR specifically binds a pMHC complex present on the IL2 agonist, resulting in functional activation and survival of the CAR-expressing cells.

In some embodiments, the CAR itself comprises an antigen binding domain (e.g., an scFv domain) that targets a pMHC complex in the IL2 agonist, for example any pMHC fusion described in Section 6.4.3. Exemplary CARs that target a pMHC complex with an HPV peptide (e.g., peptides corresponding to amino acid residues 11-19 or 82-90 of the HPV16E7 polypeptide) are disclosed in U.S. Pat. No. 10,806,780 B2, which is incorporated by reference herein in its entirety. In some embodiments, the CAR comprises a heavy chain variable domain (VH) and light chain variable domain (VL) amino acid sequence pair selected from any one of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530, in each case of U.S. Pat. No. 10,806,780 B2, each of which is incorporated by reference herein. In particular embodiments, the VH-VL pair comprise SEQ ID NOs. 2 and 10 of U.S. Pat. No. 10,806,780 B2, SEQ ID NOs. 34 and 42 of U.S. Pat. No. 10,806,780 B2, SEQ ID NOs. 82 and 90 of U.S. Pat. No. 10,806,780 B2, SEQ ID NOs. 194 and 202 of U.S. Pat. No. 10,806,780 B2, or SEQ ID NOs. 506 and 514 of U.S. Pat. No. 10,806,780 B2, each of which is incorporated by reference herein. CAR-IL2 agonist combination therapy with CARs targeting a pMHC with an HPV peptide can be used to treat an HPV-positive cancer, e.g., squamous cell carcinoma, e.g., cervical cancer, head and neck small cell carcinoma, anogenital cancer, and oropharyngeal cancer.

6.11.1.4. Immunotherapy of Autoimmune Disease

Chimeric antigen receptor (CAR) T cells have become powerful treatment options for blood cancers. By using the same idea of modifying T cells to efficiently target disease calls, scientists have efficiently engineered T cells with a predetermined antigen-specificity via transfection of viral vectors encoding chimeric antigen receptors (CARs). CAR-modified T cells engineered in a non-MHC restricted manner have the advantage of widespread applications, especially in transplantation and autoimmunity.

CAR-expressing Treg cells can be prepared as described in 6.11.1.2 above.

Particularly useful for CAR-IL2 agonist combination therapy are IL2 agonists comprising a targeting moiety that recognizes a cell surface antigen present on the surface of the CAR-expressing lymphocytes cells, e.g., a pMHC cloned from an autoimmune target cell.

For use in treatment of autoimmune disease, the extracellular domain of the CAR is preferably specific for a target antigen or ligand associated with the autoimmune response. Such modification causes activation of redirected Tregs at sites of inflammation to suppress the proinflammatory effector-type immune responses. Examples of autoimmune diseases targeted by CAR $T_{reg}$ therapy are multiple sclerosis, inflammatory bowel diseases (IBD), rheumatoid arthritis, systemic lupus erythematosus, Crohn's Disease, psoriasis, Type I Diabetes, Sjogren's disease, myasthenia gravis (MG), Hashimoto's thyroiditis; Graves' Disease, and uveitis.

In particular embodiments, the Tregs are engineered to express a CAR targeting an antigen or ligand specific to:

inflammatory bowel disease (IBD), wherein the antigen or ligand is one that is expressed in diseased colon or ileum;

rheumatoid arthritis, wherein the antigen or ligand is an epitope of collagen or an antigen present in joints;

Type I diabetes mellitus or autoimmune insulitis, wherein the antigen or ligand is a pancreatic p cell antigen;

multiple sclerosis, wherein the antigen or ligand is, for example, a myelin basic protein (MBP) antigen or MOG-1 or MOG2-2, or a neuronal antigen;

autoimmune thyroiditis, wherein the antigen or ligand is a thyroid antigen;

autoimmune gastritis, wherein the antigen or ligand is a gastric antigen;

autoimmune uveitis or uveoretinitis, wherein the antigen or ligand is S-antigen or another uveal or retinal antigen;

autoimmune orchitis, wherein the antigen or ligand is a testicular antigen;

autoimmune oophoritis, wherein the antigen or ligand is an ovarian antigen;

psoriasis, wherein the antigen or ligand is a keratinocyte antigen or another antigen present in dermis or epidermis;

vitiligo, where the antigen or ligand is a melanocyte antigen such as melanin or tyrosinase;

autoimmune prostatitis, wherein the antigen or ligand is a prostate antigen;

any undesired immune response, wherein the antigen or ligand is an activation antigen or other antigen expressed on T effector cells present at the site of the undesired response;

tissue rejection, wherein the antigen or ligand is the MHC specific to the transplanted tissue; and an inflammatory condition, wherein the antigen or ligand is one that is expressed on nonlymphoid cells of the hemopoietic lineage that participate in inflammation.

In one embodiment, T cells can be engineered to express chimeric autoantigen receptor (CAAR) T cells to specifically eliminate B cells that are responsible for autoimmune diseases.

Accordingly, reference to CAR-expressing T cells includes reference to CAAR-expressing unless the context dictates otherwise.

7. EXAMPLES

7.1. Materials and Methods

7.1.1. Production of IL2 and IL15 Agonists

Constructs encoding the IL2 and IL15 muteins (identified with an IL2M_ or IL15M_designation, as appropriate), with or without a targeting moiety (identified with a T designation), described (or containing modules described) in Tables 5A and 5B below, as well as Fc controls were generated. The constructs were expressed in Expi293F™ cells by transient transfection (Thermo Fisher Scientific). Proteins in Expi293F supernatant were purified using the ProteinMaker system (Protein BioSolutions, Gaithersburg, MD) with HiTrap Protein G HP columns (GE Healthcare). After single step elution, the muteins were neutralized, dialyzed into a final buffer of phosphate buffered saline (PBS) with 5% glycerol, aliquoted and stored at −80° C.

TABLE 5A

| Molecule/ Module | Alternate Name | Description | Sequence |
|---|---|---|---|
| IL2 | IL2 | Recombinant human IL2 (source: BD Pharmingen™) | APTSSSTKKTQLQLEHLLLDLQMILNGINNYKNPKLTRMLTFKFYM PKKATELKHLQCLEEELKPLEEVLNLAQSKNFHLRPRDLISNINVI VLELKGSETTFMCEYADETATIVEFLNRWITFCQSIISTLT (SEQ ID NO: 2) |
| IL2M0 | IL2 Mutein 0 | Human IL2 (WT)-GGGGS-Fc Fc is from SEQ ID NO: 31 of WO2014/121087, which is an IgG4 with reduced effector function | APTSSSTKKTQLQLEHLLLDLQMILNGINNYKNPKLTRMLTAKFAM PKKATELKHLQCLEEELKPLEEVLNGAQSKNFHLRPRDLISNINVI VLELKGSETTFMCEYADETATIVEFLNRWITFCQSIISTLTGGGGS ESKYGPPCPPCPAPPVAGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGK (SEQ ID NO: 98) |
| IL2M1 | IL2 Mutein 1 | CD122-biased human IL2 (F42A,Y45A,L72G)-GGGGS-Fc Fc is from SEQ ID NO: 31 of WO2014/121087, which is an IgG4 with reduced effector function | APTSSSTKKTQLQLEHLLLDLQMILNGINNYKNPKLTRMLTFKFYM PKKATELKHLQCLEEELKPLEEVLNLAQSKNFHLRPRDLISNINVI VLELKGSETTFMCEYADETATIVEFLNRWITFCQSIISTLTGGGGS ESKYGPPCPPCPAPPVAGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGK (SEQ ID NO: 99) |
| IL2M2 | IL2 Mutein 2 | Human IL2-(GGGGS)4-human IL-2Rα-GGGGS-Fc IL2 interacts with IL-2Rα in this fusion protein to form inactive head-to-tail dimers that slowly dissociate into an active monomer, with ~99.5% of a population believed to be in the inactive dimeric form. Fc is from SEQ ID NO: 31 of WO2014/121087, which is an IgG4 with reduced effector function | APTSSSTKKTQLQLEHLLLDLQMILNGINNYKNPKLTRMLTFKFYM PKKATELKHLQCLEEELKPLEEVLNLAQSKNFHLRPRDLISNINVI VLELKGSETTFMCEYADETATIVEFLNRWITFCQSIISTLTGGGGS GGGGSGGGGSGGGGSELCDDDPPEIPHATFKAMAYKEGTMLNCECK RGFRRIKSGSLYMLCTGNSSHSSWDNQCQCTSSATRNTTKQVTPQP EEQKERKTTEMQSPMQPVDQASLPGHCREPPPWENEATERIYHFVV GQMVYYQCVQGYRALHRGPAESVCKMTHGKTRWTQPQLICTGGGGS ESKYGPPCPPCPAPPVAGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGK (SEQ ID NO: 100) |
| IL2M3 | IL2 Mutein 3 | Fc-(GGGGS)3-human IL2-Rα-(GGGGS)5-human IL2 fusion IL2 interacts with IL-2Rα in this fusion protein to form inactive head-to-tail dimers that slowly dissociate into an active monomer, with ~99.5% of a population believed to be in the inactive dimeric form. Fc is from SEQ ID NO: 31 of WO2014/121087, which is an IgG4 with reduced effector function | ESKYGPPCPPCPAPPVAGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGKGG GGSGGGGSGGGGSELCDDDPPEIPHATFKAMAYKEGTMLNCECKRG FRRIKSGSLYMLCTGNSSHSSWDNQCQCTSSATRNTTKQVTPQPEE QKERKTTEMQSPMQPVDQASLPGHCREPPPWENEATERIYHFVVGQ MVYYQCVQGYRALHRGPAESVCKMTHGKTRWTQPQLICTGGGGSG GGGSGGGGSGGGGSGGGGSAPTSSSTKKTQLQLEHLLLDLQMILNG INNYKNPKLTRMLTFKFYMPKKATELKHLQCLEEELKPLEEVLNLA QSKNFHLRPRDLISNINVIVLELKGSETTFMCEYADETATIVEFLN RWITFCQSIISTLT (SEQ ID NO: 101) |

TABLE 5A-continued

| Molecule/ Module | Alternate Name | Description | Sequence |
|---|---|---|---|
| IL2M4 | IL2 Mutein 4 | Fc-GGGGS-human IL2(C125A) IL2(C125A) is an IL2 variant in which cysteine 125 is mutated to alanine to reduce aggregation. The IL2 component is not known to exhibit receptor bias. Fc is human IgG1 with N297G mutation to remove glycosylation at this site | DKTHTCPPCPAPELLGGPSVFLFPPKPKDTLMISRTPEVTCVVVDV SHEDPEVKFNWYVDGVEVHNAKTKPREEQYGSTYRVVSVLTVLHQD WLNGKEYKCKVSNKALPAPIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPGGGGG SAPTSSSTKKTQLQLEHLLLDLQMILNGINNYKNPKLTRMLTFKFY MPKKATELKHLQCLEEELKPLEEVLNLAQSKNFHLRPRDLISNINV IVLELKGSETTFMCEYADETATIVEFLNRWITFAQSIISTLT (SEQ ID NO: 102) |
| IL2M5 | IL2 Mutein 5 | Fc-GGGGS-human IL2 (N88D, C125A) fusion. N88D is a mutation of asparagine 88 to aspartic acid. IL2 variants with this mutation have reduced binding to CD122 and therefore are considered CD25 biased. C125A is a mutation of cysteine 125 alanine to reduce aggregation. Fc is human IgG1 with N297G mutation to remove glycosylation at this site | DKTHTCPPCPAPELLGGPSVFLFPPKPKDTLMISRTPEVTCVVVDV SHEDPEVKFNWYVDGVEVHNAKTKPREEQYGSTYRVVSVLTVLHQD WLNGKEYKCKVSNKALPAPIEKTISKAKGQPREPQVYTLPPSREEM TKNQVSLTCLVKGFYPSDIAVEWESNGQPENNYKTTPPVLDSDGSF FLYSKLTVDKSRWQQGNVFSCSVMHEALHNHYTQKSLSLSPGGGGG SAPTSSSTKKTQLQLEHLLLDLQMILNGINNYKNPKLTRMLTFKFY MPKKATELKHLQCLEEELKPLEEVLNLAQSKNFHLRPRDLISDINV IVLELKGSETTFMCEYADETATIVEFLNRWITFAQSIISTLT (SEQ ID NO: 103) |
| IL2M6 | IL2 Mutein 6 | Fc-(GGGGS)$_3$-hIL2(H16A, F42A) (Also referred to as Fc-(GGGGS)$_3$-hIL2(2m)) | ESKYGPPCPPCPAPPVAGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGKGG GGGSGGGGSGGGGSAPTSSSTKKTQLQLEALLLDLQMILNGINNYKN PKLTRMLTAKFYMPKKATELKHLQCLEEELKPLEEVLNLAQSKNFH LRPRDLISNINVIVLELKGSETTFMCEYADETATIVEFLNRWITFC QSIISTLT (SEQ ID NO: 104) |
| IL2M7 | IL2 Mutein 7 | hIL2(H16A, F42A)-GGGGS-IgG4st_Fc_holestar (Also referred to as hIL2(2m)-GGGGS-IgG4st_Fc_holestar) Fc is from SEQ ID NO: 31 of WO2014/121087, which is an IgG4 with reduced effector function, with addition hole and star mutations | APTSSSTKKTQLQLEALLLDLQMILNGINNYKNPKLTRMLTAKFYM PKKATELKHLQCLEEELKPLEEVLNLAQSKNFHLRPRDLISNINVI VLELKGSETTFMCEYADETATIVEFLNRWITFCQSIISTLTGGGGS ESKYGPPCPPCPAPPVAGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLSCAVKGFYPSDIAVEWESNGQPENNYKTTPPVLDSDGS FFLYSRLTVDKSRWQEGNVFSCSVMHEALHNRFTQKSLSLSPGK (SEQ ID NO: 105) |
| IL15M1 | IL15 Mutein 1 | Human IL15-(GGGGS)5-human IL15Ra-(GGGGS)4-Fc fusion Fc is from SEQ ID NO: 31 of WO2014/121087, which is an IgG4 with reduced effector function | NWVNVISDLKKIEDLIQSMHIDATLYTESDVHPSCKVTAMKCFLLE LQVISLESGDASIHDTVENLIILANNSLSSNGNVTESGCKECEELE EKNIKEFLQSFVHIVQMFINTSGGGGSGGGGSGGGGSGGGGSGGGG SITCPPPMSVEHADIWVKSYSLYSRERYICNSGFKRKAGTSSLTEC VLNKATNVAHWTTPSLKCIRDPALVHQRPAPPGGGGSGGGGSGGGG SGGGGSESKYGPPCPPCPAPPVAGPSVFLFPPKPKDTLMISRTPEV TCVVVDVSQEDPEVQFNWYVDGVEVHNAKTKPREEQFNSTYRVVSV LTVLHQDWLNGKEYKCKVSNKGLPSSIEKTISKAKGQPREPQVYTL PPSQEEMTKNQVSLTCLVKGFYPSDIAVEWESNGQPENNYKTTPPV LDSDGSFFLYSRLTVDKSRWQEGNVFSCSVMHEALHNHYTQKSLSL SLGK (SEQ ID NO: 106) |
| IL15M2 | IL15 Mutein 2 | Fc-(GGGGS)$_3$-human IL15Ra-(GGGGS)$_4$-human IL15 fusion Fc is from SEQ ID NO: 31 of WO2014/121087, which is an IgG4 with reduced effector function | ESKYGPPCPPCPAPPVAGPSVFLFPPKPKDTLMISRTPEVTCVVVD VSQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGKGG GGSGGGGSGGGGSITCPPPMSVEHADIWVKSYSLYSRERYICNSGF KRKAGTSSLTECVLNKATNVAHWTTPSLKCIRDPALVHQRPAPPGG GGSGGGGSGGGGSGGGGSNWVNVISDLKKIEDLIQSMHIDATLYTE SDVHPSCKVTAMKCFLLELQVISLESGDASIHDTVENLIILANNSL SSNGNVTESGCKECEELEEKNIKEFLQSFVHIVQMFINTS (SEQ ID NO: 107) |
| T1 | Targeting moiety 1 | Anti-murine PD1 antibody | T1 comprises the T6 comprises the Fab of an anti-PD1 antibody |
| T2 | Targeting moiety 2 | CMVpp65(495-503)-GCGGS-(GGGGS)$_2$-hB2m-(GGGGS)$_4$-hHLA.A2 peptide-MHC targeting moiety | NLVPMVATVGCGGSGGGGSGGGGSIQRTPKIQVYSRHPAENGKSNF LNCYVSGFHPSDIEVDLLKNGERIEKVEHSDLSFSKDWSFYLLYYT EFTPTEKDEYACRVNHVTLSQPKIVKWDRDMGGGGSGGGGSGGGGS GGGGSGSHSMRYFFTSVSRPGRGEPRFIAVGYVDDTQFVRFDSDAA SQRMEPRAPWIEQEGPEYWDGETRKVKAHSQTHRVDLGTLRGCYNQ SEAGSHTVQRMYGCDVGSDWRFLRGYHQYAYDGKDYIALKEDLRSW |

TABLE 5A-continued

| Molecule/ Module | Alternate Name | Description | Sequence |
|---|---|---|---|
| | | | TAADMAAQTTKHKWEAAHVAEQLRAYLEGTCVEWLRRYLENGKETL QRTDAPKTHMTHHAVSDHEATLRCWALSFYPAEITLTWQRDGEDQT QDTELVETRPAGDGTFQKWAAVVVPSGQEQRYTCHVQHEGLPKPLT LRWEP (SEQ ID NO: 108) |
| T3 | Targeting moiety 3 | HPV16E7(11-19)-GCGGS-(GGGGS)$_2$-hB2m-(GGGGS)$_4$-hHLA.A2 peptide-MHC targeting moiety | YMLDLQPETGCGGSGGGGSGGGGSIQRTPKIQVYSRHPAENGKSNF LNCYVSGFHPSDIEVDLLKNGERIEKVEHSDLSFSKDWSFYLLYYT EFTPTEKDEYACRVNHVTLSQPKIVKWDRDMGGGGSGGGGSGGGGS GGGGSGSHSMRYFFTSVSRPGRGEPRFIAVGYVDDTQFVRFDSDAA SQRMEPRAPWIEQEGPEYWDGETRKVKAHSQTHRVDLGTLRGCYNQ SEAGSHTVQRMYGCDVGSDWRFLRGYHQYAYDGKDYIALKEDLRSW TAADMAAQTTKHKWEAAHVAEQLRAYLEGTCVEWLRRYLENGKETL QRTDAPKTHMTHHAVSDHEATLRCWALSFYPAEITLTWQRDGEDQT QDTELVETRPAGDGTFQKWAAVVVPSGQEQRYTCHVQHEGLPKPLT LRWEP (SEQ ID NO: 109) |
| T4 | Targeting moiety 4 | OVA(257-264)-GCGGS-(GGGGS)2-mB2m-(GGGGS)4-mH2Kb peptide-MHC targeting moiety | SIINFEKLGCGGSGGGGSGGGGSIQKTPQIQVYSRHPPENGKPNIL NCYVTQFHPPHIEIQMLKNGKKIPKVEMSDMSFSKDWSFYILAHTE FTPTETDTYACRVKHASMAEPKTVYWDRDMGGGGSGGGGSGGGGSG GGGSGPHSLRYFVTAVSRPGLGEPRYMEVGYVDDTEFVRFDSDAEN PRYEPRARWMEQEGPEYWERETQKAKGNEQSFRVDLRTLLGCYNQS KGGSHTIQVISGCEVGSDGRLLRGYQQYAYDGCDYIALNEDLKTWT AADMAALITKHKWEQAGEAERLRAYLEGTCVEWLRRYLKNGNATLL RTDSPKAHVTHHSRPEDKVTLRCWALGFYPADITLTWQLNGEELIQ DMELVETRPAGDGTFQKWASVVVPLGKEQYYTCHVYHQGLPEPLTL RWEPPPSTVSNMA (SEQ ID NO: 110) |
| T5 | Targeting moiety 5 | MuLV p15E-GCGGS-(GGGGS)$_2$-mB2m-(GGGGS)$_4$-mH2Kb peptide-MHC targeting moiety | KSPWFTTLGCGGSGGGGSGGGGSIQKTPQIQVYSRHPPENGKPNIL NCYVTQFHPPHIEIQMLKNGKKIPKVEMSDMSFSKDWSFYILAHTE FTPTETDTYACRVKHASMAEPKTVYWDRDMGGGGSGGGGSGGGGSG GGGSGPHSLRYFVTAVSRPGLGEPRYMEVGYVDDTEFVRFDSDAEN PRYEPRARWMEQEGPEYWERETQKAKGNEQSFRVDLRTLLGCYNQS KGGSHTIQVISGCEVGSDGRLLRGYQQYAYDGCDYIALNEDLKTWT AADMAALITKHKWEQAGEAERLRAYLEGTCVEWLRRYLKNGNATLL RTDSPKAHVTHHSRPEDKVTLRCWALGFYPADITLTWQLNGEELIQ DMELVETRPAGDGTFQKWASVVVPLGKEQYYTCHVYHQGLPEPLTL RWEPPPSTVSNMA (SEQ ID NO: 111) |
| T6 | Targeting moiety 6 | Anti LAG3 Antibody | T6 comprises a Fab of an anti-LAG3 antibody |
| T7 | Targeting moiety 7 | T3 (i.e., HPV16E7(11-19)-GCGGS-(GGGGS)$_2$-hB2m-(GGGGS)$_4$-hHLA.A2)-(GGGGS)$_4$-Fc (knob) | YMLDLQPETGCGGSGGGGSGGGGSIQRTPKIQVYSRHPAENGKSNF LNCYVSGFHPSDIEVDLLKNGERIEKVEHSDLSFSKDWSFYLLYYT EFTPTEKDEYACRVNHVTLSQPKIVKWDRDMGGGGSGGGGSGGGGS GGGGSGSHSMRYFFTSVSRPGRGEPRFIAVGYVDDTQFVRFDSDAA SQRMEPRAPWIEQEGPEYWDGETRKVKAHSQTHRVDLGTLRGCYNQ SEAGSHTVQRMYGCDVGSDWRFLRGYHQYAYDGKDYIALKEDLRSW TAADMAAQTTKHKWEAAHVAEQLRAYLEGTCVEWLRRYLENGKETL QRTDAPKTHMTHHAVSDHEATLRCWALSFYPAEITLTWQRDGEDQT QDTELVETRPAGDGTFQKWAAVVVPSGQEQRYTCHVQHEGLPKPLT LRWEPGGGGSGGGGSGGGGSGGGGSESKYGPPCPPCPAPPVAGPSV FLFPPKPKDTLMISRTPEVTCVVVDVSQEDPEVQFNWYVDGVEVHN AKTKPREEQFNSTYRVVSVLTVLHQDWLNGKEYKCKVSNKGLPSSI EKTISKAKGQPREPQVYTLPPSQEEMTKNQVSLWCLVKGFYPSDIA VEWESNGQPENNYKTTPPVLDSDGSFFLYSRLTVDKSRWQEGNVFS CSVMHEALHNHYTQKSLSLSLGK (SEQ ID NO: 112) |
| T8 | Targeting moiety 8 | T2 (i.e., CMVpp65(495-503)-GCGGS-(GGGGS)$_2$-hB2m-(GGGGS)$_4$-hHLA.A2)-(GGGGS)$_4$-Fc (knob) | NLVPMVATVGCGGSGGGGSGGGGSIQRTPKIQVYSRHPAENGKSNF LNCYVSGFHPSDIEVDLLKNGERIEKVEHSDLSFSKDWSFYLLYYT EFTPTEKDEYACRVNHVTLSQPKIVKWDRDMGGGGSGGGGSGGGGS GGGGSGSHSMRYFFTSVSRPGRGEPRFIAVGYVDDTQFVRFDSDAA SQRMEPRAPWIEQEGPEYWDGETRKVKAHSQTHRVDLGTLRGCYNQ SEAGSHTVQRMYGCDVGSDWRFLRGYHQYAYDGKDYIALKEDLRSW TAADMAAQTTKHKWEAAHVAEQLRAYLEGTCVEWLRRYLENGKETL QRTDAPKTHMTHHAVSDHEATLRCWALSFYPAEITLTWQRDGEDQT QDTELVETRPAGDGTFQKWAAVVVPSGQEQRYTCHVQHEGLPKPLT LRWEPGGGGSGGGGSGGGGSGGGGSESKYGPPCPPCPAPPVAGPSV FLFPPKPKDTLMISRTPEVTCVVVDVSQEDPEVQFNWYVDGVEVHN AKTKPREEQFNSTYRVVSVLTVLHQDWLNGKEYKCKVSNKGLPSSI EKTISKAKGQPREPQVYTLPPSQEEMTKNQVSLWCLVKGFYPSDIA VEWESNGQPENNYKTTPPVLDSDGSFFLYSRLTVDKSRWQEGNVFS CSVMHEALHNHYTQKSLSLSLGK (SEQ ID NO: 113) |
| T9 | Targeting moiety 9 | CMVpp65(495-503)-GCGGS-(GGGGS)$_2$-hB2m (CMVpp65(495-503) in HLA-A*0201) | NLVPMVATVGCGGSGGGGSGGGGSIQRTPKIQVYSRHPAENGKSNF LNCYVSGFHPSDIEVDLLKNGERIEKVEHSDLSFSKDWSFYLLYYT EFTPTEKDEYACRVNHVTLSQPKIVKWDRDM (SEQ ID NO: 114) |

TABLE 5A-continued

| Molecule/ Module | Alternate Name | Description | Sequence |
|---|---|---|---|
| T10 | Targeting moiety 10 | HPV16E7(11-19)-GCGGS-(GGGGS)2-hB2m (HPV16E7(11-19) in HLA-A*0201) | YMLDLQPETGCGGSGGGGSGGGGSIQRTPKIQVYSRHPAENGKSNF LNCYVSGFHPSDIEVDLLKNGERIEKVEHSDLSFSKDWSFYLLYYT EFTPTEKDEYACRVNHVTLSQPKIVKWDRDM (SEQ ID NO: 115) |

TABLE 5B

| Molecule | Alternate Name | Description | Sequence |
|---|---|---|---|
| T1-IL2M3 | Anti-mPD1-IL2 Mutein 3 | IL2 Mutein 3 with an N-terminal anti-PD1 antibody | IL2 Mutein 3 was linked to the C-terminal of the heavy chain of an anti-PD1 antibody via a (GGGGS)3 linker (SEQ ID NO: 6). |
| T2-IL2M3 | CMVpp65_scpMHC-IL2 Mutein 3 | CMVpp65(495-503)-GCGGS-(GGGGS)2-hB2m-(GGGGS)4-hHLA.A2-(GGGGS)4-Fc-hIL2-Rα-hIL2<br>Fc is from SEQ ID NO: 31 of WO2014/121087, which is an IgG4 with reduced effector function | NLVPMVATVGCGGSGGGGSGGGGSIQRTPKIQVYSRHPAENGKS NFLNCYVSGFHPSDIEVDLLKNGERIEKVEHSDLSFSKDWSFYL LYYTEFTPTEKDEYACRVNHVTLSQPKIVKWDRDMGGGGSGGGG SGGGGSGGGGSGSHSMRYFFTSVSRPGRGEPRFIAVGYVDDTQF VRFDSDAASQRMEPRAPWIEQEGPEYWDGETRKVKAHSQTHRVD LGTLRGCYNQSEAGSHTVQRMYGCDVGSDWRFLRGYHQYAYDGK DYIALKEDLRSWTAADMAAQTTKHKWEAAHVAEQLRAYLEGTCV EWLRRYLENGKETLQRTDAPKTHMTHHAVSDHEATLRCWALSFY PAEITLTWQRDGEDQTQDTELVETRPAGDGTFQKWAAVVVPSGQ EQRYTCHVQHEGLPKPLTLRWEPGGGGSGGGGSGGGGSGGGGSE SKYGPPCPPCPAPPVAGPSVFLFPPKPKDTLMISRTPEVTCVVV DVSQEDPEVQFNWYVDGVEVHNAKTKPREEQFNSTYRVVSVLTV LHQDWLNGKEYKCKVSNKGLPSSIEKTISKAKGQPREPQVYTLP PSQEEMTKNQVSLTCLVKGFYPSDIAVEWESNGQPENNYKTTPP VLDSDGSFFLYSRLTVDKSRWQEGNVFSCSVMHEALHNHYTQKS LSLSLGK (SEQ ID NO: 116) |
| T2-IL2M6 | CMVpp65_scpMHC-IL2 Mutein 6 | CMVpp65(495-503)-GCGGS-(GGGGS)2-hB2m-(GGGGS)4-hHLA.A2-(GGGGS)4-Fc-(GGGGS)3-hIL2(H16A, F42A)<br>(Also referred to as CMVpp65(495-503)-GCGGS-(GGGGS)2-hB2m-(GGGGS)4-hHLA.A2-(GGGGS)4-Fc-(GGGGS)3-hIL2(2m))<br>Fc is from SEQ ID NO: 31 of WO2014/121087, which is an IgG4 with reduced effector function | NLVPMVATVGCGGSGGGGSGGGGSIQRTPKIQVYSRHPAENGKS NFLNCYVSGFHPSDIEVDLLKNGERIEKVEHSDLSFSKDWSFYL LYYTEFTPTEKDEYACRVNHVTLSQPKIVKWDRDMGGGGSGGGG SGGGGSGGGGSGSHSMRYFFTSVSRPGRGEPRFIAVGYVDDTQF VRFDSDAASQRMEPRAPWIEQEGPEYWDGETRKVKAHSQTHRVD LGTLRGCYNQSEAGSHTVQRMYGCDVGSDWRFLRGYHQYAYDGK DYIALKEDLRSWTAADMAAQTTKHKWEAAHVAEQLRAYLEGTCV EWLRRYLENGKETLQRTDAPKTHMTHHAVSDHEATLRCWALSFY PAEITLTWQRDGEDQTQDTELVETRPAGDGTFQKWAAVVVPSGQ EQRYTCHVQHEGLPKPLTLRWEPGGGGSGGGGSGGGGSGGGGSE SKYGPPCPPCPAPPVAGPSVFLFPPKPKDTLMISRTPEVTCVVV DVSQEDPEVQFNWYVDGVEVHNAKTKPREEQFNSTYRVVSVLTV LHQDWLNGKEYKCKVSNKGLPSSIEKTISKAKGQPREPQVYTLP PSQEEMTKNQVSLTCLVKGFYPSDIAVEWESNGQPENNYKTTPP VLDSDGSFFLYSRLTVDKSRWQEGNVFSCSVMHEALHNHYTQKS LSLSLGKGGGGSGGGGSGGGGSAPTSSSTKKTQLQLEALLLDLQ MILNGINNYKNPKLTRMLTAKFYMPKKATELKHLQCLEEELKPL EEVLNLAQSKNFHLRPRDLISNINVIVLELKGSETTFMCEYADE TATIVEFLNRWITFCQSIISTLT (SEQ ID NO: 117) |
| T3-IL2M3 | HPV16E7_scpMHC-IL2 Mutein 3 | HPV16E7(11-19)-GCGGS-(GGGGS)2-hB2m-(GGGGS)4-hHLA.A2-(GGGGS)4-Fc-hIL-2Rα-hIL2<br>Fc is from SEQ ID NO: 31 of WO2014/121087, which is an IgG4 with reduced effector function | YMLDLQPETGCGGSGGGGSGGGGSIQRTPKIQVYSRHPAENGKS NFLNCYVSGFHPSDIEVDLLKNGERIEKVEHSDLSFSKDWSFYL LYYTEFTPTEKDEYACRVNHVTLSQPKIVKWDRDMGGGGSGGGG SGGGGSGGGGSGSHSMRYFFTSVSRPGRGEPRFIAVGYVDDTQF VRFDSDAASQRMEPRAPWIEQEGPEYWDGETRKVKAHSQTHRVD LGTLRGCYNQSEAGSHTVQRMYGCDVGSDWRFLRGYHQYAYDGK DYIALKEDLRSWTAADMAAQTTKHKWEAAHVAEQLRAYLEGTCV EWLRRYLENGKETLQRTDAPKTHMTHHAVSDHEATLRCWALSFY PAEITLTWQRDGEDQTQDTELVETRPAGDGTFQKWAAVVVPSGQ EQRYTCHVQHEGLPKPLTLRWEPGGGGSGGGGSGGGGSGGGGSE SKYGPPCPPCPAPPVAGPSVFLFPPKPKDTLMISRTPEVTCVVV DVSQEDPEVQFNWYVDGVEVHNAKTKPREEQFNSTYRVVSVLTV LHQDWLNGKEYKCKVSNKGLPSSIEKTISKAKGQPREPQVYTLP PSQEEMTKNQVSLTCLVKGFYPSDIAVEWESNGQPENNYKTTPP VLDSDGSFFLYSRLTVDKSRWQEGNVFSCSVMHEALHNHYTQKS LSLSLGKGGGGSGGGGSGGGGSELCDDDPPEIPHATFKAMAYKE GTMLNCECKRGFRRIKSGSLYMLCTGNSSHSSWDNQCQCTSSAT RNTTKQVTPQPEEQKERKTTEMQSPMQPVDQASLPGHCREPPPW ENEATERIYHFVVGQMVYYQCVQGYRALHRGPAESVCKMTHGKT |

TABLE 5B-continued

| Molecule | Alternate Name | Description | Sequence |
|---|---|---|---|
| | | | RWTQPQLICTGGGGSGGGGSGGGGSGGGGSGGGGSAPTSSSTK KTQLQLEHLLLDLQMILNGINNYKNPKLTRMLTFKFYMPKKATE LKHLQCLEEELKPLEEVLNLAQSKNFHLRPRDLISNINVIVLEL KGSETTFMCEYADETATIVEFLNRWITFCQSIISTLT (SEQ ID NO: 118) |
| T3-IL2M6 | HPV16E7_scpMHC-IL2 Mutein 6 | HPV16E7(11-19)-GCGGS-GGGGS)₂-(hB2m-(GGGGS)₄-hHLA.A2-(GGGGS)₄-Fc-(GGGGS)₃-hIL2(H16A, F42A) (Also referred to as HPV16E7(11-19)-GCGGS-(GGGGS)₂-hB2m-(GGGGS)₄-hHLA.A2-(GGGGS)₄-Fc-(GGGGS)₃-hIL2(2m)) Fc is from SEQ ID NO: 31 of WO2014/121087, which is an IgG4 with reduced effector function | YMLDLQPETGCGGSGGGGSGGGGSIQRTPKIQVYSRHPAENGKS NFLNCYVSGFHPSDIEVDLLKNGERIEKVEHSDLSFSKDWSFYL LYYTEFTPTEKDEYACRVNHVTLSQPKIVKWDRDMGGGGSGGGGG SGGGGSGGGGSGSHSMRYFFTSVSRPGRGEPRFIAVGYVDDTQF VRFDSDAASQRMEPRAPWIEQEGPEYWDGETRKVKAHSQTHRVD LGTLRGCYNQSEAGSHTVQRMYGCDVGSDWRFLRGYHQYAYDGK DYIALKEDLRSWTAADMAAQTTKHKWEAAHVAEQLRAYLEGTCV EWLRRYLENGKETLQRTDAPKTHMTHHAVSDHEATLRCWALSFY PAEITLTWQRDGEDQTQDTELVETRPAGDGTFQKWAAVVVPSGQ EQRYTCHVQHEGLPKPLTLRWEPGGGGSGGGGSGGGGSGGGGSE SKYGPPCPPCPAPPVAGPSVFLFPPKPKDTLMISRTPEVTCVVV DVSQEDPEVQFNWYVDGVEVHNAKTKPREEQFNSTYRVVSVLTV LHQDWLNGKEYKCKVSNKGLPSSIEKTISKAKGQPREPQVYTLP PSQEEMTKNQVSLTCLVKGFYPSDIAVEWESNGQPENNYKTTPP VLDSDGSFFLYSRLTVDKSRWQEGNVFSCSVMHEALHNHYTQKS LSLSLGKGGGGSGGGGSGGGGSAPTSSSTKKTQLQLEALLLDLQ MILNGINNYKNPKLTRMLTAKFYMPKKATELKHLQCLEEELKPL EEVLNLAQSKNFHLRPRDLISNINVIVLELKGSETTFMCEYADE TATIVEFLNRWITFCQSIISTLT (SEQ ID NO: 119) |
| T4-IL2M6 | Ova_scpMHC-IL2 Mutein 6 | OVA(257-264)-GCGGS-(GGGGS)2-mB2m-(GGGGS)₄-mH2Kb-(GGGGS)₄-Fc-(GGGGS)₃-hIL2(H16A, F42A) (Also referred to as OVA(257-264)-GCGGS-(GGGGS)₂-mB2m-(GGGGS)₄-mH2Kb-(GGGGS)₄-Fc-(GGGGS)₃-hIL2(2m)) Fc is from SEQ ID NO: 31 of WO2014/121087, which is an IgG4 with reduced effector function | SIINFEKLGCGGSGGGGSGGGGSIQKTPQIQVYSRHPPENGKPN ILNCYVTQFHPPHIEIQMLKNGKKIPVEMSDMSFSKDWSFYIL AHTEFTPTETDTYACRVKHASMAEPKTVYWDRDMGGGGSGGGGS GGGGSGGGGSGPHSLRYFVTAVSRPGLGEPRYMEVGYVDDTEFV RFDSDAENPRYEPRARWMEQEGPEYWERETQKAKGNEQSFRVDL RTLLGCYNQSKGGSHTIQVISGCEVGSDGRLLRGYQQYAYDGCD YIALNEDLKTWTAADMAALITKHKWEQAGEAERLRAYLEGTCVE WLRRYLKNGNATLLRTDSPKAHVTHHSRPEDKVTLRCWALGFYP ADITLTWQLNGEELIQDMELVETRPAGDGTFQKWASVVVPLGKE QYYTCHVYHQGLPEPLTLRWEPPPSTVSNMAGGGGSGGGGSGGG GSGGGGSESKYGPPCPPCPAPPVAGPSVFLFPPKPKDTLMISRT PEVTCVVVDVSQEDPEVQFNWYVDGVEVHNAKTKPREEQFNSTY RVVSVLTVLHQDWLNGKEYKCKVSNKGLPSSIEKTISKAKGQPR EPQVYTLPPSQEEMTKNQVSLTCLVKGFYPSDIAVEWESNGQPE NNYKTTPPVLDSDGSFFLYSRLTVDKSRWQEGNVFSCSVMHEAL HNHYTQKSLSLSLGKGGGGSGGGGSGGGGSAPTSSSTKKTQLQL EALLLDLQMILNGINNYKNPKLTRMLTAKFYMPKKATELKHLQC LEEELKPLEEVLNLAQSKNFHLRPRDLISNINVIVLELKGSETT FMCEYADETATIVEFLNRWITFCQSIISTLT (SEQ ID NO: 120) |
| T5-IL2M6 | MuLV p15E_scpMHC-IL2 Mutein 6 | MuLV p15E-GCGGS-(GGGGS)₂-mB2m-(GGGGS)₄-mH2Kb-(GGGGS)₄-Fc-(GGGGS)3-hIL2(H16A, F42A) (Also referred to as MuLV p15E-GCGGS-(GGGGS)2-mB2m-(GGGGS)₄-mH2Kb-(GGGGS)₄-Fc-(GGGGS)₃-hIL2(2m)) Fc is from SEQ ID NO: 31 of WO2014/121087, which is an IgG4 with reduced effector function | KSPWFTTLGCGGSGGGGSGGGGSIQKTPQIQVYSRHPPENGKPN ILNCYVTQFHPPHIEIQMLKNGKKIPVEMSDMSFSKDWSFYIL AHTEFTPTETDTYACRVKHASMAEPKTVYWDRDMGGGGSGGGGS GGGGSGGGGSGPHSLRYFVTAVSRPGLGEPRYMEVGYVDDTEFV RFDSDAENPRYEPRARWMEQEGPEYWERETQKAKGNEQSFRVDL RTLLGCYNQSKGGSHTIQVISGCEVGSDGRLLRGYQQYAYDGCD YIALNEDLKTWTAADMAALITKHKWEQAGEAERLRAYLEGTCVE WLRRYLKNGNATLLRTDSPKAHVTHHSRPEDKVTLRCWALGFYP ADITLTWQLNGEELIQDMELVETRPAGDGTFQKWASVVVPLGKE QYYTCHVYHQGLPEPLTLRWEPPPSTVSNMAGGGGSGGGGSGGG GSGGGGSESKYGPPCPPCPAPPVAGPSVFLFPPKPKDTLMISRT PEVTCVVVDVSQEDPEVQFNWYVDGVEVHNAKTKPREEQFNSTY RVVSVLTVLHQDWLNGKEYKCKVSNKGLPSSIEKTISKAKGQPR EPQVYTLPPSQEEMTKNQVSLTCLVKGFYPSDIAVEWESNGQPE NNYKTTPPVLDSDGSFFLYSRLTVDKSRWQEGNVFSCSVMHEAL HNHYTQKSLSLSLGKGGGGSGGGGSGGGGSAPTSSSTKKTQLQL EALLLDLQMILNGINNYKNPKLTRMLTAKFYMPKKATELKHLQC LEEELKPLEEVLNLAQSKNFHLRPRDLISNINVIVLELKGSETT FMCEYADETATIVEFLNRWITFCQSIISTLT (SEQ ID NO: 121) |
| T6-IL2M3 | Anti-mLAG3-IL2 Mutein 3 | IL2 Mutein 3 with an N-terminal anti-LAG3 antibody | IL2 Mutein 3 was linked to the C-terminal of the heavy chain of an anti-LAG3 antibody via a (GGGGS)3 linker (SEQ ID NO: 6). |

7.1.2. Intracellular Staining of pSTAT5 on Human PBMCs

Cryopreserved human PBMCs were thawed and rested overnight in media without IL-2. The next day, cells were treated with serial dilutions of different IL-2 variants, then fixed with BD Cytofix™ fixation buffer at 37° C. for 12 min. Cells were then permeabilized with pre-chilled BD Phosflow™ Perm Buffer III for 20 min on ice. Cells were then washed twice with FACS buffer (PBS+2% FBS), followed by incubation with a staining cocktail containing Alexa Fluor® 647-conjugated anti-STAT5 pY694 (BD Biosciences) at room temperature for 45 min in the dark. To identity different lymphocyte populations in PBMCs, the following panel of antibodies were also included in the staining cocktail: BUV496-anti-CD8, BUV395-anti-CD4, BV421-anti-NKp46, BV711-anti-CD56, BV786-anti-CD3, Alexa Fluor® 488-anti-FoxP3, PE-anti-CD25 (BD Biosciences). Cells were washed twice with FACS buffer before data acquisition on a BD LSRFortessa™ X-20 flow cytometer. The raw data were analyzed using FlowJo v10.

7.1.3. Size-Exclusion Chromatography and Multiangle Light Scattering

Size-exclusion ultra-performance liquid chromatography (SEC) coupled with multiangle light scattering (MALS) were employed to assess the oligomeric state of different muteins. SEC analysis was conducted on a Waters Acquity UPLC H-Class system. 10 μg of each protein sample was injected into a two-column tandem setup consisting of Acquity BEH SEC columns (200 Å, 1.7 μm, 4.6×150 mm). Flow rate was set at 0.3 ml/min. Mobile phase buffer contains 10 mM sodium phosphate, 500 mM NaCl, pH 7.0. UV absorbance at 280 nm, light scattering and refractive index changes were monitored using Wyatt Optilab T-Rex and Wyatt-uDawn Treos LS Detector.

7.1.4. FACS Binding Assay

To analyze binding of antibody-IL2 muteins to target antigens on cell surface, HEK293 cell stably expressing antigen targets were collected and resuspended in FACS buffer (PBS+2% FBS). For each binding assay, 50,000-100,000 cells were incubated with serial dilutions of IL-2 muteins in FACS buffer at 4° C. for 30 minutes. Cells were then washed twice with FACS buffer, and incubated with 1:500 dilution of APC-F(ab)'2 anti-mouse IgG Fcγ fragment (Jackson ImmunoResearch Laboratories) for 30 minutes at 4° C. At the end of the incubation, cells were washed twice with FACS buffer and analyzed on BD FACSCelesta™ flow cytometer.

7.1.5. Tumor Inoculation, Treatment and Measurement

A total of $3 \times 10^5$ MC38 cells were injected subcutaneously (s.c.) into the flank of 6-8 weeks old female C57BL/6J mice (Jackson Laboratory). Mice were randomized when tumor size reached 80-100 mm³ and were treated intraperitoneally with different IL-2/IL-15 agonists.

The treatments were repeated four more times every other day or semiweekly. Tumors were measured semiweekly using a digital caliper and the tumor sizes were calculated as length x width²/2. In tumor studies where survival were recorded, loss of survival was defined as death or when tumor reached 20 mm in any dimension or 2250 mm³ in total volume.

7.1.6. FACS Analyses of Tumor, Spleen and Blood

Tumors were harvested and processed using gentle MACS™ dissociator (Miltenyi Biotec.) to generate single-cell suspensions. The cells were counted and then stained with a cocktail of fluorescently-labeled antibodies diluted in BD Horizon Brilliant Buffer.

Spleen and blood were collected from tumor- or non-tumor-bearing mice after treatment with IL2 muteins. Spleens were mashed through a 70-μm Corning® cell strainer to generate single-cell suspensions. Spleen and blood were then treated with ACK lysing buffer (Lonza) to lyse red blood cells (RBCs). After RBC lysis, lymphocytes were counted and stained with antibody cocktails diluted in BD Horizon Brilliant Buffer. All stained samples were analyzed on a BD LSRFortessa™ X-20 flow cytometer. The raw data were processed using FlowJo v10.

7.1.7. Antigen-Specific T cells and Chimeric Antigen Receptor (CAR) T-Cell

Ovalbumin (257-264)-specific mouse OT-1 T cells were isolated from the spleen of an OT-1 TCR transgenic mouse (Jackson Laboratory). CMV pp65(495-503)-specific human T cells were expanded from the PBMCs of a CMV+ donor and obtained from ASTARTE Biologics (Cat. #1049). CAR T cells were generated by stimulating CD3+ T cells with CD3/CD28 microbeads plus 100 U/ml recombinant human IL2 prior to transduction with lentivirus at an MOI=5. The transduced cells were then expanded for 17 days with CD3/CD28 microbeads plus 100 U/ml recombinant human IL2 before exchanging media with CTS supplemented OpTmizer™ media (Gibco) lacking IL2. Following an overnight culture at 37° C. and 5% $CO_2$, a pSTAT5 assay was performed as described in Section 7.1.2.

7.2. Example 1: Activity of IL-2Rα Attenuated IL2 Muteins In Vitro

Figure 4C:
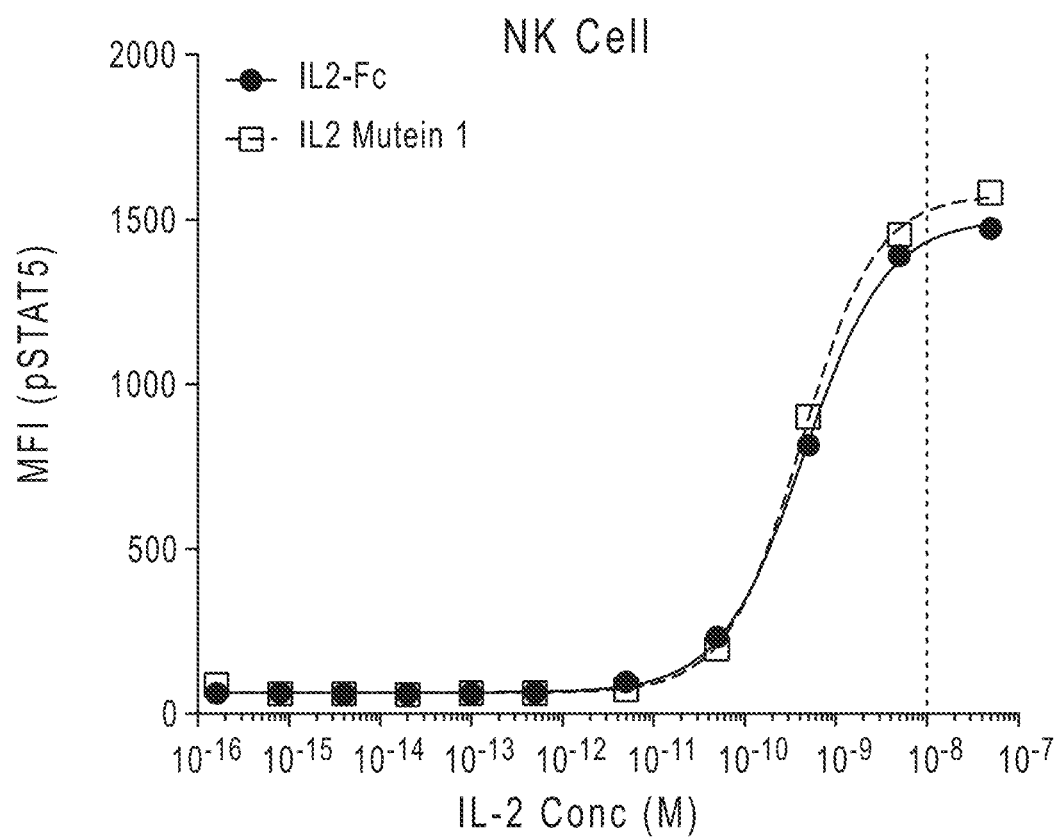

To test the ability of IL2 M1 to trigger IL2 receptor signaling in various immune cell populations, $4 \times 10^5$ human PBMCs were stimulated with increasing concentrations of IL2M0 or IL2M1 for 20 min at 37° C. As an indicator of IL2 receptor-mediated signaling, levels of intracellular STAT5 phosphorylation were measured by flow cytometry in immune cell subsets as described in Section 7.1.2. FIGS. 4A-4C show STAT5 activity in gated Tregs (FIG. 4A), CD8+ T cells (FIG. 4B) and NK cells (FIG. 4C). Compared to IL2M0, IL2 M1 remains equally active on CD8+ T and NK cells which lack detectable IL-2Rα expression. However, its activity on IL-2Rα+ Tregs is several orders of magnitude lower than that of IL2-Fc. Therefore, IL2M1 loses the preferentially activity on Tregs over other effector cell populations in vitro.

Figure 5A:
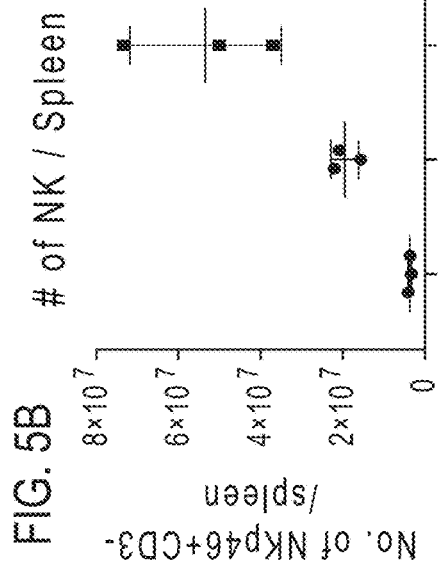
FIGS. 5A-5D show selective expansion of NK (FIG. 5B) and CD8+ T cells (FIG. 5C-5D) relative to Tregs (FIG. 5A) by IL2M1 in vivo, whereas IL2M0 (referred to as IL2-Fc in figure) preferentially expands Tregs (FIGS. 5A-5D).
Figure 5C:
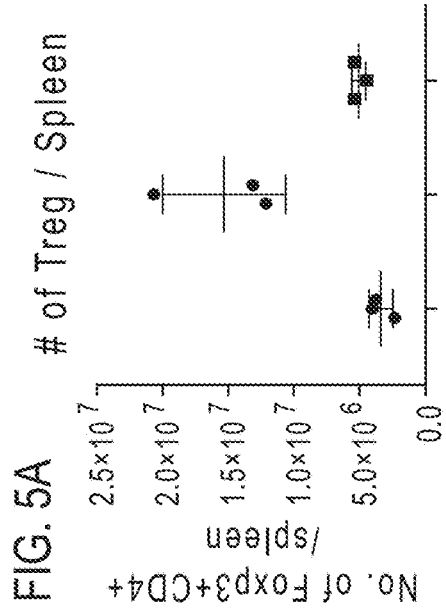
Figure 5B:
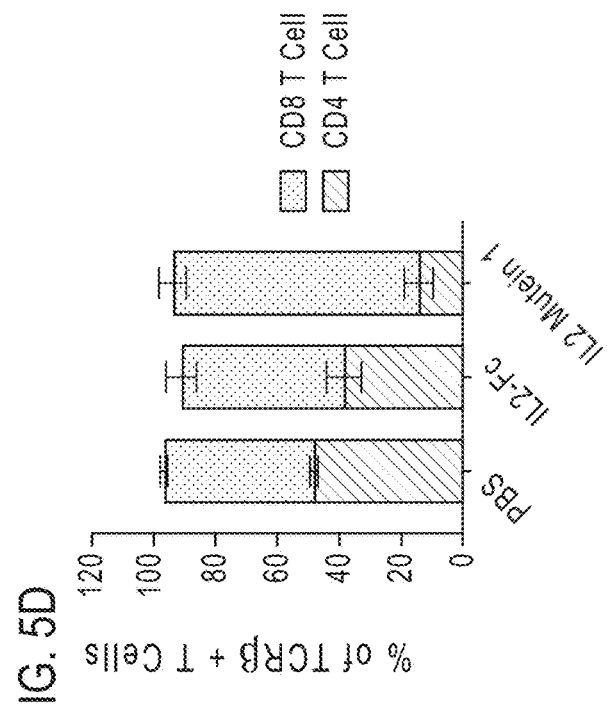
Figure 5D:
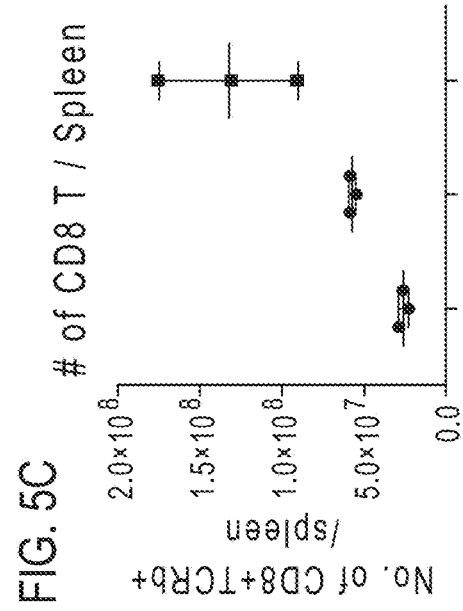

7.3. Example 2: Activity of IL-2Rα Attenuated IL2 Muteins on Immune Cell Populations In Vivo C57BL/6J mice received daily intraperitoneal injection of PBS, 15 μg IL2M0 or IL2M1 for six consecutive days. One day after the last injection, spleens were harvested for flow cytometric analysis. Numbers of Tregs, NK cells and CD8+ T cells in the spleens of treated mice are shown in FIGS. 5A-5C, respectively. Relative frequencies of CD8+ and CD4+ T cells within TCRβ+ T cells were quantified (FIG. 5D).

While IL2M0 (IL2-Fc) preferentially expands Tregs in vivo, such Treg-selectivity was abolished in IL2M1 (a CD122-biased human IL2-Fc fusion). In contrast, IL2M1 induces specific expansion of NK and CD8+ T cells with minimal effect on the Treg population. Thus, IL2M1 can remodel the peripheral lymphocyte compartment by selectively expanding the effector cell populations.

7.4. Example 3: Anti-Tumor Activity of IL2 and IL-2Rα Attenuated IL2 Muteins as Monotherapies and in Combination with Anti-PD1

Figure 6A:
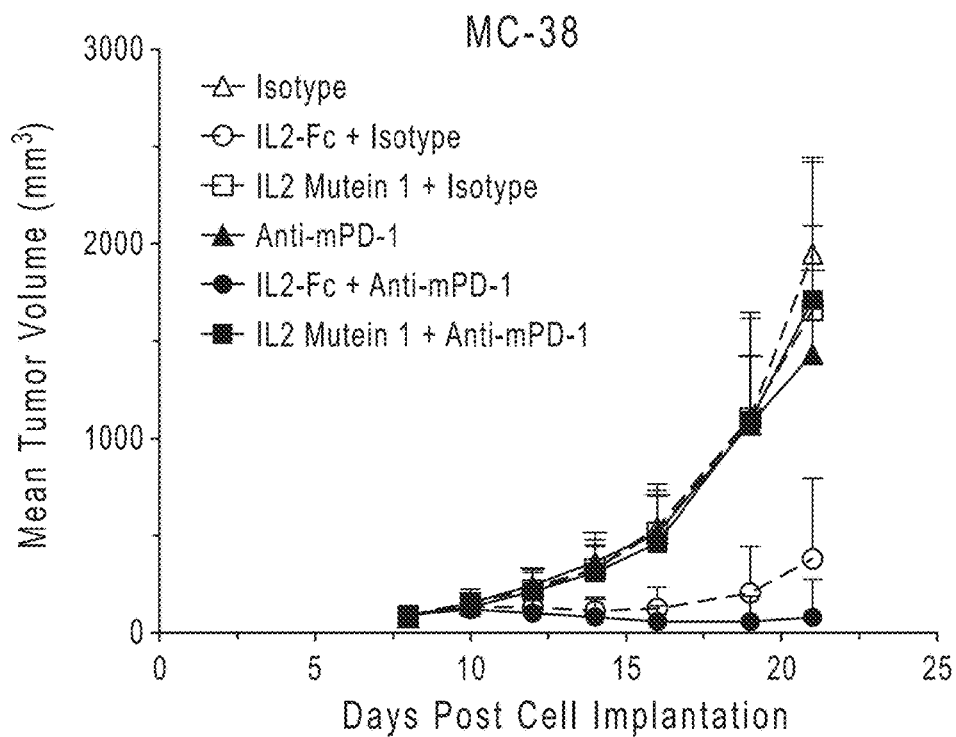
FIGS. 6A-6B show average tumor volumes (mm³+SD) (FIG. 6A) and Kaplan-Meier survival curves (FIG. 6B) of mice treated with IL2 muteins and/or anti-PD1 antibodies.
Figure 6B:
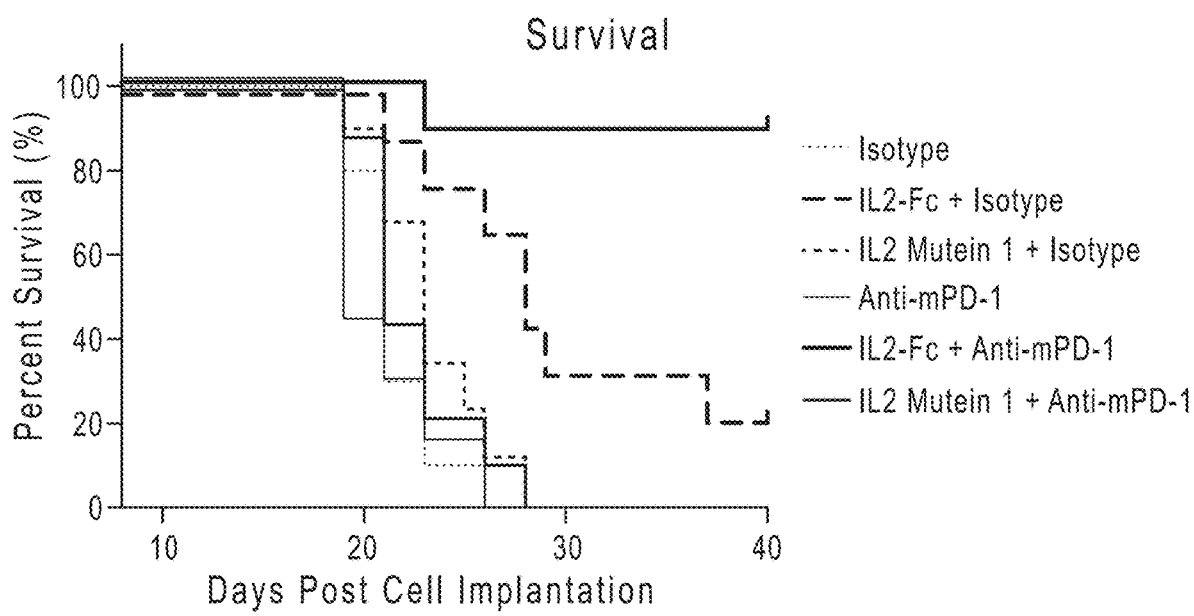

C57BL/6J mice were inoculated s.c. with $3 \times 10^5$ MC38 tumor cells on day 0 and were randomized on day 8 when average tumor size reached 100 mm$^3$. Mice were then treated intraperitoneally with isotype (10 mg/kg), IL2M0 (0.75 mg/kg)+isotype (10 mg/kg), IL2M1 (0.75 mg/kg)+ isotype (10 mg/kg), anti-mPD1 (10 mg/kg), IL2M0 (0.75 mg/kg)+anti-mPD1 (10 mg/kg), or IL2M1 (0.75 mg/kg)+ anti-mPD1 (10 mg/kg) every other day (for IL2M0 and IL2M1) or semi-weekly (for isotype and anti-mPD1) for five total injections. FIG. 6 shows average tumor volumes (mm$^3$+SD) (FIG. 6A) and Kaplan-Meier survival curves (FIG. 6B) in each treatment group. Loss of survival was defined as death or when tumor reached 20 mm in any dimension or 2250 mm$^3$ in total volume.

As a monotherapy, IL2M0 (IL2-Fc) significantly inhibits the progression of established tumors. Combining it with anti-PD1 further synergistically promotes tumor regression and the durability of tumor-free survival. Surprisingly, despite its ability to specifically expand NK and CD8+ T cells, the CD122-biased IL2M1 displays little antitumor effect, even in the presence of anti-PD1.

7.5. Example 4: Dosing Study of IL2M0

C57BL/6J mice were inoculated s.c. with 3×10$^5$ MC38 tumor cells on day 0 and were randomized on day 8 when average tumor size reached 90 mm$^3$. Mice were then treated intraperitoneally with indicated doses of IL2M0 every other day for five total injections. FIG. 7 shows average tumor volumes (mm$^3$+SD) (FIG. 7A), Kaplan-Meier survival curves (FIG. 7B), and individual tumor growth curve (7C.1-7C.5). Loss of survival was defined as death or when tumor reached 20 mm in any dimension or 2250 mm$^3$ in total volume.

This study shows that the anti-tumor efficacy of IL2M0 is highly dependent on the dose injected, with the highest dose being most efficacious. Effect was observed starting from 5 μg/dose, and increasing the dose to 10 μg and 20 μg/dose resulted in better tumor control and survival benefit.

7.6. Example 5: Anti-Tumor Activity and Toxicity of IL2M1 as Compared to IL2M0

In two different studies, C57BL/6J mice were inoculated s.c. with 3×10$^5$ MC38 tumor cells on day 0 and were randomized on day 8 when average tumor size reached 90 mm$^3$ (study #1), or on 7 when average tumor size reached 70 mm$^3$ (study #2). Mice were then treated intraperitoneally with indicated doses of IL2M0 or IL2 M1 every other day for five total injections. Average tumor volumes (mm$^3$+SD) (FIG. 8A-8B, showing results of study #1 and study #2, respectively) and percentage of body weight changes (FIG. 8C, from study #2) for each treatment group were shown. Arrows indicate the days of treatment.

IL2M1 remained ineffective in controlling tumor progression up to 40 ug/dose, whereas 10 μg/dose of IL2M0 resulted in significant delay of tumor growth (FIG. 8A). Modest efficacy was observed when IL2M1 was dosed at 75 or 100 μg/dose (FIG. 8B). However, at these doses, it caused severe toxicity including significant weight loss (FIG. 8C), hypoactivity and increased mortality rate. It remains to be determined if the efficacy observed in high dose IL2M1 groups was caused by anti-tumor immunity or tumor malnutrition resulting from the sickness of the host mice.

Despite being less effective than the 10 μg/dose of IL2M0 in controlling tumor growth, the 100 μg/dose of IL2M1 did induce massive expansion of peripheral NK and CD8+ T cells, with a less profound effect on Tregs than that induced by the 10 μg/dose of IL2M0. However, such massive expansion of peripheral effector cell populations did not translate into a more effective antitumor response.

7.7. Example 6: Anti-Tumor Activity and Toxicity of an IL15 Mutein

IL15 shares the same β/γ receptor subunits with IL2, but it does not bind to IL2-Rα. IL15 is usually expressed as part of an IL15/IL15Rα complex on the surface of myeloid cells which is then presented to activate surrounding lymphocytes (FIG. 1). IL15M1, which is comprises an IL15-IL15Rα fusion, is believed to mimic the trans-presentation of IL15 by IL15Rα and specifically engage IL-2Rβ/γ, thus triggering similar signaling as IL2-Rα-attenuated IL2 muteins (e.g., IL2M1).

The anti-tumor activity and toxicity of IL15M1 were tested. C57BL/6J mice were inoculated s.c. with 3×10$^5$ MC38 tumor cells on day 0 and were randomized on day 7 when average tumor size reached 70 mm$^3$. Mice were then treated intraperitoneally with indicated doses of IL2M0 and IL15M1 every other day for five total injections. FIG. 9 shows average tumor volumes (mm$^3$+SD) (FIG. 9A) and percentage of body weight changes (FIG. 9B) in each treatment group. Arrows indicate the days of treatment. At day 11, blood from indicated groups were collected and analyzed by flow cytometry, as described in Section 7.1.6. Counts of indicated lymphocyte populations were quantified (FIGS. 9C.1-C.4).

A modest, yet dose-dependent anti-tumor efficacy was observed after IL15M1 treatment (FIG. 9A). However, similar to IL2M1, IL15M1 treatment brought about concurrent, dose-dependent toxicity in the tumor-bearing mice (FIG. 9B). IL15M1 also induced a dramatic expansion of peripheral lymphocytes, mostly NK and CD8+ T cells, but not Tregs in the blood of these tumor-bearing mice (FIGS. 9C.1-C.4). Together with the example of IL2M1, these results indicate that selectively agonizing the IL-2Rβ/γ receptor, whether by a mutant IL2 with abolished IL-2Rα binding or an IL15 mutein, has a suboptimal therapeutic index—limited efficacy in relation to toxicity. It also suggests that peripheral NK and CD8+ T cells expanded by IL2M1 and IL15M1 are inefficient in controlling tumor growth.

Figure 10B:
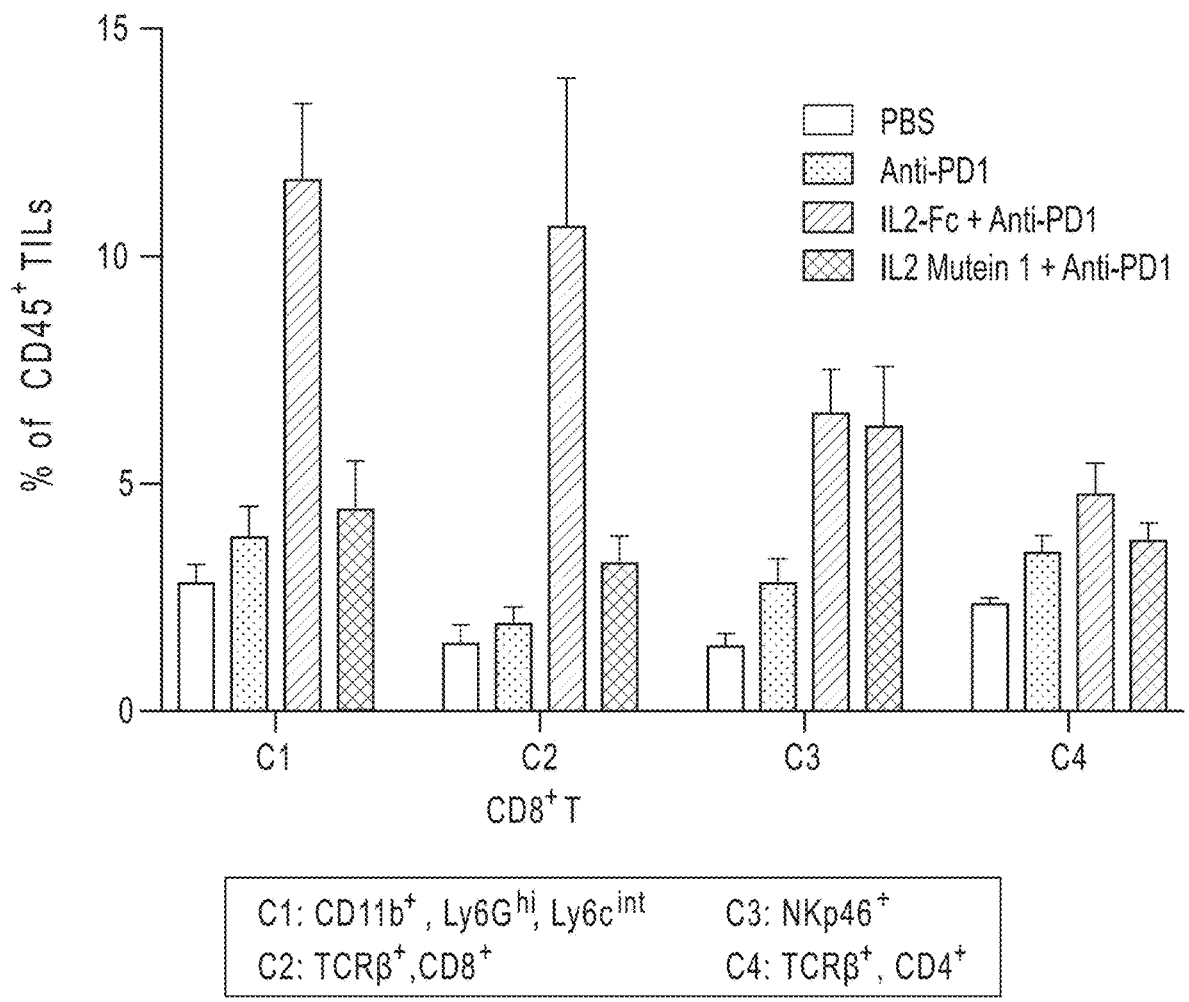

7.8. Example 7: Activity of IL-2Rα Attenuated IL2 Muteins on Intratumoral Lymphocytes C57BL/6J mice were inoculated s.c. with 3×10$^5$ MC38 tumor cells on day 0 and were randomized on day 7 when average tumor size reached 100 mm$^3$. Mice were then treated intraperitoneally with PBS, anti-mPD1 (10 mg/kg), IL2M0 (0.75 mg/kg)+anti-mPD1 (10 mg/kg), or IL2M1 (0.75 mg/kg)+anti-mPD1 (10 mg/kg) every other day. After three total doses, tumors were harvested on day 12 to isolate and analyze tumor-infiltrating lymphocytes (TILs). FIGS. 10A.1 to 10A.5 show density tSNE plots of total CD45$^+$ TILs from each treatment group. Results of quantification of the percentage of clusters 1-4 highlighted in FIGS. 10A.1 to 10A.5 within total TILs are shown in FIG. 10B. tSNE plots of total TILs overlaid with the expression of the defining markers for different lymphocyte populations are shown in FIGS. 10C.1 to 10C.7. These results show that IL2M0 induces a more pronounced expansion of CD8+ T cells in the tumor than IL2M1.

TCRβ$^+$ T cells were further gated out from total TILs. Representative FACS plots and quantification of the frequencies of Ki67$^+$IL-2Rα$^+$ cells within CD8$^+$ T cells in the tumor after each treatment are shown in FIG. 10D and FIG. 10E, respectively. Results of quantification of the densities of Ki67+IL-2Rα+CD8+ T cells in the tumor are shown in FIG. 10F. Representative FACS plots and quantification of the frequencies of FoxP3+IL-2Rα+ Tregs within CD4+ T cells in the tumor are shown in FIG. 10G and FIG. 10H. Results of quantification of the densities of FoxP3+IL-2Rα+ CD4+ Tregs in the tumor are shown in FIG. 10I. These results show that IL2M0, but not IL2M1, increases proliferating IL-2Rα+CD8+ T cells relative to Tregs in the tumor.

Figure 10J:
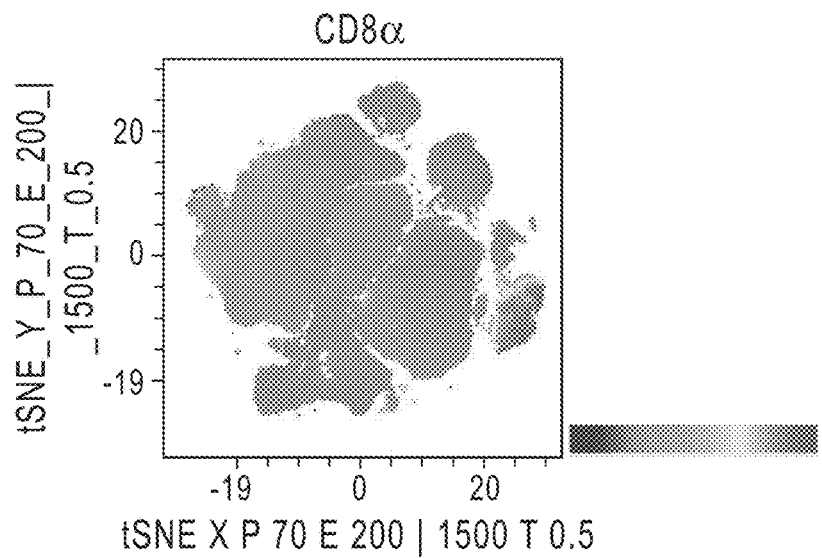
Figure 10K:
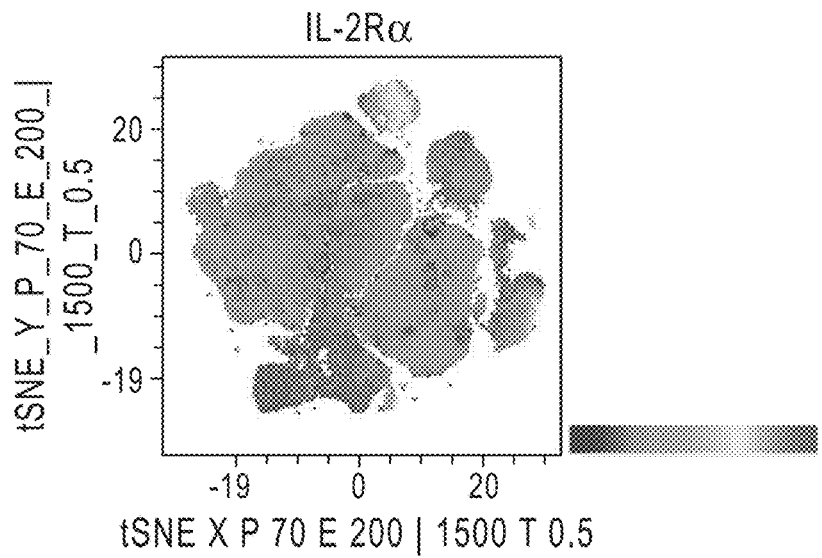
Figure 10L:
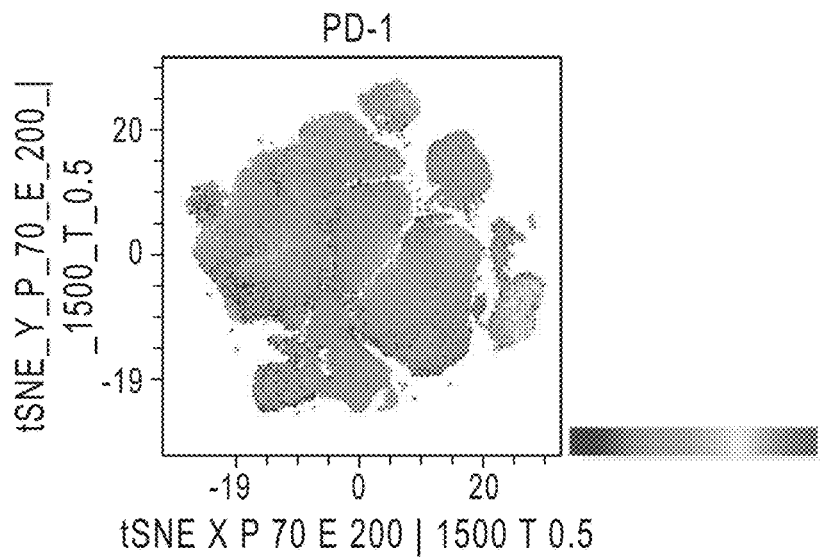

Expression of IL-2Rα and PD1 was evaluated in CD8+ TILs. tSNE plots of total CD45+ TILs were overlaid with the expression of these markers, and results are shown in FIGS. 10J-10L. The expression profiles show a subpopulation of tumor-infiltrating CD8+ T cells that co-express IL-2Rα and PD1. These results show that IL-2Rα and PD1 are co-expressed on some intratumoral CD8+ T cells in the tumor. Given the dynamic expression of these two proteins on antigen-specific CD8+ T cells after their activation, it is possible that their co-expression occurred on a broader population of CD8+ T cells at time points that were not captured here (Kalia et al., 2010, Immunity 32(1): 91-103).

Figure 10O:
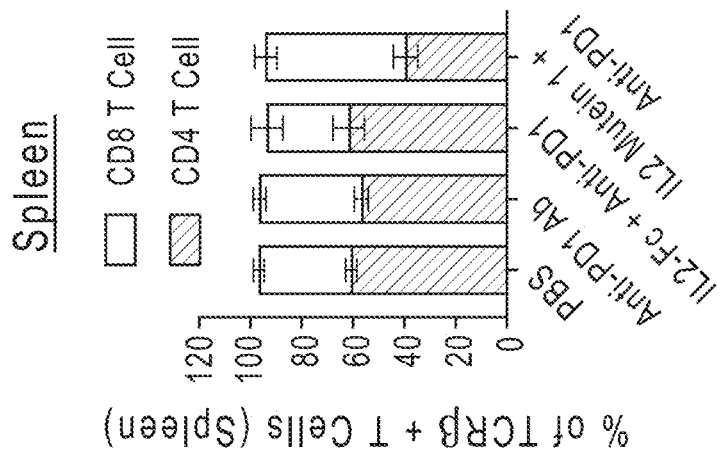
Figure 10N:
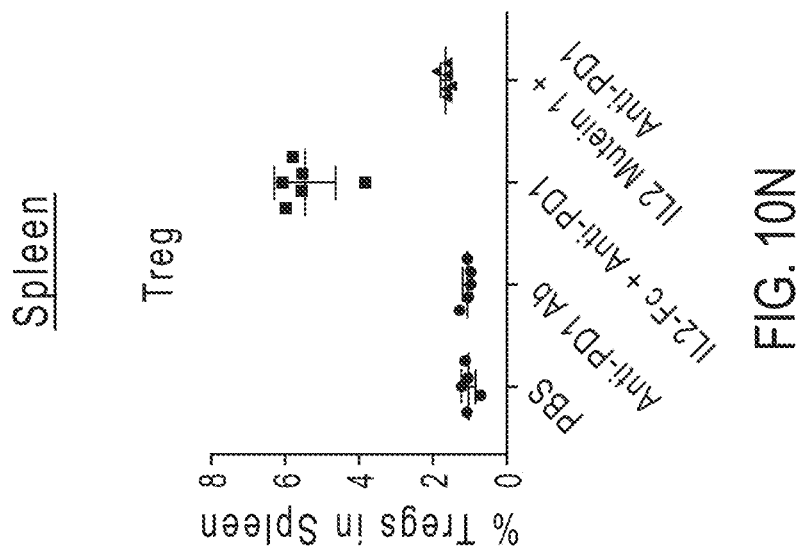
Figure 10M:
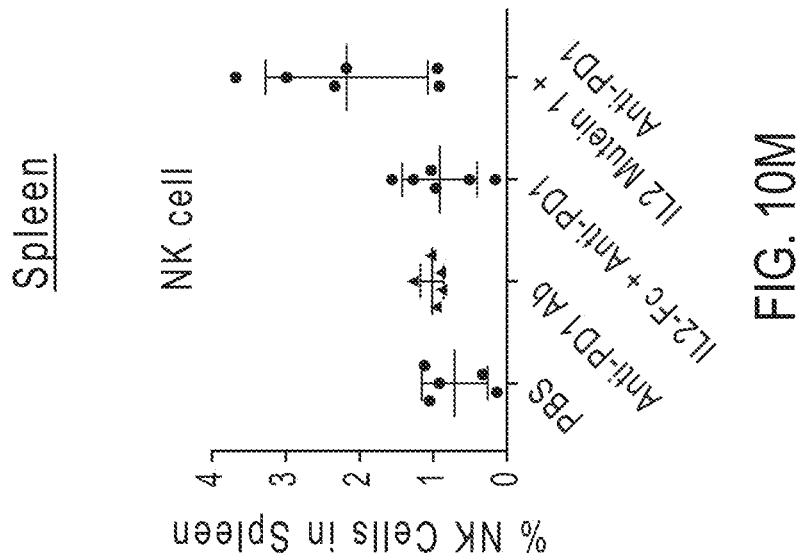
Figure 10R:
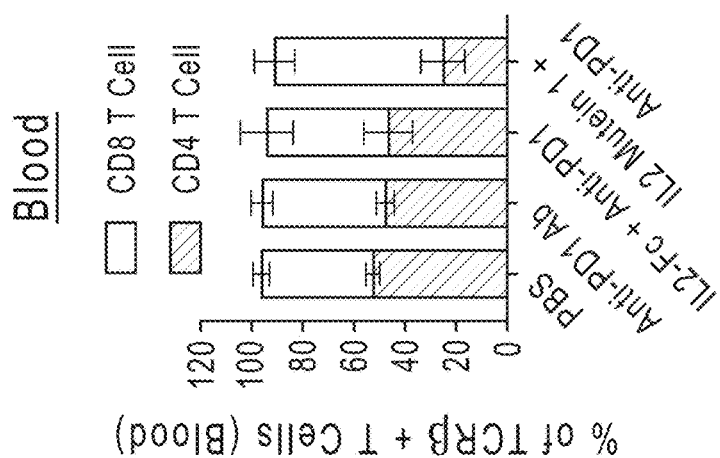
Figure 10Q:
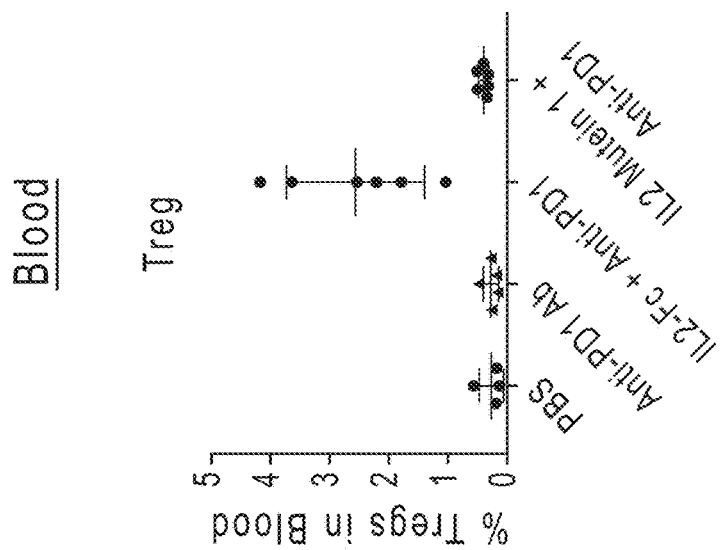
Figure 10P:
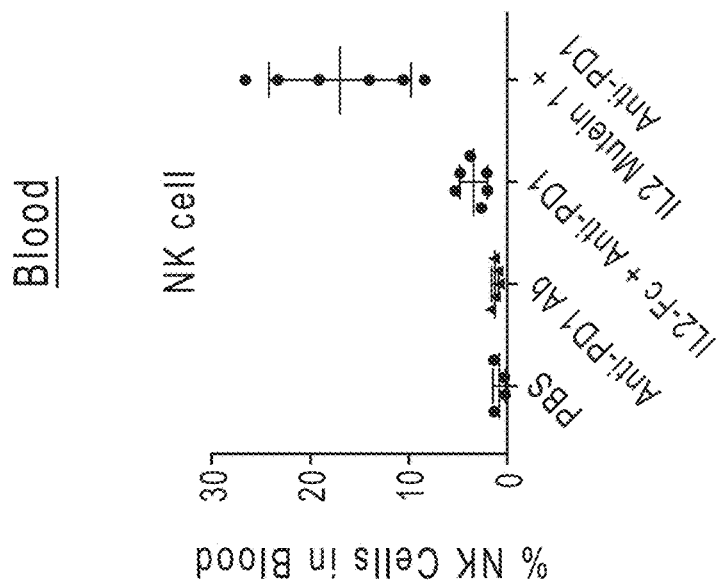

Blood and spleens were harvested from the same tumor-bearing mice for flow cytometric analysis, as described in Section 7.1.6. Results of quantification of the frequencies NK cells and Tregs in the spleen are shown in FIG. 10M and FIG. 10N. Results of quantification of the frequencies of NK cells and Tregs in the blood are shown in FIG. 10P and FIG. 10Q. Results of quantification of the relative frequencies of CD8+ and CD4+ T cells within TCRβ+ T cells in the spleen are shown in FIG. 10O and in the blood are shown in FIG. 10R. These results show that IL2M1 specifically expands NK and CD8+ T cells relative to Tregs, whereas IL2M0 preferentially expands Tregs in the spleen and blood.

The immune cell profiles induced by IL2M0 and IL2M1 are drastically different in the periphery vs. in the tumor: In the blood and spleen, IL2M0 preferentially expands Treg, whereas IL2M1 causes selective expansion of NK and CD8+ T cells. In the tumor, IL2M0 expands CD8+ T cells but not Tregs, whereas IL2M1 only slightly increases NK cells. These observations may explain why the massive expansion of peripheral NK and CD8+ T cells induced by IL-2Rα-attenuated IL2 muteins or IL15 variants does not translate into good anti-tumor responses, as such expansion is not extended to the tumor micro-environment. It also explains why IL2M0, which expands suppressive Tregs in the periphery, can induce effective antitumor immunity. When activated by antigens in the tumor, tumor-specific T cells upregulate their IL-2Rα, making them more sensitive to IL2M0 treatment. Together, these results suggest that preserving the ability to engage IL-2Rα is required for the anti-tumor efficacy of an IL2-related molecule.

7.9. Example 8: Tumor Tregs Are Less Responsive Than Splenic Tregs to IL2 Stimulation Tumor and spleen were harvested from MC38 tumor-bearing C57BL/6J mice to isolate lymphocytes as described in Section 7.1.6. Digested tumor cells were further subjected to MACS® Cell Separation with CD45 MicroBeads to enrich TILs and. 4×10⁵ TILs or 2×10⁶ splenocytes were stimulated in vitro with increasing concentrations of recombinant human IL2 for 20 min at 37° C. FIG. 11 shows percentage of cells that underwent STAT5 phosphorylation within gated Tregs (FIG. 11A) and CD8+ T cells (FIG. 11B) as determined by FACS according to the assay of Section 7.1.2.

Recombinant human IL2 showed similar EC50 on Tregs from the tumor and spleen. However, while IL2 was able to induce STAT5 phosphorylation in almost all splenic Tregs, only a fraction of tumor Tregs showed STAT5 phosphorylation after IL-2 stimulation. In contrast, CD8+ T cells from tumor respond to IL-2 treatment with a lower EC50 than those from the spleen. This result suggests tumor Tregs are less responsive than peripheral Tregs to IL2 stimulation, whereas tumor-infiltrating CD8+ T cells may be more sensitive to IL2 stimulation than their splenic counterparts. It also reveals a potential heterogeneity in the tumor Treg compartment.

7.10. Example 9: Activity of IL2M2 and IL2M3 on Lymphocyte Populations

Human PBMCs were stimulated with increasing concentrations of IL2M0, IL2M2 and IL2M3. Level of intracellular STAT5 phosphorylation was determined by FACS as described in Section 7.1.2 and results are shown in FIG. 12A for gated Tregs, FIG. 12B for CD8+ T cells, and FIG. 12C for NK cells.

IL2M2 and IL2M3 exhibited similar activities to each other on different lymphocyte populations. Compared to IL2M0, they showed reduced activities on all the cell types tested. Overall, they are attenuated on all IL2 receptors while still maintaining selectivity for IL-2Rα+ cells.

C57BL/6J mice were hydrodynamically injected with 5 μg of plasmid DNA encoding IL2M0, IL2M1, IL2M2 or IL2M3 at day 0. Proteins were continuously expressed and secreted by hepatocytes to maintain a stable serum concentration. Percentage of body weight changes for each treatment group following plasmid injection is shown in FIG. 12D. In contrast to IL2M0 and IL2M1, IL2M2 and ILM3 injection resulted in no detectable weight loss, suggestive of markedly reduced toxicity.

7.11. Example 10: Anti-Tumor Activity of IL2M2 Monotherapy in Syngeneic Mouse Models Balbc/J mice were inoculated s.c. with Colon 26 or 4T1 tumor cells on day 0 and were randomized on day 10 or 11 when average tumor size reached 80 mm³. Right after randomization, mice were hydrodynamically injected with indicated dose of plasmid DNA encoding human Fc or IL2M2 under the human ubiquitin C promoter. Proteins were continuously expressed and secreted by hepatocytes to maintain a stable serum concentration. Average tumor volumes in each treatment group were measured. Results (as mm³+SD) for the Colon 26 and 4T1 are shown in FIG. 13A and FIG. 13B. Arrows indicate the day of hydrodynamic injection.

C57BL/6J mice were inoculated s.c. with MC38 tumor cells on day 0 and were randomized on day 7 when average tumor size reached 80 mm³. Mice were then treated intraperitoneally with PBS control, IL2M0 (15 μg), or IL2M2 (50 μg) every three days for four total injections. Average tumor volumes were measured for each treatment group and results (as mm3+SD) are shown in FIG. 13C.

IL2M2 treatment, either by hydrodynamic delivery of DNA or protein injection, inhibited tumor progression in multiple syngeneic tumor models (FIG. 13). Despite being ~100× less potent than IL2M0 on multiple lymphocyte populations (FIG. 12A-C), a ~3× higher dose of IL2M2 was able to achieve comparable anti-tumor efficacy to IL2M0.

7.12. Example 11: Activity of IL2M4 and IL2M5 on Lymphocyte Populations

Human PBMCs were stimulated with increasing concentrations of IL2M4 (an Fc-IL2 fusion protein) or IL2M5. Level of intracellular STAT5 phosphorylation were measured by FACS as described in Section 7.1.2. Results are shown in FIG. 14 for gated Tregs (FIG. 14A), CD8+ T cells (FIG. 14B) and NK cells (FIG. 14C).

Compared to IL2M4, IL2M5 shows reduced activities on all the cell types tested. However, the degree of attenuation varied among different lymphocyte populations, with IL-2Rα– NK and CD8+ T cells being more affected than the IL-2Rα+ Tregs. Overall, IL2M5 is generally attenuated but has increased selectivity for IL-2Rα+ cells.

7.13. Example 12: Anti-Tumor Efficacy of IL2M5 Monotherapy

Figure 15A:
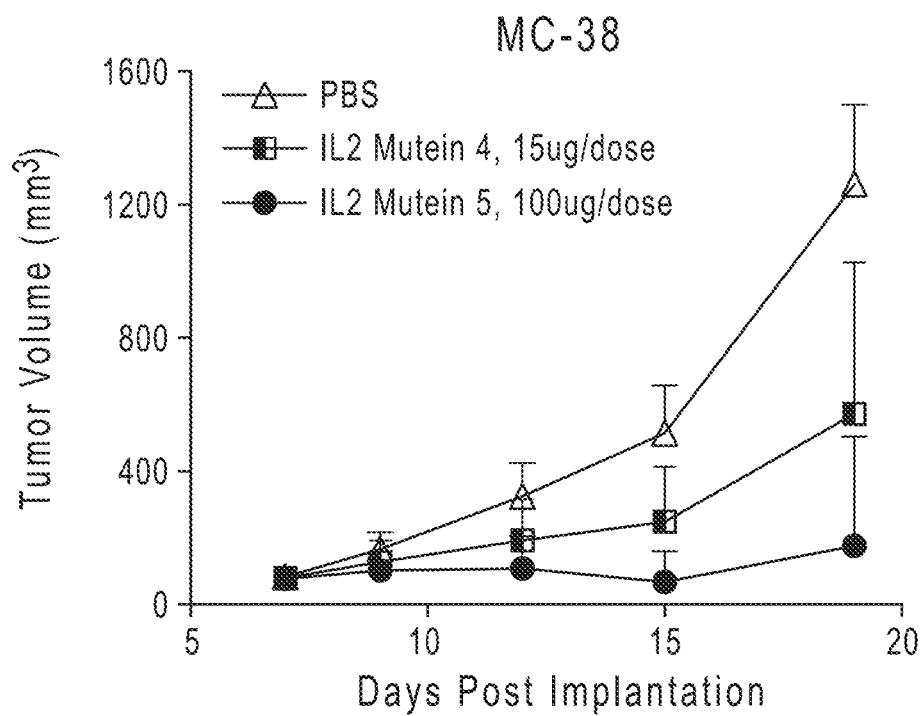
Figure 15B:
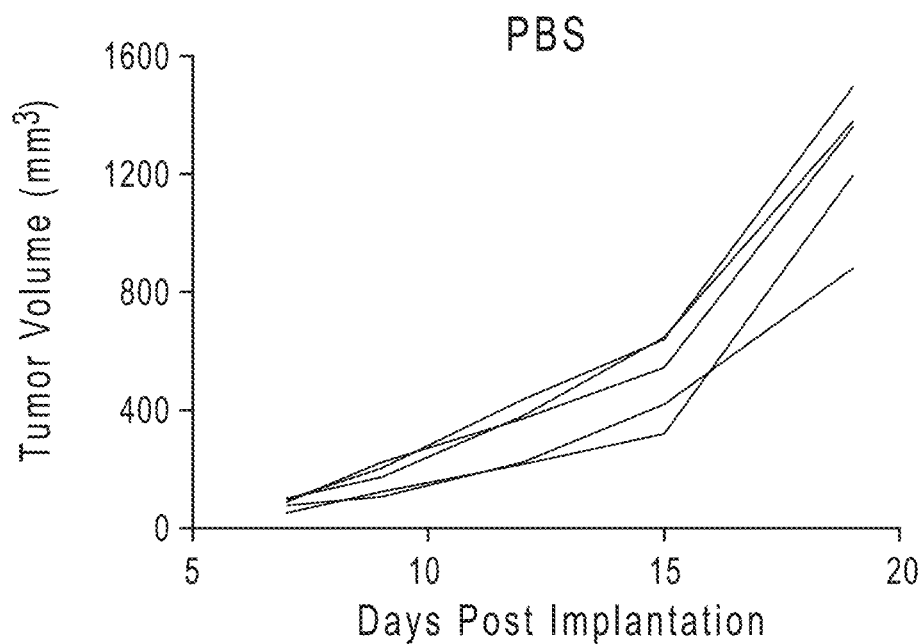
Figure 15C:
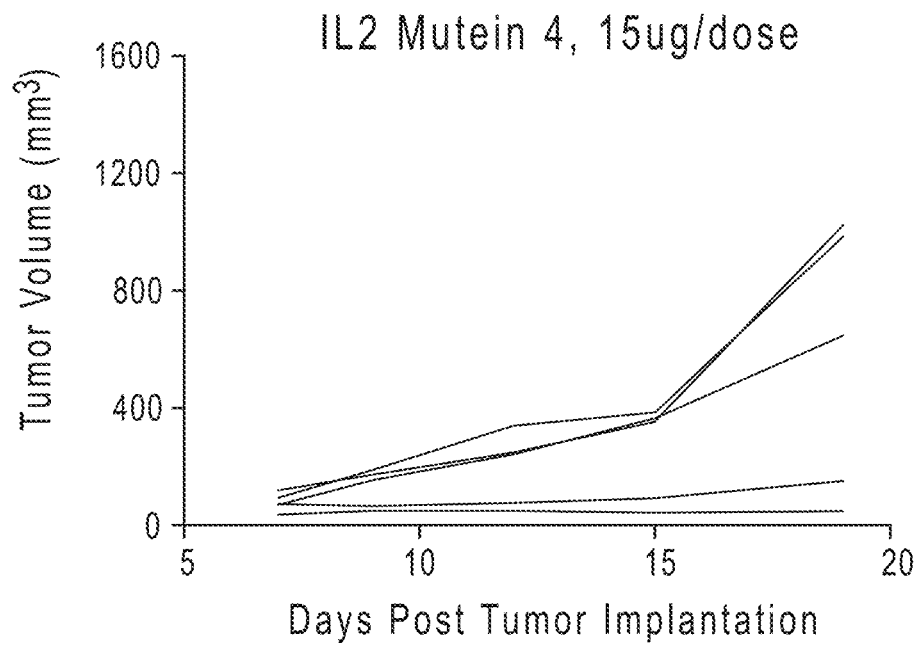
Figure 15D:
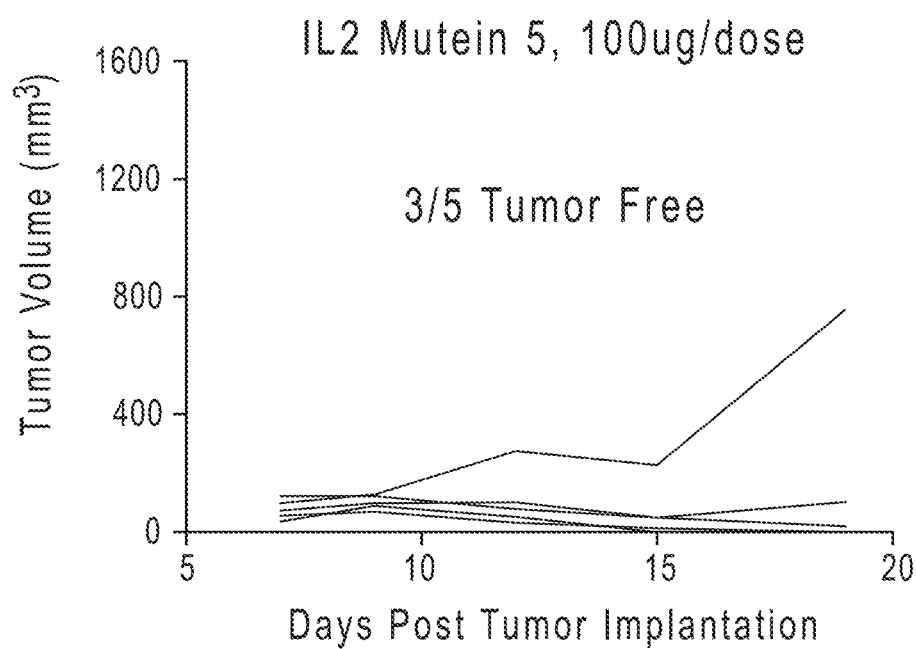

C57BL/6J mice were inoculated s.c. with MC38 tumor cells on day 0 and were randomized on day 7 when average tumor size reached 80 mm$^3$. Mice were then treated intraperitoneally with PBS, IL2M4 (15 µg), or IL2M5 (100 µg) every three days for four total injections. Average tumor volumes were measured. The results (in mm$^3$+SD) for each treatment group are shown in FIG. 15A and for individual tumors in FIGS. 15B to 15D.

Given that IL2M5 is highly attenuated compared to IL2M4, it was used at a higher dose in tumor studies. Despite being >100× less potent than IL2M4 on multiple lymphocyte populations (FIG. 14A-C), a ~6× higher dose of IL2M5 achieved a more efficacious tumor control than IL2M4. Full tumor regression and tumor-free survival was observed in three out of five mice treated with 100 µg/dose of IL2M5.

7.14. Example 13: Oligomerization States of IL-2Rα-Containing Muteins

Figure 3B:
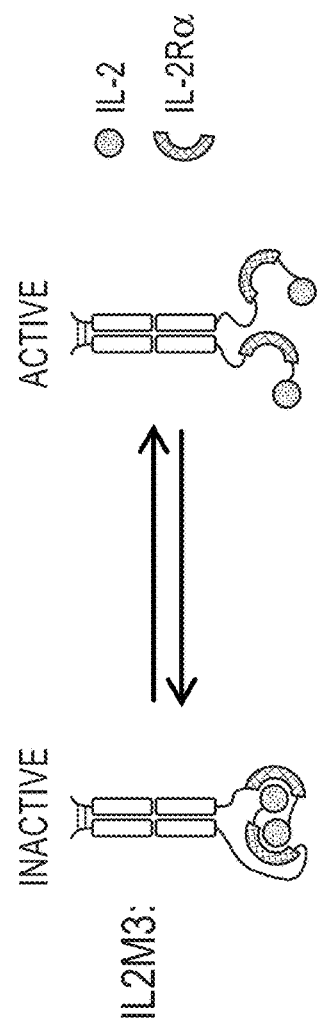

Size-exclusion ultra-performance liquid chromatography (SEC) coupled with multiangle light scattering (MALS) were employed to assess the oligomeric state of IL2M2 and IL2M3. IL2M2 contains multiple high molecular weight species, with the predominant species (~60%) exhibiting a molar mass consistent with a dimer of dimer (FIG. 16A). In contrast, IL2M3 is less prone to oligomerization. It exists predominantly as a dimer (~77%), along with two minor high molecular weight species (FIG. 16B). Arrows indicate the determined molecular weight and relative percentage of each major population. The equilibrium between different structures is illustrated in FIGS. 3A and 3B (for IL2M2 and IL2M3, respectively).

7.15. Example 14: T1-IL2M3 Retains Binding to Cell Surface PD1

The binding of T1-IL2M3, containing an anti-PD1 targeting moiety, was evaluated by FACS as described in Section 7.1.4. As shown in FIG. 17, T1-IL2M3 and the parental anti-mPD1 antibody showed comparable binding to human HEK293 cell stably expressing mouse PD1 on its surface, suggesting target-binding is minimally affected by fusing the antibody to IL2M3.

7.16. Example 15: T1-IL2M3 Shows Superior Anti-Tumor Efficacy to the Combination of Anti PD1 & IL2M3

C57BL/6J mice were inoculated s.c. with 3×10$^5$ MC38 tumor cells on day 0 and were randomized on day 7 when average tumor size reached 100 mm$^3$. Mice were then treated intraperitoneally with isotype (1 mg/kg), anti-mPD1 (1 mg/kg), isotype-IL2M3 (0.5 mg/kg)+anti-mPD1 (0.33 mg/kg), isotype-IL2M3 (1.5 mg/kg)+anti-mPD1 (1 mg/kg), T1-IL2M3 (0.5 mg/kg)+isotype (0.33 mg/kg), or T1-IL2M3 (1.5 mg/kg)+isotype (1 mg/kg) semi-weekly for five total injections.

Average tumor volumes were measured. The results (in mm$^3$+SD) for each treatment group are shown in FIG. 18A and for individual tumors in FIGS. 18B.1 to 18B.4.

While isotype-IL2M3+anti-PD1 was not able to confer tumor control, T1-IL2M3+isotype showed great efficacy at both doses tested, with more mice undergoing complete tumor regression at the higher dose. The amount of IL2M3 moiety delivered in 0.5 mg/kg dose of T1-IL2M3 is very low, equivalent to 5.7 µg/dose of IL2M3. This result reveals the superior anti-tumor efficacy of T1-IL2M3 to the combination of anti-PD1 & IL2M3. It also suggests that PD1-targeting greatly reduced the amount of IL2M3 required to achieve efficient tumor control.

Blood was collected from the tumor-bearing mice on day 15 and analyzed by FACS. The frequencies of CD44$^{high}$CD62L$^{low}$ W cells and PD1$^+$ cells within CD8$^+$ T cells and FoxP3$^+$IL-2Rα$^+$ Tregs within CD4$^+$ T cells are shown in FIGS. 18C.1-18D.2 and FIGS. 18E.1-18E.2, respectively.

Compared to the non-targeted isotype-IL2M3, T1-IL2M3 induces specific expansion of activated effector memory CD8+ T cells that are CD44$^{hi}$CD62L$^{lo}$ and PD1$^+$. At the same time, T1-IL2M3 causes less undesired proliferation of Tregs than isotype-IL2M3. This result demonstrates that T1-IL2M3 fusion is able to redirect IL2M3 to antigen-activated CD8+ T cells that express PD1. Activated T cells upregulate PD1, resulting in T cell inhibition. T1-IL2M3 can specifically re-activate and expand these cells by stimulating IL2 signaling, in addition to blocking PD1 signaling in these cells. A schematic of the proposed mechanism of action for T1-IL2M3 is shown in FIG. 19.

7.17. Example 16: Anti-mPD1-IL2 Mutein 3 Fusion Shows Superior Anti-Tumor Efficacy to the Combination of Isotype-IL2 Mutein 3 and the Parental Anti-PD1 Antibody in Several Murine Syngeneic Tumor Models The therapeutic efficacy of T1 IL2M3 (an anti-mPD1-IL2 Mutein 3) was assessed in murine syngeneic tumor models of lung, skin, breast and colon cancer (using LLC1, B16F10, 4T1, and colon-26 tumor cells, respectively) in two different mouse strains (C57BL/6J and BALB/cJ).

C57BL/6J mice were (a) inoculated s.c. with 2×10$^5$ LLC1 tumor cells on day 0 and were randomized on day 7 when average tumor size reached 90 mm$^3$, or (b) inoculated s.c. with 3×10$^5$ B16F10 tumor cells on day 0 and were randomized on day 7 when average tumor size reached 80 mm$^3$. Mice were then treated intraperitoneally with isotype (1 mg/kg), isotype-IL2 Mutein 3 (1.5 mg/kg)+anti-mPD1 (1 mg/kg), or anti-mPD1-IL2 Mutein 3 (1.5 mg/kg)+isotype (1 mg/kg) semi-weekly for four or five total injections.

BALB/cJ mice were (a) inoculated s.c. with 5×10$^5$ 4T1 tumor cells on day 0 and were randomized on day 8 when average tumor size reached 60 mm$^3$, or (b) inoculated s.c. with 1×10$^6$ Colon-26 tumor cells on day 0 and were randomized on day 12 when average tumor size reached 100 mm$^3$. Mice were then treated intraperitoneally with isotype (1 mg/kg), isotype-IL2 Mutein 3 (0.5 mg/kg)+anti-mPD1

(0.33 mg/kg), or anti-mPD1-IL2 Mutein 3 (0.5 mg/kg)+isotype (0.33 mg/kg) semi-weekly for five total injections.

Average tumor volumes (mm³+SEM) in each treatment group are shown in FIGS. 20A-20D. Arrows indicate the days of treatment.

In all the models studied, anti-mPD1-IL2 Mutein 3 displayed better anti-tumor activity than the combination of isotype-IL2 Mutein 3 and anti-mPD1. Anti-mPD1-IL2 Mutein 3 treatment resulted in complete tumor regression in most of the treated mice in the Colon-26 model (FIG. 20D). In other models (LLC1, B16F10, 4T1) which had been shown to be resistant to general immunotherapies (Mosely et al., 2016, Cancer Immunol Res 5(1):29-41), anti-mPD1-IL2 Mutein 3 was able to delay the progression of established tumors (FIGS. 20A-20C).

7.18. Example 17: Anti-mLAG3-IL2 Mutein 3 Fusion Displays Better Anti-Tumor Efficacy than the Combination of Anti-LAG3+Isotype-IL2 Mutein 3

C57BL/6J mice were inoculated s.c. with MC38 tumor cells on day 0 and were randomized on day 10 when average tumor size reached 50 mm³. Mice were then treated intraperitoneally with isotype (1 mg/kg), anti-mLAG3 (1 mg/kg), isotype-IL2 Mutein 3 (0.5 mg/kg)+anti-mLAG3 (0.33 mg/kg), isotype-IL2 Mutein 3 (1.5 mg/kg)+anti-mLAG3 (1 mg/kg), T6-IL2M3 (anti-mLAG3-IL2 Mutein 3) (0.5 mg/kg)+isotype (0.33 mg/kg), or T6-IL2M3 (anti-mLAG3-IL2 Mutein 3) (1.5 mg/kg)+isotype (1 mg/kg) semi-weekly for five total injections.

Separately, C57BL/6J mice were inoculated s.c. with MC38 tumor cells on day 0 and were randomized on day 9 when average tumor size reached 80 mm³. Mice were then treated intraperitoneally with isotype (0.33 mg/kg), isotype-IL2 Mutein 3 (0.5 mg/kg)+anti-mLAG3 (0.33 mg/kg)+anti-mPD1 (0.33 mg/kg), anti-mLAG3-IL2 Mutein 3 (0.5 mg/kg)+isotype (0.33 mg/kg), anti-mLAG3-IL2 Mutein 3 (0.5 mg/kg)+anti-mPD1 (0.33 mg/kg), or anti-mLAG3-IL2 Mutein 3 (0.5 mg/kg)+anti-mPD1 (5 mg/kg) semi-weekly for four total injections.

Average tumor volumes (mm³+SEM) in each treatment group are shown in FIGS. 21A-21B. Arrows indicate the days of treatment.

The molar amount of IL2M3 moiety delivered by a 0.5 mg/kg dose of isotype-IL2 Mutein 3 or anti-mLAG3-IL2 Mutein 3 is equivalent to that in a 5.7 µg/kg dose of IL2M2 or IL2M3. While isotype-IL2 Mutein 3+anti-mLAG3 was not able to confer tumor control at the studied doses, anti-mLAG3-IL2 Mutein 3+isotype showed augmented anti-tumor efficacy in a dose-dependent manner (FIG. 21A). This result provides another example that tumor-responsive T cell-targeting can enhance the antitumor efficacy of IL2M3 by reducing the amount of IL2M3 required to achieve an efficient tumor control.

While anti-mLAG3-IL2M3 alone conferred a partial control of tumor growth, its combination with anti-mPD1 resulted in greatly enhanced efficacy, with more mice achieving complete tumor regression (FIG. 21B). This result suggests that combining IL2 Mutein 3 targeted by a non-competing tumor-reactive T cell-targeting antibody with PD1 blockade can lead to a more robust anti-tumor immunity.

7.19. Example 18: A Peptide MHC-IL2 Mutein Fusion Allows Selective Stimulation of Antigen-Specific Mouse CD8 T Cells 1.5×10⁶ total splenocytes from an OT-I TCR transgenic mouse (obtained from the Jackson Laboratory) or a control C57BL/6J mouse were stimulated with increasing concentrations of T4-IL2M6 or T5-IL2M6 for 20 min at 37° C. Intracellular STAT5 phosphorylation in gated CD8+ T cells was evaluated by flow cytometry as described in Section 7.1.2.

Results are shown in FIG. 22B. Compared to T5-IL2M6, which targets TCRs against an irrelevant antigen, T4-IL2M6 shows two orders of magnitude higher potency in inducing STAT5 phosphorylation in T4-specific CD8+ OT-I T cells, but not on non-specific CD8+ T cells from a control mouse.

The levels of intracellular STAT5 phosphorylation on gated conventional CD4⁺ T cells and Tregs from the splenocytes of the same mice were measured.

Results are shown in FIGS. 23A-23B. Comparable activity was observed for T4-IL2M6 and T5-IL2M6 on both cell types. Unlike CD8⁺ T cells, conventional CD4⁺ T cells and Tregs from the same OT-I mouse do not express the T4-specific OT-I TCR. Therefore, the selectivity of T4-IL2M6 was abolished on these cells.

7.20. Example 19: A pMHC-IL2 Mutein Fusion Allows Selective Stimulation of Antigen-Specific Human CD8⁺ T Cells 1.5×10⁴ CMV pp65-specific human CD8+ T cells were stimulated with increasing concentrations of T2-IL2M6 or T3-IL2M6 for 20 min at 37° C. Level of intracellular STAT5 phosphorylation was evaluated by flow cytometry as described in Section 7.1.2.

Results are shown in FIG. 24. Compared to T3-IL2M6, which targets TCRs against HPV 16E7 antigen, T2-IL2M6 shows several orders of magnitude higher potency in inducing STAT5 phosphorylation on these CMV pp65-specific T cells.

7.21. Example 20: Selective CAR-T Expansion by Peptide-MHC Targeted IL2 Muteins 7.21.1. Structure of CAR Constructs Chimeric antigen receptors containing a $V_L$-$V_H$ scFv recognizing T3 (comprising HLA-A2 loaded with HPV16 E7$_{11-19}$ peptide), a huCD8 transmembrane domain, a CD137 (4-1BB) co-stimulatory domain, and a CD3ζ signaling domain (as illustrated in FIG. 25A) were constructed using the $V_L$ and $V_H$ sequences of a single antibody, 17363N. As a CAR negative control, untransduced T cells from the same donor were used. This CAR was cloned into a pLVX lentiviral vector with an EF1α promoter and containing a P2A sequence upstream of the eGFP sequence for tracking CAR-transduced cells. VSV-pseudotyped lentivirus was produced for subsequent transductions to be carried out using a multiplicity of infection (MOI) of 5. Exemplary FACS profiles of cells transduced with the CAR construct are shown in FIGS. 25B-25C 7.21.2. Generation and Expansion of CAR T Cells CD3+ T cells from a donor homozygous for HLA-A2 were thawed before being stimulated at a density of 1.5×10⁶/mL with Dynabeads® Human T-Expander CD3/CD28 microbeads plus Aldesleukin (100 IU/mL) for 24 hours. Subsequently, CD3/CD28 microbeads were removed by magnetic separation and activated T cells were then transduced with the CAR construct by spinfection at 2440 rpm for 90 minutes. As a CAR negative control, untransduced T cells from the same donor were used. The transduced and untransduced cells were then supplemented with Dynabeads® Human T-Expander CD3/CD28 microbeads (1 bead per 1 T cell) and expanded in CTS supplemented OpTmizer™ media for 19 days. Cell density was maintained between 1-1.5×10⁶/mL and Aldesleukin was added to the cultures every 48 hours and maintained at 100 IU/mL. At the end of expansion, the microbeads were removed and cells were cryopreserved.

The activities of a variety of peptide-MHC targeted IL2 muteins illustrated in FIGS. 26A and 26B, containing the attenuated IL2 (H16A, F42A) (also referred to as IL2(2m)), were tested: T7-IL2M7 (which is monovalent for IL2 and has an HPV peptide-MHC complex), T8-IL2M7 ((which is monovalent for IL2 and has a CMV peptide-MHC complex), T3-IL2M6 (which is bivalent for IL2 and has an HPV peptide-MHC complex), T2-IL2M6 (which is monovalent for IL2 and has a CMV peptide-MHC complex). CAR-T cells were thawed and washed twice in complete RPMI media. Thawed cells were then rested overnight at 2.8×10⁶/mL in complete RPMI media without Aldesleukin. After an overnight rest, levels of intracellular STAT5 phosphorylation on gated CD4+ or CD8+ populations in these CAR T cells were evaluated by flow cytometry as described in Section 7.1.2.

7.21.3. Results

Results are shown in FIG. 27A (CD4+ T cells) and 27B (CD8+ T cells). By gating on CD4+ and CD8+ CAR-T cells engineered to express a CAR targeting and HPV16 E7$_{11-19}$ peptide-HLA-A2 complex, the IL2 muteins T7-IL2M7 and T3-IL2M6 (both of which have a HPV16 E7$_{11-19}$ peptide-HLA-A2 targeting moiety) show several orders of magnitude higher potency in inducing STAT5 phosphorylation relative to T8-IL2M7 and T2-IL2M6, which target CMV pp65$_{495-503}$-specific T cells.

7.22. Example 21: Selective CAR-T Expansion by Peptide-MHC Targeted IL2 Muteins 7.22.1. Generation and Expansion of CAR T Cells CD3+ T cells from a donor homozygous for HLA-A2 were thawed before being stimulated with Dynabeads® Human T-Expander CD3/CD28 Microbeads plus 3.3×10⁻¹⁰ M recombinant Aldesleukin for 48 hours. Subsequently, CD3/CD28 microbeads were removed by magnetic separation and activated T cells were then transduced with the CAR construct shown in FIG. 27A by spinfection at 2440 rpm for 90 minutes. For a CAR negative control, untransduced T cells from the same donor were used. The transduced and untransduced cells were then expanded in CTS supplemented OpTmizer™ media for 4 days with Dynabeads® Human T-Expander CD3/CD28 microbeads, added at a 1:1 ratio with T cells, plus 3.3×10⁻¹⁰ M Aldesleukin. The activated T cells were then harvested, washed two times in OpTmizer™ media, and 003/0028 microbeads were removed by magnetic separation before resting T cells overnight at 37° C. in CTS supplemented OpTmizer™ media lacking Aldesleukin. Rested transduced and untransduced T cells were resuspended and cultured at 1×10⁶/mL in CTS supplemented OpTmizer™ media in the presence of Dynabeads® human T-Expander CD3/CD28 microbeads (1 bead to 1 T cell). Each culture was then stimulated with the respective biologics at a concentration of 3.3×10⁻¹⁰ M. Each T cell expansion culture was supplemented with biologics every 48 hours and maintained at a density of 1-1.5×10⁶/mL for 17 days. On days 3, 9, 17 of expansion, T cell numbers were enumerated and an aliquot of cells was collected to quantitate changes in the ratio of viable eGFP$^{Pos}$ (CAR+) to eGFP$^{Neg}$ (non-CAR) T cells. Untransduced T cells expanded with each biologic were used to define eGFP signal for the CAR-T expansions at each time-point.

7.22.2. Characterization of CAR-T Cells

At several time-points during the expansion of CAR-T cells, an aliquot of cells was collected to quantitate viable eGFP+ (CAR+) cells by flow cytometry. To identify different T cell populations and expression of IL2Rα, a combination of the following antibodies were used: BUV395 anti-CD4 (BD Biosciences), BUV737 anti-CD4 (BD Biosciences), PE-CY7 anti-CD8 (Biolegend), APC-Cy7 anti-CD8 (Biolegend), BV605 anti-CD25 (BD Biosciences). To characterize memory T cell subsets and phenotype, BV421 anti-CCR7 (Biolegend), PE-CF594 anti-CD45RO (BD Biosciences), PerCP-Cy5.5 anti-CD45RO (BD Biosciences), BUV395 anti-PD1 (BD Biosciences), and PE-CF594 anti-CD57 (BD Biosciences). Viability was assessed using 4',6-diamidino-2-phenylindole (DAPI)(ThermoFisher) or AQUA viability dye (ThermoFisher). All samples were acquired on a BDFortessa™ X-20 or Biorad Ze5 flow cytometer. The raw data were processed using FlowJo v10.

7.22.3. Results & Discussion

To examine the potential of attenuated IL-2 valency in concert with increasing valency of a given targeting moiety to mediate selective CAR-T expansion, selective CAR-T expansion was examined in response to a series of engineered biologics. In the monovalent format, 1 copy of attenuated IL2 is combined with 1 copy of the targeting moiety. In the bivalent format, two copies of attenuated IL-2 are combined with two copies of targeting moiety. To control for non-selective expansion, a targeting moiety not recognized by the CAR-T cells (scHLA-A2 loaded with CMV pp65$_{495-503}$ peptide) was utilized. Structures of the biologics tested are illustrated in FIGS. 26A and 26B.

Results are shown in FIG. 28. As depicted in FIGS. 28A.1-28A.16, prior to the expansion of transduced T cells in response to scMHC-peptide targeted IL2 muteins (denoted as Day 0), the frequency of viable CAR-T (eGFP$^{Pos}$) cells was 38%. By day 3 of expansion, the frequency of viable CAR-T cells increased to roughly 43% for each culture except for the bivalent T3-IL2M6 construct where the frequency of CAR decreased to 36%. By day 9, the greatest degree of selective CAR-T enrichment is observed in response to monovalent T7-IL2M7 wherein the percentage of viable CAR-T cells had increased to 75%. Of note, a less prominent increase in the percentage of CAR-T was also observed in response to the monovalent T8-IL2M7 even though this biologic does not bind to the CAR scFv. While it is unlikely that this expansion resulted from a pre-existing T cell repertoire against cytomegalovirus peptide (pp65$_{495-503}$) owing to a lack of an antigen recall response using matched donor PBMC (as per the vendor), this possibility cannot be fully ruled out. Between day 9 and 17 of expansion, the percentage of CAR in response to the monovalent T7-IL2M7 and T8-IL2M7 remained similar. A slight increase in the frequency of CAR-T was observed in response to IL2 (Aldesleukin) and bivalent T3-IL2M6, whereas no further change was observed in response to bivalent T2-IL2M6.

To evaluate the potential of biologics that concomitantly bind to the scFv of a CAR and deliver attenuated IL2 signals to mediate selective expansion of CAR-T, the total number of viable T cells against the ratio of CAR-T cells (EGFP$^{Pos}$) to non-CAR-T cells EGFPNeg) was plotted. As shown in FIGS. 28B.1-B.4, selective enrichment of CAR-T occurred between day 3 and day 9 in response to T7-IL2M7 (open circle) as the ratio of eGFP$^{Pos}$/eGFP$^{Neg}$ increased from 0.73 to 3.12. In addition, the number of T cells more than doubled. By day 17, at culture termination, the greatest number of expanded total T cells was observed in response to Aldesleukin (black square) followed by monovalent T7-IL2M7 (open circle); however, the ratio of $CAR^{Pos}$ to $CAR^{Neg}$ T cells was maximal in cultures expanded with T7-IL2M7 indicating that a selective and targeted expansion of CAR-T had occurred. As shown in FIG. 28C, the absolute number of viable CAR-T cells for each expansion condition are plotted as a function of time in culture. While IL-2 (Aldesleukin) yielded the greatest number of total T cells (FIG. 28B.4), due to selective CAR-T expansion, monovalent T7-IL2M7 generated the maximal number of viable CAR-T cells (FIG. 28C). Minimal expansion of CAR-T occurred in response to monovalent T8-IL2M7 demonstrating the importance of the targeting moiety. Of note, CAR-T expansion was low in response to bivalent T3-IL2M6, potentially indicating over-activation of the CAR-T cells resulting in cell death. Alternatively, the bivalent T3-IL2M6 may cross-link separate CAR-T cells resulting in CAR-T fratricide. These studies show that the monovalent format structure is superior for mediating selective CAR-T expansion.

7.23. Example 22: In Vivo Pharmacokinetic Assessment of Peptide-MHC Targeted IL2 Muteins 7.23.1. Methods To assess the pharmacokinetics of indicated IL2 muteins in plasma, both immunocompetent C57BL/6J and immunodeficient NSG (NOD-scid IL2Rgnull) mice were intraperitoneally injected with a single dose of 12 μg of each protein. Blood samples were collected at 2, 24, 48 and 72 hr after dosing followed by centrifugation for 10 min at 10,000 RPM to isolate plasma. 1 μl of each plasma sample were analyzed by SDS-PAGE followed by immunoblotting with antibodies against human IgG Fc. 2 ng of each purified protein (spiked into 1 μl naïve plasma) were loaded onto the same gels to help estimate the absolute levels of each protein in the plasma samples.

7.23.2. Results

Results are shown in FIG. 29. Compared to IL2M0 (referred to in FIG. 29 as IL2-Fc), the targeted IL2 muteins shown in FIGS. 26A and 26B demonstrated improved PK in an avidity dependent manner. In addition, in comparison to IL2-Fc, both bivalent and monovalent constructs show delayed clearance in circulation, with the monovalent constructs (T7-IL2M7 and T8-IL2M7) being longest-lasting. This result suggests IL2 attenuation can significantly reduce its receptor-mediated clearance in an avidity-dependent manner, and therefore increases the chance for a targeted attenuated IL2 mutein to reach target cells. Despite the more durable presence in circulation, bivalent T2-IL2M6 still shows a faster elimination from the blood than the targeting moiety alone (T2-Fc), suggesting that clearance of T2-IL2M6 is mainly driven by IL2M6.

8. SPECIFIC EMBODIMENTS, CITATION OF REFERENCES

While various specific embodiments have been illustrated and described, it will be appreciated that various changes can be made without departing from the spirit and scope of the disclosure(s). The present disclosure is exemplified by the numbered embodiments set forth below.

In preferred aspects of the numbered embodiments below and the claims which follow, the IL2 domains, the IL2 receptors, Fc domains, MHC domains, β2M, and the variants thereof preferably comprise the amino acid sequences of human IL2, human IL2 receptors, human Fc domains, human MHC domains, human β2M, and variants thereof, for example variants with at least about 90%, at least about 95%, at least about 96%, at least about 97%, at least about 98%, at least about 99% or 100% sequence identity to such human sequence.

1. An IL2 agonist comprising:
    (a) an IL2 moiety comprising an IL2 domain;
    (b) optionally, a multimerization moiety;
    (c) optionally, a targeting moiety; and
    (d) optionally, a stabilization moiety.
2. The IL2 agonist of embodiment 1, which comprises an IL2 mutein having the configuration of:
    (a) IL2M0;
    (b) IL2M1;
    (c) IL2M2;
    (d) IL2M3;
    (e) IL2M4;
    (f) IL2M5;
    (g) IL2M6; or
    (h) IL2M7.
3. The IL2 agonist of embodiment 1 or embodiment 2, wherein the IL2 moiety is an IL2-Rα-biased IL2 mutein.
4. The IL2 agonist of any one of embodiments 1 to 3, wherein the IL2 moiety and/or the IL2 agonist has 50-fold to 1,000-fold attenuated binding to human IL2-Rβ as compared to wild type IL2.
5. The IL2 agonist of any one of embodiments 1 to 4, wherein the IL2 moiety and/or the IL2 agonist has up to 100-fold, up to 500-fold, up to 1,000-fold or up to 5,000-fold attenuated binding to human IL2-Rα as compared to wild-type human IL2.
6. The IL2 agonist of any one of embodiments 1 to 5, wherein the ratio of the binding affinity of IL2 agonist to the high affinity IL2 receptor to the binding affinity of the IL2 agonist to the intermediate affinity IL2 receptor is equal to or greater than the corresponding ratio for wild type IL2.
7. The IL2 agonist of any one of embodiments 1 to 6, wherein the IL2 moiety and/or the IL2 agonist has an E50 for the high affinity IL2 receptor that is 100-fold to 10,000-fold lower than the E50 for the intermediate affinity IL2 receptor.
8. The IL2 agonist of embodiment 1, wherein the IL2 moiety is an IL2-Rβ-biased IL2 mutein.
9. The IL2 agonist of embodiment 1 or embodiment 8, wherein the IL2 moiety and/or the IL2 agonist has (a) 50-fold to 1,000-fold or (b) 50-fold to 5,000-fold attenuated binding to human IL2-Rα as compared to wild type IL2.
10. The IL2 agonist of any one of embodiments 1, 8 and 9, wherein the IL2 moiety and/or the IL2 agonist has up to 50-fold attenuated binding to human IL2-Rβ as compared to wild-type human IL2.
11. The IL2 agonist of any one of embodiments 1 and 8 to 10, wherein the ratio of the binding affinity of the IL2 moiety and/or the IL2 agonist to the intermediate affinity IL2 receptor to the binding affinity of the IL2 moiety and/or the IL2 agonist to the high affinity IL2 receptor is equal to or greater than the corresponding ratio for wild type IL2.
12. The IL2 agonist of any one of embodiments 1 and 7 to 11, wherein the IL2 moiety and/or the IL2 agonist has an E50 for the high affinity IL2 receptor that is 10-fold to 100-fold lower than the E50 for the intermediate affinity IL2 receptor.
13. The IL2 agonist of any one of embodiments 1 to 12, wherein the IL2 moiety and/or the IL2 agonist has attenuated binding affinity to the high affinity IL2 receptor compared to wild type IL2.

14. The IL2 agonist of embodiment 13, wherein the binding affinity is attenuated by up to 1,000-fold or up to 5,000 fold, or wherein the binding affinity is attenuated by:
   (a) 10-fold to 1,000-fold;
   (a) 50-fold to 5,000-fold;
   (b) up to 10-fold;
   (c) up to 50-fold;
   (d) up to 100-fold; or
   (e) up to 200-fold.

15. The IL2 agonist of any one of embodiments 1 to 14, wherein the IL2 moiety and/or the IL2 agonist has higher cytokine activity on tumor reactive lymphocytes than on peripheral lymphocytes.

16. The IL2 agonist of embodiment 15, wherein the IL2 moiety and/or the IL2 agonist has at least 5-fold or at least 10-fold higher cytokine activity on tumor reactive lymphocytes than on peripheral lymphocytes.

17. The IL2 agonist of any one of embodiments 1 to 16, which has a therapeutic index of at least 1.

18. The IL2 agonist of embodiment 17, which has a therapeutic index of at least 2.

19. The IL2 agonist of embodiment 17, which has a therapeutic index of at least 5.

20. The IL2 agonist of embodiment 17, which has a therapeutic index of at least 10.

21. The IL2 agonist of embodiment 17, which has a therapeutic index of at least 50.

22. The IL2 agonist of any one of embodiments 17 to 21, which has a therapeutic index of up to 500.

23. The IL2 agonist of any one of embodiments 17 to 21, which has a therapeutic index of up to 250.

24. The IL2 agonist of any one of embodiments 1 to 23, which has a therapeutic index of about 2.

25. The IL2 agonist of any one of embodiments 1 to 23, which has a therapeutic index of about 10.

26. The IL2 agonist of any one of embodiments 1 to 23, which has a therapeutic index of about 20.

27. The IL2 agonist of any one of embodiments 1 to 23, which has a therapeutic index of about 50.

28. The IL2 agonist of any one of embodiments 1 to 23, which has a therapeutic index of about 100.

29. The IL2 agonist of any one of embodiments 1 to 23, which has a therapeutic index of about 200.

30. The IL2 agonist of any one of embodiments 1 to 29, wherein the IL2 moiety and/or the IL2 agonist is not pegylated.

31. The IL2 agonist of any one of embodiments 1 to 30, wherein the IL2 moiety and/or the IL2 agonist does not comprise a cytokine other than IL2.

32. The IL2 agonist of any one of embodiments 1 to 31, wherein the IL2 moiety and/or the IL2 agonist does not contain an anti-IL2 antibody or antibody fragment.

33. The IL2 agonist of any one of embodiments 1 to 32, wherein the IL2 moiety and/or the IL2 agonist does not contain an anti-DNA antibody or antibody fragment.

34. The IL2 agonist of any one of embodiments 1 to 33, wherein the IL2 domain does not comprise a substitution at the position D20 as compared to human IL2.

35. The IL2 agonist of any one of embodiments 1 to 34, wherein the IL2 domain does not comprise a substitution at the position Q126 as compared to human IL2.

36. The IL2 agonist of any one of embodiments 1 to 35, wherein the IL2 moiety and/or the IL2 agonist does not contain a non-binding variable domain.

37. The IL2 agonist of any one of embodiments 1 to 36, wherein the IL2 moiety comprises an IL2 domain comprising an amino acid sequence having at least about 90% sequence identity to mature human IL2.

38. The IL2 agonist of any one of embodiments 1 to 36, wherein the IL2 moiety comprises an IL2 domain comprising an amino acid sequence having at least about 93% sequence identity to mature human IL2.

39. The IL2 agonist of any one of embodiments 1 to 36, wherein the IL2 moiety comprises an IL2 domain comprising an amino acid sequence having at least about 96% sequence identity to mature human IL2.

40. The IL2 agonist of any one of embodiments 1 to 39, wherein the IL2 moiety comprises an IL2 variant which has the amino acid substitution C125S, C125A or C125V.

41. The IL2 agonist of any one of embodiments 1 to 40, wherein the IL2 domain comprises an IL2 sequence that has one or more substitutions to reduce O-linked glycosylation.

42. The IL2 agonist of embodiment 41, wherein the IL2 domain has a substitution at a position corresponding to residue 3 of human IL2.

43. The IL2 agonist of embodiment 42, wherein the amino acid substitution is T3A, T3G, T3Q, T3E, T3N, T3D, T3R, or T3K.

44. The IL2 agonist of any one of embodiments 1 to 43, wherein the IL2 domain has a substitution at a position corresponding to methionine 104 of human IL2 with a neutral amino acid.

45. The IL2 agonist of embodiment 44, wherein the neutral amino acid is alanine.

46. The IL2 agonist of any one of embodiments 1 to 45, wherein the IL2 domain is a full-length human IL2 domain.

47. The IL2 agonist of any one of embodiments 1 to 45, wherein the IL2 domain has an N-terminal alanine deletion as compared to full length mature human IL2.

48. The IL2 agonist of any one of claims 1 to 47, wherein the IL2 domain comprises an IL2 variant which has an amino acid substitution at position N88.

49. The IL2 agonist of embodiment 48, wherein the amino acid substitution is N88D.

50. The IL2 agonist of any one of claims 1 to 47, wherein the IL2 domain comprises an IL2 variant which has amino acid substitutions at positions H16 and F42.

51. The IL2 agonist of embodiment 50, wherein the amino acid substitutions are H16A and F42A.

52. The IL2 agonist of any one of embodiments 1 to 51, wherein the IL2 moiety comprises an IL-2Rα domain comprising an IL2 binding portion of IL-2Rα fused to the IL2 domain.

53. The IL2 agonist of embodiment 52, wherein the IL2-Rα domain or the IL2 binding portion of IL-2Rα is the extracellular domain of IL-2Rα or an IL2 binding portion thereof.

54. The IL2 agonist of embodiment 52 or embodiment 53, wherein the IL2-Rα domain or the IL2 binding portion comprises or consists of an amino acid sequence having at least about 90%, at least about 95%, at least about 96%, at least about 97%, at least about 98%, at least about 99% or 100% sequence identity to an IL2 binding portion of human IL-2Rα, optionally wherein said binding portion has:
   (a) at least 160 amino acids, at least 161 amino acids, at least 162 amino acids, at least 164 amino acids or at least 165 amino acids of human IL2-Rα; and/or
   (b) up to 251, up to 240, up to 230, up to 220, up to 210, up to 200, up to 190, up to 180 or up to 170 amino acids of the extracellular domain of human IL2-Rα.

55. The IL2 agonist of any one of embodiments 52 to 54, wherein the IL2-Rα domain or the IL2 binding portion has an amino acid sequence with at least about 90%, at least about 95%, at least about 96%, at least about 97%, at least about 98%, at least about 99% or 100% sequence identity to amino acids 22-186 of IL-2Rα, amino acids 22-240 of IL-2Rα, and/or amino acids 22-272 of IL-2Rα.

56. The IL2 agonist of any one of embodiments 52 to 55, wherein the IL2-Rα domain or the IL2 binding portion comprises or consists of an amino acid sequence having at least about 90%, at least about 95%, at least about 96%, at least about 97%, at least about 98%, at least about 99% or 100% sequence identity to amino acids 22-186, with or without an additional up to 5 amino acids, up to 10 amino acids, up to 15 amino acids, up to 20 amino acids, up to 30 amino acids, or up to 40 amino acids C-terminal to amino acid residue 186, of human IL2-Rα.

57. The IL2 agonist of any one of embodiments 52 to 56, wherein the IL-2Rα domain is N-terminal to the IL2 domain.

58. The IL2 agonist any one of embodiments 52 to 56, wherein the IL-2Rα domain is C-terminal to the IL2 domain.

59. The IL2 agonist of any one of embodiments 52 to 58, wherein the IL2 domain and the IL2-Rα domain are connected via a linker.

60. The IL2 agonist of embodiment 59, wherein the linker is or comprises a glycine-serine linker.

61. The IL2 agonist of embodiment 60, wherein the linker comprises the amino acid sequence G$_4$S (SEQ ID NO:57).

62. The IL2 agonist of embodiment 61, wherein the linker is or comprises a multimer of the amino acid sequence G$_4$S (SEQ ID NO:57).

63. The IL2 agonist of embodiment 62, wherein the multimer comprises 2, 3, 4, 5 or 6 repeats of the amino acid sequence G$_4$S (SEQ ID NO:57).

64. The IL2 agonist of any one of embodiments 1 to 63, which comprises a multimerization and/or a stabilization moiety.

65. The IL2 agonist of embodiment 64, wherein the multimerization moiety and/or the stabilization moiety is or comprises an Fc domain.

66. The IL2 agonist of embodiment 65, wherein the Fc domain is an IgG1, IgG2, IgG3 or IgG4 Fc domain.

67. The IL2 agonist of embodiment 65 or embodiment 66, wherein the Fc domain has reduced effector function.

68. The IL2 agonist of embodiment 67, wherein the Fc domain comprises the amino acid sequence of SEQ ID NO:31 of WO2014/121087 or a portion thereof, e.g., as sset forth in Table 4 and/or Section 6.5.1.1.

69. The IL2 agonist of any one of embodiments 1 to 68, which comprises a stabilization moiety.

70. The IL2 agonist of embodiment 69, wherein the stabilization moiety is human serum albumin, a human serum albumin binder, an XTEN, a PAS, a carbohydrate, a polysialic acid, a hydrophilic polymer, a fatty acid, or an Fc domain.

71. The IL2 agonist of embodiment 70, wherein the stabilization moiety is a human serum albumin binder.

72. The IL2 agonist of embodiment 71, wherein the human serum albumin binder is Adnectin PKE, AlbudAb, or an albumin binding domain.

73. The IL2 agonist of embodiment 72, wherein the stabilization moiety is an Fc domain.

74. The IL2 agonist of embodiment 73, wherein the Fc domain is a monomeric Fc domain.

75. The IL2 agonist of embodiment 73 or embodiment 74, wherein Fc domain has reduced effector function.

76. The IL2 agonist of embodiment 70, wherein the stabilization moiety is a hydrophilic polymer.

77. The IL2 agonist of embodiment 76, wherein the hydrophilic polymer is PEG.

78. The IL2 agonist of embodiment 77, wherein the PEG has a molecular weight ranging from about 7.5 kDa to about 80 kDa.

79. The IL2 agonist of embodiment 78, wherein the PEG has a molecular weight ranging from about 30 kDa to about 60 kDa, optionally wherein the molecular weight is about 50 kDa.

80. The IL2 agonist of any one of embodiments 76 to 79, wherein the hydrophilic molecule is attached to the IL-2Rβ binding surface of IL2.

81. The IL2 agonist of any one of embodiments 1 to 80 which is a dimer.

82. The IL2 agonist of embodiment 81, which is a homodimer.

83. The IL2 agonist of embodiment 81, which is a heterodimer.

84. The IL2 agonist of any one of embodiments 1 to 80 which is a monomer.

85. The IL2 agonist of any one of embodiments 1 to 84, which is monovalent for the IL2 moiety.

86. The IL2 agonist of any one of embodiments 1 to 85, which is bivalent for the IL2 moiety.

87. The IL2 agonist of any one of embodiments 1 to 86, which is or comprises an Orientation 1 IL2 agonist.

88. The IL2 agonist of any one of embodiments 1 to 87, which comprises:
   (a) An IL2 moiety comprising:
      (i) An IL2 or an IL2 variant (e.g., IL2 N88D) domain, with or without a substitution at C125 that reduces aggregation (e.g., C125S or C125A or C125V);
      (ii) A linker (e.g., as described in Section 6.7), e.g., a linker comprising 10 or more amino acids and/or comprising or consisting of (G$_4$S)$_n$ (SEQ ID NO:57), optionally wherein n≥2, e.g., wherein N is 3, 4, 5 or greater; and
      (iii) IL2 binding portion of IL-2Rα;
   (b) A linker (e.g., as described in Section 6.7), e.g., a linker comprising or consisting of (G$_4$S)$_n$ (SEQ ID NO:57), optionally wherein n≥1, e.g., wherein N is 1, 2, 3, 4, 5 or greater; and
   (c) An Fc domain (e.g., IgG1 or IgG4, with or without substitutions that reduce glycosylation and/or effector function as described in Section 6.5.1 and subsections thereof).

89. The IL2 agonist of any one of embodiments 1 to 86, which is or comprises an Orientation 2 IL2 agonist.

90. The IL2 agonist of any one of embodiments 1 to 89, which comprises:
   (a) An Fc domain (e.g., IgG1 or IgG4, with or without substitutions that reduce glycosylation and/or effector function as described in Section 6.5.1 and subsections thereof);
   (b) A linker (e.g., as described in Section 6.7), e.g., a linker comprising or consisting of (G$_4$S)$_n$ (SEQ ID NO:57), optionally wherein n≥1, e.g., wherein N is 1, 2, 3, 4, 5 or greater; and
   (c) An IL2 or an IL2 variant (e.g., IL2 N88D) domain, with or without a substitution at C125 that reduces aggregation (e.g., C125S or C125A or C125V).

91. The IL2 agonist of any one of embodiments 1 to 89, which comprises:
   (a) An Fc domain (e.g., IgG1 or IgG4, with or without substitutions that reduce glycosylation and/or effector function as described in Section 6.5.1 and subsections thereof);

(b) A linker (e.g., as described in Section 6.7), e.g., a linker comprising or consisting of $(G_4S)_n$ (SEQ ID NO:57), optionally wherein n≥1, e.g., wherein N is 1, 2, 3, 4, 5 or greater; and
(c) An IL2 moiety comprising:
  (i) An IL2 or an IL2 variant (e.g., IL2 N88D) domain, with or without a substitution at C125 that reduces aggregation (e.g., C125S or C125A or C125V);
  (ii) A linker (e.g., as described in Section 6.7), e.g., a linker comprising 10 or more amino acids and/or comprising or consisting of $(G_4S)_n$ (SEQ ID NO:57), optionally wherein n≥2, e.g., wherein N is 3, 4, 5 or greater; and
  (iii) An IL2 binding portion of IL2Rα.

92. The IL2 agonist of any one of embodiments 1 to 86, which is or comprises an Orientation 3 IL2 agonist.

93. The IL2 agonist of any one of embodiments 1 to 92, which comprises:
(a) An scFv or a heavy chain variable region of a Fab (associated with a corresponding light chain variable region on a separate polypeptide) (e.g., as described in Section 6.4.2 and subsections thereof);
(b) A linker (e.g., as described in Section 6.7), e.g., a linker comprising or consisting of $(G_4S)_n$ (SEQ ID NO:57), optionally wherein n≥1, e.g., wherein N is 1, 2, 3, 4, 5 or greater;
(c) An Fc domain (e.g., IgG1 or IgG4, with or without substitutions that reduce glycosylation and/or effector function as described in Section 6.5.1 and subsections thereof);
(d) A linker (e.g., as described in Section 6.7), e.g., a linker comprising or consisting of $(G_4S)_n$ (SEQ ID NO:57), optionally wherein n≥1, e.g., wherein N is 1, 2, 3, 4, 5 or greater; and
(e) An IL2 moiety comprising:
  (i) IL2 or an IL2 variant (e.g., IL2 N88D) domain, with or without a substitution at C125 that reduces aggregation (e.g., C125S, C125A or C125V);
  (ii) A linker (e.g., as described in Section 6.7), e.g., a linker comprising 10 or more amino acids and/or comprising or consisting of $(G_4S)_n$ (SEQ ID NO:57), optionally wherein n≥2, e.g., wherein N is 3, 4, 5 or greater; and
  (iii) An IL2 binding portion of IL-2Rα (e.g., as described in Section 6.3).

94. The IL2 agonist of any one of embodiments 1 to 92, which comprises:
(a) A peptide-MHC complex (e.g., as described in Section 6.4.3) comprising:
  (i) An MHC peptide;
  (ii) A linker (e.g., as described in Section 6.7 or subsections thereof, for example in Section 6.7.1);
  (iii) Optionally, a β2-microglobulin (β2m) domain;
  (iv) Optionally, a linker (e.g., as described in Section 6.7 or subsections thereof, for example in Section 6.7.1); and
  (v) MHC;
(b) Optionally, a linker (e.g., as described in Section 6.7), e.g., a linker comprising or consisting of $(G_4S)_n$ (SEQ ID NO:57), optionally wherein n≥1, e.g., wherein N is 1, 2, 3, 4, 5 or greater;
(c) An Fc domain (e.g., IgG1 or IgG4, with or without substitutions that reduce glycosylation and/or effector function as described in Section 6.5.1 and subsections thereof);
(d) A linker (e.g., as described in Section 6.7), e.g., a linker comprising or consisting of $(G_4S)_n$ (SEQ ID NO:57), optionally wherein n≥1, e.g., wherein N is 1, 2, 3, 4, 5 or greater;
(e) An IL2 moiety comprising:
  (i) An IL2 or IL2 variant (e.g., IL2 N88D) domain, with or without a substitution at C125 that reduces aggregation (e.g., C125S, C125A or C125V);
  (ii) A linker (e.g., as described in Section 6.7), e.g., a linker comprising 10 or more amino acids and/or comprising or consisting of $(G_4S)_n$ (SEQ ID NO:57), optionally wherein n≥2, e.g., wherein N is 3, 4, 5 or greater; and
  (iii) An IL2 binding portion of IL-2Rα (e.g., as described in Section 6.3).

95. The IL2 agonist of any one of embodiments 1 to 86, which is or comprises an Orientation 4 IL2 agonist.

96. The IL2 agonist of any one of embodiments 1 to 86 and 95, which comprises:
(a) A first polypeptide comprising:
  (i) A targeting moiety, e.g., peptide-MHC complex (e.g., as described in Section 6.4.3), Fab domain (e.g., as described in Section 6.4.2.2) (e.g., a heavy chain of a Fab associated with a third polypeptide comprising the light chain of the Fab), or scFv domain (e.g., as described in Section 6.4.2.1);
  (ii) An optional linker (e.g., as described in Section 6.7); and
  (iii) A first Fc domain; and
(b) A second polypeptide comprising:
  (i) IL2 moiety comprising an IL2 or IL2 variant domain (e.g., as described in Section 6.3 (e.g., an IL2 domain with the substitutions H16A, F42A, also referred to as IL2(2m)), with or without a substitution at C125 that reduces aggregation (e.g., C125S, C125A or C125V);
  (ii) An optional linker (e.g., as described in Section 6.7); and
  (iii) A second Fc domain that can dimerize (e.g., heterodimerize) with the first Fc domain (e.g., as described in Section 6.5.1.2).

97. The IL2 agonist of any one of embodiments 1 to 86, 95 and 96, which comprises:
(a) A first polypeptide, comprising:
  (i) A peptide-MHC complex (e.g., as described in Section 6.4.3) comprising:
    (1) An MHC peptide;
    (2) A linker (e.g., as described in Section 6.7 or subsections thereof, for example in Section 6.7.1);
    (3) Optionally, a β2-microglobulin (β2m) domain;
    (4) Optionally, a linker (e.g., as described in Section 6.7 or subsections thereof, for example in Section 6.7.1); and
    (5) An MHC;
  (ii) Optionally, a linker (e.g., as described in Section 6.7); and
  (iii) A first Fc domain.
(b) A second polypeptide, comprising:
  (i) An IL2 moiety comprising an IL2 or IL2 variant (e.g., IL2 H16A, F42A) domain, with or without a substitution at C125 that reduces aggregation (e.g., C125S, C125A or C125V);
  (ii) Optionally, a linker (e.g., as described in Section 6.7); and
  (iii) A second Fc domain that is not identical to, but can heterodimerize with, the first Fc domain (e.g., as described in Section 6.5.1.2).

98. The IL2 agonist of any one of embodiments 1, 87 and 88, which (a) has or comprises an amino acid sequence having the configuration of or (b) comprises the amino acid sequence of IL2M0.

99. The IL2 agonist of any one of embodiments 1, 87 and 88, which (a) has or comprises an amino acid sequence having the configuration of (e.g., IL2 moiety-optional linker-IL2Rα-optional linker-Fc domain) or (b) comprises the amino acid sequence of IL2M2.

100. The IL2 agonist of any one of embodiments 1 and 91 to 94, which (a) has or comprises an amino acid sequence having the configuration of (e.g., IL2Rα-optional linker-IL2 moiety-optional linker-Fc domain) or (b) comprises the amino acid sequence of IL2M3.

101. The IL2 agonist of any one of embodiments 1, 89 and 90, which (a) has or comprises an amino acid sequence having the configuration of (e.g., Fc domain-optional linker-IL2 moiety) or (b) comprises the amino acid sequence of IL2M4.

102. The IL2 agonist of any one of embodiments 1, 89 and 90, which (a) has or comprises an amino acid sequence having the configuration of (e.g., Fc domain-optional linker-IL2 moiety) or (b) comprises the amino acid sequence of IL2M5.

103. The IL2 agonist of any one of embodiments 1 and 95 to 97, which (a) has or comprises an amino acid sequence having the configuration of (e.g., Fc domain-optional linker-IL2 moiety) or (b) comprises the amino acid sequence of IL2M6.

104. The IL2 agonist of any one of embodiments 1 and 95 to 97, which (a) has an amino acid sequence having the configuration (e.g., IL2 moiety-optional linker-Fc domain) of IL2M7 or (b) comprises the amino acid sequence of IL2M7, in each case optionally associated with a polypeptide chain comprising a targeting moiety-optional linker-Fc domain, e.g., a polypeptide chain comprising the sequence or configuration of T7 or T8.

105. An IL2 agonist comprising:
(a) an IL2 moiety comprising an IL2 domain and an IL2 binding portion of IL2-Ra; and
(b) an Fc domain.

106. The IL2 agonist of embodiment 105, wherein the IL2 binding portion of IL2-Rα is N-terminal to the IL2 domain.

107. The IL2 agonist of embodiment 105, wherein the IL2 binding portion of IL2-Rα is C-terminal to the IL2 domain.

108. The IL2 agonist of any one of embodiments 105 to 107, wherein the Fc domain is N-terminal to the IL2 moiety.

109. The IL2 agonist of any one of embodiments 105 to 107, wherein the Fc domain is C-terminal to the IL2 moiety.

110. The IL2 agonist of any one of embodiments 105 to 109, wherein the IL2 domain and IL2 binding portion of IL2-Rα are connected via a linker, optionally wherein the linker comprises 10 or more or 15 or more amino acids.

111. The IL2 agonist of embodiment 110, wherein the linker is or comprises $G_4S$ (SEQ ID NO:57) or a multimer thereof.

112. The IL2 agonist of embodiment 111, wherein the linker comprises a single $G_4S$ (SEQ ID NO:57).

113. The IL2 agonist of embodiment 111, wherein the linker comprises two, three, four or five repeats of $G_4S$ (SEQ ID NO:57).

114. The IL2 agonist of any one of embodiments 105 to 113, wherein the IL2 moiety and the Fc domain are connected via a linker, optionally wherein the linker comprises 5 or more or 10 or more amino acids.

115. The IL2 agonist of embodiment 114, wherein the linker is or comprises $G_4S$ (SEQ ID NO:57) or a multimer thereof.

116. The IL2 agonist of embodiment 115, wherein the linker comprises a single $G_4S$ (SEQ ID NO:57).

117. The IL2 agonist of embodiment 115, wherein the linker comprises two, three, four or five repeats of $G_4S$ (SEQ ID NO:57).

118. The IL2 agonist of embodiment 105, which (a) has or comprises an amino acid sequence having the configuration of (e.g., IL2 moiety-optional linker-IL2Rα-optional linker-Fc domain) or (b) comprises the amino acid sequence of IL2M2.

119. The IL2 agonist of embodiment 105, which (a) has or comprises an amino acid sequence having the configuration of (e.g., IL2a moiety-optional linker-IL2R-optional linker-Fc domain) or (b) comprises the amino acid sequence of IL2M3.

120. The IL2 agonist of any one of embodiments 1 to 119, which comprises a targeting moiety.

121. The IL2 agonist of embodiment 120, wherein the targeting moiety:
(a) binds to a tumor associated antigen;
(b) binds to a tumor microenvironment antigen;
(c) binds to a cell surface molecule of tumor reactive lymphocytes;
(d) binds to a checkpoint inhibitor;
(e) binds to a peptide-MHC complex;
(f) is a peptide-MHC complex; or
(g) binds to an antigen associated with or targeted by an autoimmune response.

122. The IL2 agonist of embodiment 121, wherein the targeting moiety binds to a tumor associated antigen.

123. The IL2 agonist of embodiment 122, wherein the tumor associated antigen is Fibroblast Activation Protein (FAP), the A1 domain of Tenascin-C (TNC A1), the A2 domain of Tenascin-C (TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (ADAbp), cyclophilin b, colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) or an immunogenic epitopes thereo PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22

(B-cell receptor), CD23 (low binding affinity IgE receptor), CD30 (cytokine receptor), CD33 (myeloid cell surface antigen), CD40 (tumor necrosis factor receptor), IL-6R-(IL6 receptor), CD20, MCSP, PDGFβR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, the extra domain A (EDA) or extra domain B (EDB) of fibronectin, or the A1 domain of tenascin-C (TnC A1).

124. The IL2 agonist of embodiment 121 or embodiment 122, wherein the tumor associated antigen is a viral antigen.

125. The IL2 agonist of embodiment 124, wherein the viral antigen is Epstein-Barr virus LMP-1, hepatitis C virus E2 glycoprotein, HIV gp160, or HIV gp120, HPV E6, HPV E7, CMV early membrane antigen (EMA) or CMV late membrane antigen (LMA).

126. The IL2 agonist of embodiment 121, wherein the targeting moiety binds to a tumor microenvironment antigen.

127. The IL2 agonist of embodiment 126, wherein the tumor microenvironment antigen is an extracellular matrix protein.

128. The IL2 agonist of embodiment 127, wherein the extracellular matrix protein is syndecan, heparanase, integrins, osteopontin, link, cadherins, laminin, laminin type EGF, lectin, fibronectin, notch, tenascin, collagen and matrixin.

129. The IL2 agonist of embodiment 121, wherein the targeting moiety binds to a cell surface molecule of tumor lymphocytes.

130. The IL2 agonist of embodiment 129, wherein the cell surface molecule is CD27, CD28, 4-1BB (CD137), OX40, CD30, CD40, PD1, ICOS, lymphocyte function-associated antigen-1 (LFA-1), CD2, CD7, LIGHT, NKG2C, LAG3, TIM3, or B7-H3.

131. The IL2 agonist of embodiment 130, wherein the cell surface molecule is PD1.

132. The IL2 agonist of embodiment 131, wherein targeting moiety is an anti-PD1 antibody or antigen binding fragment thereof.

133. The IL2 agonist of embodiment 132, wherein the anti-PD1 antibody or antigen binding fragment thereof inhibits PD1 signaling.

134. The IL2 agonist of embodiment 132, wherein the anti-PD1 antibody or antigen binding fragment thereof does not inhibit PD1 signaling.

135. The IL2 agonist of embodiment 130, wherein the cell surface molecule is LAG3.

136. The IL2 agonist of embodiment 121, wherein the targeting moiety binds to a checkpoint inhibitor.

137. The IL2 agonist of embodiment 136, wherein the checkpoint inhibitor is CTLA-4, PD1, PDL1, PDL2, PD1, B7-H3, B7-H4, BTLA, HVEM, TIM3, GAL9, LAG3, VISTA, KIR, 2B4, CD160, CGEN-15049, CHK1, VISTA, PSGL1, or CHK2.

138. The IL2 agonist of embodiment 137, wherein the checkpoint inhibitor is PD1.

139. The IL2 agonist of embodiment 138, wherein targeting moiety is an anti-PD1 antibody or antigen binding fragment thereof.

140. The IL2 agonist of embodiment 139, wherein the anti-PD1 antibody or antigen binding fragment thereof inhibits PD1 signaling.

141. The IL2 agonist of embodiment 139, wherein the anti-PD1 antibody or antigen binding fragment thereof does not inhibit PD1 signaling.

142. The IL2 agonist of embodiment 137, wherein the checkpoint inhibitor is LAG3.

143. The IL2 agonist of embodiment 138, wherein the targeting moiety binds to an MHC-peptide complex.

144. The IL2 agonist of embodiment 143 wherein the peptide in the peptide-MHC complex comprises a tumor neoantigen.

145. The IL2 agonist of embodiment 144, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

146. The IL2 agonist of any one of embodiments 143 to 145, wherein the targeting moiety comprises an antibody or antigen binding fragment thereof having complementarity determining regions ("CDRs") comprising:
- (a) a CDR-H1 having an amino acid sequence selected from any of SEQ ID NOs: 4, 20, 36, 52, 68, 84, 100, 1 16, 132, 148, 164, 180, 196, 212, 220, 236, 252, 268, 284, 300, 316, 332, 348, 364, 380, 396, 412, 428, 444, 460, 476, 492, 508, and 524 of International Patent Publication No. WO 2019005897 A1, which are incorporated by reference herein;
- (b) a CDR-H2 having an amino acid sequence selected from any of SEQ ID NOs: 6, 22, 38, 54, 70, 86, 102, 118, 134, 150, 166, 182, 198, 214, 222, 238, 254, 270, 286, 302, 318, 334, 350, 366, 382, 414, 430, 446, 462, 478, 494, 510, and 526 of International Patent Publication No. WO 2019005897 A1, which are incorporated by reference herein;
- (c) a CDR-H3 having an amino acid sequence selected from any of SEQ ID NOs: 8, 24, 40, 56, 72, 88, 104, 120, 136, 152, 168, 184, 200, 216, 224, 240, 256, 272, 288, 304, 320, 336, 352, 368, 384, 400, 416, 432, 448, 464, 480, 496, 512, and 528 of International Patent Publication No. WO 2019005897 A1, which are incorporated by reference herein;
- (d) a CDR-L1 having an amino acid sequence selected from any of SEQ ID NOs: 12, 28, 44, 60, 76, 92, 108, 124, 140, 156, 172, 188, 204, 204, 228, 244, 260, 276, 292, 308, 324, 340, 356, 372, 388, 404, 420, 436, 452, 468, 484, 500, 516, and 532 of International Patent Publication No. WO 2019005897 A1, which are incorporated by reference herein;
- (e) a CDR-L2 having an amino acid sequence selected from any of SEQ ID NOs: 14, 30, 46, 62, 78, 94, 110, 126, 142, 158,174, 190, 206, 230, 246, 262, 278, 294, 310, 326, 342, 358, 374, 390, 406, 422, 438, 454, 470, 486, 502, 518, and 534 of International Patent Publication No. WO 2019005897 A1, which are incorporated by reference herein; and (f) a CDR-L3 having an amino acid sequence selected from an of SEQ ID NOs: 16. 32, 48, 64, 80, 96, 112, 128, 144,160, 176, 192, 208, 232, 248, 264, 280, 296, 312, 328, 344, 360, 376, 392, 408, 424, 440, 456, 472, 488, 504, 520, and 536 of International Patent Publication No. WO 2019005897 A1, which are incorporated by reference herein.

147. The IL2 agonist of embodiment 146, wherein the antibody or antigen binding fragment has VH-VL amino acid sequences selected from any of SEQ ID NOs: 2/10, 18/26, 34/42, 50/58, 66/74, 82/90, 98/106, 114/122, 130/138, 146/154, 162/170, 178/186, 194/202, 210/202, 218/226, 234/242, 250/258, 266/274, 282/290, 298/306, 314/322, 330/338, 346/354, 362/370, 378/386, 394/402, 410/418, 426/434, 442/450, 458/466, 474/482, 490/498, 506/514, and 522/530 of International Patent Publication No. WO 2019005897 A1, which are incorporated by reference herein.

148. The IL2 agonist of embodiment 147, wherein the antibody or antigen binding fragment has VH-VL amino acid sequences selected from any of SEQ ID NOs: 2/10, 34/42, 82/90, 194/202, 282/290, and 506/514 of International Patent Publication No. WO 2019005897 A1, which are incorporated by reference herein.

149. The IL2 agonist of embodiment 121, wherein the targeting moiety binds to an antigen associated with or targeted by an autoimmune response.

150. The IL2 agonist of embodiment 149, wherein the peptide is derived from gliadin, GAD 65, IA-2, insulin B chain, glatiramer acetate (GA), achetylcholine receptor (AChR), p205, insulin, thyroid-stimulating hormone, tyrosinase, TRP I, or a myelin antigen.

151. The IL2 agonist of embodiment 150, wherein the peptide is derived from IL-4R, IL-6R, or DLL4.

152. The IL2 agonist of any one of embodiments 121 to 151, wherein the targeting moiety is an antibody or antigen binding fragment thereof.

153. The IL2 agonist of embodiment 152, wherein the targeting moiety is a Fab.

154. The IL2 agonist of embodiment 152, wherein the targeting moiety is a scFv.

155. The IL2 agonist of embodiment 121, wherein the targeting moiety is a peptide-MHC complex.

156. The IL2 agonist of embodiment 155, wherein the peptide-MHC complex binds to the T cell receptor of tumor lymphocytes.

157. The IL2 agonist of embodiment 155 or embodiment 156, wherein the peptide in the peptide-MHC complex comprises a tumor neoantigen.

158. The IL2 agonist of embodiment 157, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

159. The IL2 agonist of embodiment 155, wherein the peptide in peptide-MHC complex comprises a viral antigen.

160. The IL2 agonist of embodiment 159, wherein the viral antigen is CMVpp65 or HPV16E7.

161. The IL2 agonist of any one of embodiments 155 to 160, wherein the peptide-MHC complex further comprises β2 microglobulin or a fragment thereof.

162. The IL2 agonist of embodiment 161, wherein the peptide MHC complex comprises a type I MHC domain.

163. The IL2 agonist of embodiment 162, wherein the peptide MHC complex comprises, in an N- to C-terminal orientation a MHC peptide, a linker, a β2-microglobulin domain, a linker, and a type I MHC domain.

164. The IL2 agonist of embodiment 163, wherein the linker connecting the MHC peptide and the β2-microglobulin domain comprises the amino acid sequence GCGGS (SEQ ID NO:77).

165. The IL2 agonist of any one of embodiment 155 to 160, wherein the peptide-MHC complex does not comprise β2 microglobulin or a fragment thereof.

166. The IL2 agonist of embodiment 165, wherein the peptide MHC complex comprises a type MHC domain.

167. A nucleic acid or plurality of nucleic acids encoding the IL2 agonist of any one of embodiments 1 to 166.

168. A host cell engineered to express the IL2 agonist of any one of embodiments 1 to 166 or the nucleic acid(s) of embodiment 167.

169. A method of producing the IL2 agonist of any one of embodiments 1 to 166, comprising culturing the host cell of embodiment 168 and recovering the IL2 agonist expressed thereby.

170. A pharmaceutical composition comprising the IL2 agonist of any one of embodiments 1 to 166 and an excipient.

171. A method of treating cancer, comprising administering to a subject in need thereof the IL2 agonist of any one of embodiments 1 to 166 or the pharmaceutical composition of embodiment 170.

172. A method of treating cancer, comprising administering to a subject in need thereof:
  (a) chimeric antigen receptor ("CAR") T cells ("CART cells"); and
  (b) an IL2 agonist comprising a targeting moiety that binds to the T cell receptor of the CART cells or another cell surface molecule on the CART cells, optionally wherein the targeting moiety is capable of binding to extracellular domain of the CAR.

173. The method of embodiment 172, wherein the IL2 agonist is monovalent for an IL2 moiety and/or the targeting moiety.

174. The method of embodiment 172 or embodiment 173, wherein the IL2 agonist is an IL2 agonist according to any one of embodiments 1 to 166, preferably an IL2 agonist according to any one of embodiments 94 to 97, 121, and 155 to 166.

175. The method of any one of embodiments 172 to 174, wherein the CART cells are not engineered to express a variant IL2-Rβ receptor.

176. The method of any one of embodiments 172 to 174, wherein the CART cells are not engineered to express any variant IL2 receptor.

177. The method of any one of embodiments 172 to 176, wherein the IL2 agonist is administered to the subject within one week of administration of the CART cells.

178. The method of embodiment 177, wherein the wherein the IL2 agonist is administered to the subject on the same day as the administration of the CART cells.

179. The method of any one of embodiments 172 to 178, which comprises dosing the subject with the IL2 agonist for a period of at least two weeks.

180. The method of embodiment 179, wherein the IL2 agonist is dosed by continuous infusion.

181. The method of embodiment 179, wherein the IL2 agonist is dosed by daily administration for at least a portion of the at least two-week period.

182. The method of embodiment 179, wherein the IL2 agonist is dosed according to a split dosing regimen, comprising:
   (a) administering the IL2 agonist at a first dosing frequency in the initial part of the at least two week period; and
   (b) administering IL2 agonist at a second dosing frequency in a subsequent portion of the at least two week period.

183. The method of embodiment 182, wherein the first dosing frequency is daily.

184. The method of embodiment 182 or embodiment 183, wherein the second dosing frequency is less frequent than the first dosing frequency.

185. The method of embodiment 184, wherein the second dosing frequency is weekly.

186. The method of any one of embodiments 182 to 185, wherein the subject is transitioned from the first dosing frequency to the second dosing frequency concurrently with or after exhaustion of the CART cells.

187. The method of any one of embodiments 171 to 186, which further comprises administering an anti-PD1 antibody to the subject.

188. The method of embodiment 187, wherein the anti-PD1 antibody is MDX-1106 (nivolumab), MK-3475 (pembrolizumab), MEDI-0680 (AMP-514), PDR001, REGN2810, or BGB-108.

189. The method of any one of embodiments 172 to 188, wherein the CAR is designed to target any of the targets identified in Section 6.11.1.3.

190. The method of any one of embodiments 172 to 189, wherein the CAR is configured according to Section 6.11.1.1 and subsections thereof.

191. The method of any one of embodiments 172 to 190, wherein the targeting moiety comprises a pMHC recognized by the antigen binding domain of the CAR.

192. A method of treating autoimmune disease, comprising administering to a subject in need thereof:
   (a) chimeric antigen receptor ("CAR") T cells ("CART cells"); and
   (b) an IL2 agonist comprising a targeting moiety that binds to a cell surface antigen present on the CART cells, optionally wherein the targeting moiety is capable of binding to extracellular domain of the CAR.

193. The method of embodiment 192, wherein the IL2 agonist is monovalent for an IL2 moiety and/or the targeting moiety.

194. The method of embodiment 192 or embodiment 193, wherein the IL2 agonist is an IL2 agonist according to any one of embodiments 1 to 166, preferably an IL2 agonist according to any one of embodiments 94 to 97, 121, and 155 to 166 according to any one of embodiments 94 to 97, 121, and 155 to 166.

195. The method of any one of embodiments 192 to 194, wherein the targeting moiety comprises a pMHC cloned from an autoimmune target cell and/or which is recognized by the antigen binding domain of the CAR.

196. The method of any one of embodiments 192 to 195, wherein the CART cell is a Treg cell.

197. The method of any one of embodiments 192 to 196, wherein the CAR is designed to target any of the targets identified in Section 6.11.1.4.

198. The method of any one of embodiments 192 to 197, wherein the CAR is configured according to Section 6.11.1.1 and subsections thereof.

199. An IL2 agonist comprising:
   (a) an Fc domain; an
   (b) an IL2 moiety C-terminal to the Fc domain, wherein the IL2 moiety comprises an IL2 domain and an IL2-Rα domain,
   optionally wherein the IL2 agonist has one or more features of the IL2 agonists of any one of embodiments 1 to 36.

200. The IL2 agonist of embodiment 199, wherein the IL2 domain is N-terminal to the IL2-Rα domain.

201. The IL2 agonist of embodiment 199, wherein the IL2 domain is C-terminal to the IL2-Rα domain.

202. The IL2 agonist of any one of embodiments 199 to 201, wherein the IL2 moiety comprises an IL2 domain comprising an amino acid sequence having:
   (a) at least about 90% or at least about 95% sequence identity to mature human IL2,
   (b) an N-terminal alanine deletion as compared to mature human IL2;
   (c) an IL2 variant which has an amino acid substitution at position N88 as compared to wild type IL2, optionally wherein the amino acid substitution is N88D;
   (d) the amino acid substitution C125S, C125A or C125V as compared to wild type I L2; or
   (e) any combination of (a), (b), (c) and/or (d).

203. The IL2 agonist of any one of embodiments 199 to 202, wherein the IL2-Rα domain comprises or consists of an amino acid sequence having at least about 90%, at least about 95%, at least about 96%, at least about 97%, at least about 98%, at least about 99% or 100% sequence identity to an IL2 binding portion of human IL-2Rα, optionally wherein said binding portion has:
   (a) at least 160 amino acids, at least 161 amino acids, at least 162 amino acids, at least 164 amino acids or at least 165 amino acids of human IL2-Rα; and/or
   (b) up to 251, up to 240, up to 230, up to 220, up to 210, up to 200, up to 190, up to 180 or up to 170 amino acids of the extracellular domain of human IL2-Rα.

204. The IL2 agonist of any one of embodiments 199 to 203, wherein the IL2 domain and the IL2-Rα domain are connected via a linker ("the IL2 moiety linker").

205. The IL2 agonist of embodiment 204, wherein the IL2 moiety linker is at least 10 or at least 15 amino acids in length.

206. The IL2 agonist of embodiment 204 or embodiment 205, wherein the IL2 moiety linker is or comprises a glycine-serine linker.

207. The IL2 agonist of any one of embodiments 204 to 206, wherein the IL2 moiety linker comprises the amino acid sequence $G_4S$ (SEQ ID NO:57).

208. The IL2 agonist of embodiment 207, wherein the IL2 moiety linker is or comprises a multimer of the amino acid sequence $G_4S$ (SEQ ID NO:57).

209. The IL2 agonist of embodiment 208, wherein the multimer comprises 2, 3, 4, 5, 6 or more repeats of the amino acid sequence $G_4S$ (SEQ ID NO:57).

210. The IL2 agonist of any one of embodiments 199 to 209, wherein the Fc domain and the IL2 moiety are connected via a linker (the "Fc-IL2 linker").

211. The IL2 agonist of embodiment 210, wherein the Fc-IL2 linker is at least 5 or at least 10 amino acids in length.

212. The IL2 agonist of embodiment 210 or embodiment 211, wherein the Fc-IL2 linker is or comprises a glycine-serine linker.

213. The IL2 agonist of any one of embodiments 210 to 212, wherein the Fc-IL2 linker comprises the amino acid sequence G₄S (SEQ ID NO:57).

214. The IL2 agonist of embodiment 207, wherein the Fc-IL2 linker is or comprises a multimer of the amino acid sequence G₄S (SEQ ID NO:57).

215. The IL2 agonist of embodiment 208, wherein the multimer comprises 2, 3, 4, 5, 6 or more repeats of the amino acid sequence G₄S (SEQ ID NO:57).

216. The IL2 agonist of any one of embodiments 199 to 215, wherein the Fc domain is an IgG1, IgG2, IgG3 or IgG4 Fc domain.

217. The IL2 agonist of embodiment 216, wherein the Fc domain has reduced effector function.

218. The IL2 agonist of any one of embodiments 199 to 217 which is a dimer.

219. The IL2 agonist of embodiment 218, which is a homodimer.

220. The IL2 agonist of embodiment 218, which is a heterodimer.

221. The IL2 agonist of any one of embodiments 199 to 220, which is bivalent for the IL2 moiety.

222. The IL2 agonist of any one of embodiments 199 to 221, which comprises a targeting moiety.

223. The IL2 agonist of embodiment 222, wherein the targeting moiety is N-terminal to the Fc domain.

224. The IL2 agonist of embodiment 222 or embodiment 223, wherein the targeting moiety:
  (a) binds to a tumor associated antigen;
  (b) binds to a tumor microenvironment antigen;
  (c) binds to a cell surface molecule of tumor reactive lymphocytes;
  (d) binds to a checkpoint inhibitor;
  (e) binds to a peptide-MHC complex;
  (f) is a peptide-MHC complex; or
  (g) binds to an antigen associated with or targeted by an autoimmune response.

225. The IL2 agonist of embodiment 224, wherein the targeting moiety binds to a tumor associated antigen.

226. The IL2 agonist of embodiment 225, wherein the tumor associated antigen is Fibroblast Activation Protein (FAP), the A1 domain of Tenascin-C (TNC A1), the A2 domain of Tenascin-C (TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (ADAbp), cyclophilin b, colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) or an immunogenic epitopes thereto PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22 (B-cell receptor), CD23 (low binding affinity IgE receptor), CD30 (cytokine receptor), CD33 (myeloid cell surface antigen), CD40 (tumor necrosis factor receptor), IL-6R-(IL6 receptor), CD20, MCSP, PDGFβR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, the extra domain A (EDA) or extra domain B (EDB) of fibronectin, or the A1 domain of tenascin-C (TnC A1).

227. The IL2 agonist of embodiment 224 or embodiment 225, wherein the tumor associated antigen is a viral antigen.

228. The IL2 agonist of embodiment 227, wherein the viral antigen is Epstein-Barr virus LMP-1, hepatitis C virus E2 glycoprotein, HIV gp160, or HIV gp120, HPV E6, HPV E7, CMV early membrane antigen (EMA) or CMV late membrane antigen (LMA).

229. The IL2 agonist of embodiment 224, wherein the targeting moiety binds to a tumor microenvironment antigen.

230. The IL2 agonist of embodiment 229, wherein the tumor microenvironment antigen is an extracellular matrix protein.

231. The IL2 agonist of embodiment 230, wherein the extracellular matrix protein is syndecan, heparanase, integrins, osteopontin, link, cadherins, laminin, laminin type EGF, lectin, fibronectin, notch, tenascin, collagen and matrixin.

232. The IL2 agonist of embodiment 224, wherein the targeting moiety binds to a cell surface molecule of tumor lymphocytes.

233. The IL2 agonist of embodiment 232, wherein the cell surface molecule is CD27, CD28, 4-1BB (CD137), OX40, CD30, CD40, PD1, ICOS, lymphocyte function-associated antigen-1 (LFA-1), CD2, CD7, LIGHT, NKG2C, LAG3, TIM3, or B7-H3.

234. The IL2 agonist of embodiment 233, wherein the cell surface molecule is PD1.

235. The IL2 agonist of embodiment 234, wherein targeting moiety is an anti-PD1 antibody or antigen binding fragment thereof.

236. The IL2 agonist of embodiment 233, wherein the cell surface molecule is LAG3.

237. The IL2 agonist of embodiment 224, wherein the targeting moiety binds to a checkpoint inhibitor.

238. The IL2 agonist of embodiment 237, wherein the checkpoint inhibitor is CTLA-4, PD1, PDL1, PDL2, PD1, B7-H3, B7-H4, BTLA, HVEM, TIM3, GAL9, LAG3, VISTA, KIR, 2B4, CD160, CGEN-15049, CHK1, VISTA, PSGL1, or CHK2.

239. The IL2 agonist of embodiment 238, wherein the checkpoint inhibitor is PD1.

240. The IL2 agonist of embodiment 238, wherein the checkpoint inhibitor is LAG3.

241. The IL2 agonist of embodiment 239, wherein the targeting moiety binds to an MHC-peptide complex.

242. The IL2 agonist of embodiment 241 wherein the peptide in the peptide-MHC complex comprises a tumor neoantigen.

243. The IL2 agonist of embodiment 242, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

244. The IL2 agonist of any one of embodiments 224 to 243, wherein the targeting moiety is an antibody or antigen binding fragment thereof.

245. The IL2 agonist of embodiment 244, wherein the targeting moiety is a Fab.

246. The IL2 agonist of embodiment 244, wherein the targeting moiety is a scFv.

247. The IL2 agonist of embodiment 224, wherein the targeting moiety is a peptide-MHC complex.

248. The IL2 agonist of embodiment 247, wherein the peptide-MHC complex binds to the T cell receptor of tumor lymphocytes.

249. The IL2 agonist of embodiment 247 or embodiment 248, wherein the peptide in the peptide-MHC complex comprises a tumor neoantigen.

250. The IL2 agonist of embodiment 249, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

251. The IL2 agonist of embodiment 247, wherein the peptide in peptide-MHC complex comprises a viral antigen.

252. The IL2 agonist of embodiment 251, wherein the viral antigen is CMVpp65 or HPV16E7.

253. The IL2 agonist of any one of embodiments 247 to 252, wherein the peptide-MHC complex further comprises β2 microglobulin or a fragment thereof.

254. The IL2 agonist of embodiment 253, wherein the peptide MHC complex comprises a type I MHC domain.

255. The IL2 agonist of embodiment 254, wherein the peptide MHC complex comprises, in an N- to C-terminal orientation a MHC peptide, a linker, a β2-microglobulin domain, a linker, and a type I MHC domain.

256. The IL2 agonist of embodiment 255, wherein the linker connecting the MHC peptide and the β2-microglobulin domain comprises the amino acid sequence GCGGS.

257. The IL2 agonist of any one of embodiment 247 to 252, wherein the peptide-MHC complex does not comprise β2 microglobulin or a fragment thereof.

258. The IL2 agonist of embodiment 257, wherein the peptide MHC complex comprises a type MHC domain.

259. A nucleic acid or plurality of nucleic acids encoding the IL2 agonist of any one of embodiments 199 to 258.

260. A host cell engineered to express the IL2 agonist of any one of embodiments 199 to 258 or the nucleic acid(s) of embodiment 259.

261. A method of producing the IL2 agonist of any one of embodiments 199 to 258, comprising culturing the host cell of embodiment 260 and recovering the IL2 agonist expressed thereby.

262. A pharmaceutical composition comprising the IL2 agonist of any one of embodiments 199 to 258 and an excipient.

263. A method of treating cancer, comprising administering to a subject in need thereof the IL2 agonist of any one of embodiments 199 to 258 or the pharmaceutical composition of embodiment 262.

264. A method of treating cancer, comprising administering to a subject in need thereof:
(a) chimeric antigen receptor ("CAR") T cells ("CART cells"); and
(b) an IL2 agonist according to any one of embodiments 199 to 224 comprising a targeting moiety that binds to the T cell receptor of the CART cells or another cell surface molecule on the CART cells, optionally wherein the targeting moiety is capable of binding to the extracellular domain of the CAR,
optionally wherein the CAR:
(i) wherein the CAR is designed to target any of the targets identified in Section 6.11.1.4; and/or
(ii) wherein the CAR is configured according to Section 6.11.1.1 and subsections thereof.

265. The method of embodiment 263 or embodiment 264, which further comprises administering an anti-PD1 antibody to the subject.

266. The method of embodiment 265, wherein the anti-PD1 antibody is MDX-1106 (nivolumab), MK-3475 (pembrolizumab), MEDI-0680 (AMP-514), PDR001, REGN2810, or BGB-108.

267. An IL2 agonist comprising:
(a) a first polypeptide chain comprising:
(i) a targeting moiety, e.g., a targeting moiety capable of binding to a cell surface molecule on a chimeric antigen receptor (CAR) T cell, optionally wherein the targeting moiety is capable of binding to the extracellular domain of the CAR; and
(ii) a first Fc domain C-terminal to the targeting moiety; and
(b) a second polypeptide chain comprising:
(i) an IL2 moiety; and
(ii) a second Fc domain N- or C-terminal to the IL2 moiety, optionally wherein the IL2 agonist has one or more features of the IL2 agonists of any one of embodiments 1 to 36.

268. The IL2 agonist of embodiment 267, which is a dimer.

269. The IL2 agonist of embodiment 268, which is a homodimer.

270. The IL2 agonist of embodiment 269, which is bivalent for the targeting moiety and the IL2 moiety.

271. The IL2 agonist of embodiment 270, which has the configuration depicted in FIG. 22.A.1.

272. The IL2 agonist of embodiment 270 or embodiment 271, which comprises:
(a) a first polypeptide chain comprising:
(i) a first targeting moiety capable of binding to a chimeric antigen receptor;
(ii) an optional linker;
(iii) a first Fc domain C-terminal to the targeting moiety;

(iv) an optional linker; and
(v) a first IL2 moiety C-terminal to the first Fc domain;
(b) a second polypeptide chain comprising:
(i) a second targeting moiety capable of binding to a chimeric antigen receptor;
(ii) an optional linker;
(iii) a second Fc domain C-terminal to the targeting moiety;
(iv) an optional linker; and
(v) a second IL2 moiety C-terminal to the first Fc domain.

273. The IL2 agonist of embodiment 268, which is a heterodimer.

274. The IL2 agonist of embodiment 273, which is monovalent for the targeting moiety and the IL2 moiety.

275. The IL2 agonist of embodiment 274, which has the configuration depicted in FIG. 22.A.2.

276. The IL2 agonist of embodiment 274 or embodiment 274, which comprises:
(a) a first polypeptide chain comprising:
(i) a targeting moiety capable of binding to a chimeric antigen receptor;
(ii) an optional linker; and
(iii) a first Fc domain C-terminal to the targeting moiety; and
(b) a second polypeptide chain comprising:
(i) an IL2 moiety;
(ii) an optional linker; and
(iii) a second Fc domain C-terminal to the IL2 moiety.

277. The IL2 agonist of any one of embodiments 267 to 276, wherein the IL2 moiety and/or the IL2 agonist has attenuated binding to human IL2-Rβ.

278. The IL2 agonist of any one of embodiments 267 to 277, wherein the IL2 moiety and/or the IL2 agonist has attenuated binding to human IL2-Rα.

279. The IL2 agonist of any one of embodiments 267 to 278, wherein the IL2 moiety and/or the IL2 agonist has:
(a) 50-fold to 1000-fold attenuated binding to human IL2-Rβ as compared to wild type IL2; and/or
(b) up to 100-fold attenuated binding to human IL2-Rα as compared to wild-type human IL2.

280. The IL2 agonist of any one of embodiments 267 to 279, wherein the IL2 moiety and/or the IL2 agonist has attenuated binding affinity to the high affinity IL2 receptor compared to wild type IL2.

281. The IL2 agonist of embodiment 280, wherein the binding affinity is attenuated by 10-fold to 1,000-fold.

282. The IL2 agonist of any one of embodiments 267 to 281, wherein the IL2 moiety comprises an IL2 domain comprising an amino acid sequence having:
(a) at least about 90% or at least about 95% sequence identity to mature human IL2,
(b) an N-terminal alanine deletion as compared to mature human IL2;
(c) the amino acid substitution C125S, C125A or C125V as compared to wild type IL2;
(d) the amino acid substitutions H16A and/or F42A as compared to wild type I L2; or
(e) any combination of (a), (b), (c) and/or (d).

283. The IL2 agonist of any one of embodiments 267 to 282, which lacks an IL2 binding portion of IL2-Rα.

284. The IL2 agonist of any one of embodiments 267 to 283, wherein the Fc domain is an IgG1, IgG2, IgG3 or IgG4 Fc domain.

285. The IL2 agonist of embodiment 284, wherein the Fc domain has reduced effector function.

286. The IL2 agonist of any one of embodiments 1 to 285, wherein the targeting moiety is a peptide-MHC complex.

287. The IL2 agonist of embodiment 286, wherein the peptide-MHC complex binds to the T cell receptor of tumor lymphocytes.

288. The IL2 agonist of embodiment 286 or embodiment 287, wherein the peptide in the peptide-MHC complex comprises a tumor neoantigen.

289. The IL2 agonist of embodiment 288, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

290. The IL2 agonist of embodiment 286 or embodiment 287, wherein the peptide in peptide-MHC complex comprises a viral antigen.

291. The IL2 agonist of embodiment 290, wherein the viral antigen is CMVpp65 or HPV16E7.

292. The IL2 agonist of any one of embodiments 286 to 291, wherein the peptide-MHC complex further comprises β2 microglobulin or a fragment thereof.

293. The IL2 agonist of embodiment 292, wherein the peptide MHC complex comprises a type I MHC domain.

294. The IL2 agonist of embodiment 293, wherein the peptide MHC complex comprises, in an N- to C-terminal orientation a MHC peptide, a linker, a β2-microglobulin domain, a linker, and a type I MHC domain.

295. The IL2 agonist of embodiment 294, wherein the linker connecting the MHC peptide and the β2-microglobulin domain comprises the amino acid sequence GCGGS (SEQ ID NO:77).

296. The IL2 agonist of any one of embodiment 286 to 291, wherein the peptide-MHC complex does not comprise β2 microglobulin or a fragment thereof.

297. The IL2 agonist of embodiment 296, wherein the peptide MHC complex comprises a type II MHC domain.

298. The IL2 agonist of any one of embodiments 267 to 285, wherein the targeting moiety is an antibody or antigen binding fragment thereof.

299. The IL2 agonist of embodiment 298, wherein the targeting moiety is a Fab and wherein the IL2 agonist comprises a third polypeptide chain comprising the light chain of the Fab.

300. The IL2 agonist of embodiment 298, wherein the targeting moiety is a scFv.

301. The IL2 agonist of any one of embodiments 267 to 285 and 298 to 300, wherein the targeting moiety:
(a) binds to a tumor associated antigen;
(b) binds to a tumor microenvironment antigen;
(c) binds to a cell surface molecule of tumor reactive lymphocytes;
(d) binds to a checkpoint inhibitor;
(e) binds to a peptide-MHC complex;
(f) binds to an antigen associated with or targeted by an autoimmune response.

302. The IL2 agonist of embodiment 301, wherein the targeting moiety binds to a tumor associated antigen.

303. The IL2 agonist of embodiment 302, wherein the tumor associated antigen is Fibroblast Activation Protein (FAP), the A1 domain of Tenascin-C (TNC A1), the A2 domain of Tenascin-C (TNC A2), the Extra Domain B of Fibronectin (EDB), the Melanoma-associated Chondroitin Sulfate Proteoglycan (MCSP), MART-1/Melan-A, gp100, Dipeptidyl peptidase IV (DPPIV), adenosine deaminase-binding protein (ADAbp), cyclophilin b, colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) or an immunogenic epitopes thereto PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, c-erbB-2, Her2, EGFR, IGF-1R, CD2 (T-cell surface antigen), CD3 (heteromultimer associated with the TCR), CD22 (B-cell receptor), CD23 (low binding affinity IgE receptor), CD30 (cytokine receptor), CD33 (myeloid cell surface antigen), CD40 (tumor necrosis factor receptor), IL-6R-(IL6 receptor), CD20, MCSP, PDGFβR (β-platelet-derived growth factor receptor), ErbB2 epithelial cell adhesion molecule (EpCAM), EGFR variant III (EGFRvIII), CD19, disialoganglioside GD2, ductal-epithelial mucine, gp36, TAG-72, glioma-associated antigen, β-human chorionic gonadotropin, alphafetoprotein (AFP), lectin-reactive AFP, thyroglobulin, MN-CA IX, human telomerase reverse transcriptase, RU1, RU2 (AS), intestinal carboxyl esterase, mut hsp70-2, M-CSF, prostase, prostase specific antigen (PSA), PAP, LAGA-1a, p53, prostein, PSMA, surviving and telomerase, prostate-carcinoma tumor antigen-1 (PCTA-1), ELF2M, neutrophil elastase, ephrin B2, insulin growth factor (IGF1)-I, IGF-II, IGFI receptor, 5T4, ROR1, Nkp30, NKG2D, tumor stromal antigens, the extra domain A (EDA) or extra domain B (EDB) of fibronectin, or the A1 domain of tenascin-C (TnC A1).

304. The IL2 agonist of embodiment 301 or embodiment 302, wherein the tumor associated antigen is a viral antigen.

305. The IL2 agonist of embodiment 304, wherein the viral antigen is Epstein-Barr virus LMP-1, hepatitis C virus E2 glycoprotein, HIV gp160, or HIV gp120, HPV E6, HPV E7, CMV early membrane antigen (EMA) or CMV late membrane antigen (LMA).

306. The IL2 agonist of embodiment 301, wherein the targeting moiety binds to a tumor microenvironment antigen.

307. The IL2 agonist of embodiment 306, wherein the tumor microenvironment antigen is an extracellular matrix protein.

308. The IL2 agonist of embodiment 307, wherein the extracellular matrix protein is syndecan, heparanase, integrins, osteopontin, link, cadherins, laminin, laminin type EGF, lectin, fibronectin, notch, tenascin, collagen and matrixin.

309. The IL2 agonist of embodiment 301, wherein the targeting moiety binds to a cell surface molecule of tumor lymphocytes.

310. The IL2 agonist of embodiment 309, wherein the cell surface molecule is CD27, CD28, 4-1BB (CD137), OX40, CD30, CD40, PD1, ICOS, lymphocyte function-associated antigen-1 (LFA-1), CD2, CD7, LIGHT, NKG2C, LAG3, TIM3, or B7-H3.

311. The IL2 agonist of embodiment 310, wherein the cell surface molecule is PD1.

312. The IL2 agonist of embodiment 310, wherein the cell surface molecule is LAG3.

313. The IL2 agonist of embodiment 301, wherein the targeting moiety binds to a checkpoint inhibitor.

314. The IL2 agonist of embodiment 313, wherein the checkpoint inhibitor is CTLA-4, PD1, PDL1, PDL2, PD1, B7-H3, B7-H4, BTLA, HVEM, TIM3, GAL9, LAG3, VISTA, KIR, 2B4, CD160, CGEN-15049, CHK1, VISTA, PSGL1, or CHK2.

315. The IL2 agonist of embodiment 314, wherein the checkpoint inhibitor is PD1.

316. The IL2 agonist of embodiment 314, wherein the checkpoint inhibitor is LAG3.

317. The IL2 agonist of embodiment 301, wherein the targeting moiety binds to an MHC-peptide complex.

318. The IL2 agonist of embodiment 317 wherein the peptide in the peptide-MHC complex comprises a tumor neoantigen.

319. The IL2 agonist of embodiment 318, wherein the tumor neoantigen is LCMV derived peptide gp33-41, APF (126-134), BALF (276-284), CEA (571-579), CMV pp65 (495-503), FLU-M1 (58-66), gp100 (154-162), gp100 (209-217), HBV Core (18-27), Her2/neu (369-377; V2v9); HPV E7 (11-20), HPV E7 (11-19), HPV E7 (82-90), KLK4 (11-19), LMP1 (125-133), MAG-A3 (112-120), NYESO1 (157-165, C165A), NYESO1 (157-165, C165V), p54 WT (264-272), PAP-3 (136-143), PSMA (4-12), PSMA (135-145), Survivin (96-014), Tyrosinase (369-377, 371D), or WT1 (126-134).

320. The IL2 agonist of embodiment 301, wherein the targeting moiety binds to an antigen associated with or targeted by an autoimmune response.

321. The IL2 agonist of embodiment 320, wherein the peptide is derived from gliadin, GAD 65, IA-2, insulin B chain, glatiramer acetate (GA), achetylcholine receptor (AChR), p205, insulin, thyroid-stimulating hormone, tyrosinase, TRP I, or a myelin antigen.

322. The IL2 agonist of embodiment 321, wherein the peptide is derived from IL-4R, IL-6R, or DLL4.

323. A nucleic acid or plurality of nucleic acids encoding the IL2 agonist of any one of embodiments 267 to 322.

324. A host cell engineered to express the IL2 agonist of any one of embodiments 267 to 322 or the nucleic acid(s) of embodiment 323.

325. A method of producing the IL2 agonist of any one of embodiments 267 to 322, comprising culturing the host cell of embodiment 324 and recovering the IL2 agonist expressed thereby.

326. A pharmaceutical composition comprising the IL2 agonist of any one of embodiments 267 to 322 and an excipient.

327. A method of treating cancer, comprising administering to a subject in need thereof the IL2 agonist of any one of embodiments 267 to 322 or the pharmaceutical composition of embodiment 326.

328. A method of treating cancer, comprising administering to a subject in need thereof:
(a) chimeric antigen receptor ("CAR") T cells ("CART cells"); and
(b) an IL2 agonist according to any one of embodiments 267 to 322 whose targeting moiety binds to a cell surface molecule on the chimeric antigen receptor (CAR) T cells, optionally wherein the targeting moiety is capable of binding to the extracellular domain of the CAR, optionally wherein the CAR is:
(i) designed to target any of the targets identified in Section 6.11.1.4; and/or
(ii) configured according to Section 6.11.1.1 and subsections thereof.

329. The method of embodiment 328, wherein the targeting moiety comprises a pMHC recognized by the antigen binding domain of the CAR.

330. The method of embodiment 328 or embodiment 329, wherein the CART cells are not engineered to express a variant IL2-Rβ receptor.

331. The method of any one of embodiments 328 to 330, wherein the CART cells are not engineered to express any variant IL2 receptor.

332. The method of any one of embodiments 328 to 331, wherein the IL2 agonist is administered to the subject within one week of administration of the CART cells.

333. The method of embodiment 332, wherein the wherein the IL2 agonist is administered to the subject on the same day as the administration of the CART cells.

334. The method of any one of embodiments 328 to 333, which comprises dosing the subject with the IL2 agonist for a period of at least two weeks.

335. The method of embodiment 334, wherein the IL2 agonist is dosed by continuous infusion.

336. The method of embodiment 334, wherein the IL2 agonist is dosed by daily administration for at least a portion of the at least two-week period.

337. The method of embodiment 334, wherein the IL2 agonist is dosed according to a split dosing regimen, comprising:
(a) administering the IL2 agonist at a first dosing frequency in the initial part of the at least two week period; and
(b) administering IL2 agonist at a second dosing frequency in a subsequent portion of the at least two week period.

338. The method of embodiment 337, wherein the first dosing frequency is daily.

339. The method of embodiment 337 or embodiment 338, wherein the second dosing frequency is less frequent than the first dosing frequency.

340. The method of embodiment 339, wherein the second dosing frequency is weekly.

341. The method of any one of embodiments 337 to 340, wherein the subject is transitioned from the first dosing frequency to the second dosing frequency concurrently with or after exhaustion of the CART cells.

342. The method of any one of embodiments 328 to 341, which further comprises administering an anti-PD1 antibody to the subject.

343. The method of embodiment 342, wherein the anti-PD1 antibody is MDX-1106 (nivolumab), MK-3475 (pembrolizumab), MEDI-0680 (AMP-514), PDR001, REGN2810, or BGB-108.

344. A method of treating autoimmune disease, comprising administering to a subject in need thereof:
(a) chimeric antigen receptor ("CAR") T cells ("CART cells"); and
(b) an IL2 agonist according to any one of embodiments 267 to 322 whose targeting moiety binds to a cell surface molecule on the chimeric antigen receptor (CAR) T cells, optionally wherein the targeting moiety is capable of binding to the extracellular domain of the CAR, optionally wherein the CAR is:
(i) designed to target any of the targets identified in Section 6.11.1.4; and/or
(ii) configured according to Section 6.11.1.1 and subsections thereof.

345. The method of embodiment 344, wherein the targeting moiety comprises a pMHC cloned from an autoimmune target cell.

346. The method of embodiment 344 or embodiment 345, wherein the CART cell is a Treg cell.

All publications, patents, patent applications and other documents cited in this application are hereby incorporated by reference in their entireties for all purposes to the same extent as if each individual publication, patent, patent application or other document were individually indicated to be incorporated by reference for all purposes. In the event that there is an inconsistency between the teachings of one or more of the references incorporated herein and the present disclosure, the teachings of the present specification are intended.

What is claimed is:

1. A heterodimer comprising:
   (a) a first polypeptide chain comprising, in N-to C-terminal orientation:
      (i) a peptide-MHC (pMHC) complex comprising a class I α heavy chain human HLA-A2 sequence and a peptide, the peptide comprising the amino acid sequence of HPV 16E7 (11-19), HPV 16E7 (82-90), CMV pp65 (495-503), NY-ESO-1 (157-165) mutant C165V, WT-1 (126-134), or Tyrosinase (369-377); and
      (ii) a first Fc domain; and
   (b) a second polypeptide chain comprising, in N- to C-terminal orientation:
      (i) an IL2 domain comprising an amino acid sequence having at least about 90% sequence identity to SEQ ID NO:2 and the amino acid substitutions H16A and F42A as compared to SEQ ID NO:2; and
      (ii) a second Fc domain capable of heterodimerizing with the first Fc domain.

2. The heterodimer of claim 1, which is monovalent for the pMHC complex and the IL2 domain.

3. The heterodimer of claim 1, wherein the IL2 domain comprises the amino acid sequence of SEQ ID NO: 124.

4. The heterodimer of claim 1, which lacks an IL2 binding portion of IL2-Rα.

5. A pharmaceutical composition comprising the heterodimer of claim 1 and an excipient.

6. The heterodimer of claim 1, wherein the IL2 domain comprises an amino acid sequence having at least about 95% sequence identity to SEQ ID NO: 2.

7. The heterodimer of claim 1, wherein the IL2 domain comprises an amino acid sequence having at least about 98% sequence identity to SEQ ID NO: 2.

8. The heterodimer of claim 1, wherein the first polypeptide chain comprises a linker connecting the pMHC complex and the first Fc domain.

9. The heterodimer of claim 1, wherein the second polypeptide chain comprises a linker connecting the IL2 domain and the second Fc domain.

10. The heterodimer of claim 1, wherein the pMHC complex comprises a human β2 microglobulin.

11. The heterodimer of claim 1, wherein the peptide comprises the amino acid sequence of HPV 16E7 (11-19), HPV 16E7 (82-90), or CMV pp65 (495-503).

12. The heterodimer of claim 1, wherein the peptide comprises the amino acid sequence of SEQ ID NO:7.

13. The heterodimer of claim 1, wherein the peptide comprises the amino acid sequence of SEQ ID NO:8.

* * * * *

SEQUENCE LISTING

```
<160> NUMBER OF SEQ ID NOS: 124

<210> SEQ ID NO 1
<211> LENGTH: 5
<212> TYPE: PRT
<213> ORGANISM: Unknown
<220> FEATURE:
<221> NAME/KEY: source
<223> OTHER INFORMATION: /note="Description of Unknown:
    Type I cytokine receptor motif sequence"
<220> FEATURE:
<221> NAME/KEY: MOD_RES
<222> LOCATION: (3)..(3)
<223> OTHER INFORMATION: Any amino acid

<400> SEQUENCE: 1

Trp Ser Xaa Trp Ser
```

-continued

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
    130

<210> SEQ ID NO 3
<211> LENGTH: 251
<212> TYPE: PRT
<213> ORGANISM: Homo sapiens

<400> SEQUENCE: 3

Glu Leu Cys Asp Asp Asp Pro Pro Glu Ile Pro His Ala Thr Phe Lys
1               5                   10                  15
Ala Met Ala Tyr Lys Glu Gly Thr Met Leu Asn Cys Glu Cys Lys Arg
            20                  25                  30
Gly Phe Arg Arg Ile Lys Ser Gly Ser Leu Tyr Met Leu Cys Thr Gly
        35                  40                  45
Asn Ser Ser His Ser Ser Trp Asp Asn Gln Cys Gln Cys Thr Ser Ser
    50                  55                  60
Ala Thr Arg Asn Thr Thr Lys Gln Val Thr Pro Gln Pro Glu Glu Gln
65                  70                  75                  80
Lys Glu Arg Lys Thr Thr Glu Met Gln Ser Pro Met Gln Pro Val Asp
                85                  90                  95
Gln Ala Ser Leu Pro Gly His Cys Arg Glu Pro Pro Trp Glu Asn
            100                 105                 110
Glu Ala Thr Glu Arg Ile Tyr His Phe Val Val Gly Gln Met Val Tyr
        115                 120                 125
Tyr Gln Cys Val Gln Gly Tyr Arg Ala Leu His Arg Gly Pro Ala Glu
    130                 135                 140
Ser Val Cys Lys Met Thr His Gly Lys Thr Arg Trp Thr Gln Pro Gln
145                 150                 155                 160
Leu Ile Cys Thr Gly Glu Met Glu Thr Ser Gln Phe Pro Gly Glu Glu
                165                 170                 175
Lys Pro Gln Ala Ser Pro Glu Gly Arg Pro Glu Ser Glu Thr Ser Cys 180                 185                 190
Leu Val Thr Thr Thr Asp Phe Gln Ile Gln Thr Glu Met Ala Ala Thr
                195                 200                 205

Met Glu Thr Ser Ile Phe Thr Thr Glu Tyr Gln Val Ala Val Ala Gly
            210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Thr Ile
                245                 250

<210> SEQ ID NO 4
<211> LENGTH: 165
<212> TYPE: PRT
<213> ORGANISM: Homo sapiens

<400> SEQUENCE: 4

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly
                165

<210> SEQ ID NO 5
<211> LENGTH: 219
<212> TYPE: PRT
<213> ORGANISM: Homo sapiens

<400> SEQUENCE: 5

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp

```
                   85                  90                  95

Gln Ala Ser Leu Pro Gly His Cys Arg Glu Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln
    210                 215

<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 9
<212> TYPE: PRT
<213> ORGANISM: Human papillomavirus

<400> SEQUENCE: 7

Tyr Met Leu Asp Leu Gln Pro Glu Thr
1               5

<210> SEQ ID NO 8
<211> LENGTH: 9
<212> TYPE: PRT
<213> ORGANISM: Human papillomavirus

<400> SEQUENCE: 8

Leu Leu Met Gly Thr Leu Gly Ile Val
1               5

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Arg Pro His Ala Ile Arg Arg Pro Leu Ala Leu
1               5                   10
```

```
<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Phe Leu Asp Glu Phe Met Glu Gly Val
1               5

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Leu Thr Asp Asp Arg Leu Phe Thr Cys Tyr
1               5                   10

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Val Val Met Ser Trp Ala Pro Pro Val
1               5

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Leu Leu Leu Asp Asp Leu Leu Val Ser Ile
1               5                   10

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Lys Thr Leu Thr Ser Val Phe Gln Lys
1               5

<210> SEQ ID NO 15
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 15

Glu Ala Phe Ile Gln Pro Ile Thr Arg
1               5

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Arg Pro His Val Pro Glu Ser Ala Phe
1               5

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Leu Ala Asp Glu Ala Glu Val Tyr Leu
1               5                   10

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Lys Leu Tyr Glu Glu Pro Leu Leu Lys
1               5

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Lys Ile Phe Ser Glu Val Thr Leu Lys
1               5

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 20

Glu Thr Val Ser Glu Gln Ser Asn Val
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Leu His Asp Asp Leu Leu Glu Ala
1               5

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Ile Val Glu Gly Leu Ile Thr Thr Val
1               5                   10

<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Tyr Leu Gln Tyr Val Leu Gln Ile
1               5

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Leu Phe Glu Gly Ile Asp Ile Tyr Thr
1               5                   10

<210> SEQ ID NO 25
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Phe Ile Ala Ser Asn Gly Val Lys Leu Val
```

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 26

Cys Ile Leu Gly Lys Leu Phe Thr Lys
1               5

<210> SEQ ID NO 27
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

Gln Thr Ala Cys Glu Val Leu Asp Tyr
1               5

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Ile Leu Asn Ala Met Ile Ala Lys Ile
1               5

<210> SEQ ID NO 29
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

Lys Glu Phe Glu Asp Asp Ile Ile Asn Trp
1               5                   10

<210> SEQ ID NO 30
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

Tyr Thr Asp Phe His Cys Gln Tyr Val
1               5

<210> SEQ ID NO 31

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Glu Glu Lys Arg Gly Ser Leu His Val Trp
1               5                   10

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ser Glu Leu Phe Arg Ser Gly Leu Asp Ser Tyr
1               5                   10

<210> SEQ ID NO 33
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ala Glu Pro Ile Asp Ile Gln Thr Trp
1               5

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Thr Leu Asp Trp Leu Leu Gln Thr Pro Lys
1               5                   10

<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Leu Phe Gly Asp Ile Tyr Leu Ala Ile
1               5                   10

<210> SEQ ID NO 36
<211> LENGTH: 9
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 36

Ile Leu Asp Lys Val Leu Val His Leu
1               5

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Tyr Leu Asp Ser Gly Ile His Phe
1               5

<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Lys Ile Leu Asp Ala Val Val Ala Gln Lys
1               5                   10

<210> SEQ ID NO 39
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Lys Glu Leu Glu Gly Ile Leu Leu Leu
1               5

<210> SEQ ID NO 40
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Lys Ile Asn Lys Asn Pro Lys Tyr Lys
1               5

<210> SEQ ID NO 41
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 41

Phe Leu Glu Gly Asn Glu Val Gly Lys Thr Tyr
1               5                   10

<210> SEQ ID NO 42
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Gln Gln Ile Thr Lys Thr Glu Val
1               5

<210> SEQ ID NO 43
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Cys Asp Pro His Ser Gly His Phe Val
1               5                   10

<210> SEQ ID NO 44
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ala Val Cys Pro Trp Thr Trp Leu Arg
1               5

<210> SEQ ID NO 45
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Met Glu Ile Phe Ile Glu Val Phe Ser His Phe
1               5                   10

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Arg Val Trp Asp Leu Pro Gly Val Leu Lys
1               5                   10
```

```
<210> SEQ ID NO 47
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Glu Glu Lys Leu Ile Val Val Leu Phe
1               5

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Thr Pro Asn Gln Arg Gln Asn Val Cys
1               5

<210> SEQ ID NO 49
<211> LENGTH: 232
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Asp Lys Arg Val Glu Ser Lys Tyr Gly Pro Pro Cys Pro Pro Cys Pro
1               5                   10                  15

Ala Pro Pro Val Ala Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser Gln Glu Asp Pro Glu Val Gln Phe Asn Trp Tyr Val
        50                  55                  60

Asp Gly Val Glu Val His Asn Ala Lys Thr Lys Pro Arg Glu Glu Gln
65                  70                  75                  80

Phe Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Arg Leu Thr Val Asp Lys Ser Arg Trp Gln Glu Gly Asn Val Phe
        195                 200                 205

Ser Cys Ser Val Met His Glu Ala Leu His Asn His Tyr Thr Gln Lys
        210                 215                 220

Ser Leu Ser Leu Ser Leu Gly Lys
225                 230

<210> SEQ ID NO 50
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Asp Lys Lys Val Glu Pro Lys Ser Cys Asp Lys Thr His Thr Cys Pro
1               5                   10                  15

Pro Cys Pro Ala Pro Val Ala Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Asp Val Ser Gln Glu Asp Pro Glu Val Gln Phe Asn
50                  55                  60

Trp Tyr Val Asp Gly Val Glu Val His Asn Ala Lys Thr Lys Pro Arg
65                  70                  75                  80

Glu Glu Gln Phe Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Gly Leu Pro Ser Ser Ile Glu Lys Thr Ile Ser Lys Ala Lys
        115                 120                 125

Gly Gln Pro Arg Glu Pro Gln Val Tyr Thr Leu Pro Pro Ser Arg Asp
    130                 135                 140

Glu Leu Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
    210                 215                 220

Thr Gln Lys Ser Leu Ser Leu Ser Pro Gly Lys
225                 230                 235

<210> SEQ ID NO 51
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Ala Ser Thr Lys Gly Pro Ser Val Phe Pro Leu Ala Pro Ser Ser Lys
```

```
                1               5                      10                      15
            Ser Thr Ser Gly Gly Thr Ala Ala Leu Gly Cys Leu Val Lys Asp Tyr
                            20                      25                      30

Phe Pro Glu Pro Val Thr Val Ser Trp Asn Ser Gly Ala Leu Thr Ser
                            35                      40                      45

Gly Val His Thr Phe Pro Ala Val Leu Gln Ser Ser Gly Leu Tyr Ser
                            50                      55                      60

Leu Ser Ser Val Val Thr Val Pro Ser Ser Leu Gly Thr Gln Thr
             65                      70                      75                      80

Tyr Ile Cys Asn Val Asn His Lys Pro Ser Asn Thr Lys Val Asp Lys
                            85                      90                      95

Lys Val Glu Pro Lys Ser Cys Asp Lys Thr His Thr Cys Pro Pro Cys
                            100                     105                     110

Pro Ala Pro Pro Val Ala Gly Pro Ser Val Phe Leu Phe Pro Pro Lys
                            115                     120                     125

Pro Lys Asp Thr Leu Met Ile Ser Arg Thr Pro Glu Val Thr Cys Val
             130                     135                     140

Val Val Asp Val Ser Gln Glu Asp Pro Glu Val Gln Phe Asn Trp Tyr
             145                     150                     155                     160

Val Asp Gly Val Glu Val His Asn Ala Lys Thr Lys Pro Arg Glu Glu
                            165                     170                     175

Gln Phe Asn Ser Thr Tyr Arg Val Val Ser Val Leu Thr Val Leu His
                            180                     185                     190

Gln Asp Trp Leu Asn Gly Lys Glu Tyr Lys Cys Lys Val Ser Asn Lys
                            195                     200                     205

Gly Leu Pro Ser Ser Ile Glu Lys Thr Ile Ser Lys Ala Lys Gly Gln
                            210                     215                     220

Pro Arg Glu Pro Gln Val Tyr Thr Leu Pro Pro Ser Arg Asp Glu Leu
             225                     230                     235                     240

Thr Lys Asn Gln Val Ser Leu Thr Cys Leu Val Lys Gly Phe Tyr Pro
                            245                     250                     255

Ser Asp Ile Ala Val Glu Trp Glu Ser Asn Gly Gln Pro Glu Asn Asn
                            260                     265                     270

Tyr Lys Thr Thr Pro Pro Val Leu Asp Ser Asp Gly Ser Phe Phe Leu
                            275                     280                     285

Tyr Ser Lys Leu Thr Val Asp Lys Ser Arg Trp Gln Gln Gly Asn Val
                            290                     295                     300

Phe Ser Cys Ser Val Met His Glu Ala Leu His Asn His Tyr Thr Gln
             305                     310                     315                     320

Lys Ser Leu Ser Leu Ser Pro Gly Lys
                            325

<210> SEQ ID NO 52
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Ala Ser Thr Lys Gly Pro Ser Val Phe Pro Leu Ala Pro Cys Ser Arg
 1               5                      10                      15

Ser Thr Ser Glu Ser Thr Ala Ala Leu Gly Cys Leu Val Lys Asp Tyr
                20                      25                      30
```

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 53
<211> LENGTH: 329
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Pro Val Ala Gly Pro Ser Val Phe Leu Phe Pro Pro Lys
                115                 120                 125

Pro Lys Asp Thr Leu Met Ile Ser Arg Thr Pro Glu Val Thr Cys Val
130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
                195                 200                 205

Gly Leu Pro Ser Ser Ile Glu Lys Thr Ile Ser Lys Ala Lys Gly Gln
210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
                275                 280                 285

Tyr Ser Lys Leu Thr Val Asp Lys Ser Arg Trp Gln Gln Gly Asn Val
                290                 295                 300

Phe Ser Cys Ser Val Met His Glu Ala Leu His Asn Arg Phe Thr Gln
305                 310                 315                 320

Lys Ser Leu Ser Leu Ser Pro Gly Lys
                325

<210> SEQ ID NO 54
<211> LENGTH: 326
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 54

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr

```
            65                  70                  75                  80
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                325

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(9)
<223> OTHER INFORMATION: /note="Each of amino acids 1-9 can
      independently be present or absent"

<400> SEQUENCE: 55

Gly Gly Gly Gly Gly Gly Gly Gly Gly Gly Ser
1               5                   10

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: SITE
<222> LOCATION: (2)..(10)
<223> OTHER INFORMATION: /note="Each of amino acids 2-10 can
      independently be present or absent"

<400> SEQUENCE: 56

Ser Gly Gly Gly Gly Gly Gly Gly Gly Gly
1               5                   10

<210> SEQ ID NO 57
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gly Gly Gly Gly Ser
1               5

<210> SEQ ID NO 58
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Gly Gly Gly
1

<210> SEQ ID NO 59
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Gly Gly Gly Gly
1               5

<210> SEQ ID NO 60
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Gly Gly Gly Gly Gly
1               5

<210> SEQ ID NO 61
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
```

-continued

```
      Synthetic peptide"

<400> SEQUENCE: 61

Gly Gly Gly Gly Gly Gly Gly
1               5

<210> SEQ ID NO 62
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Gly Gly Gly Gly Gly Gly Gly
1               5

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Gly Gly Gly Gly Gly Gly Gly Gly
1               5

<210> SEQ ID NO 64
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gly Ser Gly Gly Ser
1               5

<210> SEQ ID NO 65
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Gly Gly Gly Ser
1

<210> SEQ ID NO 66
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66
```

Gly Gly Ser Gly
1

<210> SEQ ID NO 67
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Gly Gly Ser Gly Gly
1               5

<210> SEQ ID NO 68
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Gly Ser Gly Ser Gly
1               5

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Ser Gly Gly Gly
1               5

<210> SEQ ID NO 70
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gly Gly Gly Ser Gly
1               5

<210> SEQ ID NO 71
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly Ser Ser Ser Gly
1               5

```
<210> SEQ ID NO 72
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gly Cys Gly Ala Ser Gly Gly Gly Gly Ser Gly Gly Gly Gly Ser
1               5                   10                  15

<210> SEQ ID NO 73
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gly Gly Gly Gly Ser Gly Gly Gly Gly Ser
1               5                   10

<210> SEQ ID NO 74
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Gly Gly Gly Ala Ser Gly Gly Gly Gly Ser Gly Gly Gly Gly Ser
1               5                   10                  15

<210> SEQ ID NO 75
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gly Gly Gly Ala Ser Gly Gly Gly Gly Ser
1               5                   10

<210> SEQ ID NO 76
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Gly Gly Gly Ser Gly Gly Gly Gly Ser Gly Gly Gly Gly Ser Gly
1               5                   10                  15

Gly Gly Gly Ser
            20

<210> SEQ ID NO 77
```

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gly Cys Gly Gly Ser
1               5

<210> SEQ ID NO 78
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Cys Pro Pro Cys
1

<210> SEQ ID NO 79
<211> LENGTH: 4
<212> TYPE: PRT
<213> ORGANISM: Homo sapiens

<400> SEQUENCE: 79

Cys Pro Ser Cys
1

<210> SEQ ID NO 80
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Glu Pro Lys Ser Cys Asp Lys Thr His Thr Cys Pro Pro Cys Pro Ala
1               5                   10                  15

Pro Pro Val Ala
            20

<210> SEQ ID NO 81
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Glu Ser Lys Tyr Gly Pro Pro Cys Pro Pro Cys Pro Ala Pro Pro Val
1               5                   10                  15

Ala

<210> SEQ ID NO 82
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 82

Cys Pro Pro Cys Pro Ala Pro Gly Gly Gly Gly Pro Ser Val Phe
1               5                   10                  15

<210> SEQ ID NO 83
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Cys Pro Pro Cys Pro Ala Pro Gly Gly Gly Pro Ser Val Phe
1               5                   10

<210> SEQ ID NO 84
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Cys Pro Pro Cys Pro Ala Pro Gly Gly Pro Ser Val Phe
1               5                   10

<210> SEQ ID NO 85
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Cys Pro Pro Cys Pro Ala Pro Gly Pro Ser Val Phe
1               5                   10

<210> SEQ ID NO 86
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 87
<211> LENGTH: 28
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 87

Leu Asp Pro Lys Leu Cys Tyr Leu Leu Asp Gly Ile Leu Phe Ile Tyr
1               5                   10                  15

Gly Val Ile Leu Thr Ala Leu Phe Leu Arg Val Lys
            20                  25

<210> SEQ ID NO 88
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 89
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala
        35                  40                  45

<210> SEQ ID NO 90
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Leu Asp Pro Lys Leu Cys Tyr Leu Leu Asp Gly Ile Leu Phe Ile Tyr
1               5                   10                  15

Gly Val Ile Leu Thr Ala Leu Phe Leu Arg Val Lys Phe Ser Arg Ser
            20                  25                  30

Ala Asp Ala Pro Ala Tyr Gln Gln Gly Gln Asn Gln Leu Tyr Asn Glu
        35                  40                  45

Leu Asn Leu Gly Arg Arg Glu Glu Tyr Asp Val Leu Asp Lys Arg Arg
    50                  55                  60

Gly Arg Asp Pro Glu Met Gly Gly Lys Pro Arg Arg Lys Asn Pro Gln
65                  70                  75                  80

Glu Gly Leu Tyr Asn Glu Leu Gln Lys Asp Lys Met Ala Glu Ala Tyr
```

```
                85                  90                  95

Ser Glu Ile Gly Met Lys Gly Glu Arg Arg Gly Lys Gly His Asp
            100                 105                 110

Gly Leu Tyr Gln Gly Leu Ser Thr Ala Thr Lys Asp Thr Tyr Asp Ala
        115                 120                 125

Leu His Met Gln Ala Leu Pro Pro Arg
    130                 135

<210> SEQ ID NO 91
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 92
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Lys Ile Glu Val Met Tyr Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro Phe Trp Val Leu Val Val Val Gly
        35                  40                  45

Gly Val Leu Ala Cys Tyr Ser Leu Leu Val Thr Val Ala Phe Ile Ile
    50                  55                  60

Phe Trp Val Arg Ser Lys Arg Ser Arg Leu Leu His Ser Asp Tyr Met
65                  70                  75                  80

Asn Met Thr Pro Arg Arg Pro Gly Pro Thr Arg Lys His Tyr Gln Pro
                85                  90                  95

Tyr Ala Pro Pro Arg Asp Phe Ala Ala Tyr Arg Ser
            100                 105

<210> SEQ ID NO 93
```

```
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 93

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 94
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Lys Ile Glu Val Met Tyr Pro Pro Tyr Leu Asp Asn Glu Lys Ser
1               5                   10                  15

Asn Gly Thr Ile Ile His Val Lys Gly Lys His Leu Cys Pro Ser Pro
                20                  25                  30

Leu Phe Pro Gly Pro Ser Lys Pro
            35                  40

<210> SEQ ID NO 95
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 96
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 96

Gly Lys Pro Ile Pro Asn Pro Leu Leu Gly Leu Asp Ser Thr
1               5                   10

<210> SEQ ID NO 97
<211> LENGTH: 9
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Ile Pro Asn Pro Leu Leu Gly Leu Asp
1               5

<210> SEQ ID NO 98
<211> LENGTH: 366
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Leu Lys
        50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Glu Ser Lys Tyr Gly Pro
130                 135                 140

Pro Cys Pro Pro Cys Pro Ala Pro Val Ala Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser Gln Glu Asp Pro Glu Val
            180                 185                 190

Gln Phe Asn Trp Tyr Val Asp Gly Val Glu Val His Asn Ala Lys Thr
        195                 200                 205

Lys Pro Arg Glu Glu Gln Phe Asn Ser Thr Tyr Arg Val Val Ser Val
210                 215                 220

Leu Thr Val Leu His Gln Asp Trp Leu Asn Gly Lys Glu Tyr Lys Cys
225                 230                 235                 240

Lys Val Ser Asn Lys Gly Leu Pro Ser Ser Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Gln Glu Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
```

```
            290                 295                 300

Gln Pro Glu Asn Asn Tyr Lys Thr Thr Pro Val Leu Asp Ser Asp
305                 310                 315                 320

Gly Ser Phe Phe Leu Tyr Ser Arg Leu Thr Val Asp Lys Ser Arg Trp
                325                 330                 335

Gln Glu Gly Asn Val Phe Ser Cys Ser Val Met His Glu Ala Leu His
                340                 345                 350

Asn His Tyr Thr Gln Lys Ser Leu Ser Leu Ser Leu Gly Lys
                355                 360                 365

<210> SEQ ID NO 99
<211> LENGTH: 366
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr Gly Gly Gly Ser Glu Ser Lys Tyr Gly Pro
130                 135                 140

Pro Cys Pro Pro Cys Pro Ala Pro Pro Val Ala Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser Gln Glu Asp Pro Glu Val
                180                 185                 190

Gln Phe Asn Trp Tyr Val Asp Gly Val Glu Val His Asn Ala Lys Thr
            195                 200                 205

Lys Pro Arg Glu Glu Gln Phe Asn Ser Thr Tyr Arg Val Val Ser Val
210                 215                 220

Leu Thr Val Leu His Gln Asp Trp Leu Asn Gly Lys Glu Tyr Lys Cys
225                 230                 235                 240

Lys Val Ser Asn Lys Gly Leu Pro Ser Ser Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Gln Glu Glu Met Thr Lys Asn Gln Val Ser Leu Thr Cys Leu Val
            275                 280                 285
```

-continued

```
Lys Gly Phe Tyr Pro Ser Asp Ile Ala Val Glu Trp Glu Ser Asn Gly
            290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Arg Leu Thr Val Asp Lys Ser Arg Trp
                325                 330                 335

Gln Glu Gly Asn Val Phe Ser Cys Ser Val Met His Glu Ala Leu His
            340                 345                 350

Asn His Tyr Thr Gln Lys Ser Leu Ser Leu Ser Leu Gly Lys
                355                 360                 365

<210> SEQ ID NO 100
<211> LENGTH: 550
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                 55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Ser Gly
130                 135                 140

Gly Gly Gly Ser Gly Gly Gly Ser Glu Leu Cys Asp Asp Asp Pro
145                 150                 155                 160

Pro Glu Ile Pro His Ala Thr Phe Lys Ala Met Ala Tyr Lys Glu Gly
                165                 170                 175

Thr Met Leu Asn Cys Glu Cys Lys Arg Gly Phe Arg Arg Ile Lys Ser
            180                 185                 190

Gly Ser Leu Tyr Met Leu Cys Thr Gly Asn Ser Ser His Ser Ser Trp
        195                 200                 205

Asp Asn Gln Cys Gln Cys Thr Ser Ser Ala Thr Arg Asn Thr Thr Lys
    210                 215                 220

Gln Val Thr Pro Gln Pro Glu Glu Gln Lys Glu Arg Lys Thr Thr Glu
225                 230                 235                 240

Met Gln Ser Pro Met Gln Pro Val Asp Gln Ala Ser Leu Pro Gly His
                245                 250                 255

Cys Arg Glu Pro Pro Pro Trp Glu Asn Glu Ala Thr Glu Arg Ile Tyr
            260                 265                 270
```

His Phe Val Val Gly Gln Met Val Tyr Tyr Gln Cys Val Gln Gly Tyr
                275                 280                 285

Arg Ala Leu His Arg Gly Pro Ala Glu Ser Val Cys Lys Met Thr His
290                 295                 300

Gly Lys Thr Arg Trp Thr Gln Pro Gln Leu Ile Cys Thr Gly Gly Gly
305                 310                 315                 320

Gly Ser Glu Ser Lys Tyr Gly Pro Pro Cys Pro Cys Pro Ala Pro
                325                 330                 335

Pro Val Ala Gly Pro Ser Val Phe Leu Phe Pro Pro Lys Pro Lys Asp
            340                 345                 350

Thr Leu Met Ile Ser Arg Thr Pro Glu Val Thr Cys Val Val Val Asp
            355                 360                 365

Val Ser Gln Glu Asp Pro Glu Val Gln Phe Asn Trp Tyr Val Asp Gly
            370                 375                 380

Val Glu Val His Asn Ala Lys Thr Lys Pro Arg Glu Glu Gln Phe Asn
385                 390                 395                 400

Ser Thr Tyr Arg Val Val Ser Val Leu Thr Val Leu His Gln Asp Trp
                405                 410                 415

Leu Asn Gly Lys Glu Tyr Lys Cys Lys Val Ser Asn Lys Gly Leu Pro
            420                 425                 430

Ser Ser Ile Glu Lys Thr Ile Ser Lys Ala Lys Gly Gln Pro Arg Glu
            435                 440                 445

Pro Gln Val Tyr Thr Leu Pro Pro Ser Gln Glu Glu Met Thr Lys Asn
            450                 455                 460

Gln Val Ser Leu Thr Cys Leu Val Lys Gly Phe Tyr Pro Ser Asp Ile
465                 470                 475                 480

Ala Val Glu Trp Glu Ser Asn Gly Gln Pro Glu Asn Asn Tyr Lys Thr
                485                 490                 495

Thr Pro Pro Val Leu Asp Ser Asp Gly Ser Phe Phe Leu Tyr Ser Arg
            500                 505                 510

Leu Thr Val Asp Lys Ser Arg Trp Gln Glu Gly Asn Val Phe Ser Cys
            515                 520                 525

Ser Val Met His Glu Ala Leu His Asn His Tyr Thr Gln Lys Ser Leu
530                 535                 540

Ser Leu Ser Leu Gly Lys
545                 550

<210> SEQ ID NO 101
<211> LENGTH: 566
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Glu Ser Lys Tyr Gly Pro Pro Cys Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr

-continued

```
                65                  70                  75                  80
Tyr Arg Val Val Ser Val Leu Thr Val Leu His Gln Asp Trp Leu Asn
                        85                  90                  95
Gly Lys Glu Tyr Lys Cys Lys Val Ser Asn Lys Gly Leu Pro Ser Ser
                        100                 105                 110
Ile Glu Lys Thr Ile Ser Lys Ala Lys Gly Gln Pro Arg Glu Pro Gln
                        115                 120                 125
Val Tyr Thr Leu Pro Pro Ser Gln Glu Glu Met Thr Lys Asn Gln Val
                        130                 135                 140
Ser Leu Thr Cys Leu Val Lys Gly Phe Tyr Pro Ser Asp Ile Ala Val
145                     150                 155                 160
Glu Trp Glu Ser Asn Gly Gln Pro Glu Asn Asn Tyr Lys Thr Thr Pro
                        165                 170                 175
Pro Val Leu Asp Ser Asp Gly Ser Phe Phe Leu Tyr Ser Arg Leu Thr
                        180                 185                 190
Val Asp Lys Ser Arg Trp Gln Glu Gly Asn Val Phe Ser Cys Ser Val
                        195                 200                 205
Met His Glu Ala Leu His Asn His Tyr Thr Gln Lys Ser Leu Ser Leu
                        210                 215                 220
Ser Leu Gly Lys Gly Gly Gly Ser Gly Gly Gly Ser Gly Gly
225                     230                 235                 240
Gly Gly Ser Glu Leu Cys Asp Asp Pro Pro Glu Ile Pro His Ala
                        245                 250                 255
Thr Phe Lys Ala Met Ala Tyr Lys Glu Gly Thr Met Leu Asn Cys Glu
                        260                 265                 270
Cys Lys Arg Gly Phe Arg Arg Ile Lys Ser Gly Ser Leu Tyr Met Leu
                        275                 280                 285
Cys Thr Gly Asn Ser Ser His Ser Ser Trp Asp Asn Gln Cys Gln Cys
                        290                 295                 300
Thr Ser Ser Ala Thr Arg Asn Thr Thr Lys Gln Val Thr Pro Gln Pro
305                     310                 315                 320
Glu Glu Gln Lys Glu Arg Lys Thr Thr Glu Met Gln Ser Pro Met Gln
                        325                 330                 335
Pro Val Asp Gln Ala Ser Leu Pro Gly His Cys Arg Glu Pro Pro Pro
                        340                 345                 350
Trp Glu Asn Glu Ala Thr Glu Arg Ile Tyr His Phe Val Val Gly Gln
                        355                 360                 365
Met Val Tyr Tyr Gln Cys Val Gln Gly Tyr Arg Ala Leu His Arg Gly
                        370                 375                 380
Pro Ala Glu Ser Val Cys Lys Met Thr His Gly Lys Thr Arg Trp Thr
385                     390                 395                 400
Gln Pro Gln Leu Ile Cys Thr Gly Gly Gly Gly Ser Gly Gly Gly
                        405                 410                 415
Gly Ser Gly Gly Gly Gly Ser Gly Gly Gly Gly Ser Gly Gly Gly Gly
                        420                 425                 430
Ser Ala Pro Thr Ser Ser Ser Thr Lys Lys Thr Gln Leu Gln Leu Glu
                        435                 440                 445
His Leu Leu Leu Asp Leu Gln Met Ile Leu Asn Gly Ile Asn Asn Tyr
                        450                 455                 460
Lys Asn Pro Lys Leu Thr Arg Met Leu Thr Phe Lys Phe Tyr Met Pro
465                     470                 475                 480
Lys Lys Ala Thr Glu Leu Lys His Leu Gln Cys Leu Glu Glu Glu Leu
                        485                 490                 495
```

```
Lys Pro Leu Glu Glu Val Leu Asn Leu Ala Gln Ser Lys Asn Phe His
            500                 505                 510

Leu Arg Pro Arg Asp Leu Ile Ser Asn Ile Asn Val Ile Val Leu Glu
        515                 520                 525

Leu Lys Gly Ser Glu Thr Thr Phe Met Cys Gly Tyr Ala Asp Glu Thr
    530                 535                 540

Ala Thr Ile Val Glu Phe Leu Asn Arg Trp Ile Thr Phe Cys Gln Ser
545                 550                 555                 560

Ile Ile Ser Thr Leu Thr
                565

<210> SEQ ID NO 102
<211> LENGTH: 364
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Ala Pro Thr Ser Ser Ser Thr Lys Lys
225                 230                 235                 240

Thr Gln Leu Gln Leu Glu His Leu Leu Leu Asp Leu Gln Met Ile Leu
                245                 250                 255

Asn Gly Ile Asn Asn Tyr Lys Asn Pro Lys Leu Thr Arg Met Leu Thr
            260                 265                 270
```

```
Phe Lys Phe Tyr Met Pro Lys Lys Ala Thr Glu Leu Lys His Leu Gln
                275                 280                 285

Cys Leu Glu Glu Glu Leu Lys Pro Leu Glu Val Leu Asn Leu Ala
290                 295                 300

Gln Ser Lys Asn Phe His Leu Arg Pro Arg Asp Leu Ile Ser Asn Ile
305                 310                 315                 320

Asn Val Ile Val Leu Glu Leu Lys Gly Ser Glu Thr Thr Phe Met Cys
                325                 330                 335

Glu Tyr Ala Asp Glu Thr Ala Thr Ile Val Glu Phe Leu Asn Arg Trp
                340                 345                 350

Ile Thr Phe Ala Gln Ser Ile Ile Ser Thr Leu Thr
                355                 360

<210> SEQ ID NO 103
<211> LENGTH: 364
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Gly Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Glu Met Thr Lys Asn Gln Val Ser
                130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
                210                 215                 220

Pro Gly Gly Gly Gly Ser Ala Pro Thr Ser Ser Ser Thr Lys Lys
225                 230                 235                 240

Thr Gln Leu Gln Leu Glu His Leu Leu Leu Asp Leu Gln Met Ile Leu
                245                 250                 255

Asn Gly Ile Asn Asn Tyr Lys Asn Pro Lys Leu Thr Arg Met Leu Thr
```

```
                260                 265                 270
Phe Lys Phe Tyr Met Pro Lys Ala Thr Glu Leu Lys His Leu Gln
            275                 280                 285

Cys Leu Glu Glu Glu Leu Lys Pro Leu Glu Glu Val Leu Asn Leu Ala
        290                 295                 300

Gln Ser Lys Asn Phe His Leu Arg Pro Arg Asp Leu Ile Ser Asp Ile
305                 310                 315                 320

Asn Val Ile Val Leu Glu Leu Lys Gly Ser Glu Thr Thr Phe Met Cys
                325                 330                 335

Glu Tyr Ala Asp Glu Thr Ala Thr Ile Val Glu Phe Leu Asn Arg Trp
            340                 345                 350

Ile Thr Phe Ala Gln Ser Ile Ile Ser Thr Leu Thr
            355                 360

<210> SEQ ID NO 104
<211> LENGTH: 376
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Gly Gly Gly Ser Gly Gly Gly Ser Gly Gly
225                 230                 235                 240

Gly Gly Ser Ala Pro Thr Ser Ser Ser Thr Lys Lys Thr Gln Leu Gln
            245                 250                 255
```

```
Leu Glu Ala Leu Leu Leu Asp Leu Gln Met Ile Leu Asn Gly Ile Asn
            260                 265                 270
Asn Tyr Lys Asn Pro Lys Leu Thr Arg Met Leu Thr Ala Lys Phe Tyr
        275                 280                 285
Met Pro Lys Lys Ala Thr Glu Leu Lys His Leu Gln Cys Leu Glu Glu
    290                 295                 300
Glu Leu Lys Pro Leu Glu Glu Val Leu Asn Leu Ala Gln Ser Lys Asn
305                 310                 315                 320
Phe His Leu Arg Pro Arg Asp Leu Ile Ser Asn Ile Asn Val Ile Val
                325                 330                 335
Leu Glu Leu Lys Gly Ser Glu Thr Thr Phe Met Cys Glu Tyr Ala Asp
            340                 345                 350
Glu Thr Ala Thr Ile Val Glu Phe Leu Asn Arg Trp Ile Thr Phe Cys
        355                 360                 365
Gln Ser Ile Ile Ser Thr Leu Thr
    370                 375

<210> SEQ ID NO 105
<211> LENGTH: 366
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Ala Pro Thr Ser Ser Ser Thr Lys Lys Thr Gln Leu Gln Leu Glu Ala
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Ala Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr Gly Gly Gly Ser Gly Ser Lys Tyr Gly Pro
    130                 135                 140
Pro Cys Pro Pro Cys Pro Ala Pro Pro Val Ala Gly Pro Ser Val Phe
145                 150                 155                 160
Leu Phe Pro Pro Lys Pro Lys Asp Thr Leu Met Ile Ser Arg Thr Pro
                165                 170                 175
Glu Val Thr Cys Val Val Val Asp Val Ser Gln Glu Asp Pro Glu Val
            180                 185                 190
Gln Phe Asn Trp Tyr Val Asp Gly Val Glu Val His Asn Ala Lys Thr
        195                 200                 205
Lys Pro Arg Glu Glu Gln Phe Asn Ser Thr Tyr Arg Val Val Ser Val
    210                 215                 220
```

```
Leu Thr Val Leu His Gln Asp Trp Leu Asn Gly Lys Glu Tyr Lys Cys
225                 230                 235                 240

Lys Val Ser Asn Lys Gly Leu Pro Ser Ser Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Gln Glu Glu Met Thr Lys Asn Gln Val Ser Leu Ser Cys Ala Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Val Ser Arg Leu Thr Val Asp Lys Ser Arg Trp
                325                 330                 335

Gln Glu Gly Asn Val Phe Ser Cys Ser Val Met His Glu Ala Leu His
                340                 345                 350

Asn Arg Phe Thr Gln Lys Ser Leu Ser Leu Ser Pro Gly Lys
                355                 360                 365

<210> SEQ ID NO 106
<211> LENGTH: 464
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Gly Gly Gly
            115                 120                 125

Ser Gly Gly Gly Gly Ser Gly Gly Gly Gly Ser Ile Thr Cys Pro Pro
        130                 135                 140

Pro Met Ser Val Glu His Ala Asp Ile Trp Val Lys Ser Tyr Ser Leu
145                 150                 155                 160

Tyr Ser Arg Glu Arg Tyr Ile Cys Asn Ser Gly Phe Lys Arg Lys Ala
                165                 170                 175

Gly Thr Ser Ser Leu Thr Glu Cys Val Leu Asn Lys Ala Thr Asn Val
            180                 185                 190

Ala His Trp Thr Thr Pro Ser Leu Lys Cys Ile Arg Asp Pro Ala Leu
        195                 200                 205

Val His Gln Arg Pro Ala Pro Gly Gly Gly Gly Ser Gly Gly Gly
```

```
            210                 215                 220
Gly Ser Gly Gly Gly Ser Gly Gly Gly Ser Glu Ser Lys Tyr
225                 230                 235                 240

Gly Pro Pro Cys Pro Pro Cys Pro Ala Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460

<210> SEQ ID NO 107
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Glu Ser Lys Tyr Gly Pro Pro Cys Pro Pro Cys Pro Ala Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110
```

```
Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Gly Gly Gly Ser Gly Gly Gly Ser Gly Gly
225                 230                 235                 240

Gly Gly Ser Ile Thr Cys Pro Pro Met Ser Val Glu His Ala Asp
                245                 250                 255

Ile Trp Val Lys Ser Tyr Ser Leu Tyr Ser Arg Glu Arg Tyr Ile Cys
            260                 265                 270

Asn Ser Gly Phe Lys Arg Lys Ala Gly Thr Ser Ser Leu Thr Glu Cys
                275                 280                 285

Val Leu Asn Lys Ala Thr Asn Val Ala His Trp Thr Thr Pro Ser Leu
        290                 295                 300

Lys Cys Ile Arg Asp Pro Ala Leu Val His Gln Arg Pro Ala Pro Pro
305                 310                 315                 320

Gly Gly Gly Gly Ser Gly Gly Gly Ser Gly Gly Gly Gly Ser Gly
                325                 330                 335

Gly Gly Gly Ser Asn Trp Val Asn Val Ile Ser Asp Leu Lys Lys Ile
                340                 345                 350

Glu Asp Leu Ile Gln Ser Met His Ile Asp Ala Thr Leu Tyr Thr Glu
            355                 360                 365

Ser Asp Val His Pro Ser Cys Lys Val Thr Ala Met Lys Cys Phe Leu
        370                 375                 380

Leu Glu Leu Gln Val Ile Ser Leu Glu Ser Gly Asp Ala Ser Ile His
385                 390                 395                 400

Asp Thr Val Glu Asn Leu Ile Ile Leu Ala Asn Asn Ser Leu Ser Ser
                405                 410                 415

Asn Gly Asn Val Thr Glu Ser Gly Cys Lys Glu Cys Glu Glu Leu Glu
                420                 425                 430

Glu Lys Asn Ile Lys Glu Phe Leu Gln Ser Phe Val His Ile Val Gln
            435                 440                 445

Met Phe Ile Asn Thr Ser
    450

<210> SEQ ID NO 108
<211> LENGTH: 419
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108
```

```
Asn Leu Val Pro Met Val Ala Thr Val Gly Cys Gly Gly Ser Gly Gly
 1               5                  10                  15
Gly Gly Ser Gly Gly Gly Ser Ile Gln Arg Thr Pro Lys Ile Gln
            20                  25                  30
Val Tyr Ser Arg His Pro Ala Glu Asn Gly Lys Ser Asn Phe Leu Asn
            35                  40                  45
Cys Tyr Val Ser Gly Phe His Pro Ser Asp Ile Glu Val Asp Leu Leu
            50                  55                  60
Lys Asn Gly Glu Arg Ile Glu Lys Val Glu His Ser Asp Leu Ser Phe
 65                  70                  75                  80
Ser Lys Asp Trp Ser Phe Tyr Leu Leu Tyr Tyr Thr Glu Phe Thr Pro
                85                  90                  95
Thr Glu Lys Asp Glu Tyr Ala Cys Arg Val Asn His Val Thr Leu Ser
            100                 105                 110
Gln Pro Lys Ile Val Lys Trp Asp Arg Asp Met Gly Gly Gly Gly Ser
            115                 120                 125
Gly Gly Gly Gly Ser Gly Gly Gly Ser Gly Gly Gly Gly Ser Gly
            130                 135                 140
Ser His Ser Met Arg Tyr Phe Phe Thr Ser Val Ser Arg Pro Gly Arg
145                 150                 155                 160
Gly Glu Pro Arg Phe Ile Ala Val Gly Tyr Val Asp Asp Thr Gln Phe
                165                 170                 175
Val Arg Phe Asp Ser Asp Ala Ala Ser Gln Arg Met Glu Pro Arg Ala
            180                 185                 190
Pro Trp Ile Glu Gln Glu Gly Pro Glu Tyr Trp Asp Gly Glu Thr Arg
            195                 200                 205
Lys Val Lys Ala His Ser Gln Thr His Arg Val Asp Leu Gly Thr Leu
            210                 215                 220
Arg Gly Cys Tyr Asn Gln Ser Glu Ala Gly Ser His Thr Val Gln Arg
225                 230                 235                 240
Met Tyr Gly Cys Asp Val Gly Ser Asp Trp Arg Phe Leu Arg Gly Tyr
            245                 250                 255
His Gln Tyr Ala Tyr Asp Gly Lys Asp Tyr Ile Ala Leu Lys Glu Asp
            260                 265                 270
Leu Arg Ser Trp Thr Ala Ala Asp Met Ala Ala Gln Thr Thr Lys His
            275                 280                 285
Lys Trp Glu Ala Ala His Val Ala Glu Gln Leu Arg Ala Tyr Leu Glu
            290                 295                 300
Gly Thr Cys Val Glu Trp Leu Arg Arg Tyr Leu Glu Asn Gly Lys Glu
305                 310                 315                 320
Thr Leu Gln Arg Thr Asp Ala Pro Lys Thr His Met Thr His His Ala
            325                 330                 335
Val Ser Asp His Glu Ala Thr Leu Arg Cys Trp Ala Leu Ser Phe Tyr
            340                 345                 350
Pro Ala Glu Ile Thr Leu Thr Trp Gln Arg Asp Gly Glu Asp Gln Thr
            355                 360                 365
Gln Asp Thr Glu Leu Val Glu Thr Arg Pro Ala Gly Asp Gly Thr Phe
            370                 375                 380
Gln Lys Trp Ala Ala Val Val Val Pro Ser Gly Gln Glu Gln Arg Tyr
385                 390                 395                 400
Thr Cys His Val Gln His Glu Gly Leu Pro Lys Pro Leu Thr Leu Arg
            405                 410                 415
Trp Glu Pro
```

<210> SEQ ID NO 109
<211> LENGTH: 419
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Tyr Met Leu Asp Leu Gln Pro Glu Thr Gly Cys Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
        50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
                100                 105                 110

Gln Pro Lys Ile Val Lys Trp Asp Arg Asp Met Gly Gly Gly Gly Ser
                115                 120                 125

Gly Gly Gly Gly Ser Gly Gly Gly Ser Gly Gly Gly Gly Ser Gly
        130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Ala Ser Gln Arg Met Glu Pro Arg Ala
                180                 185                 190

Pro Trp Ile Glu Gln Glu Gly Pro Glu Tyr Trp Asp Gly Glu Thr Arg
                195                 200                 205

Lys Val Lys Ala His Ser Gln Thr His Arg Val Asp Leu Gly Thr Leu
        210                 215                 220

Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                245                 250                 255

His Gln Tyr Ala Tyr Asp Gly Lys Asp Tyr Ile Ala Leu Lys Glu Asp
                260                 265                 270

Leu Arg Ser Trp Thr Ala Ala Asp Met Ala Ala Gln Thr Thr Lys His
            275                 280                 285

Lys Trp Glu Ala Ala His Val Ala Glu Gln Leu Arg Ala Tyr Leu Glu
290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                325                 330                 335

Val Ser Asp His Glu Ala Thr Leu Arg Cys Trp Ala Leu Ser Phe Tyr
                340                 345                 350
```

```
Pro Ala Glu Ile Thr Leu Thr Trp Gln Arg Asp Gly Glu Asp Gln Thr
            355                 360                 365

Gln Asp Thr Glu Leu Val Glu Thr Arg Pro Ala Gly Asp Gly Thr Phe
370                 375                 380

Gln Lys Trp Ala Ala Val Val Pro Ser Gly Gln Glu Gln Arg Tyr
385                 390                 395                 400

Thr Cys His Val Gln His Glu Gly Leu Pro Lys Pro Leu Thr Leu Arg
                405                 410                 415

Trp Glu Pro

<210> SEQ ID NO 110
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Ser Ile Ile Asn Phe Glu Lys Leu Gly Cys Gly Gly Ser Gly Gly Gly
1               5                   10                  15

Gly Ser Gly Gly Gly Ser Ile Gln Lys Thr Pro Gln Ile Gln Val
            20                  25                  30

Tyr Ser Arg His Pro Pro Glu Asn Gly Lys Pro Asn Ile Leu Asn Cys
            35                  40                  45

Tyr Val Thr Gln Phe His Pro Pro His Ile Glu Ile Gln Met Leu Lys
50                  55                  60

Asn Gly Lys Lys Ile Pro Lys Val Glu Met Ser Asp Met Ser Phe Ser
65                  70                  75                  80

Lys Asp Trp Ser Phe Tyr Ile Leu Ala His Thr Glu Phe Thr Pro Thr
                85                  90                  95

Glu Thr Asp Thr Tyr Ala Cys Arg Val Lys His Ala Ser Met Ala Glu
            100                 105                 110

Pro Lys Thr Val Tyr Trp Asp Arg Asp Met Gly Gly Gly Gly Ser Gly
            115                 120                 125

Gly Gly Ser Gly Gly Gly Ser Gly Gly Gly Gly Ser Gly Pro
            130                 135                 140

His Ser Leu Arg Tyr Phe Val Thr Ala Val Ser Arg Pro Gly Leu Gly
145                 150                 155                 160

Glu Pro Arg Tyr Met Glu Val Gly Tyr Val Asp Asp Thr Glu Phe Val
                165                 170                 175

Arg Phe Asp Ser Asp Ala Glu Asn Pro Arg Tyr Glu Pro Arg Ala Arg
            180                 185                 190

Trp Met Glu Gln Glu Gly Pro Glu Tyr Trp Glu Arg Glu Thr Gln Lys
            195                 200                 205

Ala Lys Gly Asn Glu Gln Ser Phe Arg Val Asp Leu Arg Thr Leu Leu
            210                 215                 220

Gly Cys Tyr Asn Gln Ser Lys Gly Gly Ser His Thr Ile Gln Val Ile
225                 230                 235                 240

Ser Gly Cys Glu Val Gly Ser Asp Gly Arg Leu Leu Arg Gly Tyr Gln
                245                 250                 255

Gln Tyr Ala Tyr Asp Gly Cys Asp Tyr Ile Ala Leu Asn Glu Asp Leu
            260                 265                 270

Lys Thr Trp Thr Ala Ala Asp Met Ala Ala Leu Ile Thr Lys His Lys
            275                 280                 285
```

```
Trp Glu Gln Ala Gly Glu Ala Glu Arg Leu Arg Ala Tyr Leu Glu Gly
            290                 295                 300

Thr Cys Val Glu Trp Leu Arg Arg Tyr Leu Lys Asn Gly Asn Ala Thr
305                 310                 315                 320

Leu Leu Arg Thr Asp Ser Pro Lys Ala His Val Thr His His Ser Arg
            325                 330                 335

Pro Glu Asp Lys Val Thr Leu Arg Cys Trp Ala Leu Gly Phe Tyr Pro
            340                 345                 350

Ala Asp Ile Thr Leu Thr Trp Gln Leu Asn Gly Glu Glu Leu Ile Gln
            355                 360                 365

Asp Met Glu Leu Val Glu Thr Arg Pro Ala Gly Asp Gly Thr Phe Gln
        370                 375                 380

Lys Trp Ala Ser Val Val Val Pro Leu Gly Lys Glu Gln Tyr Tyr Thr
385                 390                 395                 400

Cys His Val Tyr His Gln Gly Leu Pro Glu Pro Leu Thr Leu Arg Trp
            405                 410                 415

Glu Pro Pro Pro Ser Thr Val Ser Asn Met Ala
            420                 425

<210> SEQ ID NO 111
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Lys Ser Pro Trp Phe Thr Thr Leu Gly Cys Gly Gly Ser Gly Gly Gly
1               5                   10                  15

Gly Ser Gly Gly Gly Gly Ser Ile Gln Lys Thr Pro Gln Ile Gln Val
            20                  25                  30

Tyr Ser Arg His Pro Pro Glu Asn Gly Lys Pro Asn Ile Leu Asn Cys
        35                  40                  45

Tyr Val Thr Gln Phe His Pro Pro His Ile Glu Ile Gln Met Leu Lys
    50                  55                  60

Asn Gly Lys Lys Ile Pro Lys Val Glu Met Ser Asp Met Ser Phe Ser
65                  70                  75                  80

Lys Asp Trp Ser Phe Tyr Ile Leu Ala His Thr Glu Phe Thr Pro Thr
                85                  90                  95

Glu Thr Asp Thr Tyr Ala Cys Arg Val Lys His Ala Ser Met Ala Glu
            100                 105                 110

Pro Lys Thr Val Tyr Trp Asp Arg Asp Met Gly Gly Gly Gly Ser Gly
            115                 120                 125

Gly Gly Ser Gly Gly Gly Gly Ser Gly Gly Gly Gly Ser Gly Pro
        130                 135                 140

His Ser Leu Arg Tyr Phe Val Thr Ala Val Ser Arg Pro Gly Leu Gly
145                 150                 155                 160

Glu Pro Arg Tyr Met Glu Val Gly Tyr Val Asp Asp Thr Glu Phe Val
                165                 170                 175

Arg Phe Asp Ser Asp Ala Glu Asn Pro Arg Tyr Glu Pro Arg Ala Arg
            180                 185                 190

Trp Met Glu Gln Glu Gly Pro Glu Tyr Trp Glu Arg Glu Thr Gln Lys
            195                 200                 205
```

```
Ala Lys Gly Asn Glu Gln Ser Phe Arg Val Asp Leu Arg Thr Leu Leu
    210                 215                 220

Gly Cys Tyr Asn Gln Ser Lys Gly Gly Ser His Thr Ile Gln Val Ile
225                 230                 235                 240

Ser Gly Cys Glu Val Gly Ser Asp Gly Arg Leu Leu Arg Gly Tyr Gln
                245                 250                 255

Gln Tyr Ala Tyr Asp Gly Cys Asp Tyr Ile Ala Leu Asn Glu Asp Leu
            260                 265                 270

Lys Thr Trp Thr Ala Ala Asp Met Ala Ala Leu Ile Thr Lys His Lys
                275                 280                 285

Trp Glu Gln Ala Gly Glu Ala Glu Arg Leu Arg Ala Tyr Leu Glu Gly
    290                 295                 300

Thr Cys Val Glu Trp Leu Arg Arg Tyr Leu Lys Asn Gly Asn Ala Thr
305                 310                 315                 320

Leu Leu Arg Thr Asp Ser Pro Lys Ala His Val Thr His His Ser Arg
                325                 330                 335

Pro Glu Asp Lys Val Thr Leu Arg Cys Trp Ala Leu Gly Phe Tyr Pro
            340                 345                 350

Ala Asp Ile Thr Leu Thr Trp Gln Leu Asn Gly Glu Glu Leu Ile Gln
                355                 360                 365

Asp Met Glu Leu Val Glu Thr Arg Pro Ala Gly Asp Gly Thr Phe Gln
    370                 375                 380

Lys Trp Ala Ser Val Val Pro Leu Gly Lys Glu Gln Tyr Tyr Thr
385                 390                 395                 400

Cys His Val Tyr His Gln Gly Leu Pro Glu Pro Leu Thr Leu Arg Trp
            405                 410                 415

Glu Pro Pro Pro Ser Thr Val Ser Asn Met Ala
            420                 425

<210> SEQ ID NO 112
<211> LENGTH: 667
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Tyr Met Leu Asp Leu Gln Pro Glu Thr Gly Cys Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Ser
        115                 120                 125

Gly Gly Gly Gly Ser Gly Gly Gly Ser Gly Gly Gly Gly Ser Gly
```

```
                130             135             140
Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Thr Gln Phe
                165                 170                 175

Val Arg Phe Asp Ser Asp Ala Ala Ser Gln Arg Met Glu Pro Arg Ala
                180                 185                 190

Pro Trp Ile Glu Gln Glu Gly Pro Glu Tyr Trp Asp Gly Glu Thr Arg
                195                 200                 205

Lys Val Lys Ala His Ser Gln Thr His Arg Val Asp Leu Gly Thr Leu
210                 215                 220

Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                245                 250                 255

His Gln Tyr Ala Tyr Asp Gly Lys Asp Tyr Ile Ala Leu Lys Glu Asp
                260                 265                 270

Leu Arg Ser Trp Thr Ala Ala Asp Met Ala Ala Gln Thr Thr Lys His
                275                 280                 285

Lys Trp Glu Ala Ala His Val Ala Glu Gln Leu Arg Ala Tyr Leu Glu
290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                325                 330                 335

Val Ser Asp His Glu Ala Thr Leu Arg Cys Trp Ala Leu Ser Phe Tyr
                340                 345                 350

Pro Ala Glu Ile Thr Leu Thr Trp Gln Arg Asp Gly Glu Asp Gln Thr
                355                 360                 365

Gln Asp Thr Glu Leu Val Glu Thr Arg Pro Ala Gly Asp Gly Thr Phe
                370                 375                 380

Gln Lys Trp Ala Ala Val Val Pro Ser Gly Gln Glu Gln Arg Tyr
385                 390                 395                 400

Thr Cys His Val Gln His Glu Gly Leu Pro Lys Pro Leu Thr Leu Arg
                405                 410                 415

Trp Glu Pro Gly Gly Gly Ser Gly Gly Gly Ser Gly Gly Gly
                420                 425                 430

Gly Ser Gly Gly Gly Ser Glu Ser Lys Tyr Gly Pro Pro Cys Pro
                435                 440                 445

Pro Cys Pro Ala Pro Pro Val Ala Gly Pro Ser Val Phe Leu Phe Pro
450                 455                 460

Pro Lys Pro Lys Asp Thr Leu Met Ile Ser Arg Thr Pro Glu Val Thr
465                 470                 475                 480

Cys Val Val Val Asp Val Ser Gln Glu Asp Pro Glu Val Gln Phe Asn
                485                 490                 495

Trp Tyr Val Asp Gly Val Glu Val His Asn Ala Lys Thr Lys Pro Arg
                500                 505                 510

Glu Glu Gln Phe Asn Ser Thr Tyr Arg Val Val Ser Val Leu Thr Val
                515                 520                 525

Leu His Gln Asp Trp Leu Asn Gly Lys Glu Tyr Lys Cys Lys Val Ser
                530                 535                 540

Asn Lys Gly Leu Pro Ser Ser Ile Glu Lys Thr Ile Ser Lys Ala Lys
545                 550                 555                 560
```

```
Gly Gln Pro Arg Glu Pro Gln Val Tyr Thr Leu Pro Pro Ser Gln Glu
                565                 570                 575

Glu Met Thr Lys Asn Gln Val Ser Leu Trp Cys Leu Val Lys Gly Phe
                580                 585                 590

Tyr Pro Ser Asp Ile Ala Val Glu Trp Glu Ser Asn Gly Gln Pro Glu
            595                 600                 605

Asn Asn Tyr Lys Thr Thr Pro Pro Val Leu Asp Ser Asp Gly Ser Phe
610                 615                 620

Phe Leu Tyr Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Leu Gly Lys
                660                 665

<210> SEQ ID NO 113
<211> LENGTH: 667
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Asn Leu Val Pro Met Val Ala Thr Val Gly Cys Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
                35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
                100                 105                 110

Gln Pro Lys Ile Val Lys Trp Asp Arg Asp Met Gly Gly Gly Gly Ser
            115                 120                 125

Gly Gly Gly Gly Ser Gly Gly Gly Ser Gly Gly Gly Gly Ser Gly
        130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Ala Ser Gln Arg Met Glu Pro Arg Ala
            180                 185                 190

Pro Trp Ile Glu Gln Glu Gly Pro Glu Tyr Trp Asp Gly Glu Thr Arg
        195                 200                 205

Lys Val Lys Ala His Ser Gln Thr His Arg Val Asp Leu Gly Thr Leu
    210                 215                 220

Arg Gly Cys Tyr Asn Gln Ser Glu Ala Gly Ser His Thr Val Gln Arg
225                 230                 235                 240
```

-continued

```
Met Tyr Gly Cys Asp Val Gly Ser Asp Trp Arg Phe Leu Arg Gly Tyr
                245                 250                 255
His Gln Tyr Ala Tyr Asp Gly Lys Asp Tyr Ile Ala Leu Lys Glu Asp
            260                 265                 270
Leu Arg Ser Trp Thr Ala Ala Asp Met Ala Ala Gln Thr Thr Lys His
        275                 280                 285
Lys Trp Glu Ala Ala His Val Ala Glu Gln Leu Arg Ala Tyr Leu Glu
    290                 295                 300
Gly Thr Cys Val Glu Trp Leu Arg Arg Tyr Leu Glu Asn Gly Lys Glu
305                 310                 315                 320
Thr Leu Gln Arg Thr Asp Ala Pro Lys Thr His Met Thr His His Ala
                325                 330                 335
Val Ser Asp His Glu Ala Thr Leu Arg Cys Trp Ala Leu Ser Phe Tyr
            340                 345                 350
Pro Ala Glu Ile Thr Leu Thr Trp Gln Arg Asp Gly Glu Asp Gln Thr
        355                 360                 365
Gln Asp Thr Glu Leu Val Glu Thr Arg Pro Ala Gly Asp Gly Thr Phe
    370                 375                 380
Gln Lys Trp Ala Ala Val Val Val Pro Ser Gly Gln Glu Gln Arg Tyr
385                 390                 395                 400
Thr Cys His Val Gln His Glu Gly Leu Pro Lys Pro Leu Thr Leu Arg
                405                 410                 415
Trp Glu Pro Gly Gly Gly Ser Gly Gly Gly Ser Gly Gly
            420                 425                 430
Gly Ser Gly Gly Gly Ser Glu Ser Lys Tyr Gly Pro Pro Cys Pro
        435                 440                 445
Pro Cys Pro Ala Pro Pro Val Ala Gly Pro Ser Val Phe Leu Phe Pro
    450                 455                 460
Pro Lys Pro Lys Asp Thr Leu Met Ile Ser Arg Thr Pro Glu Val Thr
465                 470                 475                 480
Cys Val Val Val Asp Val Ser Gln Glu Asp Pro Glu Val Gln Phe Asn
                485                 490                 495
Trp Tyr Val Asp Gly Val Glu Val His Asn Ala Lys Thr Lys Pro Arg
            500                 505                 510
Glu Glu Gln Phe Asn Ser Thr Tyr Arg Val Val Ser Val Leu Thr Val
        515                 520                 525
Leu His Gln Asp Trp Leu Asn Gly Lys Glu Tyr Lys Cys Lys Val Ser
    530                 535                 540
Asn Lys Gly Leu Pro Ser Ser Ile Glu Lys Thr Ile Ser Lys Ala Lys
545                 550                 555                 560
Gly Gln Pro Arg Glu Pro Gln Val Tyr Thr Leu Pro Pro Ser Gln Glu
                565                 570                 575
Glu Met Thr Lys Asn Gln Val Ser Leu Trp Cys Leu Val Lys Gly Phe
            580                 585                 590
Tyr Pro Ser Asp Ile Ala Val Glu Trp Glu Ser Asn Gly Gln Pro Glu
        595                 600                 605
Asn Asn Tyr Lys Thr Thr Pro Pro Val Leu Asp Ser Asp Gly Ser Phe
    610                 615                 620
Phe Leu Tyr Ser Arg Leu Thr Val Asp Lys Ser Arg Trp Gln Glu Gly
625                 630                 635                 640
Asn Val Phe Ser Cys Ser Val Met His Glu Ala Leu His Asn His Tyr
                645                 650                 655
Thr Gln Lys Ser Leu Ser Leu Ser Leu Gly Lys
```

<210> SEQ ID NO 114
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 114

Asn Leu Val Pro Met Val Ala Thr Val Gly Cys Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met
        115                 120

<210> SEQ ID NO 115
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 115

Tyr Met Leu Asp Leu Gln Pro Glu Thr Gly Cys Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met
        115                 120

<210> SEQ ID NO 116
<211> LENGTH: 667
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Asn Leu Val Pro Met Val Ala Thr Val Gly Cys Gly Gly Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
                35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
                100                 105                 110

Gln Pro Lys Ile Val Lys Trp Asp Arg Asp Met Gly Gly Gly Ser
            115                 120                 125

Gly Gly Gly Gly Ser Gly Gly Gly Ser Gly Gly Gly Ser Gly
        130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Ala Ser Gln Arg Met Glu Pro Arg Ala
                180                 185                 190

Pro Trp Ile Glu Gln Glu Gly Pro Glu Tyr Trp Asp Gly Glu Thr Arg
            195                 200                 205

Lys Val Lys Ala His Ser Gln Thr His Arg Val Asp Leu Gly Thr Leu
            210                 215                 220

Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                245                 250                 255

His Gln Tyr Ala Tyr Asp Gly Lys Asp Tyr Ile Ala Leu Lys Glu Asp
                260                 265                 270

Leu Arg Ser Trp Thr Ala Ala Asp Met Ala Ala Gln Thr Thr Lys His
            275                 280                 285

Lys Trp Glu Ala Ala His Val Ala Glu Gln Leu Arg Ala Tyr Leu Glu
            290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                325                 330                 335

Val Ser Asp His Glu Ala Thr Leu Arg Cys Trp Ala Leu Ser Phe Tyr
                340                 345                 350

Pro Ala Glu Ile Thr Leu Thr Trp Gln Arg Asp Gly Glu Asp Gln Thr
            355                 360                 365

Gln Asp Thr Glu Leu Val Glu Thr Arg Pro Ala Gly Asp Gly Thr Phe
370                 375                 380

```
Gln Lys Trp Ala Ala Val Val Pro Ser Gly Gln Glu Gln Arg Tyr
385                 390                 395                 400

Thr Cys His Val Gln His Glu Gly Leu Pro Lys Pro Leu Thr Leu Arg
            405                 410                 415

Trp Glu Pro Gly Gly Gly Gly Ser Gly Gly Gly Gly Ser Gly Gly Gly
        420                 425                 430

Gly Ser Gly Gly Gly Gly Ser Glu Ser Lys Tyr Gly Pro Pro Cys Pro
        435                 440                 445

Pro Cys Pro Ala Pro Pro Val Ala Gly Pro Ser Val Phe Leu Phe Pro
        450                 455                 460

Pro Lys Pro Lys Asp Thr Leu Met Ile Ser Arg Thr Pro Glu Val Thr
465                 470                 475                 480

Cys Val Val Val Asp Val Ser Gln Glu Asp Pro Glu Val Gln Phe Asn
                485                 490                 495

Trp Tyr Val Asp Gly Val Glu Val His Asn Ala Lys Thr Lys Pro Arg
            500                 505                 510

Glu Glu Gln Phe Asn Ser Thr Tyr Arg Val Val Ser Val Leu Thr Val
            515                 520                 525

Leu His Gln Asp Trp Leu Asn Gly Lys Glu Tyr Lys Cys Lys Val Ser
        530                 535                 540

Asn Lys Gly Leu Pro Ser Ser Ile Glu Lys Thr Ile Ser Lys Ala Lys
545                 550                 555                 560

Gly Gln Pro Arg Glu Pro Gln Val Tyr Thr Leu Pro Pro Ser Gln Glu
                565                 570                 575

Glu Met Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
        610                 615                 620

Phe Leu Tyr Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Leu Gly Lys
            660                 665

<210> SEQ ID NO 117
<211> LENGTH: 815
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Asn Leu Val Pro Met Val Ala Thr Val Gly Cys Gly Gly Ser Gly Gly
1               5                   10                  15

Gly Gly Ser Gly Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
        35                  40                  45

Cys Tyr Val Ser Gly Phe His Pro Ser Asp Ile Glu Val Asp Leu Leu
    50                  55                  60

Lys Asn Gly Glu Arg Ile Glu Lys Val Glu His Ser Asp Leu Ser Phe
```

```
                65                  70                  75                  80
Ser Lys Asp Trp Ser Phe Tyr Leu Leu Tyr Tyr Thr Glu Phe Thr Pro
                    85                  90                  95

Thr Glu Lys Asp Glu Tyr Ala Cys Arg Val Asn His Val Thr Leu Ser
                100                 105                 110

Gln Pro Lys Ile Val Lys Trp Asp Arg Asp Met Gly Gly Gly Gly Ser
                115                 120                 125

Gly Gly Gly Gly Ser Gly Gly Gly Ser Gly Gly Gly Gly Ser Gly
130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                    165                 170                 175

Val Arg Phe Asp Ser Asp Ala Ala Ser Gln Arg Met Glu Pro Arg Ala
                180                 185                 190

Pro Trp Ile Glu Gln Glu Gly Pro Glu Tyr Trp Asp Gly Glu Thr Arg
                195                 200                 205

Lys Val Lys Ala His Ser Gln Thr His Arg Val Asp Leu Gly Thr Leu
210                 215                 220

Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                    245                 250                 255

His Gln Tyr Ala Tyr Asp Gly Lys Asp Tyr Ile Ala Leu Lys Glu Asp
                260                 265                 270

Leu Arg Ser Trp Thr Ala Ala Asp Met Ala Ala Gln Thr Thr Lys His
                275                 280                 285

Lys Trp Glu Ala Ala His Val Ala Glu Gln Leu Arg Ala Tyr Leu Glu
290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                    325                 330                 335

Val Ser Asp His Glu Ala Thr Leu Arg Cys Trp Ala Leu Ser Phe Tyr
                340                 345                 350

Pro Ala Glu Ile Thr Leu Thr Trp Gln Arg Asp Gly Glu Asp Gln Thr
                355                 360                 365

Gln Asp Thr Glu Leu Val Glu Thr Arg Pro Ala Gly Asp Gly Thr Phe
370                 375                 380

Gln Lys Trp Ala Ala Val Val Pro Ser Gly Gln Glu Gln Arg Tyr
385                 390                 395                 400

Thr Cys His Val Gln His Glu Gly Leu Pro Lys Pro Leu Thr Leu Arg
                    405                 410                 415

Trp Glu Pro Gly Gly Gly Gly Ser Gly Gly Gly Gly Ser Gly Gly Gly
                420                 425                 430

Gly Ser Gly Gly Gly Ser Glu Ser Lys Tyr Gly Pro Pro Cys Pro
        435                 440                 445

Pro Cys Pro Ala Pro Pro Val Ala Gly Pro Ser Val Phe Leu Phe Pro
450                 455                 460

Pro Lys Pro Lys Asp Thr Leu Met Ile Ser Arg Thr Pro Glu Val Thr
465                 470                 475                 480

Cys Val Val Val Asp Val Ser Gln Glu Asp Pro Glu Val Gln Phe Asn
                    485                 490                 495
```

Trp Tyr Val Asp Gly Val Glu Val His Asn Ala Lys Thr Lys Pro Arg
            500                 505                 510

Glu Glu Gln Phe Asn Ser Thr Tyr Arg Val Val Ser Val Leu Thr Val
            515                 520                 525

Leu His Gln Asp Trp Leu Asn Gly Lys Glu Tyr Lys Cys Lys Val Ser
530                 535                 540

Asn Lys Gly Leu Pro Ser Ser Ile Glu Lys Thr Ile Ser Lys Ala Lys
545                 550                 555                 560

Gly Gln Pro Arg Glu Pro Gln Val Tyr Thr Leu Pro Pro Ser Gln Glu
            565                 570                 575

Glu Met Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
            595                 600                 605

Asn Asn Tyr Lys Thr Thr Pro Pro Val Leu Asp Ser Asp Gly Ser Phe
            610                 615                 620

Phe Leu Tyr Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
            645                 650                 655

Thr Gln Lys Ser Leu Ser Leu Ser Leu Gly Lys Gly Gly Gly Gly Ser
            660                 665                 670

Gly Gly Gly Gly Ser Gly Gly Gly Ser Ala Pro Thr Ser Ser Ser
            675                 680                 685

Thr Lys Lys Thr Gln Leu Gln Leu Glu Ala Leu Leu Leu Asp Leu Gln
            690                 695                 700

Met Ile Leu Asn Gly Ile Asn Asn Tyr Lys Asn Pro Lys Leu Thr Arg
705                 710                 715                 720

Met Leu Thr Ala Lys Phe Tyr Met Pro Lys Lys Ala Thr Glu Leu Lys
            725                 730                 735

His Leu Gln Cys Leu Glu Glu Glu Leu Lys Pro Leu Glu Glu Val Leu
            740                 745                 750

Asn Leu Ala Gln Ser Lys Asn Phe His Leu Arg Pro Arg Asp Leu Ile
            755                 760                 765

Ser Asn Ile Asn Val Ile Val Leu Glu Leu Lys Gly Ser Glu Thr Thr
770                 775                 780

Phe Met Cys Glu Tyr Ala Asp Glu Thr Ala Thr Ile Val Glu Phe Leu
785                 790                 795                 800

Asn Arg Trp Ile Thr Phe Cys Gln Ser Ile Ile Ser Thr Leu Thr
            805                 810                 815

<210> SEQ ID NO 118
<211> LENGTH: 1005
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Tyr Met Leu Asp Leu Gln Pro Glu Thr Gly Cys Gly Ser Gly Gly
1               5                   10                  15

Gly Gly Ser Gly Gly Gly Ser Ile Gln Arg Thr Pro Lys Ile Gln
            20                  25                  30

-continued

```
Val Tyr Ser Arg His Pro Ala Glu Asn Gly Lys Ser Asn Phe Leu Asn
         35                  40                  45

Cys Tyr Val Ser Gly Phe His Pro Ser Asp Ile Glu Val Asp Leu Leu
 50                  55                  60

Lys Asn Gly Glu Arg Ile Glu Lys Val Glu His Ser Asp Leu Ser Phe
 65                  70                  75                  80

Ser Lys Asp Trp Ser Phe Tyr Leu Leu Tyr Tyr Thr Glu Phe Thr Pro
                 85                  90                  95

Thr Glu Lys Asp Glu Tyr Ala Cys Arg Val Asn His Val Thr Leu Ser
             100                 105                 110

Gln Pro Lys Ile Val Lys Trp Asp Arg Asp Met Gly Gly Gly Gly Ser
         115                 120                 125

Gly Gly Gly Gly Ser Gly Gly Gly Ser Gly Gly Gly Gly Ser Gly
     130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                 165                 170                 175

Val Arg Phe Asp Ser Asp Ala Ala Ser Gln Arg Met Glu Pro Arg Ala
             180                 185                 190

Pro Trp Ile Glu Gln Glu Gly Pro Glu Tyr Trp Asp Gly Glu Thr Arg
         195                 200                 205

Lys Val Lys Ala His Ser Gln Thr His Arg Val Asp Leu Gly Thr Leu
     210                 215                 220

Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                 245                 250                 255

His Gln Tyr Ala Tyr Asp Gly Lys Asp Tyr Ile Ala Leu Lys Glu Asp
             260                 265                 270

Leu Arg Ser Trp Thr Ala Ala Asp Met Ala Ala Gln Thr Thr Lys His
         275                 280                 285

Lys Trp Glu Ala Ala His Val Ala Glu Gln Leu Arg Ala Tyr Leu Glu
     290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                 325                 330                 335

Val Ser Asp His Glu Ala Thr Leu Arg Cys Trp Ala Leu Ser Phe Tyr
             340                 345                 350

Pro Ala Glu Ile Thr Leu Thr Trp Gln Arg Asp Gly Glu Asp Gln Thr
         355                 360                 365

Gln Asp Thr Glu Leu Val Glu Thr Arg Pro Ala Gly Asp Gly Thr Phe
     370                 375                 380

Gln Lys Trp Ala Ala Val Val Val Pro Ser Gly Gln Glu Gln Arg Tyr
385                 390                 395                 400

Thr Cys His Val Gln His Glu Gly Leu Pro Lys Pro Leu Thr Leu Arg
                 405                 410                 415

Trp Glu Pro Gly Gly Gly Ser Gly Gly Gly Gly Ser Gly Gly Gly
         420                 425                 430

Gly Ser Gly Gly Gly Ser Glu Ser Lys Tyr Gly Pro Pro Cys Pro
     435                 440                 445

Pro Cys Pro Ala Pro Pro Val Ala Gly Pro Ser Val Phe Leu Phe Pro
```

```
            450                 455                 460
Pro Lys Pro Lys Asp Thr Leu Met Ile Ser Arg Thr Pro Glu Val Thr
465                 470                 475                 480

Cys Val Val Asp Val Ser Gln Glu Asp Pro Glu Val Gln Phe Asn
                485                 490                 495

Trp Tyr Val Asp Gly Val Glu Val His Asn Ala Lys Thr Lys Pro Arg
                500                 505                 510

Glu Glu Gln Phe Asn Ser Thr Tyr Arg Val Val Ser Val Leu Thr Val
                515                 520                 525

Leu His Gln Asp Trp Leu Asn Gly Lys Glu Tyr Lys Cys Lys Val Ser
        530                 535                 540

Asn Lys Gly Leu Pro Ser Ser Ile Glu Lys Thr Ile Ser Lys Ala Lys
545                 550                 555                 560

Gly Gln Pro Arg Glu Pro Gln Val Tyr Thr Leu Pro Pro Ser Gln Glu
                565                 570                 575

Glu Met Thr Lys Asn Gln Val Ser Leu Thr Cys Leu Val Lys Gly Phe
                580                 585                 590

Tyr Pro Ser Asp Ile Ala Val Glu Trp Glu Ser Asn Gly Gln Pro Glu
                595                 600                 605

Asn Asn Tyr Lys Thr Thr Pro Pro Val Leu Asp Ser Asp Gly Ser Phe
610                 615                 620

Phe Leu Tyr Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Leu Gly Lys Gly Gly Gly Gly Ser
                660                 665                 670

Gly Gly Gly Gly Ser Gly Gly Gly Ser Glu Leu Cys Asp Asp Asp
                675                 680                 685

Pro Pro Glu Ile Pro His Ala Thr Phe Lys Ala Met Ala Tyr Lys Glu
                690                 695                 700

Gly Thr Met Leu Asn Cys Glu Cys Lys Arg Gly Phe Arg Arg Ile Lys
705                 710                 715                 720

Ser Gly Ser Leu Tyr Met Leu Cys Thr Gly Asn Ser Ser His Ser Ser
                725                 730                 735

Trp Asp Asn Gln Cys Gln Cys Thr Ser Ser Ala Thr Arg Asn Thr Thr
                740                 745                 750

Lys Gln Val Thr Pro Gln Pro Glu Glu Gln Lys Glu Arg Lys Thr Thr
                755                 760                 765

Glu Met Gln Ser Pro Met Gln Pro Val Asp Gln Ala Ser Leu Pro Gly
770                 775                 780

His Cys Arg Glu Pro Pro Pro Trp Glu Asn Glu Ala Thr Glu Arg Ile
785                 790                 795                 800

Tyr His Phe Val Val Gly Gln Met Val Tyr Tyr Gln Cys Val Gln Gly
                805                 810                 815

Tyr Arg Ala Leu His Arg Gly Pro Ala Glu Ser Val Cys Lys Met Thr
                820                 825                 830

His Gly Lys Thr Arg Trp Thr Gln Pro Gln Leu Ile Cys Thr Gly Gly
                835                 840                 845

Gly Gly Gly Ser Gly Gly Gly Gly Ser Gly Gly Gly Gly Ser Gly Gly
                850                 855                 860

Gly Gly Ser Gly Gly Gly Gly Ser Ala Pro Thr Ser Ser Ser Thr Lys
865                 870                 875                 880
```

```
Lys Thr Gln Leu Gln Leu Glu His Leu Leu Asp Leu Gln Met Ile
            885                 890                 895

Leu Asn Gly Ile Asn Asn Tyr Lys Asn Pro Lys Leu Thr Arg Met Leu
            900                 905                 910

Thr Phe Lys Phe Tyr Met Pro Lys Ala Thr Glu Leu Lys His Leu
            915                 920                 925

Gln Cys Leu Glu Glu Leu Lys Pro Leu Glu Glu Val Leu Asn Leu
            930                 935                 940

Ala Gln Ser Lys Asn Phe His Leu Arg Pro Arg Asp Leu Ile Ser Asn
945                 950                 955                 960

Ile Asn Val Ile Val Leu Glu Leu Lys Gly Ser Glu Thr Thr Phe Met
            965                 970                 975

Cys Glu Tyr Ala Asp Glu Thr Ala Thr Ile Val Glu Phe Leu Asn Arg
            980                 985                 990

Trp Ile Thr Phe Cys Gln Ser Ile Ile Ser Thr Leu Thr
            995                 1000                1005

<210> SEQ ID NO 119
<211> LENGTH: 815
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Tyr Met Leu Asp Leu Gln Pro Glu Thr Gly Cys Gly Gly Ser Gly
1               5                   10                  15

Gly Gly Ser Gly Gly Gly Gly Ser Ile Gln Arg Thr Pro Lys Ile Gln
                20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
        50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Ser
            115                 120                 125

Gly Gly Gly Gly Ser Gly Gly Gly Ser Gly Gly Gly Gly Ser Gly
        130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Ala Ser Gln Arg Met Glu Pro Arg Ala
            180                 185                 190

Pro Trp Ile Glu Gln Glu Gly Pro Glu Tyr Trp Asp Gly Glu Thr Arg
            195                 200                 205

Lys Val Lys Ala His Ser Gln Thr His Arg Val Asp Leu Gly Thr Leu
        210                 215                 220
```

```
Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                245                 250                 255

His Gln Tyr Ala Tyr Asp Gly Lys Asp Tyr Ile Ala Leu Lys Glu Asp
            260                 265                 270

Leu Arg Ser Trp Thr Ala Ala Asp Met Ala Ala Gln Thr Thr Lys His
        275                 280                 285

Lys Trp Glu Ala Ala His Val Ala Glu Gln Leu Arg Ala Tyr Leu Glu
    290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                325                 330                 335

Val Ser Asp His Glu Ala Thr Leu Arg Cys Trp Ala Leu Ser Phe Tyr
            340                 345                 350

Pro Ala Glu Ile Thr Leu Thr Trp Gln Arg Asp Gly Glu Asp Gln Thr
        355                 360                 365

Gln Asp Thr Glu Leu Val Glu Thr Arg Pro Ala Gly Asp Gly Thr Phe
    370                 375                 380

Gln Lys Trp Ala Ala Val Val Pro Ser Gly Gln Glu Gln Arg Tyr
385                 390                 395                 400

Thr Cys His Val Gln His Glu Gly Leu Pro Lys Pro Leu Thr Leu Arg
                405                 410                 415

Trp Glu Pro Gly Gly Gly Gly Ser Gly Gly Gly Gly Ser Gly Gly Gly
            420                 425                 430

Gly Ser Gly Gly Gly Gly Ser Glu Ser Lys Tyr Gly Pro Pro Cys Pro
        435                 440                 445

Pro Cys Pro Ala Pro Pro Val Ala Gly Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser Gln Glu Asp Pro Glu Val Gln Phe Asn
                485                 490                 495

Trp Tyr Val Asp Gly Val Glu Val His Asn Ala Lys Thr Lys Pro Arg
            500                 505                 510

Glu Glu Gln Phe Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540

Asn Lys Gly Leu Pro Ser Ser Ile Glu Lys Thr Ile Ser Lys Ala Lys
545                 550                 555                 560

Gly Gln Pro Arg Glu Pro Gln Val Tyr Thr Leu Pro Pro Ser Gln Glu
                565                 570                 575

Glu Met Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
    610                 615                 620

Phe Leu Tyr Ser Arg Leu Thr Val Asp Lys Ser Arg Trp Gln Glu Gly
625                 630                 635                 640

Asn Val Phe Ser Cys Ser Val Met His Glu Ala Leu His Asn His Tyr
```

-continued

```
                    645                 650                 655
Thr Gln Lys Ser Leu Ser Leu Ser Leu Gly Lys Gly Gly Gly Ser
                660                 665                 670

Gly Gly Gly Gly Ser Gly Gly Gly Ser Ala Pro Thr Ser Ser Ser
                675                 680                 685

Thr Lys Lys Thr Gln Leu Gln Leu Glu Ala Leu Leu Leu Asp Leu Gln
                690                 695                 700

Met Ile Leu Asn Gly Ile Asn Asn Tyr Lys Asn Pro Lys Leu Thr Arg
705                 710                 715                 720

Met Leu Thr Ala Lys Phe Tyr Met Pro Lys Ala Thr Glu Leu Lys
                725                 730                 735

His Leu Gln Cys Leu Glu Glu Glu Leu Lys Pro Leu Glu Glu Val Leu
                740                 745                 750

Asn Leu Ala Gln Ser Lys Asn Phe His Leu Arg Pro Arg Asp Leu Ile
                755                 760                 765

Ser Asn Ile Asn Val Ile Val Leu Glu Leu Lys Gly Ser Glu Thr Thr
                770                 775                 780

Phe Met Cys Glu Tyr Ala Asp Glu Thr Ala Thr Ile Val Glu Phe Leu
785                 790                 795                 800

Asn Arg Trp Ile Thr Phe Cys Gln Ser Ile Ile Ser Thr Leu Thr
                805                 810                 815
```

<210> SEQ ID NO 120
<211> LENGTH: 823
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

```
Ser Ile Ile Asn Phe Glu Lys Leu Gly Cys Gly Gly Ser Gly Gly Gly
1               5                   10                  15

Gly Ser Gly Gly Gly Gly Ser Ile Gln Lys Thr Pro Gln Ile Gln Val
                20                  25                  30

Tyr Ser Arg His Pro Pro Glu Asn Gly Lys Pro Asn Ile Leu Asn Cys
                35                  40                  45

Tyr Val Thr Gln Phe His Pro Pro His Ile Glu Ile Gln Met Leu Lys
                50                  55                  60

Asn Gly Lys Lys Ile Pro Lys Val Glu Met Ser Asp Met Ser Phe Ser
65                  70                  75                  80

Lys Asp Trp Ser Phe Tyr Ile Leu Ala His Thr Glu Phe Thr Pro Thr
                85                  90                  95

Glu Thr Asp Thr Tyr Ala Cys Arg Val Lys His Ala Ser Met Ala Glu
                100                 105                 110

Pro Lys Thr Val Tyr Trp Asp Arg Asp Met Gly Gly Gly Gly Ser Gly
                115                 120                 125

Gly Gly Gly Ser Gly Gly Gly Gly Ser Gly Gly Gly Gly Ser Gly Pro
                130                 135                 140

His Ser Leu Arg Tyr Phe Val Thr Ala Val Ser Arg Pro Gly Leu Gly
145                 150                 155                 160

Glu Pro Arg Tyr Met Glu Val Gly Tyr Val Asp Asp Thr Glu Phe Val
                165                 170                 175

Arg Phe Asp Ser Asp Ala Glu Asn Pro Arg Tyr Glu Pro Arg Ala Arg
                180                 185                 190
```

```
Trp Met Glu Gln Glu Gly Pro Glu Tyr Trp Arg Glu Thr Gln Lys
        195                 200                 205
Ala Lys Gly Asn Glu Gln Ser Phe Arg Val Asp Leu Arg Thr Leu Leu
210             215                 220
Gly Cys Tyr Asn Gln Ser Lys Gly Gly Ser His Thr Ile Gln Val Ile
225                 230                 235                 240
Ser Gly Cys Glu Val Gly Ser Asp Gly Arg Leu Leu Arg Gly Tyr Gln
                245                 250                 255
Gln Tyr Ala Tyr Asp Gly Cys Asp Tyr Ile Ala Leu Asn Glu Asp Leu
            260                 265                 270
Lys Thr Trp Thr Ala Ala Asp Met Ala Ala Leu Ile Thr Lys His Lys
        275                 280                 285
Trp Glu Gln Ala Gly Glu Ala Glu Arg Leu Arg Ala Tyr Leu Glu Gly
    290                 295                 300
Thr Cys Val Glu Trp Leu Arg Arg Tyr Leu Lys Asn Gly Asn Ala Thr
305                 310                 315                 320
Leu Leu Arg Thr Asp Ser Pro Lys Ala His Val Thr His His Ser Arg
                325                 330                 335
Pro Glu Asp Lys Val Thr Leu Arg Cys Trp Ala Leu Gly Phe Tyr Pro
            340                 345                 350
Ala Asp Ile Thr Leu Thr Trp Gln Leu Asn Gly Glu Glu Leu Ile Gln
        355                 360                 365
Asp Met Glu Leu Val Glu Thr Arg Pro Ala Gly Asp Gly Thr Phe Gln
    370                 375                 380
Lys Trp Ala Ser Val Val Val Pro Leu Gly Lys Glu Gln Tyr Tyr Thr
385                 390                 395                 400
Cys His Val Tyr His Gln Gly Leu Pro Glu Pro Leu Thr Leu Arg Trp
                405                 410                 415
Glu Pro Pro Pro Ser Thr Val Ser Asn Met Ala Gly Gly Gly Gly Ser
            420                 425                 430
Gly Gly Gly Gly Ser Gly Gly Gly Gly Ser Gly Gly Gly Gly Ser Glu
        435                 440                 445
Ser Lys Tyr Gly Pro Pro Cys Pro Pro Cys Pro Ala Pro Pro Val Ala
    450                 455                 460
Gly Pro Ser Val Phe Leu Phe Pro Pro Lys Pro Lys Asp Thr Leu Met
465                 470                 475                 480
Ile Ser Arg Thr Pro Glu Val Thr Cys Val Val Val Asp Val Ser Gln
                485                 490                 495
Glu Asp Pro Glu Val Gln Phe Asn Trp Tyr Val Asp Gly Val Glu Val
            500                 505                 510
His Asn Ala Lys Thr Lys Pro Arg Glu Glu Gln Phe Asn Ser Thr Tyr
        515                 520                 525
Arg Val Val Ser Val Leu Thr Val Leu His Gln Asp Trp Leu Asn Gly
    530                 535                 540
Lys Glu Tyr Lys Cys Lys Val Ser Asn Lys Gly Leu Pro Ser Ser Ile
545                 550                 555                 560
Glu Lys Thr Ile Ser Lys Ala Lys Gly Gln Pro Arg Glu Pro Gln Val
                565                 570                 575
Tyr Thr Leu Pro Pro Ser Gln Glu Glu Met Thr Lys Asn Gln Val Ser
            580                 585                 590
Leu Thr Cys Leu Val Lys Gly Phe Tyr Pro Ser Asp Ile Ala Val Glu
        595                 600                 605
```

Trp Glu Ser Asn Gly Gln Pro Glu Asn Asn Tyr Lys Thr Thr Pro Pro
            610                 615                 620

Val Leu Asp Ser Asp Gly Ser Phe Phe Leu Tyr Ser Arg Leu Thr Val
625                 630                 635                 640

Asp Lys Ser Arg Trp Gln Glu Gly Asn Val Phe Ser Cys Ser Val Met
            645                 650                 655

His Glu Ala Leu His Asn His Tyr Thr Gln Lys Ser Leu Ser Leu Ser
            660                 665                 670

Leu Gly Lys Gly Gly Gly Gly Ser Gly Gly Gly Ser Gly Gly Gly
            675                 680                 685

Gly Ser Ala Pro Thr Ser Ser Ser Thr Lys Lys Thr Gln Leu Gln Leu
690                 695                 700

Glu Ala Leu Leu Leu Asp Leu Gln Met Ile Leu Asn Gly Ile Asn Asn
705                 710                 715                 720

Tyr Lys Asn Pro Lys Leu Thr Arg Met Leu Thr Ala Lys Phe Tyr Met
            725                 730                 735

Pro Lys Lys Ala Thr Glu Leu Lys His Leu Gln Cys Leu Glu Glu Glu
            740                 745                 750

Leu Lys Pro Leu Glu Glu Val Leu Asn Leu Ala Gln Ser Lys Asn Phe
            755                 760                 765

His Leu Arg Pro Arg Asp Leu Ile Ser Asn Ile Asn Val Ile Val Leu
            770                 775                 780

Glu Leu Lys Gly Ser Glu Thr Thr Phe Met Cys Glu Tyr Ala Asp Glu
785                 790                 795                 800

Thr Ala Thr Ile Val Glu Phe Leu Asn Arg Trp Ile Thr Phe Cys Gln
            805                 810                 815

Ser Ile Ile Ser Thr Leu Thr
            820

<210> SEQ ID NO 121
<211> LENGTH: 823
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Lys Ser Pro Trp Phe Thr Thr Leu Gly Cys Gly Gly Ser Gly Gly Gly
1               5                   10                  15

Gly Ser Gly Gly Gly Gly Ser Ile Gln Lys Thr Pro Gln Ile Gln Val
            20                  25                  30

Tyr Ser Arg His Pro Pro Glu Asn Gly Lys Pro Asn Ile Leu Asn Cys
            35                  40                  45

Tyr Val Thr Gln Phe His Pro Pro His Ile Glu Ile Gln Met Leu Lys
50                  55                  60

Asn Gly Lys Lys Ile Pro Lys Val Glu Met Ser Asp Met Ser Phe Ser
65                  70                  75                  80

Lys Asp Trp Ser Phe Tyr Ile Leu Ala His Thr Glu Phe Thr Pro Thr
            85                  90                  95

Glu Thr Asp Thr Tyr Ala Cys Arg Val Lys His Ala Ser Met Ala Glu
            100                 105                 110

Pro Lys Thr Val Tyr Trp Asp Arg Asp Met Gly Gly Gly Gly Ser Gly
            115                 120                 125

Gly Gly Gly Ser Gly Gly Gly Gly Ser Gly Gly Gly Gly Ser Gly Pro

```
            130                 135                 140
His Ser Leu Arg Tyr Phe Val Thr Ala Val Ser Arg Pro Gly Leu Gly
145                 150                 155                 160

Glu Pro Arg Tyr Met Glu Val Gly Tyr Val Asp Thr Glu Phe Val
                165                 170                 175

Arg Phe Asp Ser Asp Ala Glu Asn Pro Arg Tyr Glu Pro Arg Ala Arg
                180                 185                 190

Trp Met Glu Gln Glu Gly Pro Glu Tyr Trp Glu Arg Glu Thr Gln Lys
            195                 200                 205

Ala Lys Gly Asn Glu Gln Ser Phe Arg Val Asp Leu Arg Thr Leu Leu
        210                 215                 220

Gly Cys Tyr Asn Gln Ser Lys Gly Gly Ser His Thr Ile Gln Val Ile
225                 230                 235                 240

Ser Gly Cys Glu Val Gly Ser Asp Gly Arg Leu Leu Arg Gly Tyr Gln
                245                 250                 255

Gln Tyr Ala Tyr Asp Gly Cys Asp Tyr Ile Ala Leu Asn Glu Asp Leu
                260                 265                 270

Lys Thr Trp Thr Ala Ala Asp Met Ala Ala Leu Ile Thr Lys His Lys
            275                 280                 285

Trp Glu Gln Ala Gly Glu Ala Glu Arg Leu Arg Ala Tyr Leu Glu Gly
        290                 295                 300

Thr Cys Val Glu Trp Leu Arg Arg Tyr Leu Lys Asn Gly Asn Ala Thr
305                 310                 315                 320

Leu Leu Arg Thr Asp Ser Pro Lys Ala His Val Thr His His Ser Arg
                325                 330                 335

Pro Glu Asp Lys Val Thr Leu Arg Cys Trp Ala Leu Gly Phe Tyr Pro
                340                 345                 350

Ala Asp Ile Thr Leu Thr Trp Gln Leu Asn Gly Glu Glu Leu Ile Gln
            355                 360                 365

Asp Met Glu Leu Val Glu Thr Arg Pro Ala Gly Asp Gly Thr Phe Gln
        370                 375                 380

Lys Trp Ala Ser Val Val Val Pro Leu Gly Lys Glu Gln Tyr Tyr Thr
385                 390                 395                 400

Cys His Val Tyr His Gln Gly Leu Pro Glu Pro Leu Thr Leu Arg Trp
                405                 410                 415

Glu Pro Pro Pro Ser Thr Val Ser Asn Met Ala Gly Gly Gly Gly Ser
                420                 425                 430

Gly Gly Gly Gly Ser Gly Gly Gly Ser Gly Gly Gly Gly Ser Glu
            435                 440                 445

Ser Lys Tyr Gly Pro Pro Cys Pro Pro Cys Pro Ala Pro Pro Val Ala
450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser Gln
                485                 490                 495

Glu Asp Pro Glu Val Gln Phe Asn Trp Tyr Val Asp Gly Val Glu Val
                500                 505                 510

His Asn Ala Lys Thr Lys Pro Arg Glu Glu Gln Phe Asn Ser Thr Tyr
            515                 520                 525

Arg Val Val Ser Val Leu Thr Val Leu His Gln Asp Trp Leu Asn Gly
        530                 535                 540

Lys Glu Tyr Lys Cys Lys Val Ser Asn Lys Gly Leu Pro Ser Ser Ile
545                 550                 555                 560
```

Glu Lys Thr Ile Ser Lys Ala Lys Gly Gln Pro Arg Glu Pro Gln Val
                565                 570                 575

Tyr Thr Leu Pro Pro Ser Gln Glu Glu Met Thr Lys Asn Gln Val Ser
            580                 585                 590

Leu Thr Cys Leu Val Lys Gly Phe Tyr Pro Ser Asp Ile Ala Val Glu
        595                 600                 605

Trp Glu Ser Asn Gly Gln Pro Glu Asn Asn Tyr Lys Thr Thr Pro Pro
610                 615                 620

Val Leu Asp Ser Asp Gly Ser Phe Phe Leu Tyr Ser Arg Leu Thr Val
625                 630                 635                 640

Asp Lys Ser Arg Trp Gln Glu Gly Asn Val Phe Ser Cys Ser Val Met
                645                 650                 655

His Glu Ala Leu His Asn His Tyr Thr Gln Lys Ser Leu Ser Leu Ser
            660                 665                 670

Leu Gly Lys Gly Gly Gly Gly Ser Gly Gly Gly Gly Ser Gly Gly Gly
        675                 680                 685

Gly Ser Ala Pro Thr Ser Ser Ser Thr Lys Lys Thr Gln Leu Gln Leu
    690                 695                 700

Glu Ala Leu Leu Leu Asp Leu Gln Met Ile Leu Asn Gly Ile Asn Asn
705                 710                 715                 720

Tyr Lys Asn Pro Lys Leu Thr Arg Met Leu Thr Ala Lys Phe Tyr Met
                725                 730                 735

Pro Lys Lys Ala Thr Glu Leu Lys His Leu Gln Cys Leu Glu Glu Glu
            740                 745                 750

Leu Lys Pro Leu Glu Glu Val Leu Asn Leu Ala Gln Ser Lys Asn Phe
        755                 760                 765

His Leu Arg Pro Arg Asp Leu Ile Ser Asn Ile Asn Val Ile Val Leu
770                 775                 780

Glu Leu Lys Gly Ser Glu Thr Thr Phe Met Cys Glu Tyr Ala Asp Glu
785                 790                 795                 800

Thr Ala Thr Ile Val Glu Phe Leu Asn Arg Trp Ile Thr Phe Cys Gln
                805                 810                 815

Ser Ile Ile Ser Thr Leu Thr
            820

<210> SEQ ID NO 122
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(25)
<223> OTHER INFORMATION: /note="This sequence can include 2-5 'Gly Gly
      Gly Gly Ser' repeating units"

<400> SEQUENCE: 122

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 123
<211> LENGTH: 30
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(30)
<223> OTHER INFORMATION: /note="This sequence can include 2-6 'Gly Gly
      Gly Gly Ser' repeating units"

<400> SEQUENCE: 123

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 124
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Ser Ala Pro Thr Ser Ser Ser Thr Lys Lys Thr Gln Leu Gln Leu Glu
1               5                   10                  15

Ala Leu Leu Leu Asp Leu Gln Met Ile Leu Asn Gly Ile Asn Asn Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
        130
```